(12) United States Patent
Fabio et al.

(10) Patent No.: US 10,439,151 B2
(45) Date of Patent: Oct. 8, 2019

(54) ORGANIC MOLECULES, ESPECIALLY FOR USE IN ORGANIC OPTOELECTRONIC DEVICES

(71) Applicant: CYNORA GMBH, Bruchsal (DE)

(72) Inventors: Martina Fabio, Karlsruhe Durlach (DE); Larissa Bergmann, Karlsruhe (DE); Daniel Zink, Bruchsal (DE)

(73) Assignee: CYNORA GMBH, Bruchsal (DE)

( * ) Notice: Subject to any disclaimer, the term of this patent is extended or adjusted under 35 U.S.C. 154(b) by 0 days.

(21) Appl. No.: 15/685,166

(22) Filed: Aug. 24, 2017

(65) Prior Publication Data

US 2018/0062086 A1 Mar. 1, 2018

(30) Foreign Application Priority Data

Aug. 25, 2016 (DE) .......................... 10 2016 115 854
Sep. 15, 2016 (DE) .......................... 10 2016 117 390
Feb. 24, 2017 (DE) .......................... 10 2017 103 942
Mar. 16, 2017 (DE) .......................... 10 2017 105 691

(51) Int. Cl.
*H01L 51/54* (2006.01)
*C09K 11/06* (2006.01)
(Continued)

(52) U.S. Cl.
CPC ........ *H01L 51/0072* (2013.01); *C07D 209/86* (2013.01); *C07D 209/88* (2013.01);
(Continued)

(58) Field of Classification Search
CPC .. C07D 209/86; C07D 209/88; C07D 401/00; C07D 401/10; C07D 401/14; C07D 403/00; C07D 403/10; C07D 403/14; C07D 405/00; C07D 405/10; C07D 405/14; C07D 487/00; C07D 487/02; C07D 487/04; C07D 493/00; C07D 493/02; C07D 493/04; C07D 519/00; C09K 11/06; C09K 2211/00; C09K 2211/10; C09K 2211/1007; C09K 2211/1014; C09K 2211/1029; C09K 2211/1018; C09K 2211/1044; H01L 51/0032; H01L 51/0003; H01L 51/001; H01L 51/005; H01L 51/006; H01L 51/0067; H01L 51/0071; H01L 51/0072;
(Continued)

(56) References Cited

U.S. PATENT DOCUMENTS

2009/0072727 A1* 3/2009 Takeda .................. C09K 11/06
313/504

FOREIGN PATENT DOCUMENTS

CN 105051014 A 11/2015
CN 106966955 A 7/2017
(Continued)

OTHER PUBLICATIONS

Machine translation of JP2011-256143. (Year: 2011).*

Primary Examiner — Andrew K Bohaty
(74) Attorney, Agent, or Firm — Ryan, Mason & Lewis, LLP

(57) ABSTRACT

The invention relates to an organic molecule, especially for use in optoelectronic components. According to the invention, the organic molecule contains
a first chemical unit having a structure of formula I

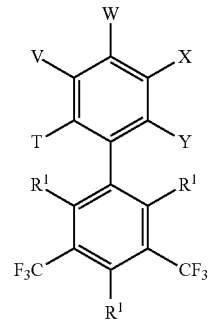

Formula I and two second chemical units each having a structure of formula II

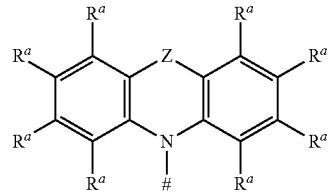

Formula II wherein the first chemical unit is joined to each of the two second chemical units via a single bond;
wherein:
T, V is independently an attachment point of the single bond between the chemical unit of formula I and a chemical unit of formula II or is H; and
W, X, Y is independently an attachment point of the single bond between the chemical unit of formula I and a chemical unit of formula II or is selected from the group consisting of H, CN and $CF_3$; and
wherein exactly one radical selected from W, X and Y is CN or $CF_3$ and exactly two radicals selected from the group consisting of T, V, W, X and Y are an attachment
(Continued)

point of the single bond between the first chemical unit and a second chemical unit.

16 Claims, 21 Drawing Sheets

(51) Int. Cl.
  *H01L 51/00* (2006.01)
  *C07D 209/86* (2006.01)
  *C07D 209/88* (2006.01)
  *C07D 405/14* (2006.01)
  *C07D 487/04* (2006.01)
  *C07D 493/04* (2006.01)
  *C07D 401/14* (2006.01)
  *C07D 403/14* (2006.01)
  *C07D 519/00* (2006.01)
  *H01L 51/50* (2006.01)
  *H01L 51/52* (2006.01)

(52) U.S. Cl.
  CPC ......... *C07D 401/14* (2013.01); *C07D 403/14* (2013.01); *C07D 405/14* (2013.01); *C07D 487/04* (2013.01); *C07D 493/04* (2013.01); *C07D 519/00* (2013.01); *C09K 11/06* (2013.01); *H01L 51/0071* (2013.01); *H01L 51/0073* (2013.01); *C09K 2211/1007* (2013.01); *C09K 2211/1014* (2013.01); *C09K 2211/1018* (2013.01); *C09K 2211/1029* (2013.01); *C09K 2211/1044* (2013.01); *H01L 51/001* (2013.01); *H01L 51/0003* (2013.01); *H01L 51/0096* (2013.01); *H01L 51/5012* (2013.01); *H01L 51/5072* (2013.01); *H01L 51/5088* (2013.01); *H01L 51/5096* (2013.01); *H01L 51/5206* (2013.01); *H01L 51/5221* (2013.01); *Y02E 10/549* (2013.01)

(58) Field of Classification Search
  CPC ............. H01L 51/0073; H01L 51/0074; H01L 51/0096; H01L 51/50; H01L 51/5012; H01L 51/5016; H01L 51/5071; H01L 51/5088; H01L 51/5096; H01L 51/5206; H01L 51/5221; H01L 2251/5376
  USPC ....... 428/690, 691, 917, 411.4, 336; 427/58, 427/66; 313/500–512; 257/40, 88–104, 257/E51.001–E51.052; 252/301.16–301.35
  See application file for complete search history.

(56) References Cited

FOREIGN PATENT DOCUMENTS

| EP | 2709183 A1 | 3/2014 |
|---|---|---|
| JP | 2011256143 A * | 12/2011 |
| JP | 2011256143 A | 12/2011 |
| WO | 2014183080 A1 | 11/2014 |
| WO | 2015066354 A1 | 5/2015 |
| WO | 2015175678 A1 | 11/2015 |

* cited by examiner

ORGANIC MOLECULES, ESPECIALLY FOR USE IN ORGANIC OPTOELECTRONIC DEVICES

CROSS-REFERENCE TO RELATED APPLICATIONS

This application claims priority to German Patent Application No. 10 2016 115 854.2 filed Aug. 25, 2016, German Patent Application No. 10 2016 117 390.8 filed Sep. 15, 2016, German Patent Application No. 10 2017 103 942.2 filed Feb. 24, 2017, and German Patent Application No. 10 2017 105 691.2 filed Mar. 16, 2017, the disclosures of which are incorporated by reference herein in their entireties.

FIELD OF INVENTION

The invention relates to purely organic molecules and to the use thereof in organic light-emitting diodes (OLEDs) and in other organic optoelectronic devices.

SUMMARY

The problem addressed by the present invention was that of providing molecules suitable for use in optoelectronic devices.

The problem is solved by the invention, which provides a new class of organic molecules.

The organic molecules according to the invention are purely organic molecules, i.e. do not have any metal ions, and are thus delimited from the metal complexes known for use in organic optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
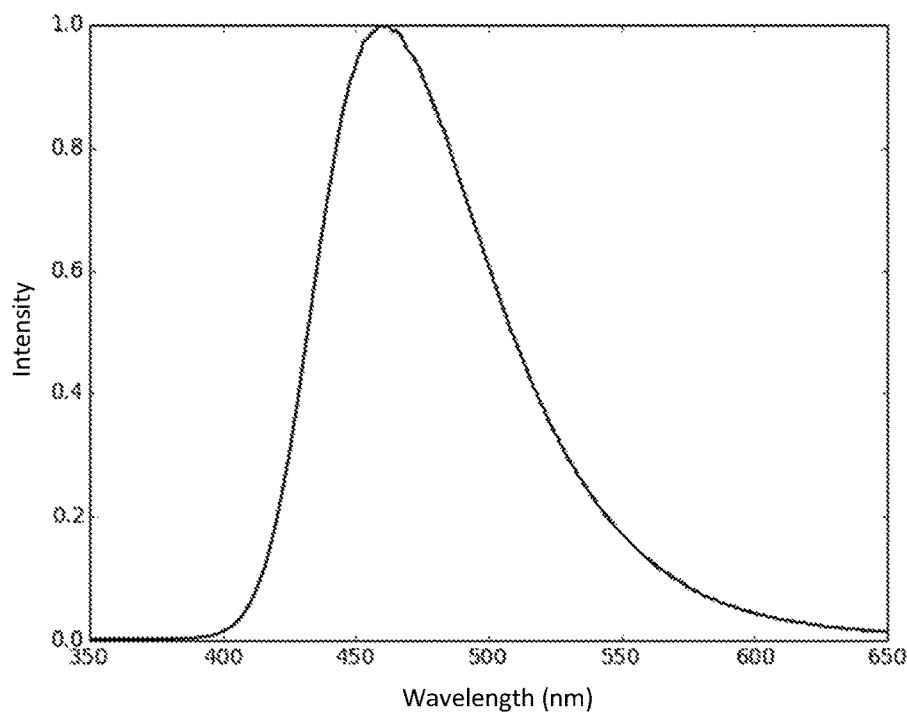
FIG. 1 illustrates an emission spectrum of Example 1 (10% in PMMA).

Exemplary embodiments of the invention will now be discussed in further detail. This invention may, however, be embodied in many different forms and should not be construed as limited to the embodiments set forth herein.

The organic molecules according to the invention are notable for emissions in the blue, sky blue or green spectral region. The photoluminescence quantum yields of the organic molecules according to the invention are especially 20% or more. The molecules according to the invention especially exhibit thermally activated delayed fluorescence (TADF). The use of the molecules according to the invention in an optoelectronic device, for example an organic light-emitting diode (OLED), leads to higher efficiencies of the device. Corresponding OLEDs have higher stability than OLEDs with known emitter materials and a comparable colour.

The blue spectral region is understood here to mean the visible range from 420 nm to 470 nm. The sky blue spectral region is understood here to mean the range from 470 nm to 499 nm. The green spectral region is understood here to mean the range from 500 nm to 599 nm. The emission maximum here is within the respective range.

The organic molecules contain a first chemical unit comprising or consisting of a structure of formula I:

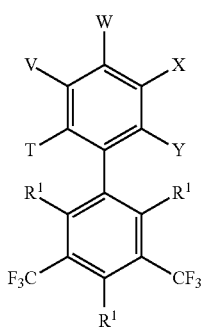

Formula I and
  two second chemical units D each comprising or consisting of, identically or differently at each instance, a structure of formula II

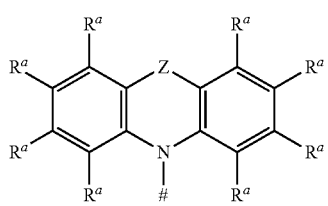

Formula II

In these molecules, the first chemical unit is joined to each of the two second chemical units via a single bond.

T is an attachment point of the single bond between the chemical unit of formula I and a chemical unit D or H.

V is an attachment point of the single bond between the chemical unit of formula I and a chemical unit D or H.

W is an attachment point of the single bond between the chemical unit of formula I and a chemical unit D or selected from the group consisting of H, CN and $CF_3$.

X is an attachment point of the single bond between the chemical unit of formula I and a chemical unit D or selected from the group consisting of H, CN and $CF_3$.

Y is an attachment point of the single bond between the chemical unit of formula I and a chemical unit D or selected from the group consisting of H, CN and $CF_3$.

# is an attachment point of the single bond between the respective chemical unit D and the chemical unit of formula I.

Z is the same or different at each instance and is a direct bond or selected from the group consisting of $CR^3R^4$, $C=CR^3R^4$, $C=O$, $C=NR^3$, $NR^3$, O, $SiR^3R^4$, S, S(O) and $S(O)_2$.

$R^1$ is the same or different at each instance and is H, deuterium, a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium, or an aromatic or heteroaromatic ring system which has 5 to 15 aromatic ring atoms and may be substituted in each case by one or more $R^6$ radicals.

$R^a$, $R^3$ and $R^4$ is the same or different at each instance and is H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^5$ radicals, where one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^5$ radicals, or an aryloxy or heteroaryloxy group which has 5 to 60 aromatic ring atoms and may be substituted in each case by one or more $R^5$ radicals, or a diarylamino group, diheteroarylamino group or arylheteroarylamino group which has 10 to 40 aromatic ring atoms and may be substituted in each case by one or more $R^5$ radicals.

$R^5$ is the same or different at each instance and is H, deuterium, $N(R^6)_2$, OH, $Si(R^6)_3$, $B(OR^6)_2$, $OSO_2R^6$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^6$ radicals, where one or more nonadjacent $CH_2$ groups may be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^6$ radicals, or an aryloxy or heteroaryloxy group which has 5 to 60 aromatic ring atoms and may be substituted in each case by one or more $R^6$ radicals, or a diarylamino group, diheteroarylamino group or arylheteroarylamino group which has 10 to 40 aromatic ring atoms and may be substituted in each case by one or more $R^6$ radicals.

$R^6$ is the same or different at each instance and is H, deuterium, OH, $CF_3$, CN, F, a linear alkyl, alkoxy or thioalkoxy group having 1 to 5 carbon atoms or a linear alkenyl or alkynyl group having 2 to 5 carbon atoms or a branched or cyclic alkyl, alkenyl, alkynyl, alkoxy or thioalkoxy group having 3 to 5 carbon atoms, where one or more hydrogen atoms may be replaced by deuterium, CN, $CF_3$ or $NO_2$; or an aromatic or heteroaromatic ring system having 5 to 60 aromatic ring atoms or an aryloxy or heteroaryloxy group having 5 to 60 aromatic ring atoms or a diarylamino group, diheteroarylamino group or arylheteroarylamino group having 10 to 40 aromatic ring atoms.

According to the invention, each of the $R^a$, $R^3$, $R^4$ or $R^5$ radicals together with one or more further $R^a$, $R^3$, $R^4$ or $R^5$ radicals may form a mono- or polycyclic, aliphatic, aromatic and/or benzofused ring system.

According to the invention, exactly one radical selected from W, X and Y is CN or $CF_3$ and exactly two radicals selected from the group consisting of T, V, W, X and Y are an attachment point of a single bond between the chemical unit of formula I and a chemical unit D.

In one embodiment, $R^1$ is the same or different at each instance and is H, methyl or phenyl.

In one embodiment, W is CN.

In a further embodiment of the organic molecules, the chemical group D is the same or different at each instance and comprises or consists of a structure of the formula IIa:

Formula IIa

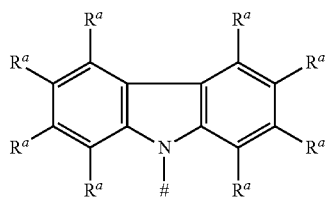

where the definitions for formula I and II are applicable to # and $R^a$.

In a further embodiment of the organic molecules according to the invention, the chemical unit D is the same or different at each instance and comprises or consists of a structure of the formula IIb, of the formula IIb-2, of the formula IIb-3 or of the formula IIb-4:

Formula IIb

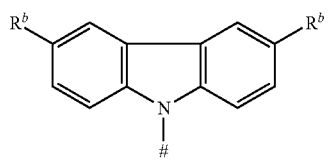

Formula IIb-2

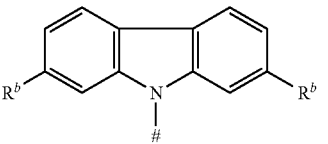

Formula IIb-3

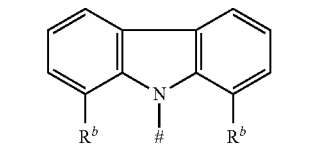

Formula IIb-4

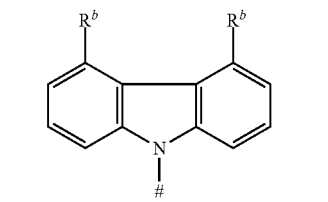

where
$R^5$ is the same or different at each instance and is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^5$ radicals, where one or more nonadjacent $CH_2$ groups may be replaced by $R^5C=CR^5$, $C\equiv C$, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^5$ radicals, or an aryloxy or heteroaryloxy group which has 5 to 60 aromatic ring atoms and may be substituted in each case by one or more $R^5$ radicals, or a diarylamino group, diheteroarylamino group or arylheteroarylamino group which has 10 to 40 aromatic ring atoms and may be substituted in each case by one or more $R^5$ radicals. For the rest, the definitions given above are applicable.

In a further embodiment of the organic molecules according to the invention, the chemical unit D is the same or different at each instance and comprises or consists of a structure of the formula IIc, of the formula IIc-2, of the formula IIc-3 or of the formula IIc-4:

Formula IIc

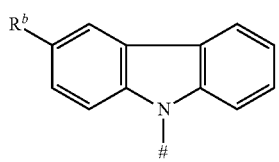

Formula IIc-2

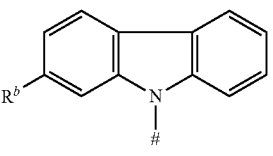

Formula IIc-3

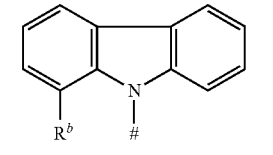

Formula IIc-4

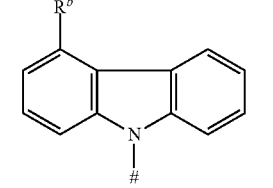

where the definitions given above are applicable.

In a further embodiment of the organic molecules according to the invention, $R^b$ independently at each instance is selected from the group consisting of Me, $^iPr$, $^tBu$, CN, $CF_3$, Ph which may be substituted in each case by one or more radicals selected from Me, $^iPr$, $^tBu$, CN, $CF_3$ and Ph, pyridinyl which may be substituted in each case by one or more radicals selected from Me, $^i$Pr, $^t$Bu, CN, CF$_3$ and Ph, pyrimidinyl which may be substituted in each case by one or more radicals selected from Me, $^i$Pr, $^t$Bu, CN, CF$_3$ and Ph, carbazolyl which may be substituted in each case by one or more radicals selected from Me, $^i$Pr, $^t$Bu, CN, CF$_3$ and Ph, triazinyl which may be substituted in each case by one or more radicals selected from Me, $^i$Pr, $^t$Bu, CN, CF$_3$ and Ph, and N(Ph)$_2$.

The following are illustrative embodiments of the chemical group D:

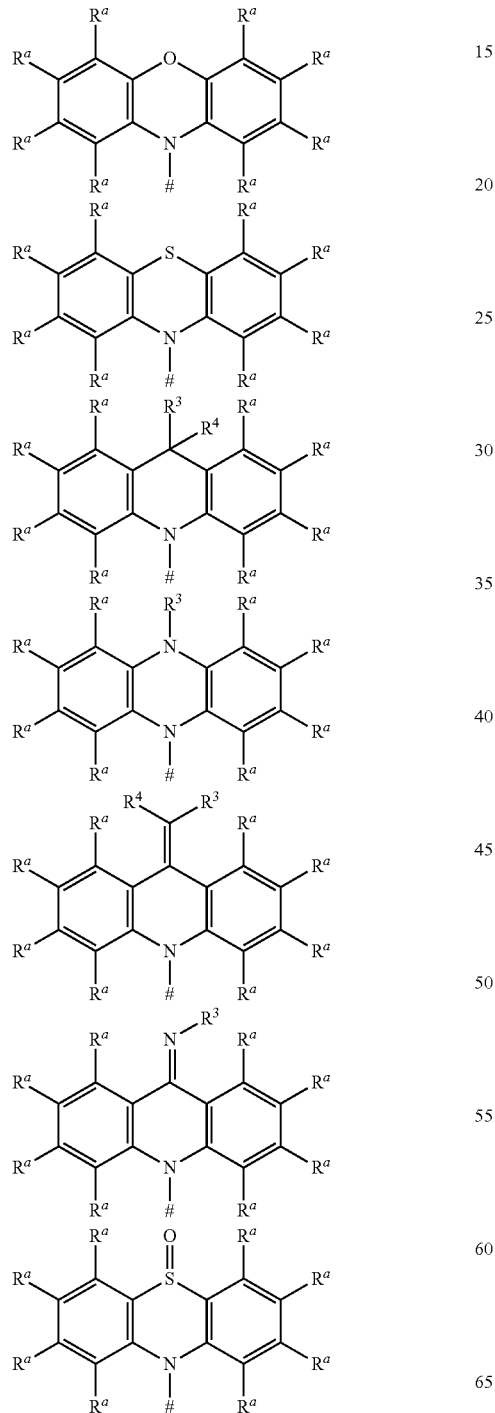

-continued

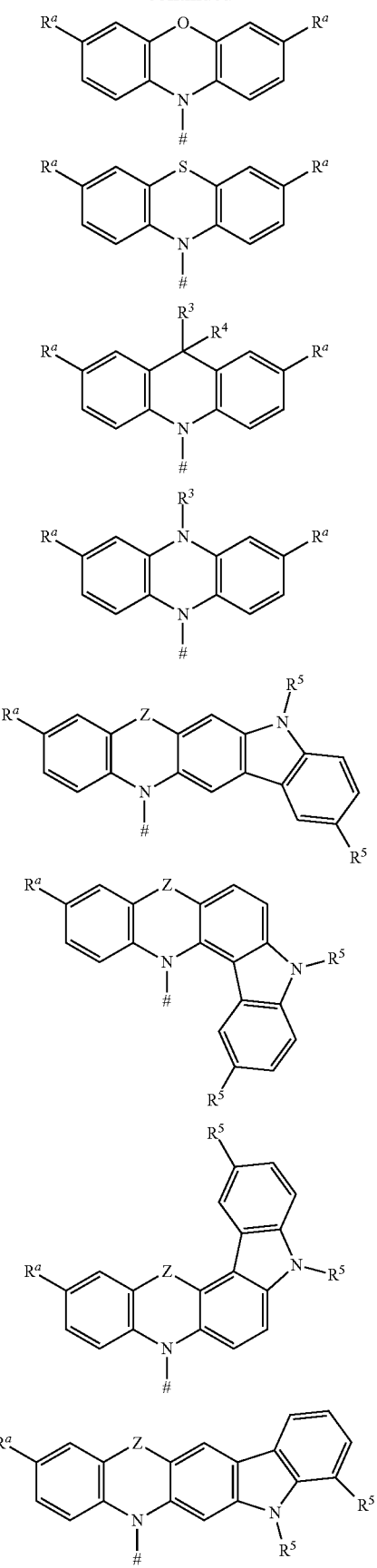

-continued
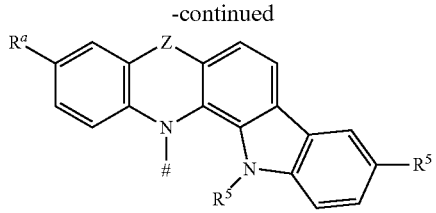
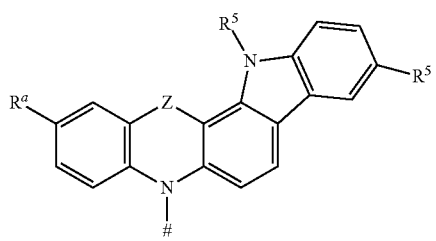
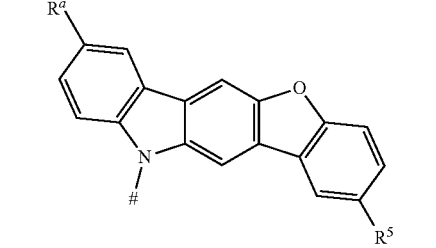
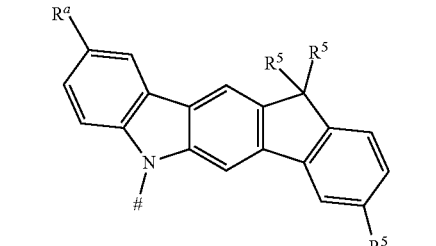
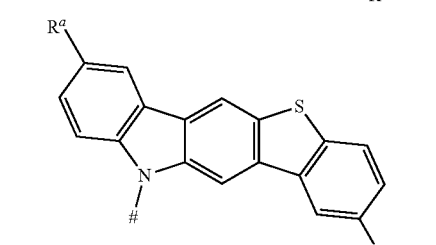
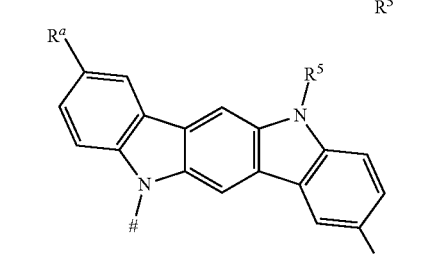
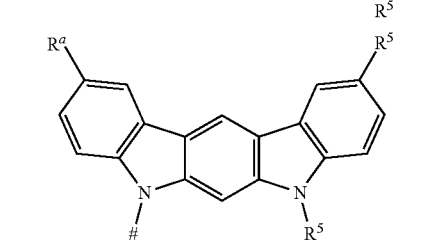
-continued
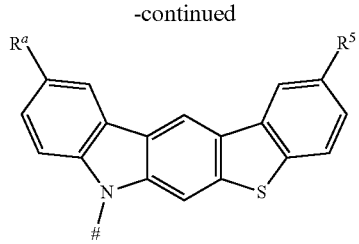
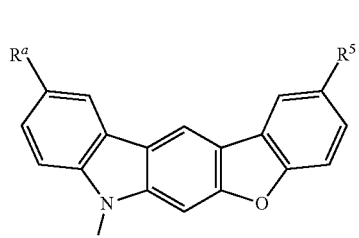
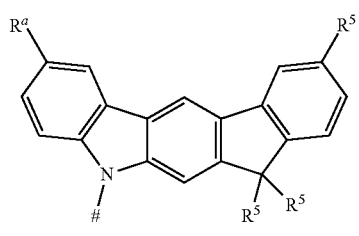
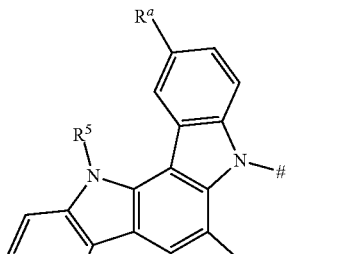
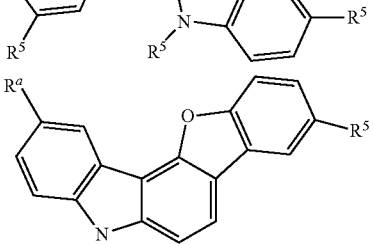
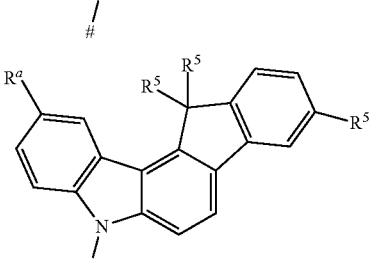
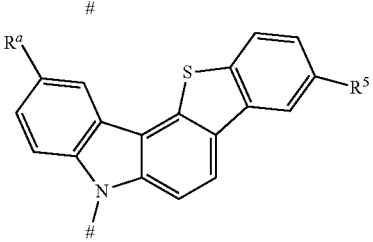

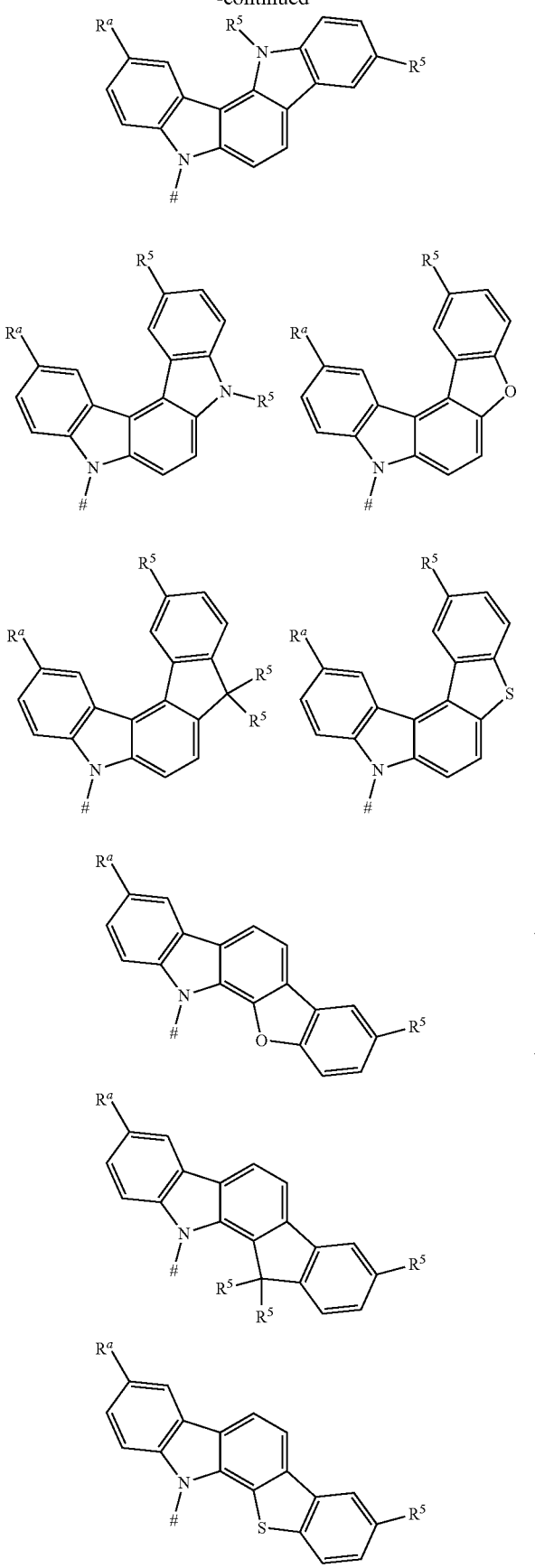
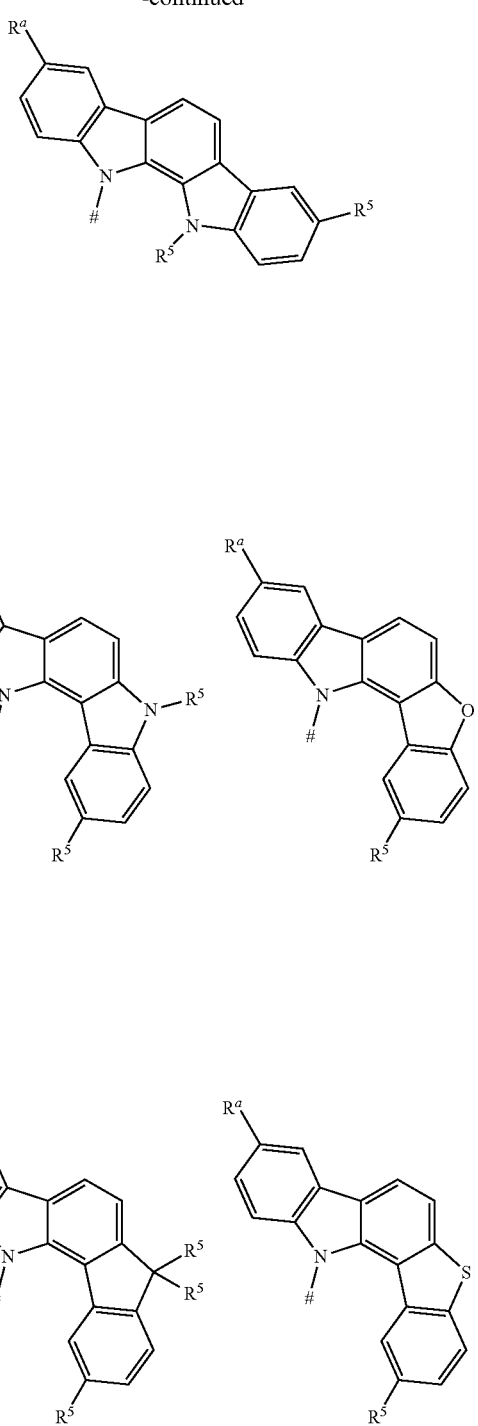

where the definitions given above are applicable to #, Z, $R^a$, $R^3$, $R^4$ and $R^5$. In one embodiment, the $R^5$ radical is the same or different at each instance and is selected from the group consisting of H, methyl, ethyl, phenyl and mesityl. In one embodiment, $R^a$ is the same or different at each instance and is selected from the group consisting of H, methyl (Me), i-propyl ($CH(CH_3)_2$) ($^i$Pr), t-butyl ($^t$Bu), phenyl (Ph), CN, $CF_3$ and diphenylamine ($NPh_2$).

In one embodiment, the organic molecules according to the invention have a structure of the formula III:

Formula III

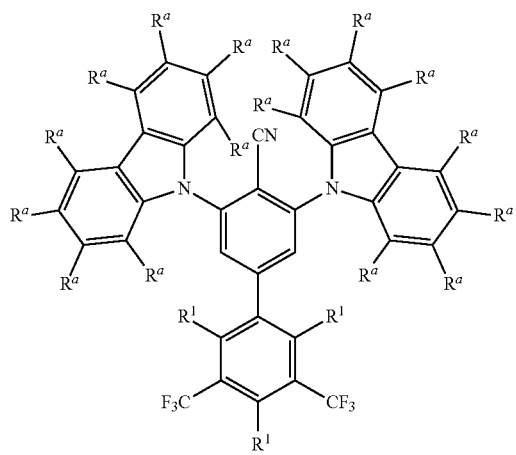

where the definitions given above are applicable.

In a further embodiment, the organic molecules according to the invention comprise a structure of the formula IIIa:

Formula IIIa

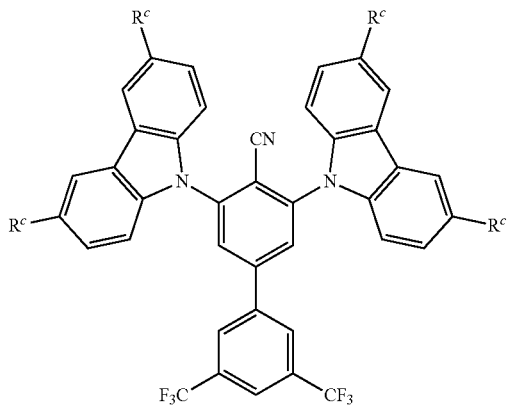

where $R^c$ independently at each instance is selected from the group consisting of Me, $^i$Pr, $^t$Bu, CN, CF$_3$, Ph which may be substituted in each case by one or more radicals selected from Me, $^i$Pr, $^t$Bu, CN, CF$_3$ and Ph, pyridinyl which may be substituted in each case by one or more radicals selected from Me, $^i$Pr, $^t$Bu, CN, CF$_3$ and Ph, pyrimidinyl which may be substituted in each case by one or more radicals selected from Me, $^i$Pr, $^t$Bu, CN, CF$_3$ and Ph, carbazolyl which may be substituted in each case by one or more radicals selected from Me, $^i$Pr, $^t$Bu, CN, CF$_3$ and Ph, triazinyl which may be substituted in each case by one or more radicals selected from Me, $^i$Pr, $^t$Bu, CN, CF$_3$ and Ph, and N(Ph)$_2$.

In a further embodiment, the organic molecules according to the invention comprise a structure of the formula IIIb:

Formula IIIb

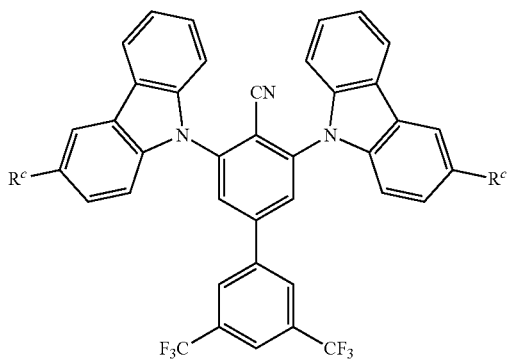

where the definitions given above are applicable.

In a further embodiment, the organic molecules according to the invention comprise a structure of the formula IIIc:

Formula IIIc

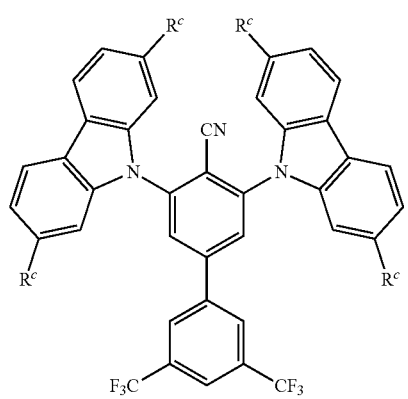

where the definitions given above are applicable.

In a further embodiment, the organic molecules according to the invention comprise a structure of the formula IIId:

Formula IIId

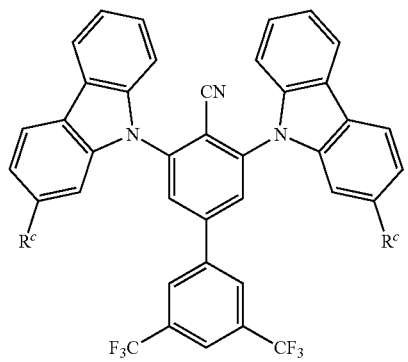

where the definitions given above are applicable.

In a further embodiment, the organic molecules according to the invention comprise a structure of the formula IIIe:

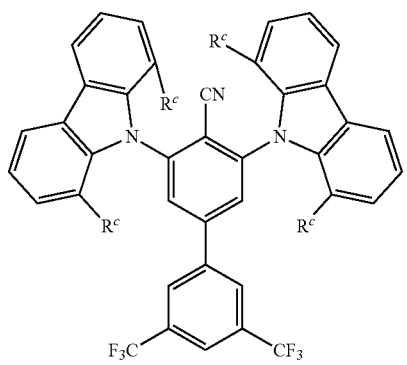

Formula IIIe where the definitions given above are applicable.

In a further embodiment, the organic molecules according to the invention comprise a structure of the formula IIIf:

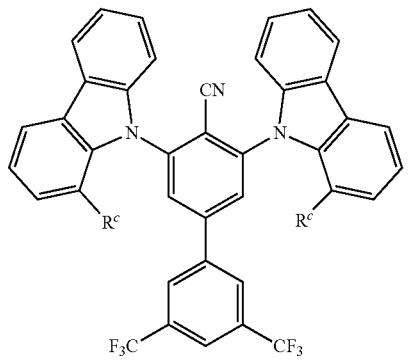

Formula IIIf where the definitions given above are applicable.

In a further embodiment, the organic molecules according to the invention comprise a structure of the formula IIIg:

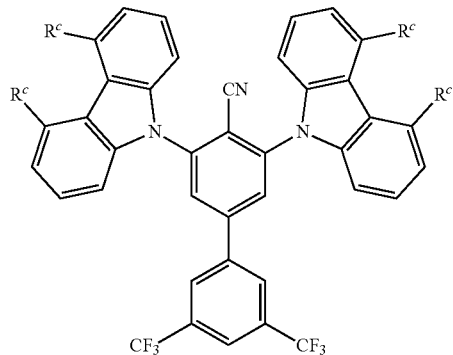

Formula IIIg where the definitions given above are applicable.

In a further embodiment, the organic molecules according to the invention comprise a structure of the formula IIIh:

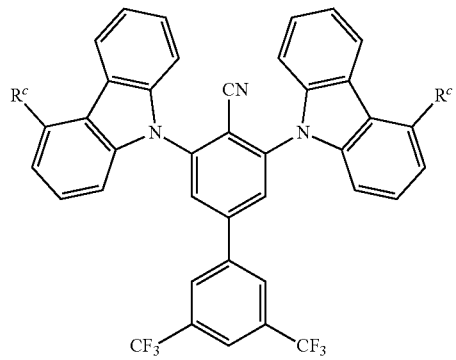

Formula IIIh where the definitions given above are applicable.

In one embodiment, the organic molecules according to the invention comprise a structure of the formula IV:

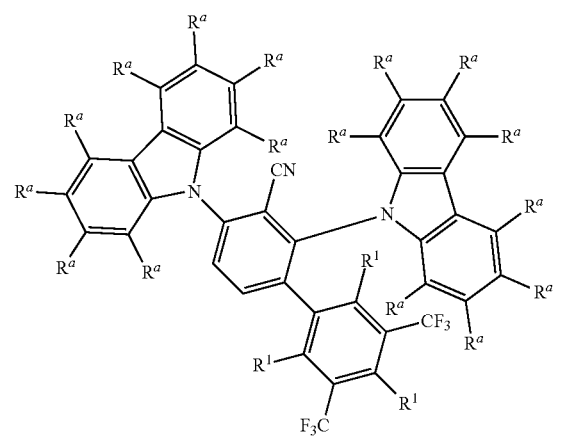

Formula IV where the definitions given above are applicable.

In a further embodiment, the organic molecules according to the invention comprise a structure of the formula IVa:

Formula IVa where the definitions given above are applicable.

In a further embodiment, the organic molecules according to the invention comprise a structure of the formula IVb:

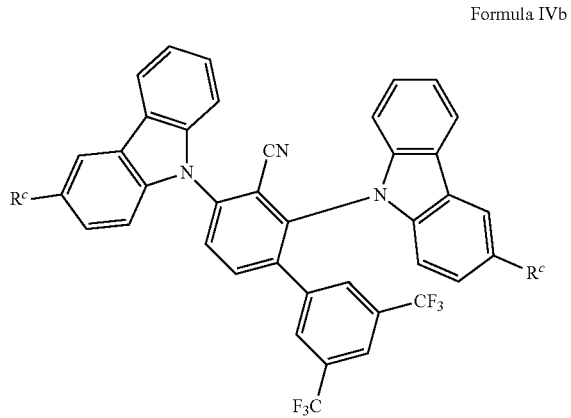

Formula IVb where the definitions given above are applicable.

In a further embodiment, the organic molecules according to the invention comprise a structure of the formula IVc:

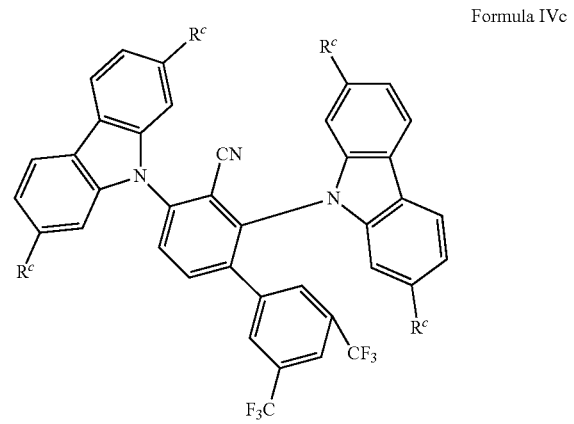

Formula IVc where the definitions given above are applicable.

In a further embodiment, the organic molecules according to the invention comprise a structure of the formula IVd:

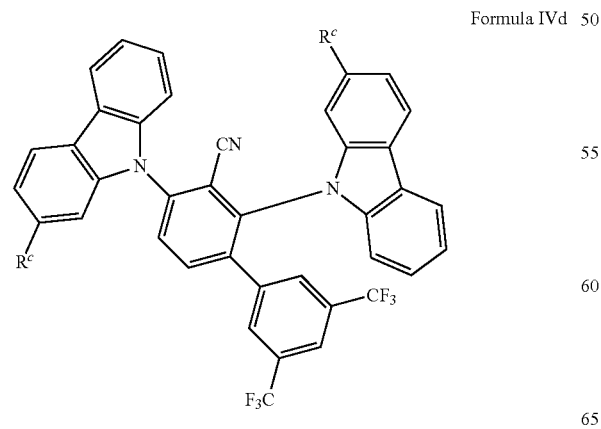

Formula IVd where the definitions given above are applicable.

In a further embodiment, the organic molecules according to the invention comprise a structure of the formula IVe:

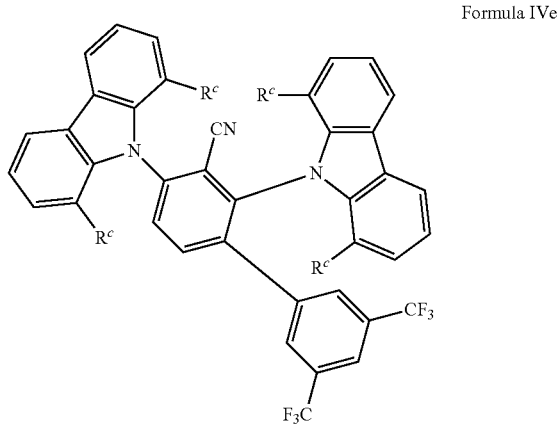

Formula IVe where the definitions given above are applicable.

In a further embodiment, the organic molecules according to the invention comprise a structure of the formula IVf:

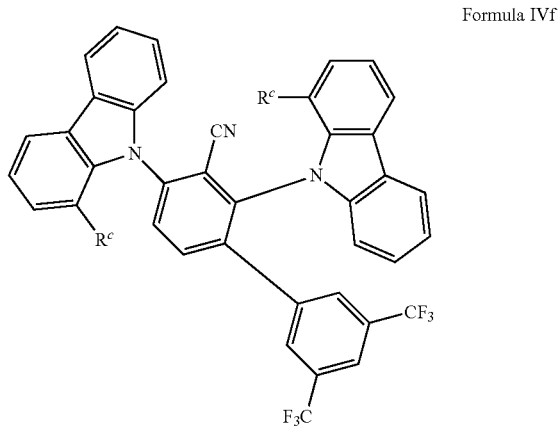

Formula IVf where the definitions given above are applicable.

In a further embodiment, the organic molecules according to the invention comprise a structure of the formula IVg:

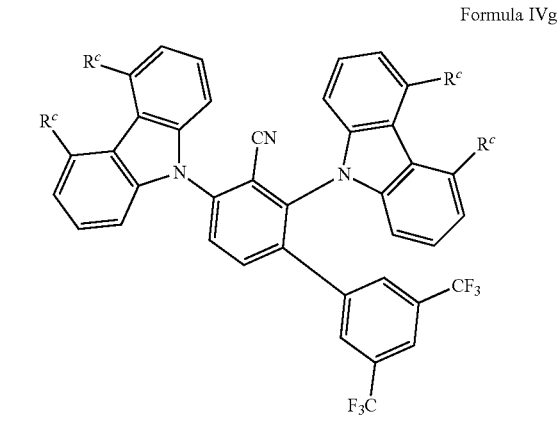

Formula IVg where the definitions given above are applicable.

In a further embodiment, the organic molecules according to the invention comprise a structure of the formula IVh:

Formula IVh

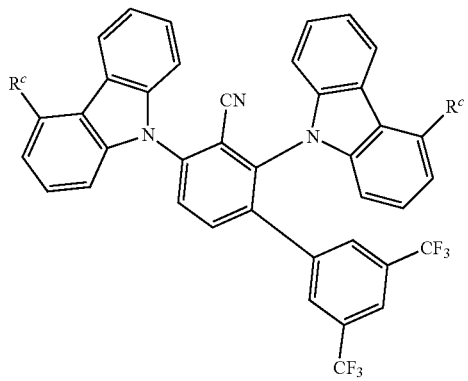

where the definitions given above are applicable.

In one embodiment, the organic molecules according to the invention comprise a structure of the formula V:

Formula V

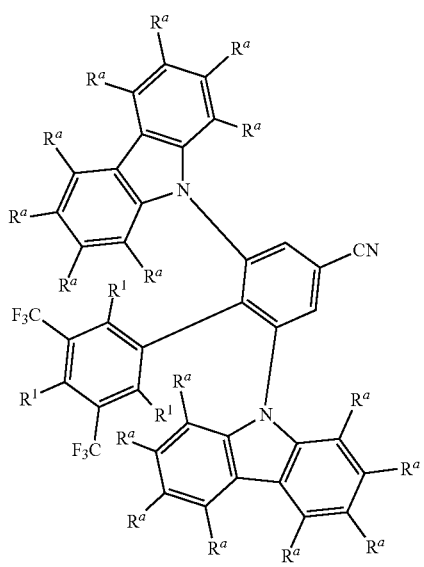

where the definitions given above are applicable.

In a further embodiment, the organic molecules according to the invention comprise a structure of the formula Va:

Formula Va

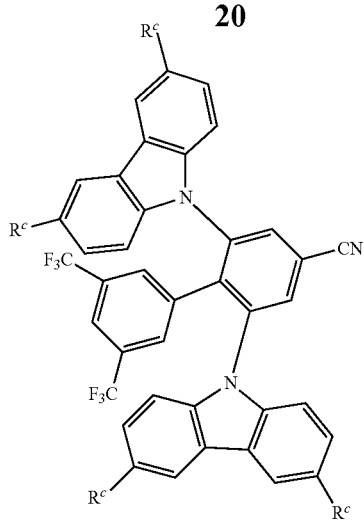

where the definitions given above are applicable.

In a further embodiment, the organic molecules according to the invention comprise a structure of the formula Vb:

Formula Vb

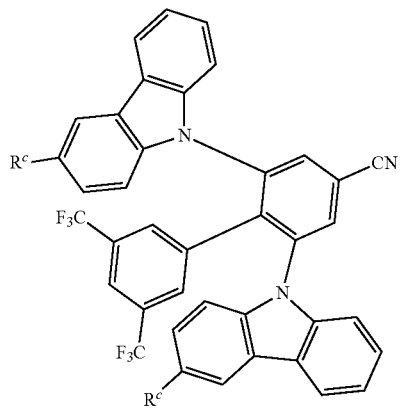

where the definitions given above are applicable.

In a further embodiment, the organic molecules according to the invention comprise a structure of the formula Vc:

Formula Vc

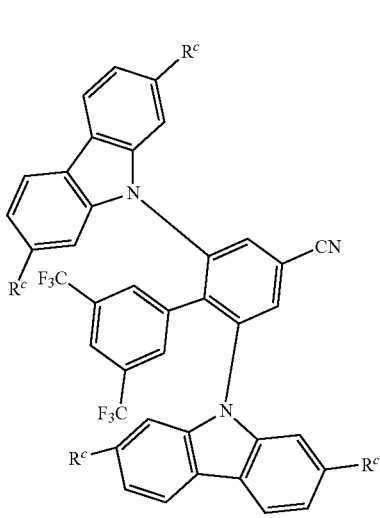

where the definitions given above are applicable.

In a further embodiment, the organic molecules according to the invention comprise a structure of the formula Vd:

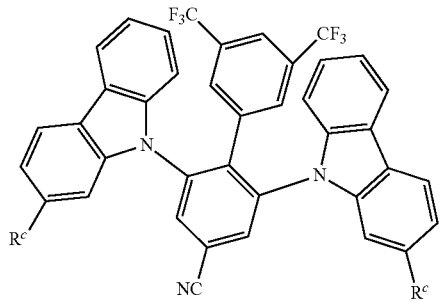

Formula Vd where the definitions given above are applicable.

In a further embodiment, the organic molecules according to the invention comprise a structure of the formula Ve:

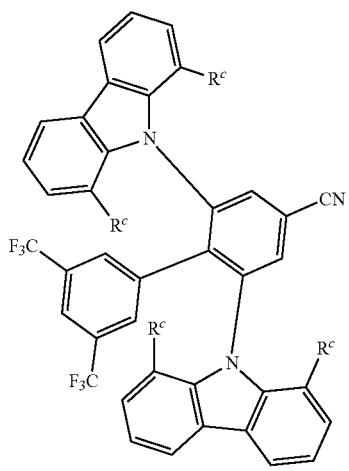

Formula Ve where the definitions given above are applicable.

In a further embodiment, the organic molecules according to the invention comprise a structure of the formula Vf:

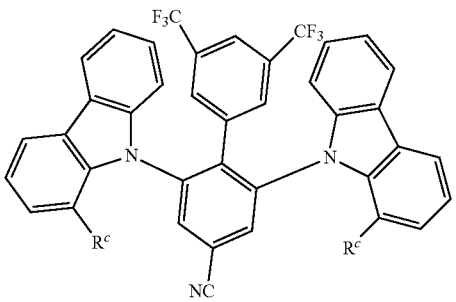

Formula Vf where the definitions given above are applicable.

In a further embodiment, the organic molecules according to the invention comprise a structure of the formula Vg:

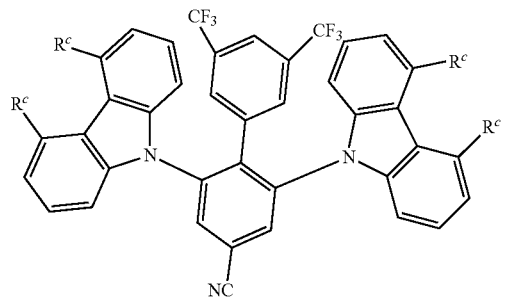

Formula Vg where the definitions given above are applicable.

In a further embodiment, the organic molecules according to the invention comprise a structure of the formula Vh:

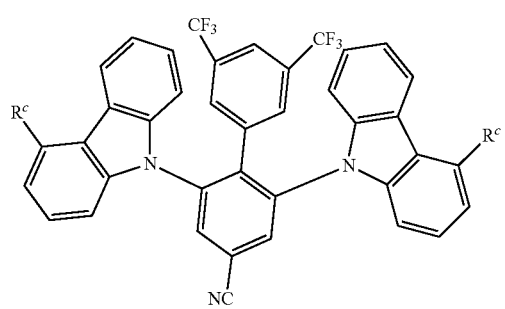

Formula Vh where the definitions given above are applicable.

In one embodiment, the organic molecules according to the invention comprise a structure of the formula VI:

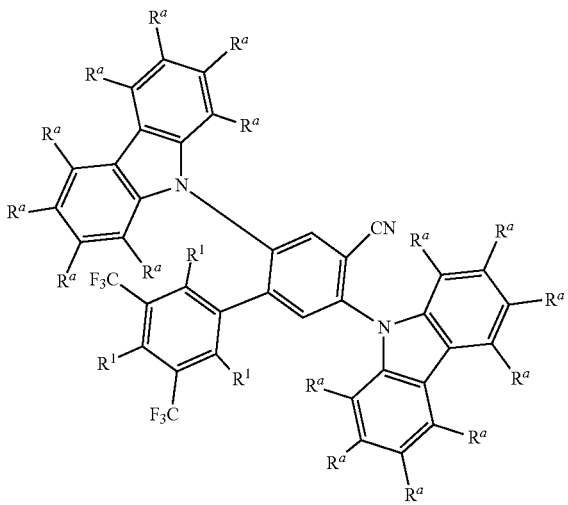

Formula VI where the definitions given above are applicable.

In a further embodiment, the organic molecules according to the invention comprise a structure of the formula VIa:

Formula VIa

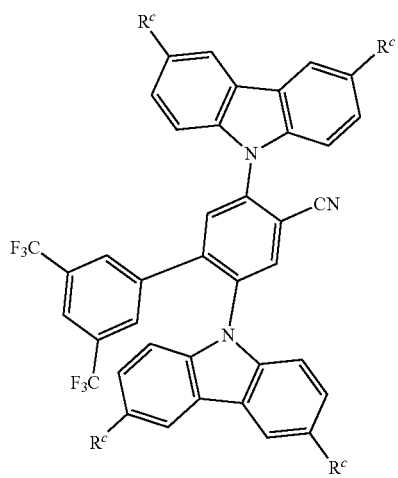

where the definitions given above are applicable.

In a further embodiment, the organic molecules according to the invention comprise a structure of the formula VIb:

Formula VIb

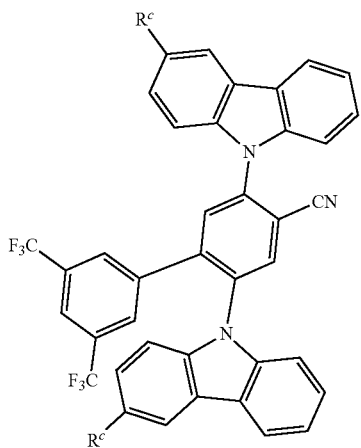

where the definitions given above are applicable.

In a further embodiment, the organic molecules according to the invention comprise a structure of the formula VIc:

Formula VIc

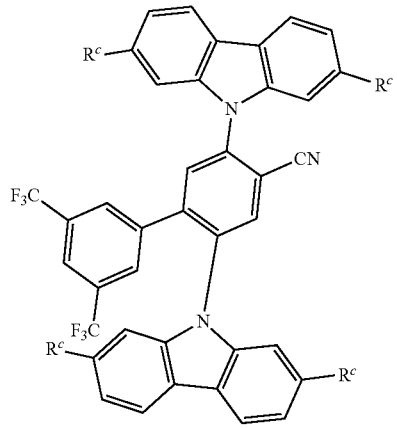

where the definitions given above are applicable.

In a further embodiment, the organic molecules according to the invention comprise a structure of the formula VId:

Formula VId

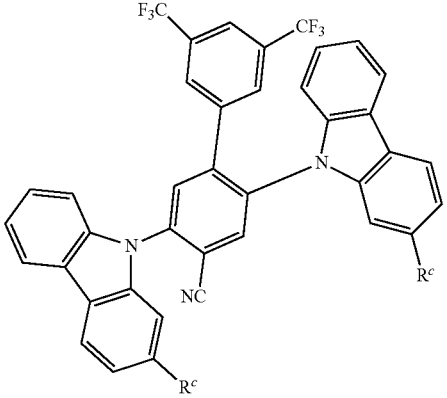

where the definitions given above are applicable.

In a further embodiment, the organic molecules according to the invention comprise a structure of the formula VIe:

Formula VIe

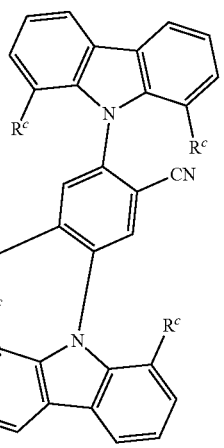

where the definitions given above are applicable.

In a further embodiment, the organic molecules according to the invention comprise a structure of the formula VIf:

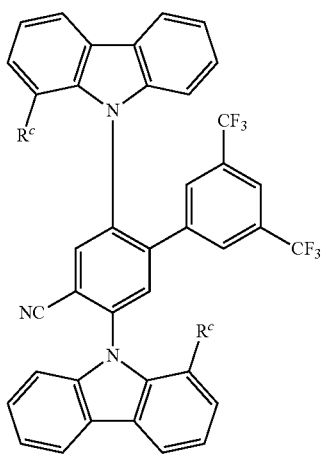

Formula VIf where the definitions given above are applicable.

In a further embodiment, the organic molecules according to the invention comprise a structure of the formula VIg:

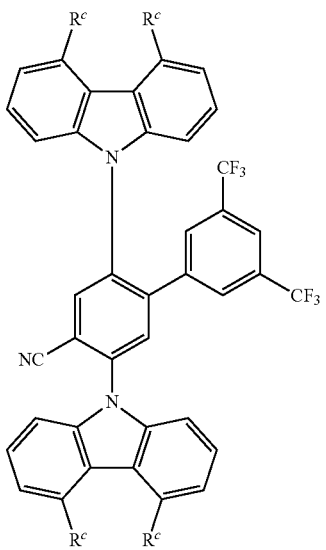

Formula VIg where the definitions given above are applicable.

In a further embodiment, the organic molecules according to the invention comprise a structure of the formula VIh:

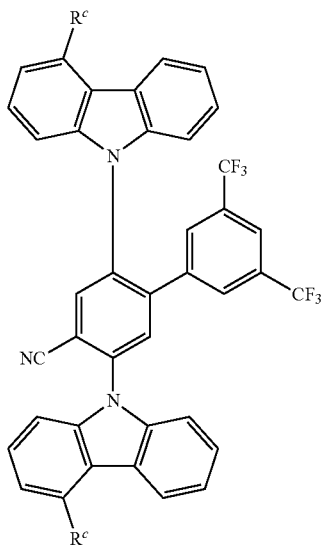

Formula VIh where the definitions given above are applicable.

In one embodiment, the organic molecules according to the invention comprise a structure of the formula VII:

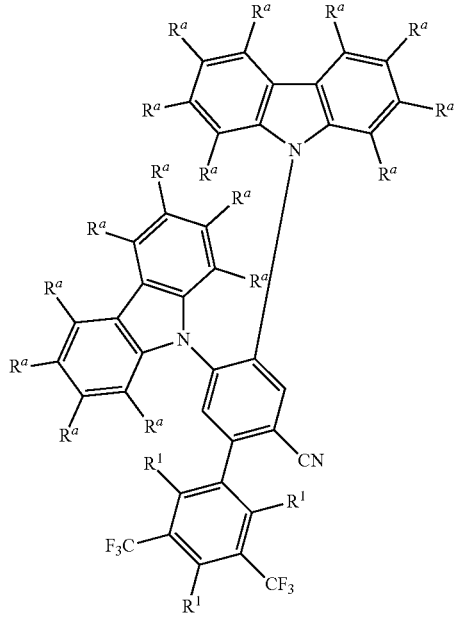

Formula VII where the definitions given above are applicable.

In a further embodiment, the organic molecules according to the invention comprise a structure of the formula VIIa:

Formula VIIa

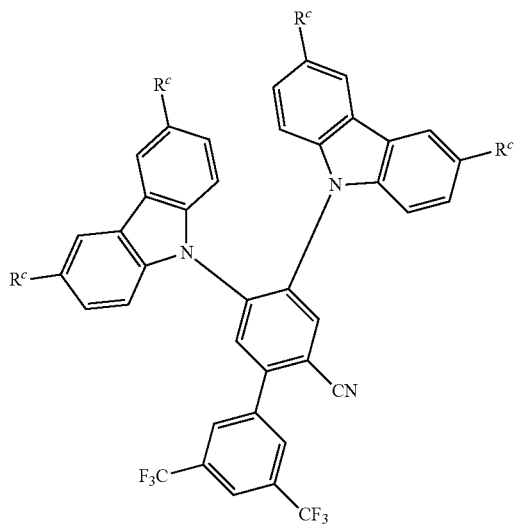

where the definitions given above are applicable.

In a further embodiment, the organic molecules according to the invention comprise a structure of the formula VIIb:

Formula VIIb

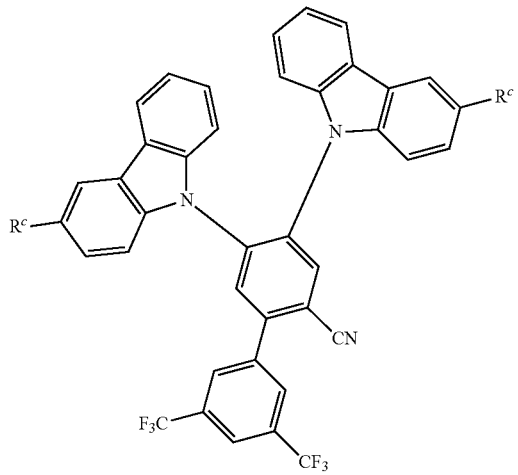

where the definitions given above are applicable.

In a further embodiment, the organic molecules according to the invention comprise a structure of the formula VIIc:

Formula VIIc

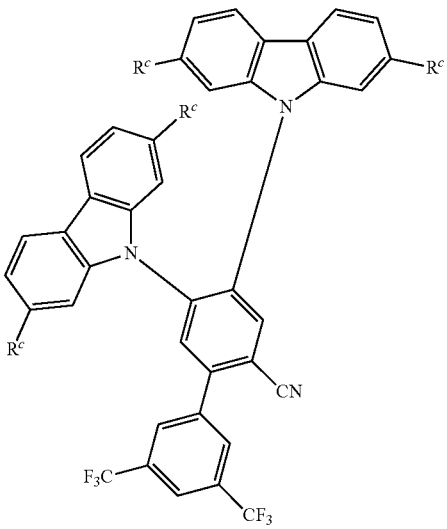

where the definitions given above are applicable.

In a further embodiment, the organic molecules according to the invention comprise a structure of the formula VIId:

Formula VIId

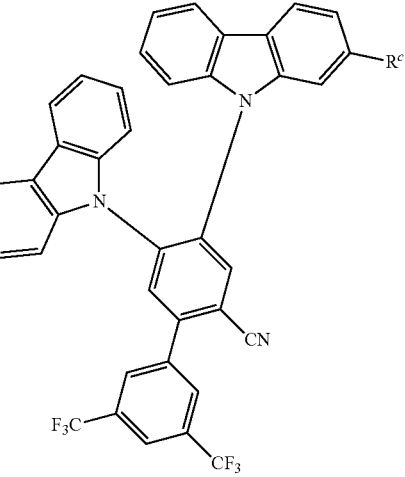

where the definitions given above are applicable.

In a further embodiment, the organic molecules according to the invention comprise a structure of the formula VIIe:

Formula VIIe

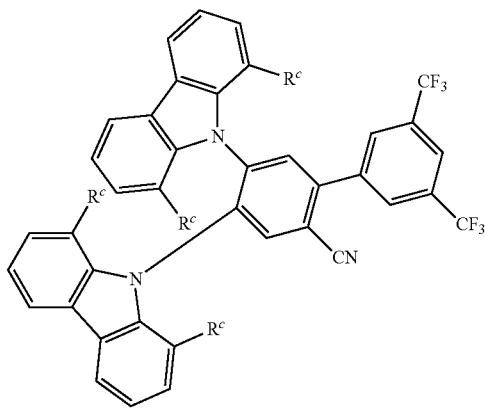

where the definitions given above are applicable.

In a further embodiment, the organic molecules according to the invention comprise a structure of the formula VIIf:

Formula VIIf

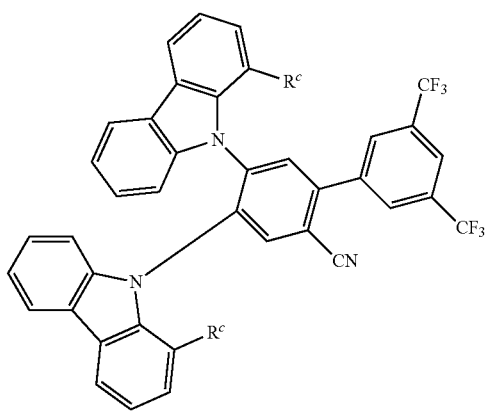

where the definitions given above are applicable.

In a further embodiment, the organic molecules according to the invention comprise a structure of the formula VIIg:

Formula VIIg

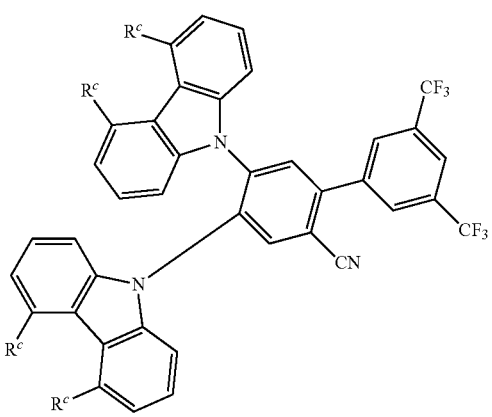

where the definitions given above are applicable.

In a further embodiment, the organic molecules according to the invention comprise a structure of the formula VIIh:

Formula VIIh

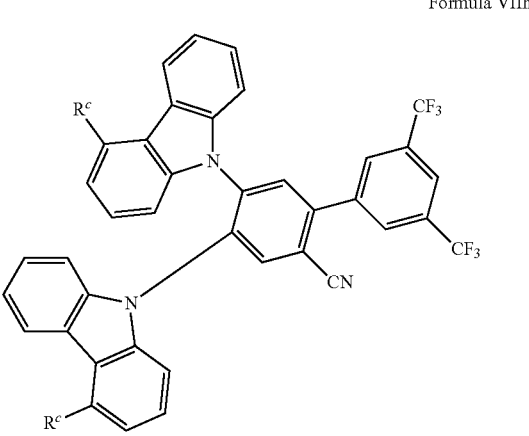

where the definitions given above are applicable.

In one embodiment, the organic molecules according to the invention comprise a structure of the formula VIII:

Formula VIII

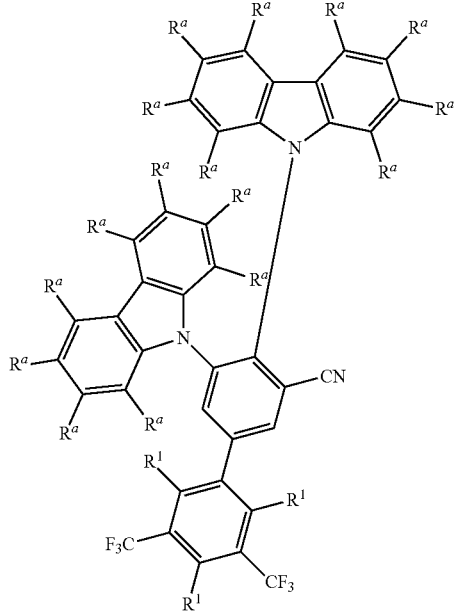

where the definitions given above are applicable.

In one embodiment, $R^c$ independently at each instance is selected from the group consisting of Me, $^iPr$, $^tBu$, Ph which may be substituted in each case by one or more radicals selected from Me, $^iPr$, $^tBu$, CN, $CF_3$ and Ph, and carbazolyl which may be substituted in each case by one or more radicals selected from Me, $^iPr$, $^tBu$ and Ph.

In the context of this invention, an aryl group contains 6 to 60 aromatic ring atoms; a heteroaryl group contains 5 to 60 aromatic ring atoms, of which at least one is a heteroatom. The heteroatoms are especially N, O and/or S. If, in the description of particular embodiments of the invention, other definitions departing from the definition mentioned are given, for example with regard to the number of aromatic ring atoms or of heteroatoms present, these are applicable.

An aryl group or heteroaryl group is understood to mean a simple aromatic cycle, i.e. benzene, or a simple heteroaromatic cycle, for example pyridine, pyrimidine or thiophene, or a heteroaromatic polycycle, for example phenanthrene, quinoline or carbazole. A fused (annelated) aromatic or heteroaromatic polycycle in the context of the present application consists of two or more mutually condensed simple aromatic or heteroaromatic cycles.

An alkyl or heteroaryl group which may be substituted in each case by the abovementioned radicals and which may be joined via any desired positions to the aromatic or heteroaromatic system is especially understood to mean groups derived from benzene, naphthalene, anthracene, phenanthrene, pyrene, dihydropyrene, chrysene, perylene, fluoranthene, benzanthracene, benzphenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the groups mentioned.

A cyclic alkyl, alkoxy or thioalkoxy group is understood here to mean a monocyclic, bicyclic or polycyclic group.

In the context of the present invention, a $C_1$- to $C_{40}$-alkyl group in which individual hydrogen atoms or $CH_2$ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]-octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

One embodiment of the invention relates to organic molecules having a $\Delta E(S_1\text{-}T_1)$ value between the lowermost excited singlet state ($S_1$) and the triplet state ($T_1$) below it of not higher than 5000 cm$^{-1}$, especially not higher than 3000 cm$^{-1}$, or not higher than 1500 cm$^{-1}$ or 1000 cm$^{-1}$, and/or an emission lifetime of not more than 150 µs, especially of not more than 100 µs, of not more than 50 µs, or of not more than 10 µs, and/or a main emission band having a half-height width of less than 0.55 eV, especially less than 0.50 eV, less than 0.48 eV, or less than 0.45 eV.

The organic molecules especially exhibit an emission maximum between 420 and 500 nm, between 430 and 480 nm, especially between 450 and 470 nm.

The molecules especially have a blue material index (BMI), the quotient of the PLQY (in %) and its $CIE_y$ colour coordinates of the light emitted by the molecule according to the invention, of greater than 150, especially of greater than 200, of greater than 250 or of greater than 300.

In a further aspect, the invention relates to a process for preparing an organic molecule according to the invention of the type described here (with a possible further conversion), wherein a 2,4,6-$R^1$-substituted 3,5-bis(trifluoromethyl)phenylboronic acid or a corresponding 2,4,6-$R^1$-substituted 3,5-bis(trifluoromethyl)phenylboronic ester is used as reactant.

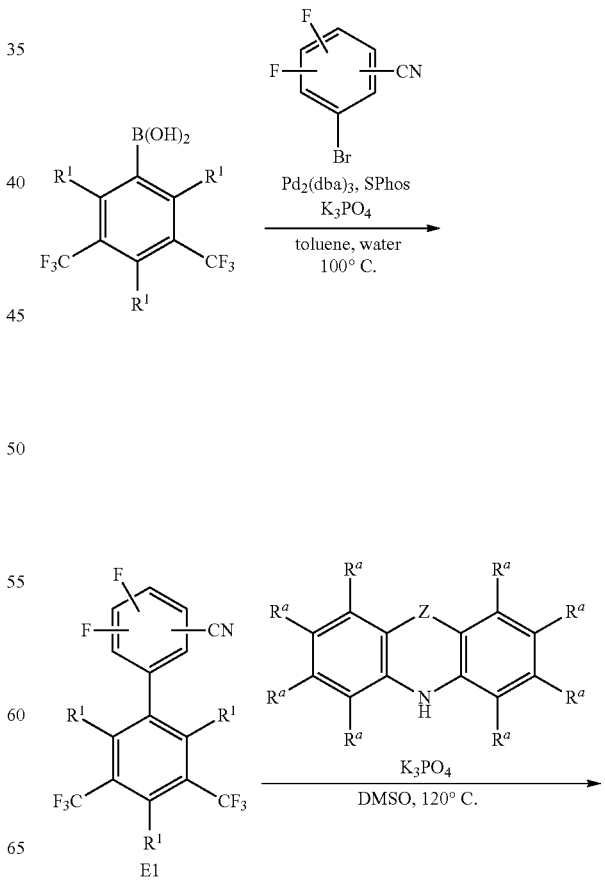

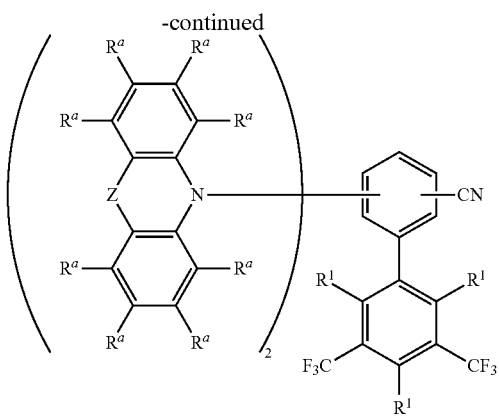

In the above scheme, in one embodiment, the chemical CN group is replaced by $CF_3$.

In one embodiment, a 2,4,6-$R^1$-substituted 3,5-bis(trifluoromethyl)phenylboronic acid or a corresponding 2,4,6-$R^1$-substituted 3,5-bis(trifluoromethyl)phenylboronic ester as reactant is reacted with a bromodifluorobenzonitrile in a palladium-catalysed cross-coupling reaction. It is possible here to use, by way of example, in accordance with the invention, 4-bromo-2,6-difluorobenzonitrile, 4-bromo-2,5-difluorobenzonitrile, 4-bromo-3,5-difluorobenzonitrile, 3-bromo-2,6-difluorobenzonitrile, 3-bromo-5,6-difluorobenzonitrile and 2-bromo-4,5-difluorobenzonitrile. The product is obtained by deprotonation of the corresponding amine, followed by nucleophilic substitution of the two fluorine groups. In this case, a nitrogen heterocycle is reacted with a reactant E1 in the manner of a nucleophilic aromatic substitution. Typical conditions include the use of a base, for example tribasic potassium phosphate or sodium hydride, in an aprotic polar solvent, for example dimethyl sulphoxide (DMSO) or N,N-dimethylformamide (DMF).

In a further aspect, the invention relates to the use of the organic molecules as luminescent emitters or as host material in an organic optoelectronic device, especially where the organic optoelectronic device is selected from the group consisting of:
  organic light-emitting diodes (OLEDs),
  light-emitting electrochemical cells,
  OLED sensors, especially in gas and vapour sensors not hermetically shielded from the outside,
  organic diodes,
  organic solar cells,
  organic transistors,
  organic field-effect transistors,
  organic lasers and
  down-conversion elements.

In a further aspect, the invention relates to a composition comprising or consisting of:
  (a) at least one organic molecule according to the invention, especially as emitter and/or host, and
  (b) at least one, i.e. one or more, emitter and/or host material(s) other than the organic molecule according to the invention, and
  (c) optionally one or more dyes and/or one or more organic solvents.

In one embodiment, the composition according to the invention consists of an organic molecule according to the invention and one or more host materials. The host material(s) especially has/have triplet ($T_1$) and singlet ($S_1$) energy levels at higher energy than the triplet ($T_1$) and singlet ($S_1$) energy levels of the organic molecule according to the invention. In one embodiment, the composition, as well as the organic molecule according to the invention, includes an electron-dominant and a hole-dominant host material. The highest occupied orbital (HOMO) and the lowest unoccupied orbital (LUMO) of the hole-dominant host material are especially at higher energy than those of the electron-dominant host material. The HOMO of the hole-dominant host material is at lower energy than the HOMO of the organic molecule according to the invention, while the LUMO of the electron-dominant host material is at higher energy than the LUMO of the organic molecule according to the invention. In order to avoid exciplex formation between emitter and host material(s), the materials should be chosen such that the energy gaps between the respective orbitals are small. The gap between the LUMO of the electron-dominant host material and the LUMO of the organic molecule according to the invention is especially less than 0.5 eV, preferably less than 0.3 eV, even more preferably less than 0.2 eV. The gap between the HOMO of the hole-dominant host material and the HOMO of the organic molecule according to the invention is especially less than 0.5 eV, preferably less than 0.3 eV, even more preferably less than 0.2 eV.

In a further aspect, the invention relates to an organic optoelectronic device comprising an organic molecule according to the invention or a composition according to the invention. The organic optoelectronic device especially takes the form of a device selected from the group consisting of organic light-emitting diode (OLED); light-emitting electrochemical cell; OLED sensor, especially gas and vapour sensors that are not hermetically shielded from the outside; organic diode; organic solar cell; organic transistor; organic field effect transistor; organic laser and down-conversion element.

An organic optoelectronic device comprising
  a substrate,
  an anode and
  a cathode, where the anode or cathode has been applied to the substrate, and
  at least one light-emitting layer which is arranged between anode and cathode and includes an organic molecule according to the invention is a further embodiment of the invention.

In one embodiment, the optoelectronic device is an OLED. A typical OLED comprises, for example, the following layer structure:
  1. Substrate (carrier material)
  2. Anode
  3. Hole injection layer (HIL)
  4. Hole transport layer (HTL)
  5. Electron blocking layer (EBL)
  6. Emitting layer (EML)
  7. Hole blocking layer (HBL)
  8. Electron transport layer (ETL)
  9. Electron injection layer (EIL)
  10. Cathode.

Individual layers here are present merely in an optional manner. In addition, two or more of these layers may be combined. And it is possible for individual layers to be present more than once in the component.

In one embodiment, at least one electrode of the organic component is translucent. "Translucent" refers here to a layer which is transparent to visible light. The translucent layer here may be clear and see-through, i.e. transparent, or at least partly light-absorbing and/or partly light-scattering, such that the translucent layer, for example, may also have a diffuse or milky appearance. More particularly, a layer referred to here as translucent is very substantially transparent, such that, in particular, the absorption of light is as low as possible.

In a further embodiment, the organic component, especially an OLED, comprises an inverted structure. It is a feature of the inverted structure that the cathode is on the substrate and the other layers are applied in a correspondingly inverted manner.

1. Substrate (carrier material)
2. Cathode
3. Electron injection layer (EIL)
4. Electron transport layer (ETL)
5. Hole blocking layer (HBL)
6. Emission layer/emitting layer (EML)
7. Electron blocking layer (EBL)
8. Hole transport layer (HTL)
9. Hole injection layer (HIL)
10. Anode Individual layers here are present merely in an optional manner. In addition, two or more of these layers may be combined. And it is possible for individual layers to be present more than once in the component.

In one embodiment, in the inverted OLED, the anode layer of the typical structure, for example an ITO (indium tin oxide) layer, is connected as the cathode.

In a further embodiment, the organic component, especially an OLED, has a stacked structure. The individual OLEDs here are arranged one on top of another and not one alongside another as usual. A stacked structure can enable the generation of mixed light. For example, this structure can be used in the generation of white light, which is produced by forming the entire visible spectrum, typically by the combination of the emitted light from blue, green and red emitters. In addition, with practically the same efficiency and identical luminance, it is possible to achieve significantly longer lifetimes compared to standard OLEDs. For the stacked structure, it is optionally possible to use what is called a charge generation layer (CGL) between two OLEDs. This consists of an n-doped layer and a p-doped layer, the n-doped layer typically being applied closer to the anode.

In one embodiment—called a tandem OLED—two or more emission layers occur between the anode and cathode. In one embodiment, three emission layers are arranged one on top of another, where one emission layer emits red light, one emission layer emits green light and one emission layer emits blue light, and there are optionally further charge generation, blocker or transport layers applied between the individual emission layers. In a further embodiment, the respective emission layers are applied in a directly adjacent manner. In a further embodiment, there is one charge generation layer in each case between the emission layers. In addition, in an OLED, it is possible to combine directly adjacent emission layers and emission layers separated by charge generation layers.

It is also possible to arrange an encapsulation on top of the electrodes and the organic layers. The encapsulation may take the form, for example, of a glass lid or the form of a thin-film encapsulation.

The carrier material used in the optoelectronic device may, for example, be glass, quartz, plastic, metal, a silicon wafer or any other suitable solid or flexible, optionally transparent material. The carrier material may include, for example, one or more materials in the form of a layer, a film, a sheet or a laminate.

Anodes used in the optoelectronic device may, for example, be transparent conductive metal oxides, for example ITO (indium tin oxide), zinc oxide, tin oxide, cadmium oxide, titanium oxide, indium oxide or aluminium zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides.

HIL materials used may, for example, be PEDOT:PSS (poly-3,4-ethylenedioxythiophene:polystyrenesulphonic acid), PEDOT (poly-3,4-ethylenedioxythiophene), m-MTDATA (4,4',4"-tris[phenyl(m-tolyl)amino]triphenylamine), spiro-TAD (2,2',7,7'-tetrakis(N,N-diphenylamino)-9,9-spirobifluorene), DNTPD (4,4'-bis[N-[4-{N,N-bis(3-methylphenyl)amino}phenyl]-N-phenylamino]biphenyl), NPB (N,N'-bis-(1-naphthalenyl)-N,N'-bisphenyl-(1,1'-biphenyl)-4,4'-diamine), NPNPB (N,N'-diphenyl-N,N'-di-[4-(N,N-diphenylamino)phenyl]benzene), MeO-TPD (N,N,N',N'-tetrakis(4-methoxyphenyl)benzene), HAT-CN (1,4,5,8,9,11-hexaazatriphenylenehexacarbonitrile) or spiro-NPD (N,N'-diphenyl-N,N'-bis(1-naphthyl)-9,9'-spirobifluorene-2,7-diamine). By way of example, the layer thickness is 10-80 nm. In addition, it is possible to use small molecules (e.g. copper phthalocyanine (CuPc, e.g. thickness 10 nm)) or metal oxides, by way of example $MoO_3$, $V_2O_5$.

HTL materials used may be tertiary amines, carbazole derivatives, polystyrenesulphonic acid-doped polyethylenedioxythiophene, camphorsulphonic acid-doped polyaniline, poly-TPD (poly(4-butylphenyldiphenylamine), [alpha]-NPD (poly(4-butylphenyldiphenylamine)), TAPC (4,4'-cyclohexylidenebis[N,N-bis(4-methylphenyl)benzeneamine]), TCTA (tris(4-carbazoyl-9-ylphenyl)amine), 2-TNATA (4,4',4"-tris[2-naphthyl(phenyl)amino]triphenylamine), spiro-TAD, DNTPD, NPB, NPNPB, MeO-TPD, HAT-CN or TrisPcz (9,9'-diphenyl-6-(9-phenyl-9H-carbazol-3-yl)-9H,9'H-3,3'-bicarbazole). By way of example, the layer thickness is 10 nm to 100 nm.

The HTL may comprise a p-doped layer having an inorganic or organic dopant in an organic hole-conducting matrix. Inorganic dopants used may, for example, be transition metal oxides, for instance vanadium oxide, molybdenum oxide or tungsten oxide. Organic dopants used may, for example, be tetrafluorotetracyanoquinodimethane (F4-TCNQ), copper pentafluorobenzoate (Cu(I)pFBz) or transition metal complexes. By way of example, the layer thickness is 10 nm to 100 nm.

Electron blocker layer materials used may, for example, be mCP (1,3-bis(carbazol-9-yl)benzene), TCTA, 2-TNATA, mCBP (3,3-di(9H-carbazol-9-yl)biphenyl), tris-Pcz (9,9'-diphenyl-6-(9-phenyl-9H-carbazol-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene). By way of example, the layer thickness is 10 nm to 50 nm.

The emitter layer EML or emission layer consists of or comprises emitter material or a mixture including at least two emitter materials and optionally one or more host materials. Suitable host materials are, for example, mCP, TCTA, 2-TNATA, mCBP, CBP (4,4'-bis(N-carbazolyl)biphenyl), Sif87 (dibenzo[b,d]thiophen-2-yltriphenylsilane), Sif88 (dibenzo[b,d]thiophen-2-yl)diphenylsilane), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluoren-2-yl)-1,3,5-triazine) and/ or DPEPO (bis[2-((oxo)diphenylphosphino)phenyl]ether). In one embodiment, the EML contains 50%-80% by weight, preferably 60%-75% by weight, of a host material selected from the group consisting of CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl) phenyl]-9H-carbazole and 9-[3,5-bis(2-dibenzothiophenyl) phenyl]-9H-carbazole; 10%-45% by weight, preferably 15%-30% by weight, of T2T and 5%-40% by weight, preferably 10%-30% by weight, of an organic molecule according to the invention as emitter. For emitter material which emits in the green or in the red or a mixture comprising at least two emitter materials, the standard matrix materials are suitable, such as CBP. For emitter material which emits in the blue or a mixture comprising at least two emitter materials, it is possible to use UHG matrix materials (ultra-high-energy gap materials) (see, for example, M. E. Thompson et al., Chem. Mater. 2004, 16, 4743), or other so-called wide-gap matrix materials. By way of example, the layer thickness is 10 nm to 250 nm.

The hole blocker layer HBL may include, for example, BCP (2,9-dimethyl-4,7-diphenyl-1,10-phenanthroline= bathocuproin), bis(2-methyl-8-hydroxyquinolinato)-(4-phenylphenolato)aluminium(III) (BAlq), NBphen (2,9-bis (naphthalen-2-yl)-4,7-diphenyl-1,10-phenanthroline), Alq3 (aluminium tris(8-hydroxyquinoline)), T2T, TSPO1 (diphenyl-4-triphenylsilylphenylphosphine oxide) or TCB/TCP (1,3,5-tris(N-carbazolyl)benzene/1,3,5-tris(carbazol)-9-yl) benzene). By way of example, the layer thickness is 10 nm to 50 nm.

The electron transport layer ETL may include, for example, materials based on $AlQ_3$, TSPO1, BPyTP2 (2,7-di(2,2'-bipyridin-5-yl)triphenyl), NBPhen, Sif87, Sif88, BmPyPhB (1,3-bis[3,5-di(pyridin-3-yl)phenyl]benzene) or BTB (4,4'-bis[2-(4,6-diphenyl-1,3,5-triazinyl)]-1,1'-biphenyl). By way of example, the layer thickness is 10 nm to 200 nm.

Materials used in a thin electron injection layer EIL may, for example, be CsF, LiF, 8-hydroxyquinolinolatolithium (Liq), $Li_2O$, $BaF_2$, MgO or NaF.

Materials used in the cathode layer may be metals or alloys, for example Al, Al>AlF, Ag, Pt, Au, Mg, Ag:Mg. Typical layer thicknesses are 100 nm to 200 nm. In particular, one or more metals that are stable under air and/or self-passivating, for example through formation of a thin protective oxide layer, are used.

Suitable materials for encapsulation are, for example, aluminium oxide, vanadium oxide, zinc oxide, zirconium oxide, titanium oxide, hafnium oxide, lanthanum oxide, tantalum oxide.

In one embodiment of the organic optoelectronic device according to the invention, the organic molecule according to the invention is used as emission material in a light-emitting layer EML, where it is used either in the form of a pure layer or in combination with one or more host materials.

One embodiment of the invention relates to organic optoelectronic devices having an external quantum efficiency (EQE) at 1000 $cd/m^2$ of greater than 5%, especially of greater than 8%, especially of greater than 10%, or of greater than 13%, or of greater than 16% and especially of greater than 20%, and/or an emission maximum at a wavelength between 420 nm and 500 nm, especially between 430 nm and 490 nm, or between 440 nm and 480 nm and especially between 450 nm and 470 nm, and/or an LT80 value at 500 $cd/m^2$ of greater than 30 h, especially of greater than 70 h, or of greater than 100 h, or of greater than 150 h and especially of greater than 200 h.

The proportion by mass of the organic molecule according to the invention in the emitter layer EML, in a further embodiment in a light-emitting layer in optical light-emitting devices, especially in OLEDs, is between 1% and 80%. In one embodiment of the organic optoelectronic device according to the invention, the light-emitting layer is applied to a substrate, preferably with application of an anode and a cathode to the substrate and application of the light-emitting layer between the anode and cathode.

The light-emitting layer, in one embodiment, may have exclusively an organic molecule according to the invention in 100% concentration, with the anode and the cathode applied to the substrate, and the light-emitting layer applied between the anode and cathode.

In one embodiment of the organic optoelectronic device according to the invention, a hole- and electron-injecting layer has been applied between the anode and cathode, and a hole- and electron-transporting layer between the hole- and electron-injecting layer, and the light-emitting layer between the hole- and electron-transporting layer.

The organic optoelectronic device, in a further embodiment of the invention, has: a substrate, an anode, a cathode and at least one hole- and one electron-injecting layer, and at least one hole- and one electron-transporting layer, and at least one light-emitting layer including an organic molecule according to the invention and one or more host materials, the triplet ($T_1$) and singlet ($S_1$) energy levels of which are at higher energy than the triplet ($T_1$) and singlet ($S_1$) energy levels of the organic molecule, with the anode and cathode applied to the substrate, and the hole- and electron-injecting layer applied between the anode and cathode, and the hole- and electron-transporting layer applied between the hole- and electron-injecting layer, and the light-emitting layer applied between the hole- and electron-transporting layer.

In a further aspect, the invention relates to a process for producing an optoelectronic component. This is done using an organic molecule according to the invention.

In one embodiment, the production process encompasses the processing of the organic molecule according to the invention by means of a vacuum evaporation method or from a solution.

The invention also includes a process for producing an optoelectronic device according to the invention, in which at least one layer of the optoelectronic device
   is coated by a sublimation method,
   is coated by an OVPD (organic vapour phase deposition) method,
   is coated by a carrier gas sublimation, and/or
   is produced from solution or by a printing method.

In the production of the optoelectronic device according to the invention, known methods are used. In general, the layers are applied individually to a suitable substrate in successive deposition process steps. In the gas phase deposition, it is possible to employ the commonly used methods, such as thermal evaporation, chemical gas phase deposition (CVD), physical gas phase deposition (PVD). For active-matrix OLED (AMOLED) displays, deposition is effected on an AMOLED backplane as substrate.

Alternatively, it is possible to apply layers from solutions or dispersions in suitable solvents. Illustrative suitable coating methods are spin-coating, dip-coating and jet printing methods. The individual layers can be produced in accor-

EXAMPLES

General Synthesis Scheme I

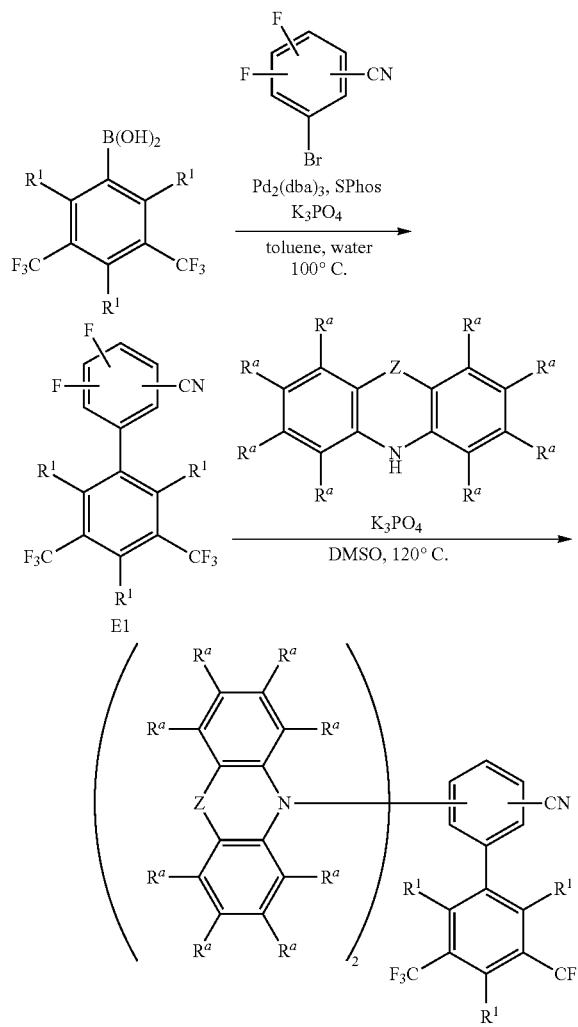

General Synthesis Method GM1:

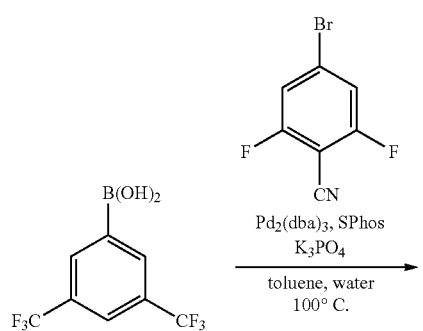

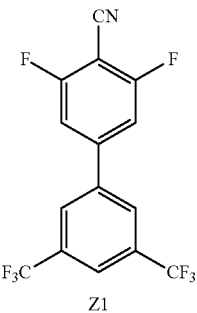

3,5-Bis(trifluoromethyl)phenylboronic acid (1.50 equivalents), 4-bromo-2,6-difluorobenzonitrile (1.00 equivalent), $Pd_2(dba)_3$ (0.02 equivalent), 2-dicyclohexylphosphino-2',6'-dimethoxybiphenyl (SPhos) (0.08 equivalent) and tribasic potassium phosphate (2.50 equivalents) are stirred under nitrogen in a toluene/water mixture (ratio 20:1) at 100° C. for 16 h. Subsequently, the reaction mixture is added to saturated sodium chloride solution and extracted twice with ethyl acetate. The combined organic phases are washed with saturated sodium chloride solution and dried over $MgSO_4$, and the solvent is removed. The product is filtered through a little silica gel and then recrystallized. The product is obtained in solid form.

It is also possible in accordance with the invention to use a corresponding boronic ester rather than a boronic acid.

General Synthesis Method GM2:

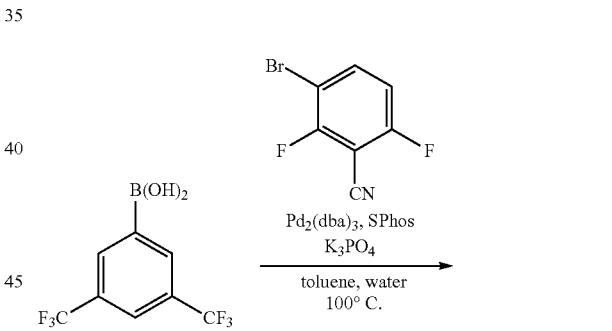

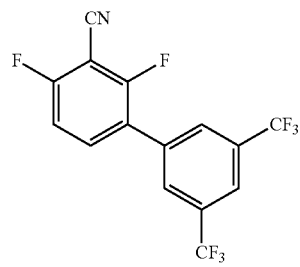

The synthesis of Z2 is effected analogously to GM1, by reaction of 3,5-bis(trifluoromethyl)phenylboronic acid with 3-bromo-2,6-difluorobenzonitrile.

General Synthesis Method GM3:

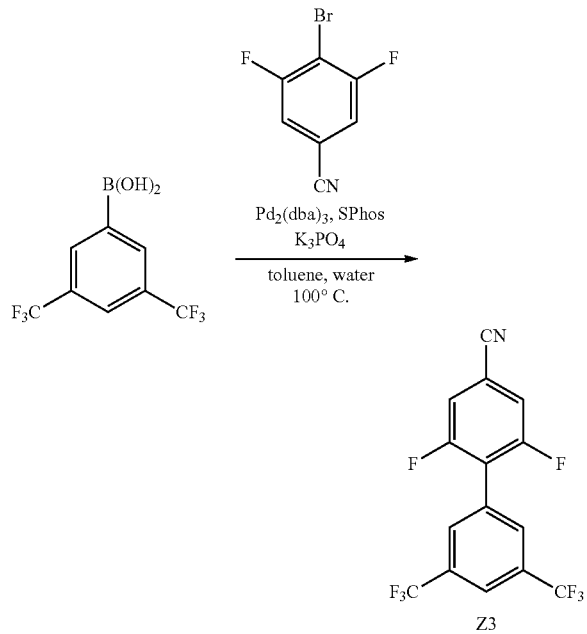

The synthesis of Z3 is effected analogously to GM1, by reaction of 3,5-bis(trifluoromethyl)phenylboronic acid with 4-bromo-3,5-difluorobenzonitrile.

General Synthesis Method GM4:

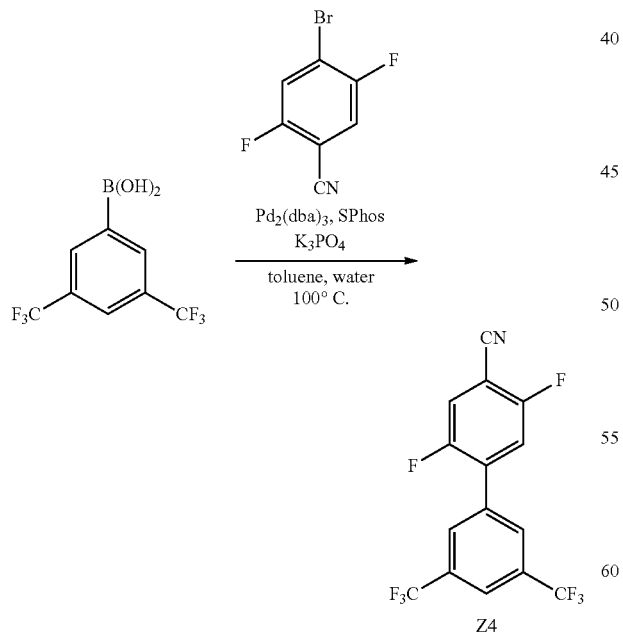

The synthesis of Z4 is effected analogously to GM1, by reaction of 3,5-bis(trifluoromethyl)phenylboronic acid with 4-bromo-2,5-difluorobenzonitrile.

General Synthesis Method GM5:

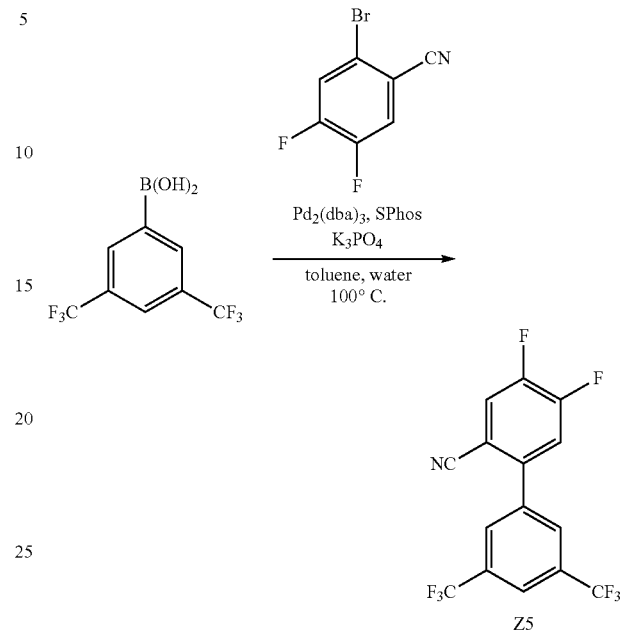

The synthesis of Z5 is effected analogously to GM1, by reaction of 3,5-bis(trifluoromethyl)phenylboronic acid with 2-bromo-4,5-difluorobenzonitrile.

General Synthesis Method GM6:

The synthesis of Z6 is effected analogously to GM1, by reaction of 3,5-bis(trifluoromethyl)phenylboronic acid with 3-bromo-5,6-difluorobenzonitrile.

General Synthesis Method GM7:
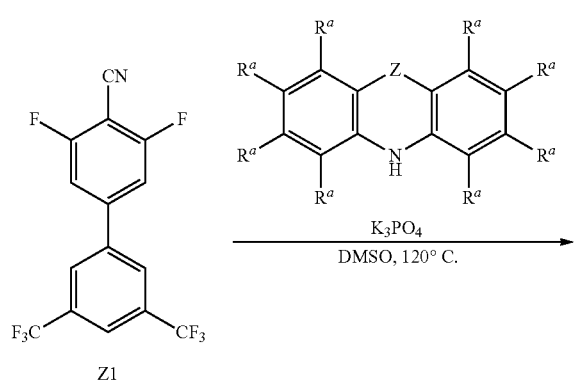
Z1
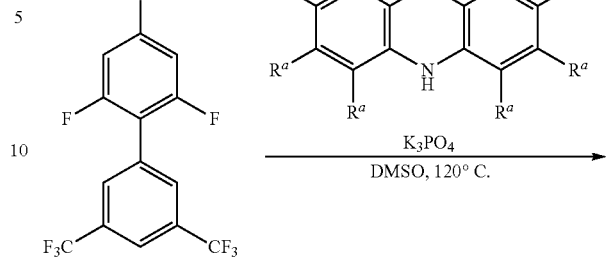
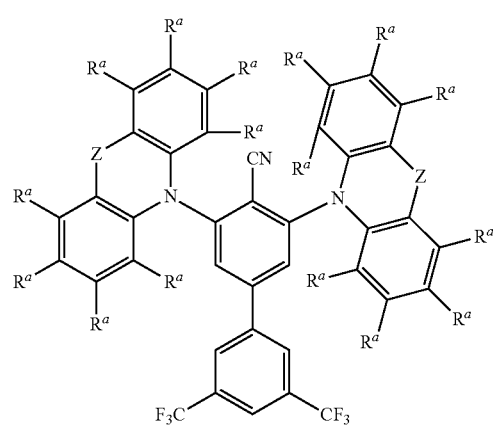
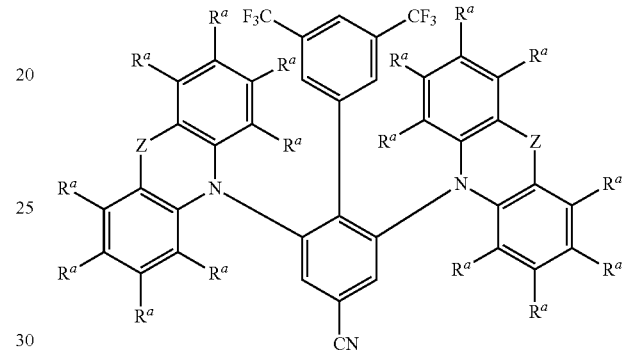
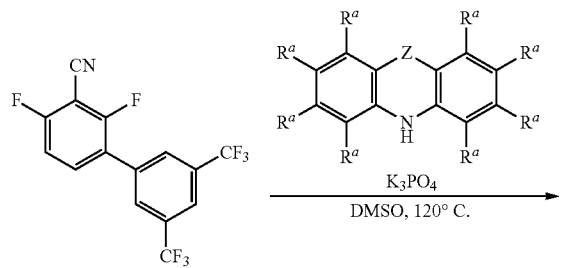
Z2
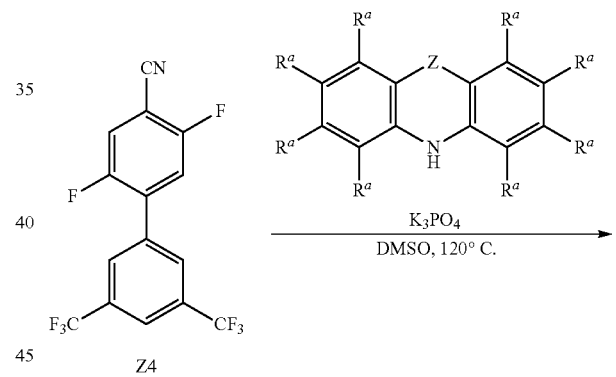
Z4
-continued
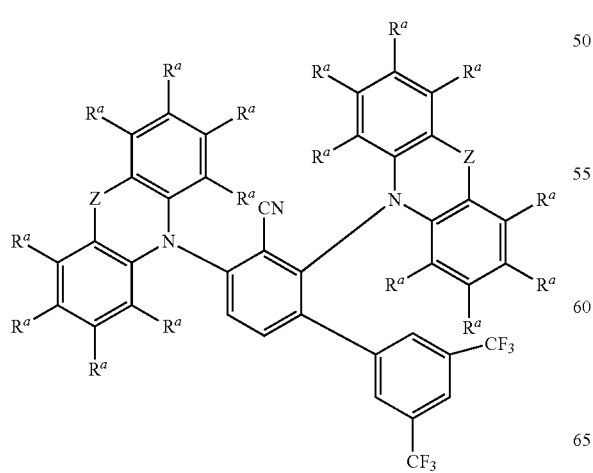
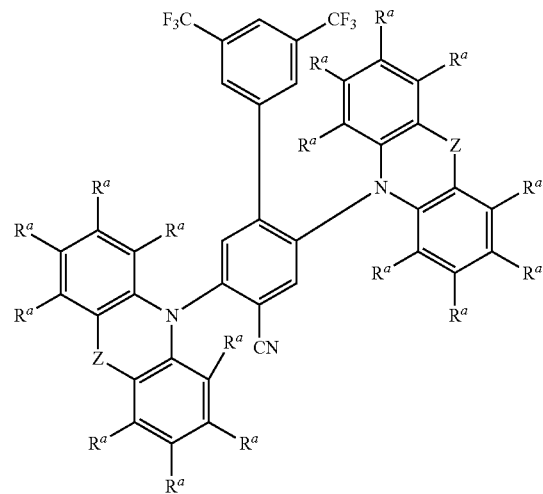

-continued

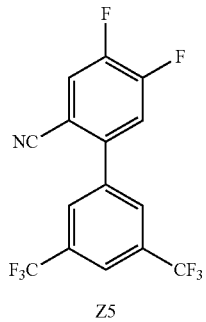
Z5

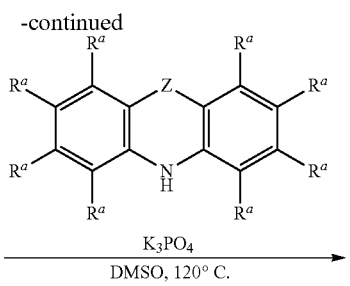

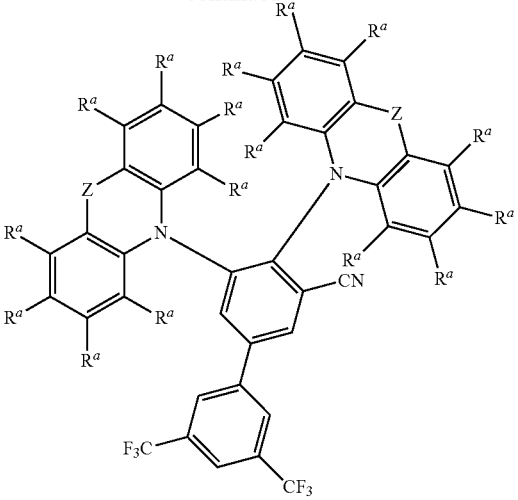

-continued

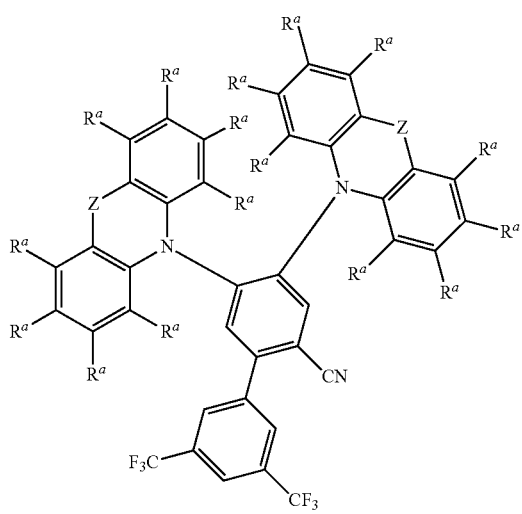

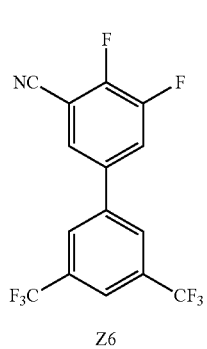
Z6

Z1, Z2, Z3, Z4, Z5 or Z6 (1.00 equivalent of each), the appropriate donor molecule D-H (2.00 equivalents) and tribasic potassium phosphate (4.00 equivalents) are suspended in DMSO under nitrogen and stirred at 110° C. (16 h). Subsequently, the reaction mixture is added to saturated sodium chloride solution and extracted three times with dichloromethane. The combined organic phases are washed twice with saturated sodium chloride solution and dried over magnesium sulphate, and the solvent is then removed. The crude product was finally purified by recrystallization from toluene or via flash chromatography. The product is obtained in solid form.

Specifically, D-H corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), a 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole).

Photophysical Measurements
Pretreatment of Optical Glassware

All glassware (cuvettes and substrates made from quartz glass, diameter: 1 cm) was cleaned after each use: Three rinses each time with dichloromethane, acetone, ethanol, demineralized water, placing in 5% Hellmanex solution for 24 h, thorough rinsing-out with demineralized water. For drying, the optical glassware was blown dry with nitrogen.

Sample Preparation, Film: Spin-coating
Instrument: Spin150, SPS euro.
Sample concentration corresponded to 10 mg/ml, made up in toluene or chlorobenzene.
Programme: 1) 3 s at 400 rpm; 2) 20 s at 1000 rpm at 1000 rpm/s. 3) 10 s at 4000 rpm at 1000 rpm/s. After coating, the films were dried at 70° C. under air on an LHG precision hotplate for 1 min.

Photoluminescence Spectroscopy and TCSPC
Steady-state emission spectroscopy was conducted with a Horiba Scientific fluorescence spectrometer, model: Fluoro-Max-4, equipped with a 150 W xenon arc lamp, excitation and emission monochromators and a Hamamatsu R928 photomultiplier tube, and also a "time-correlated single-photon counting" (TCSPC) option. Emission and excitation spectra were corrected by means of standard correction curves.

The emission decay times were likewise measured with this system using the TCSPC method with the FM-2013 accessories and a TCSPC hub from Horiba Yvon Jobin. Excitation sources:
NanoLED 370 (wavelength: 371 nm, pulse duration: 1.1 ns)
NanoLED 290 (wavelength: 294 nm, pulse duration: <1 ns)
SpectraLED 310 (wavelength: 314 nm)
SpectraLED 355 (wavelength: 355 nm).

The evaluation (exponential fitting) was effected with the DataStation software package and the DAS 6 evaluation software. The fit was reported by the chi-squared method $$c^2 = \sum_{k=1}^{i} \frac{(e_i - o_i)^2}{e_i}$$

with $e_i$: parameter predicted by the fit and $o_i$: parameter measured.

Determination of Quantum Efficiency

The photoluminescence quantum yield (PLQY) was measured by means of an Absolute PL Quantum Yield Measurement C9920-03G system from Hamamatsu Photonics. This consists of a 150 W xenon gas discharge lamp, automatically adjustable Czerny-Turner monochromators (250-950 nm) and an Ulbricht sphere with highly reflective Spectralon coating (a Teflon derivative), connected via a glass fibre cable to a PMA-12 multichannel detector with a BT (back-thinned) CCD chip having 1024×122 pixels (size 24×24 µm). The quantum efficiency and the CIE coordinates were evaluated with the aid of the U6039-05 software, version 3.6.0.

The emission maximum is reported in nm, the quantum yield φ in %, and the CIE colour coordinates as x,y values.

The photoluminescence quantum yield was determined according to the following protocol:
1) Performance of quality assurance: The reference material used is anthracene in ethanol with known concentration.
2) Determining the excitation wavelength: First of all, the absorption maximum of the organic molecule was determined and it was excited therewith.
3) Performance of sample analysis: The absolute quantum yield of degassed solutions and films was determined under a nitrogen atmosphere.

The calculation was effected within the system according to the following equation:

$$\Phi_{PL} = \frac{n_{photon}, \text{emitted}}{n_{photon}, \text{absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

with the photon count $n_{photon}$ and the intensity Int.

Production and Characterization of Organic Electroluminescent Devices from the Gas Phase With the organic molecules according to the invention, it is possible to create OLED devices by means of vacuum sublimation methodology. If a layer contains two or more components, the ratio of these is reported in percent by mass.

These as yet unoptimized OLEDs can be characterized in a standard manner; for this purpose, the electroluminescent spectra, the external quantum efficiency (measured in %) as a function of brightness, calculated from the light detected by the photodiode, and the current are recorded. The lifetime of the OLEDs can be determined from the plot of the electroluminescence spectra against time. The LT50 value reported corresponds here to the time at which the luminance has dropped to 50% of the starting value. Analogously, the LT70 value corresponds to the time at which the luminance has dropped to 70% of the starting value. The values reported are calculated from the average of the different pixels of an OLED. The spectra depicted each show a measurement series for a pixel.

HPLC-MS:

HPLC-MS spectroscopy was measured with an Agilent HPLC system (1100 series) connected to an MS detector (Thermo LTQ XL). For the HPLC, an Eclipse Plus C18 column from Agilent with a particle size of 3.5 µm, a length of 150 mm and an internal diameter of 4.6 mm was used. No pre-column was employed and operation was effected at room temperature with the solvents acetonitrile, water and tetrahydrofuran in these concentrations:

| Solvent A: | $H_2O$ (90%) | MeCN (10%) |
|---|---|---|
| Solvent B: | $H_2O$ (10%) | MeCN (90%) |
| Solvent C: | THF (100%) | |

An injection volume of 15 µl and a concentration of 10 µg/ml with this gradient was employed:

| Flow rate [ml/min] | Time [min] | A[%] | B[%] | C[%] | Pressure [bar] |
|---|---|---|---|---|---|
| 0.3 | 0 | 80 | 20 | — | 115 |
| 0.3 | 5 | 80 | 20 | — | 115 |
| 0.3 | 14 | 0 | 90 | 10 | 65 |
| 0.3 | 25 | 0 | 90 | 10 | 65 |
| 0.3 | 26 | 80 | 20 | — | 115 |
| 0.3 | 33 | 80 | 20 | — | 115 |

The sample was ionized by APCI (atmospheric pressure chemical ionization).

Example 1

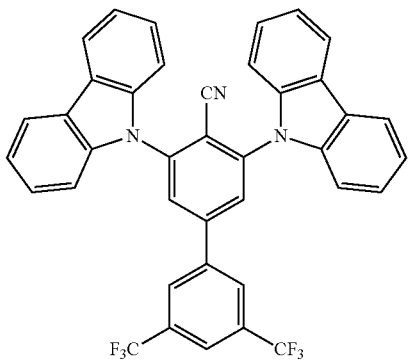 [SMILES: N#Cc1c(-n2c3ccccc3c3ccccc32)cc(-c2cc(C(F)(F)F)cc(C(F)(F)F)c2)cc1-n1c2ccccc2c2ccccc21]

Example 1 was prepared according to GM1 (99% yield) and GM7 (40% yield).

MS (HPLC-MS), m/z (Retention time): 643, (18.60 min)

$R_f$=0.68 (cyclohexane/ethyl acetate 5:1).

FIG. 1 shows the emission spectrum of Example 1 (10% in PMMA). The emission maximum is at 461 nm. The photoluminescence quantum yield (PLQY) is 84% and the half-height width is 0.43 eV.

Example 2

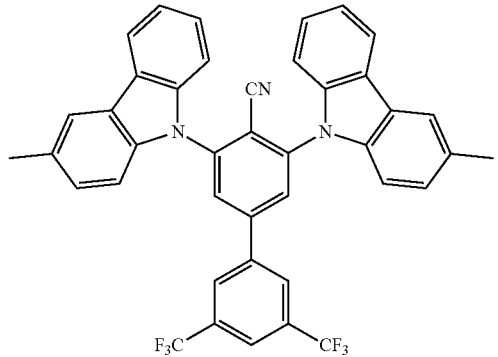

Example 2 was prepared according to GM1 (99% yield) and GM7 (47% yield).

MS (HPLC-MS), m/z (Retention time): 673, (20.05 min)

$R_f$=0.71 (cyclohexane/ethyl acetate 5:1).

Figure 2:
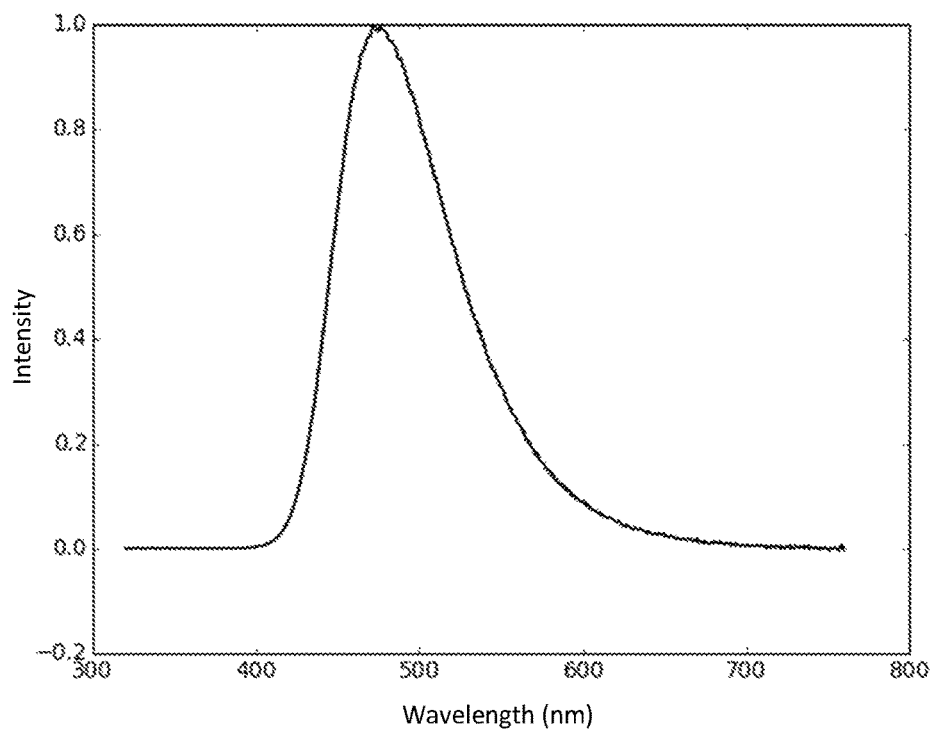
FIG. 2 illustrates an emission spectrum of Example 2 (10% in PMMA).

FIG. 2 shows the emission spectrum of Example 2 (10% in PMMA). The emission maximum is at 476 nm. The photoluminescence quantum yield (PLQY) is 84% and the half-height width is 0.44 eV. The emission decay time is 63 µs.

Example 3

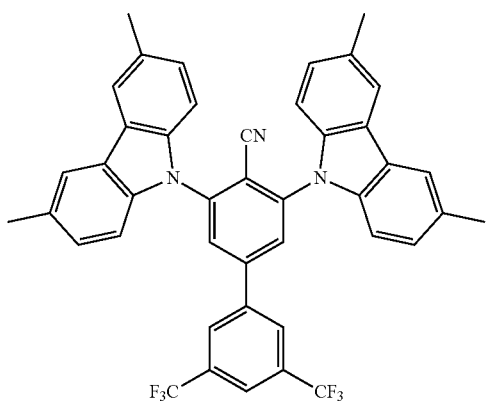

Example 3 was prepared according to GM1 (99% yield) and GM7 (77% yield).

MS (HPLC-MS), m/z (Retention time): 702, (21.51 min)

$R_f$=0.83 (cyclohexane/ethyl acetate 5:1)

Figure 3:
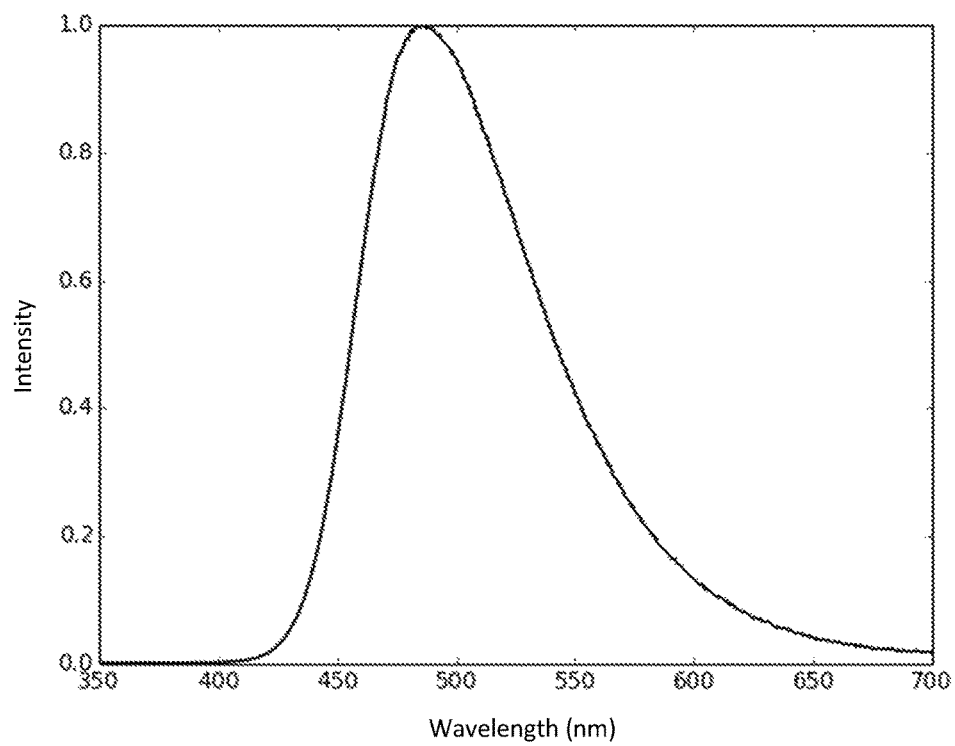
FIG. 3 illustrates an emission spectrum of Example 3 (10% in PMMA).

FIG. 3 shows the emission spectrum of Example 3 (10% in PMMA). The emission maximum is at 486 nm. The photoluminescence quantum yield (PLQY) is 74% and the half-height width is 0.43 eV. The emission decay time is 12 µs.

Example 4

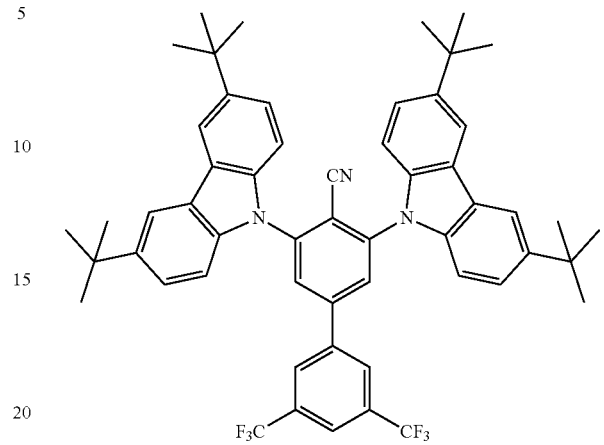

Example 4 was prepared according to GM1 (99% yield) and GM7 (89% yield).

$R_f$=0.84 (cyclohexane/ethyl acetate 5:1).

Figure 4:
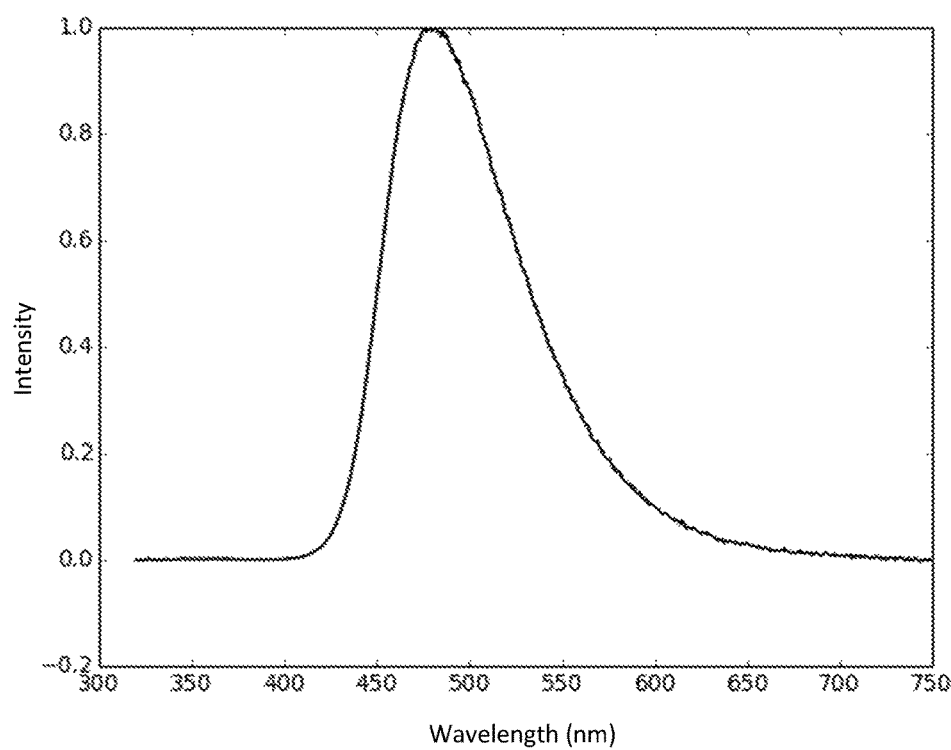
FIG. 4 illustrates an emission spectrum of Example 4 (10% in PMMA).

FIG. 4 shows the emission spectrum of Example 4 (10% in PMMA). The emission maximum is at 478 nm. The photoluminescence quantum yield (PLQY) is 78% and the half-height width is 0.43 eV. The emission decay time is 14 µs.

Example 5

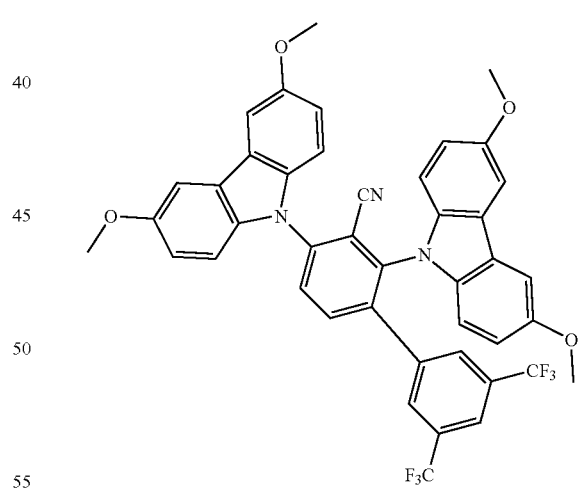

Example 5 was prepared according to GM2 (52% yield) and GM7 (70% yield).

MS (HPLC-MS), m/z (Retention time): 765, (14.45 min)

$R_f$=0.13 (cyclohexane/ethyl acetate 5:1).

Figure 5:
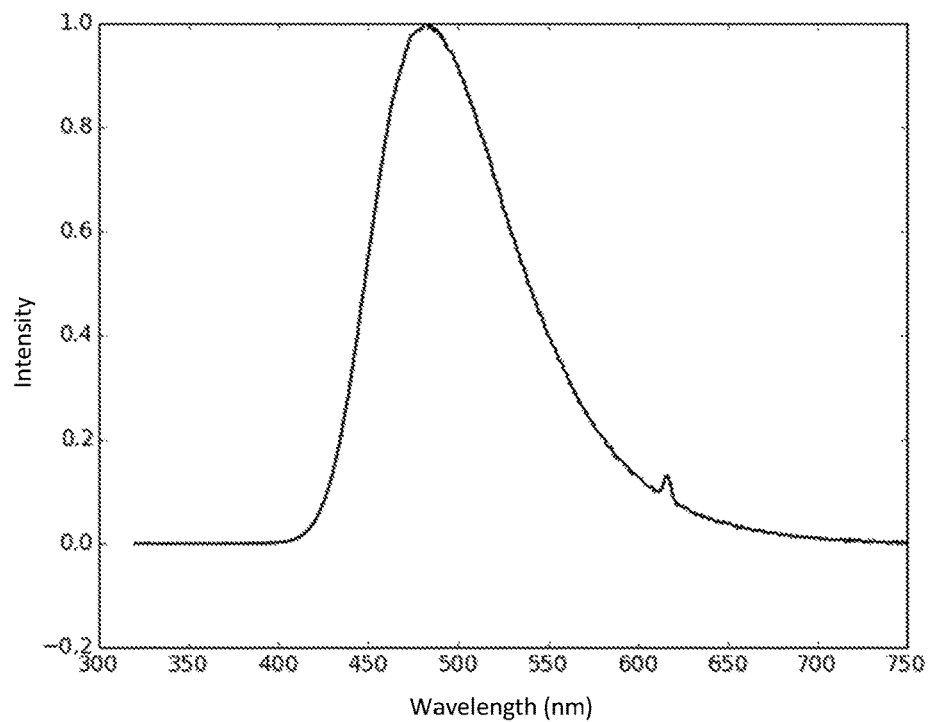
FIG. 5 illustrates an emission spectrum of Example 5 (10% in PMMA).

FIG. 5 shows the emission spectrum of Example 5 (10% in PMMA). The emission maximum is at 483 nm. The photoluminescence quantum yield (PLQY) is 68% and the half-height width is 0.46 eV. The emission decay time is 34 µs.

Example 6

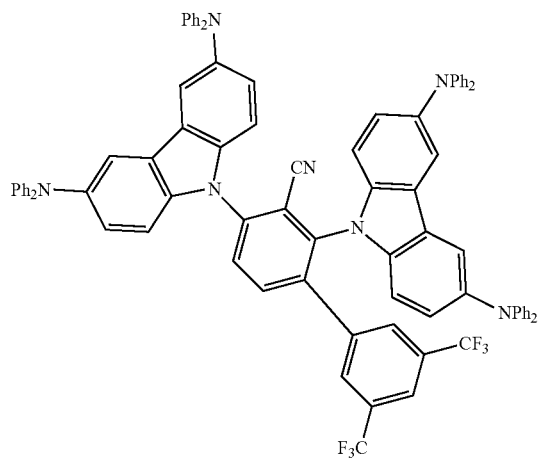

Example 6 was prepared according to GM2 (52% yield) and GM7 (69% yield).

MS (HPLC-MS), m/z (Retention time): 1304, (31.17 min)

$R_f$=0.69 (cyclohexane/ethyl acetate 5:1).

Figure 6:
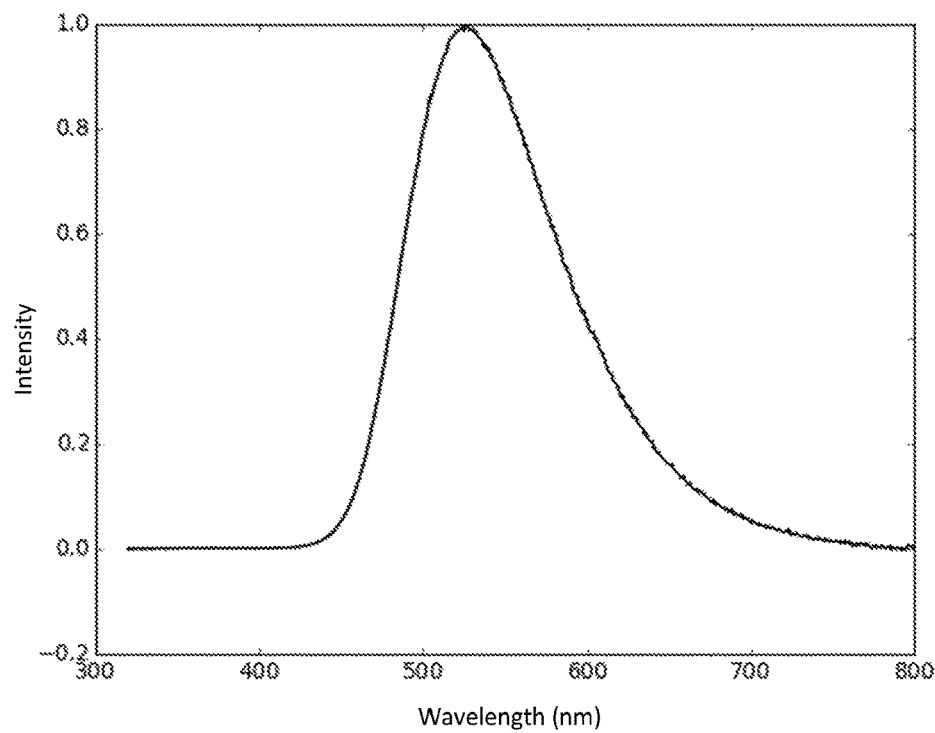
FIG. 6 illustrates an emission spectrum of Example 6 (10% in PMMA).

FIG. 6 shows the emission spectrum of Example 6 (10% in PMMA). The emission maximum is at 528 nm. The photoluminescence quantum yield (PLQY) is 45% and the half-height width is 0.46 eV. The emission decay time is 3 μs.

Example 7

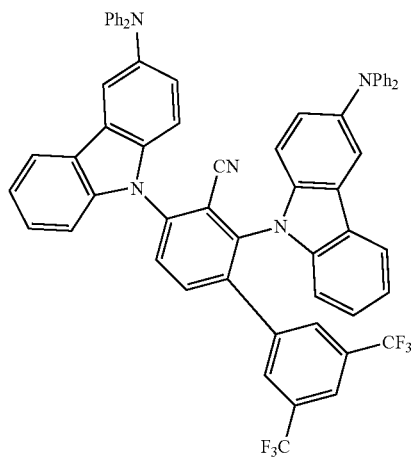

Example 7 was prepared according to GM2 (52% yield) and GM7 (74% yield).

MS (HPLC-MS), m/z (Retention time): 980, (22.38 min)

$R_f$=0.56 (cyclohexane/ethyl acetate 5:1).

Figure 7:
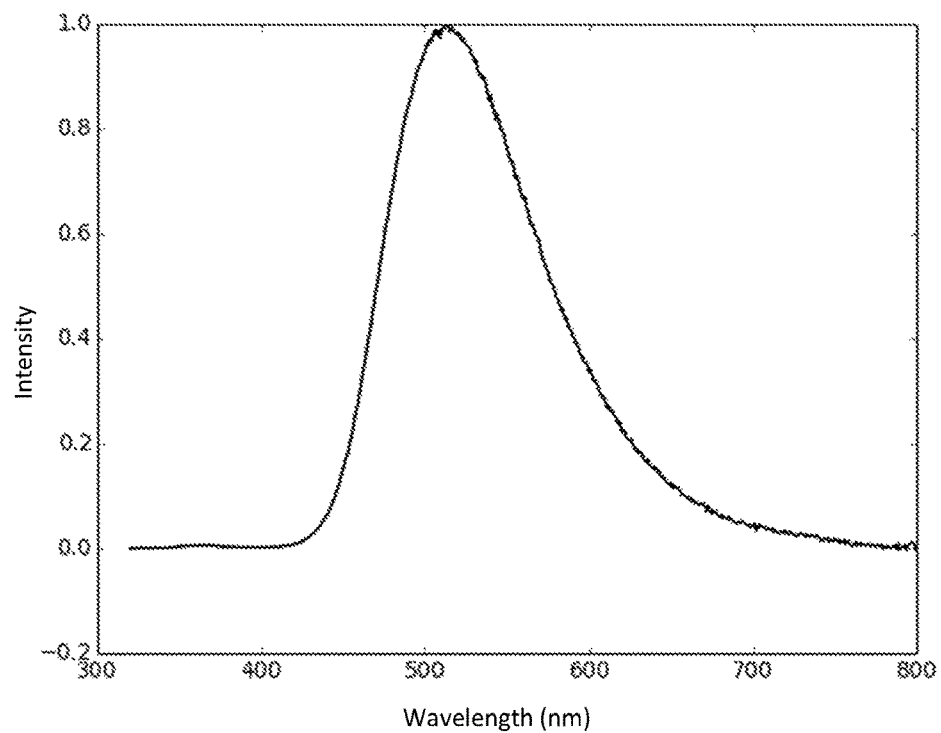
FIG. 7 illustrates an emission spectrum of Example 7 (10% in PMMA).

FIG. 7 shows the emission spectrum of Example 7 (10% in PMMA). The emission maximum is at 516 nm. The photoluminescence quantum yield (PLQY) is 44% and the half-height width is 0.49 eV. The emission decay time is 3 μs.

Example 8

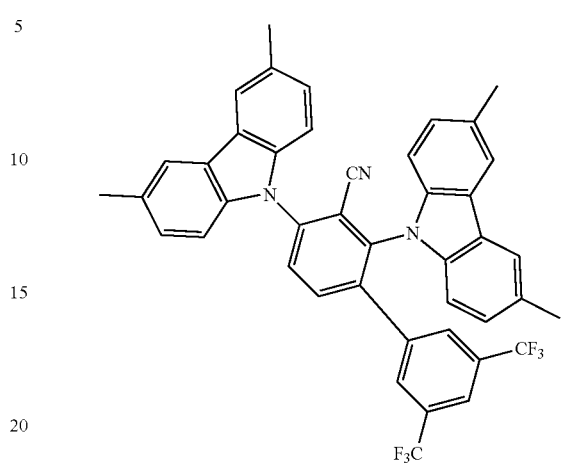

Example 8 was prepared according to GM2 (52% yield) and GM7 (38% yield).

MS (HPLC-MS), m/z (Retention time): 702, (19.55 min)

$R_f$=0.70 (cyclohexane/ethyl acetate 5:1).

Figure 8:
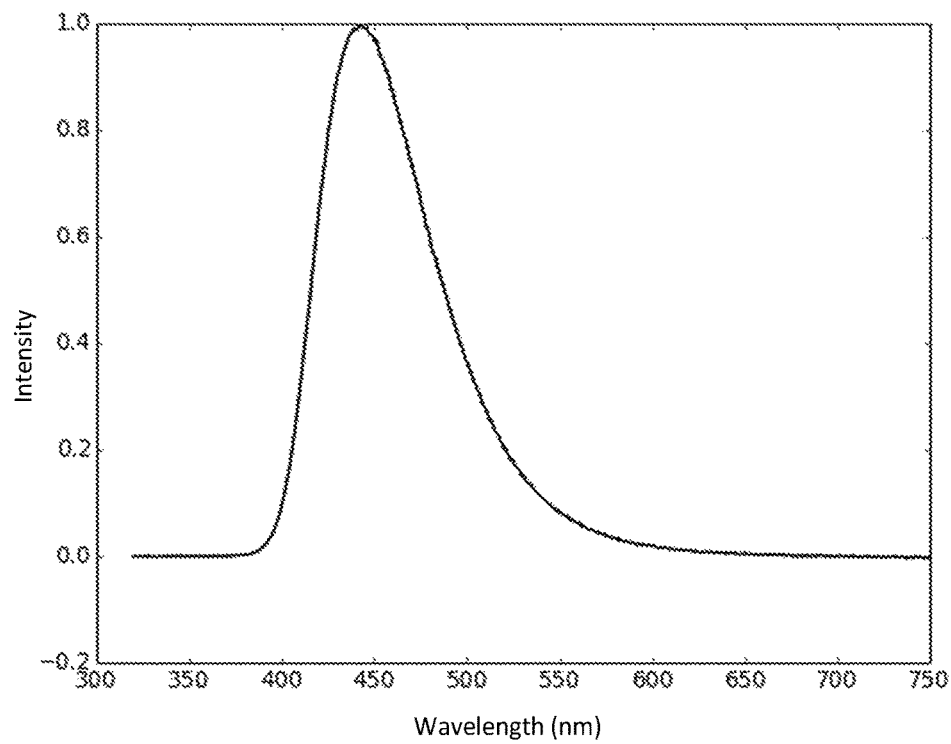
FIG. 8 illustrates an emission spectrum of Example 8 (10% in PMMA).

FIG. 8 shows the emission spectrum of Example 8 (10% in PMMA). The emission maximum is at 442 nm. The photoluminescence quantum yield (PLQY) is 71% and the half-height width is 0.44 eV.

Example 9

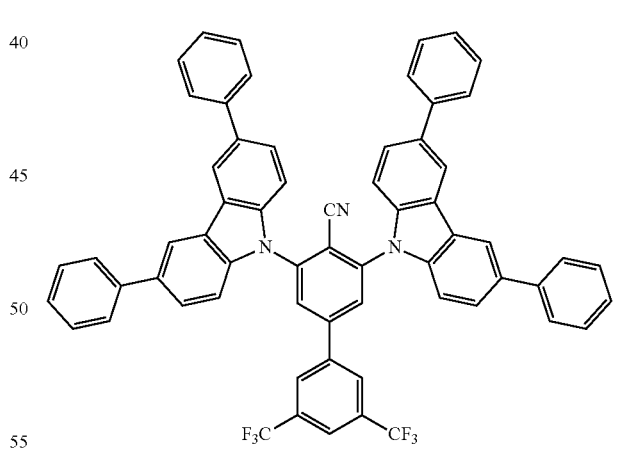

Example 9 was prepared according to GM1 (99% yield) and GM7 (47% yield).

MS (HPLC-MS), m/z (Retention time): 593, (10.67 min)

Figure 9:
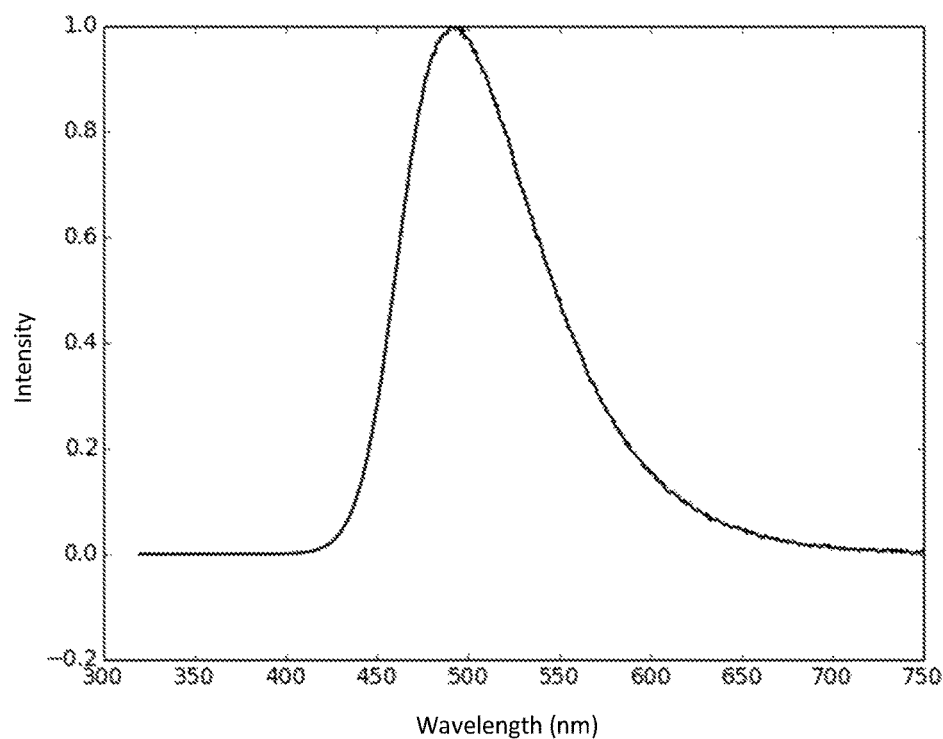
FIG. 9 illustrates an emission spectrum of Example 9 (10% in PMMA).

FIG. 9 shows the emission spectrum of Example 9 (10% in PMMA). The emission maximum is at 492 nm. The photoluminescence quantum yield (PLQY) is 84% and the half-height width is 0.41 eV. The emission decay time is 7 μs.

Example 10

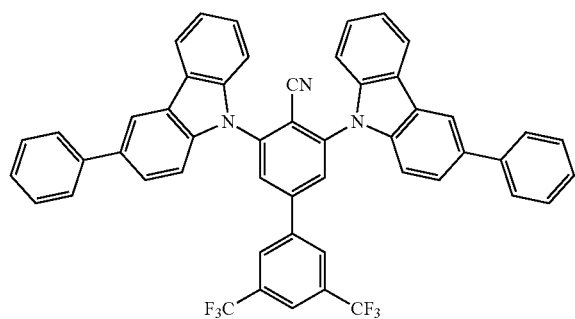 [SMILES: N#Cc1c(-n2c3ccccc3c3cc(-c4ccccc4)ccc32)cc(-c2cc(C(F)(F)F)cc(C(F)(F)F)c2)cc1-n1c2ccccc2c2cc(-c3ccccc3)ccc21]

Example 10 was prepared according to GM1 (99% yield) and GM7 (74% yield).

MS (HPLC-MS), m/z (Retention time): 797, (21.35 min)

$R_f$=0.48 (cyclohexane/ethyl acetate 5:1)

Figure 10:
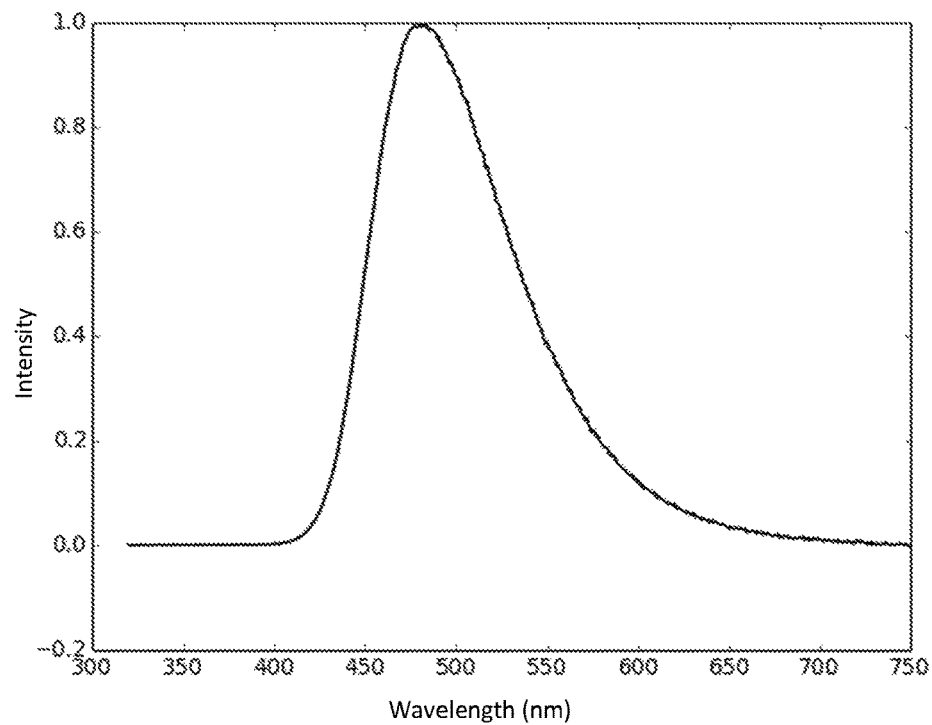
FIG. 10 illustrates an emission spectrum of Example 10 (10% in PMMA).

FIG. 10 shows the emission spectrum of Example 10 (10% in PMMA). The emission maximum is at 481 nm. The photoluminescence quantum yield (PLQY) is 80% and the half-height width is 0.45 eV. The emission decay time is 41 µs.

Example 11

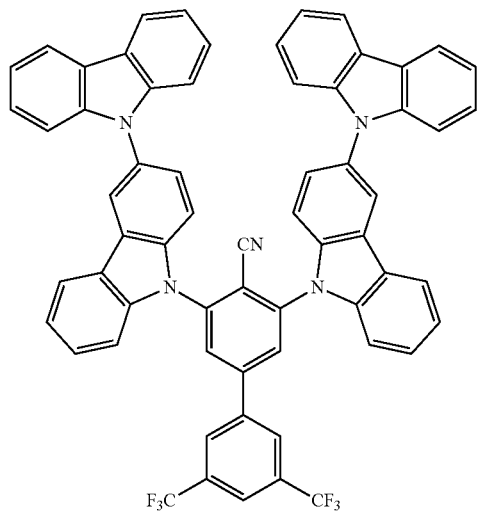 [SMILES: N#Cc1c(-n2c3ccccc3c3cc(-n4c5ccccc5c5ccccc54)ccc32)cc(-c2cc(C(F)(F)F)cc(C(F)(F)F)c2)cc1-n1c2ccccc2c2cc(-n3c4ccccc4c4ccccc43)ccc21]

Example 11 was prepared according to GM1 (99% yield) and GM7 (81% yield).

MS (HPLC-MS), m/z (Retention time): 975, (25.15 min)

$R_f$=0.65 (cyclohexane/ethyl acetate 5:1)

Figure 11:
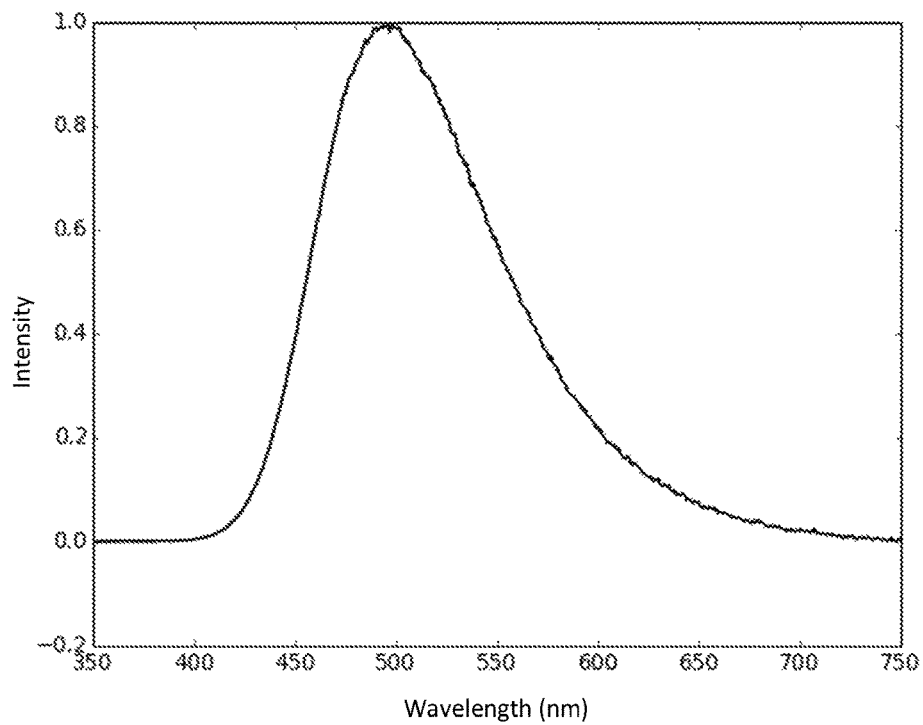
FIG. 11 illustrates an emission spectrum of Example 11 (10% in PMMA).

FIG. 11 shows the emission spectrum of Example 11 (10% in PMMA). The emission maximum is at 496 nm. The photoluminescence quantum yield (PLQY) is 59% and the half-height width is 0.50 eV. The emission decay time is 22 µs.

Example 12

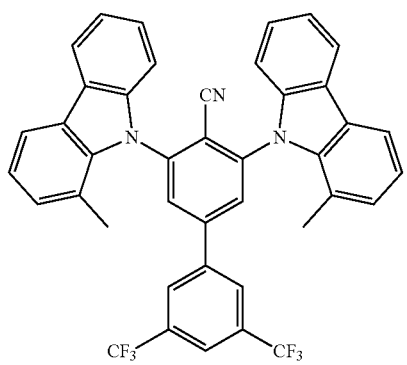 [SMILES: Cc1cccc2c3ccccc3n(-c3cc(-c4cc(C(F)(F)F)cc(C(F)(F)F)c4)cc(-n4c5ccccc5c5cccc(C)c54)c3C#N)c12]

Example 12 was prepared according to GM1 (99% yield) and GM7 (16% yield).

MS (HPLC-MS), m/z (Retention time): 673, (19.01 min)

$R_f$=0.67 (cyclohexane/ethyl acetate 5:1).

Figure 12:
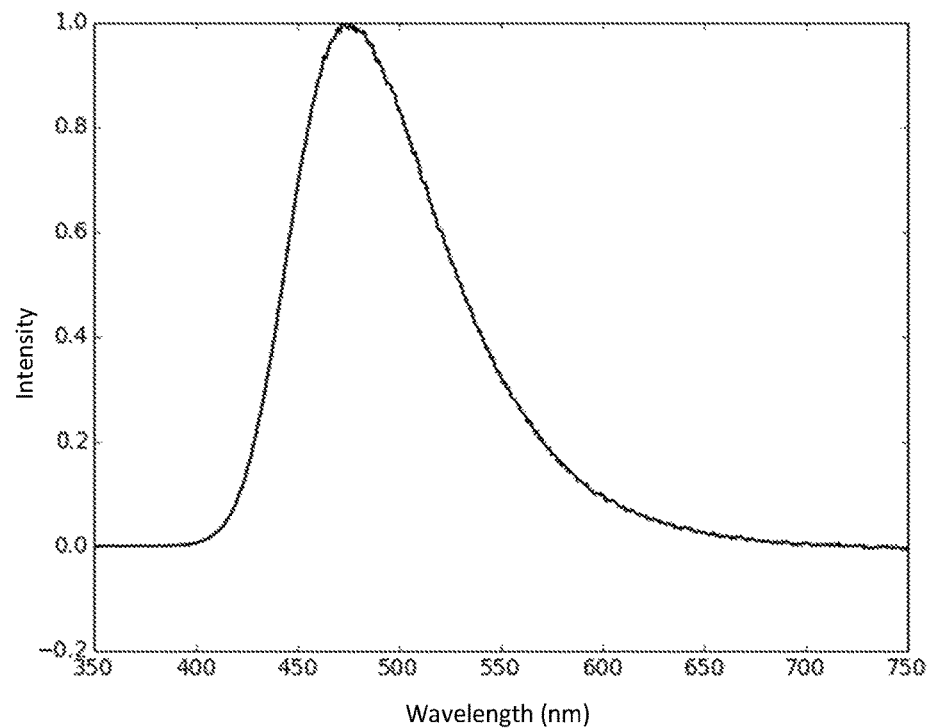
FIG. 12 illustrates an emission spectrum of Example 12 (10% in PMMA).

FIG. 12 shows the emission spectrum of Example 12 (10% in PMMA). The emission maximum is at 476 nm. The photoluminescence quantum yield (PLQY) is 76% and the half-height width is 0.46 eV.

Example 13

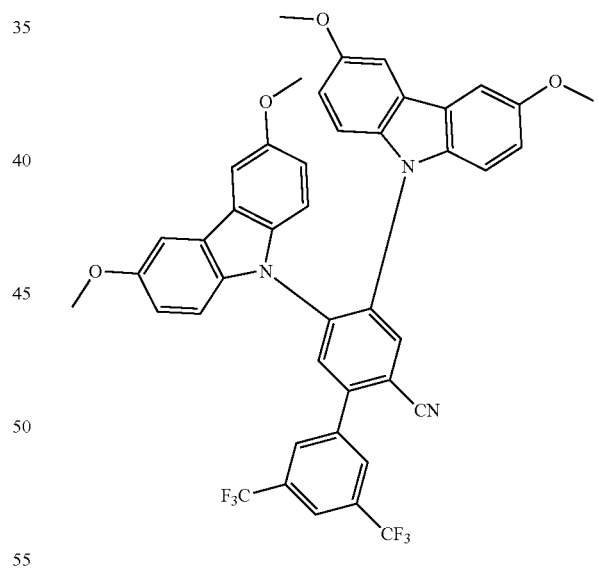

Example 13 was prepared according to GM5 (94% yield) and GM7 (53% yield).

$R_f$=0.2 (cyclohexane/ethyl acetate 5:1).

$^1$H-NMR (500 MHz, CDCl$_3$): d=8.28 (s, 1 H), 8.18 (s, 1 H), 8.07 (s, 1 H), 8.00 (s, 1 H), 7.29-7.31 (m, 4 H), 7.04 (dd, 4 H), 6.75 (td, 4 H), 3.85 (s, 6 H), 3.87 (s, 6 H) ppm.

Figure 13:
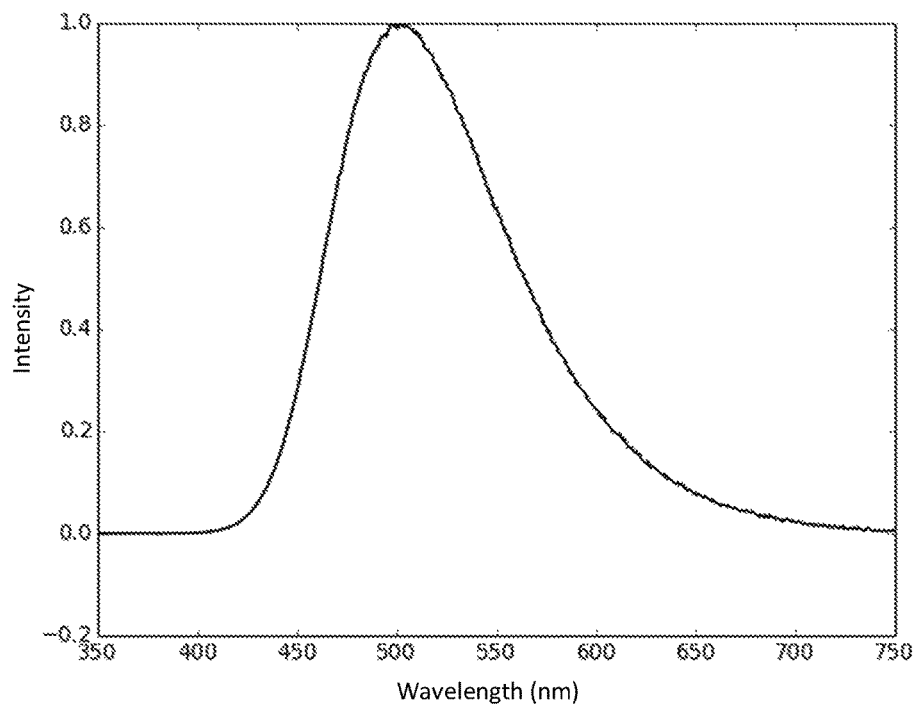
FIG. 13 illustrates an emission spectrum of Example 13 (10% in PMMA).

FIG. 13 shows the emission spectrum of Example 13 (10% in PMMA). The emission maximum is at 502 nm. The photoluminescence quantum yield (PLQY) is 75% and the half-height width is 0.49 eV.

Example 14

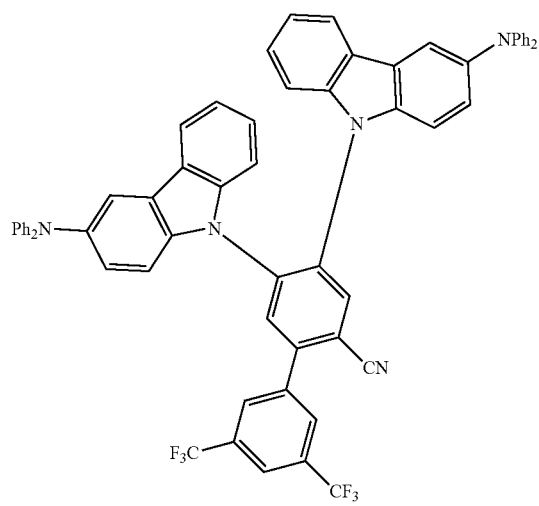

Example 14 was prepared according to GM5 (94% yield) and GM7 (71% yield).

$R_f$=0.7 (cyclohexane/ethyl acetate 5:1).

$^1$H-NMR (500 MHz, CDCl$_3$): d=8.41 (d, 1 H), 8.26 (s, 2 H), 8.12 (d, 2 H), 7.72 (q, 2 H), 7.61 (dd, 1 H), 7.56 (dd, 1 H), 7.40 (t, 1 H), 7.27-7.34 (m, 1 H), 7.14-7.22 (m, 9 H), 7.01-7.16 (m, 4 H), 6.92-6.97 (m, 12 H), 6.85 (td, 1 H), 6.60 (dd, 1 H), 6.55 (td, 1 H) ppm.

Figure 14:
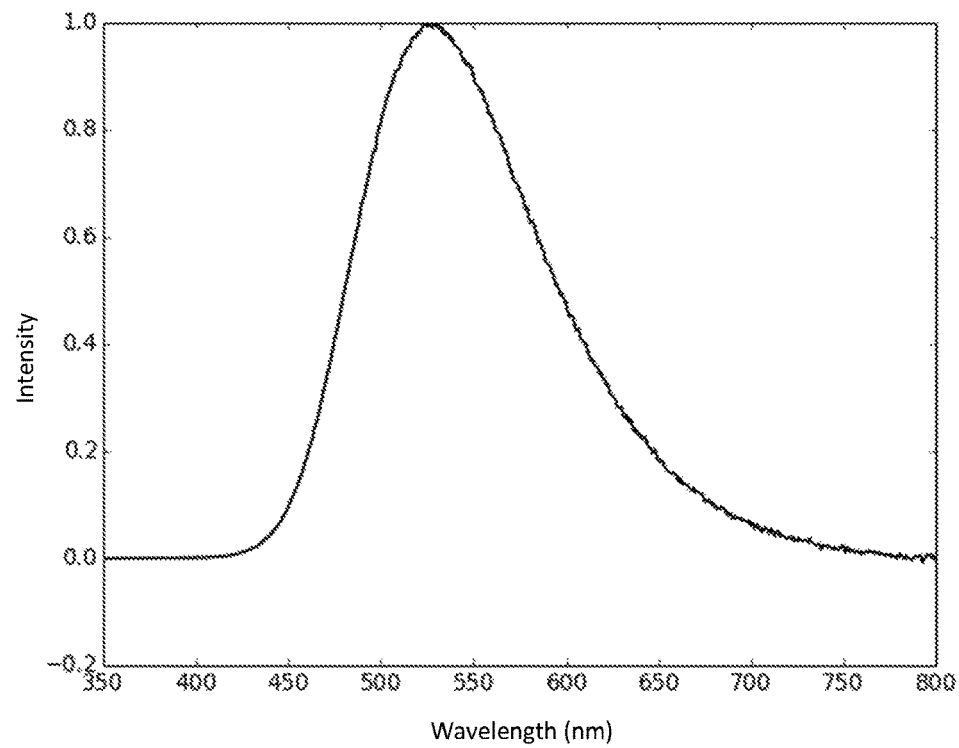
FIG. 14 illustrates an emission spectrum of Example 14 (10% in PMMA).

FIG. 14 shows the emission spectrum of Example 14 (10% in PMMA). The emission maximum is at 527 nm. The photoluminescence quantum yield (PLQY) is 49% and the half-height width is 0.50 eV. The emission decay time is 9 μs.

Example 15

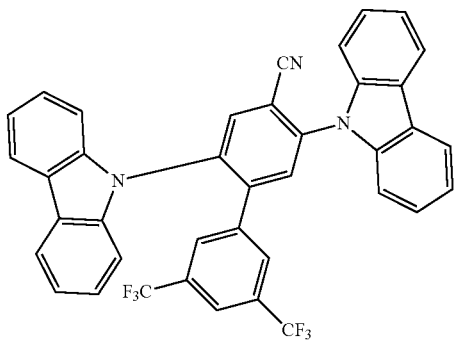 [SMILES: N#Cc1cc(-n2c3ccccc3c3ccccc32)c(-c2cc(C(F)(F)F)cc(C(F)(F)F)c2)cc1-n1c2ccccc2c2ccccc21]

Example 15 was prepared according to GM4 (88% yield) and GM7 (79% yield).

MS (HPLC-MS), m/z (Retention time): 645, (18.61 min)

$R_f$=0.55 (cyclohexane/ethyl acetate 5:1).

Figure 15:
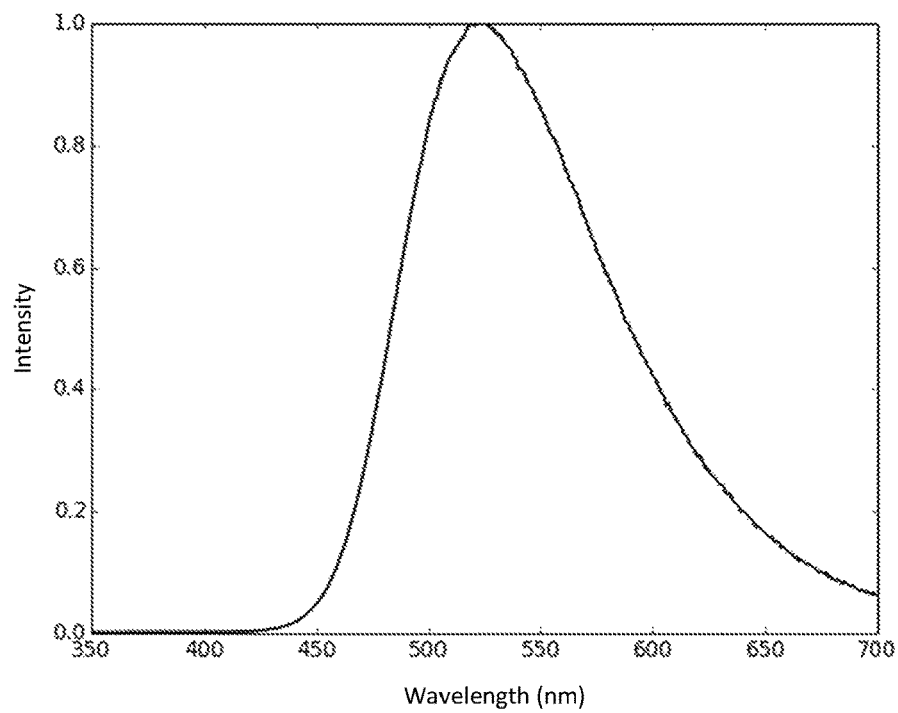
FIG. 15 illustrates an emission spectrum of Example 15 (10% in PMMA).

FIG. 15 shows the emission spectrum of Example 15 (10% in PMMA). The emission maximum is at 450 nm. The photoluminescence quantum yield (PLQY) is 78% and the half-height width is 0.42 eV.

Example 16

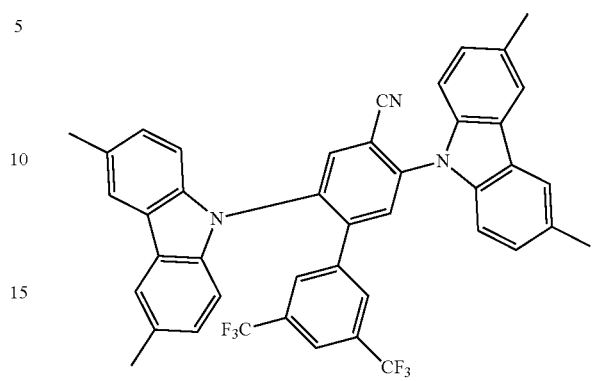

Example 16 was prepared according to GM4 (88% yield) and GM7 (99% yield).

MS (HPLC-MS), m/z (Retention time): 702, (21.47 min)

$R_f$=0.74 (cyclohexane/ethyl acetate 5:1).

Figure 16:
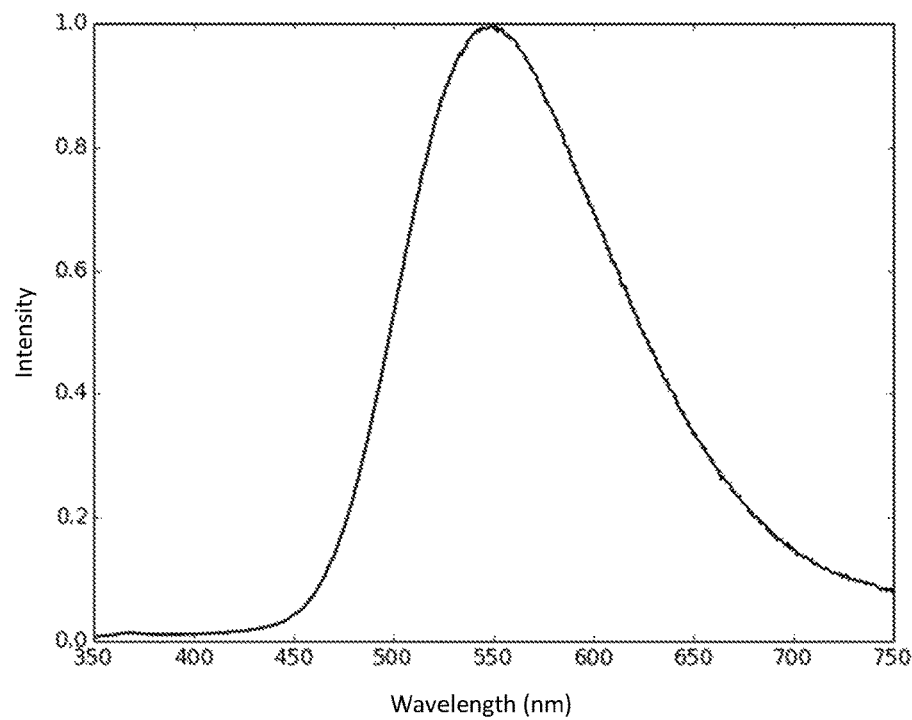
FIG. 16 illustrates an emission spectrum of Example 16 (10% in PMMA).

FIG. 16 shows the emission spectrum of Example 16 (10% in PMMA). The emission maximum is at 471 nm. The photoluminescence quantum yield (PLQY) is 92% and the half-height width is 0.41 eV.

Example 17

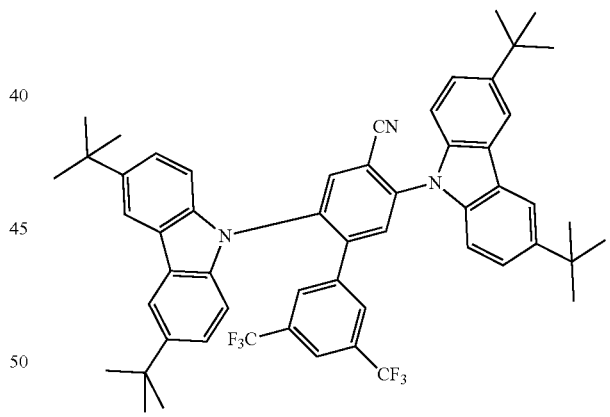

Example 17 was prepared according to GM4 (88% yield) and GM7 (99% yield).

$^1$H-NMR (500 MHz, CDCl$_3$): d=8.26 (s, 1H, Ar—H), 8.19 (d, 2H, Ar—H), 8.02 (d, 2H, Ar—H), 7.87 (s, 1H, Ar—H), 7.56 (dd, 2H, Ar—H), 7.45 (bs, 1H, Ar—H), 7.38-7.35 (m, 4H, Ar—H), 7.22-7.21 (m, 2H, Ar—H), 6.98 (d, 2H, Ar—H), 1.43 (s, 18H, CH$_3$), 1.41 (s, 18H, CH$_3$) ppm.

Figure 17:
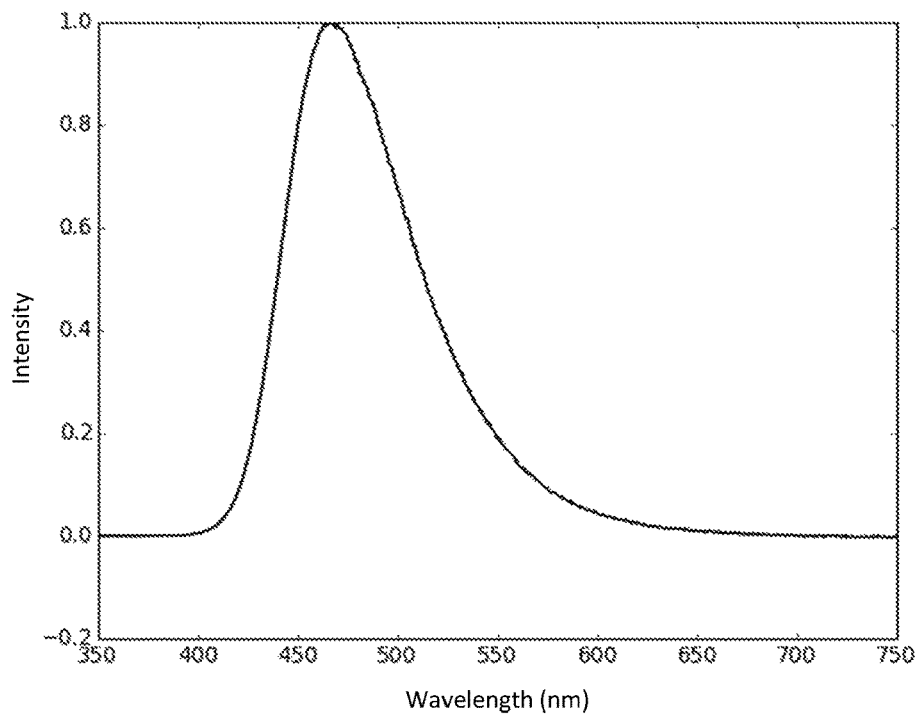
FIG. 17 illustrates an emission spectrum of Example 17 (10% in PMMA).

FIG. 17 shows the emission spectrum of Example 17 (10% in PMMA). The emission maximum is at 466 nm. The photoluminescence quantum yield (PLQY) is 94% and the half-height width is 0.41 eV.

Example 18

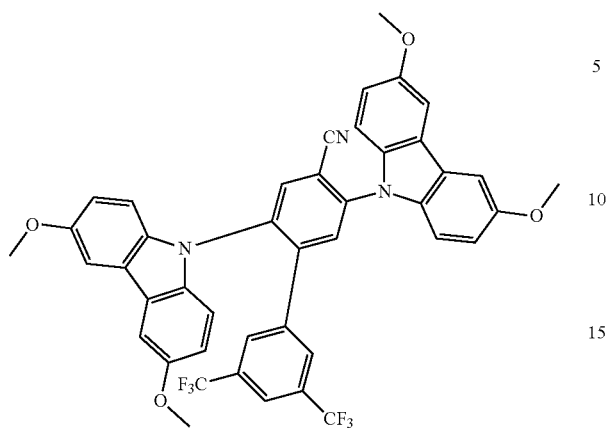

Figure 18:
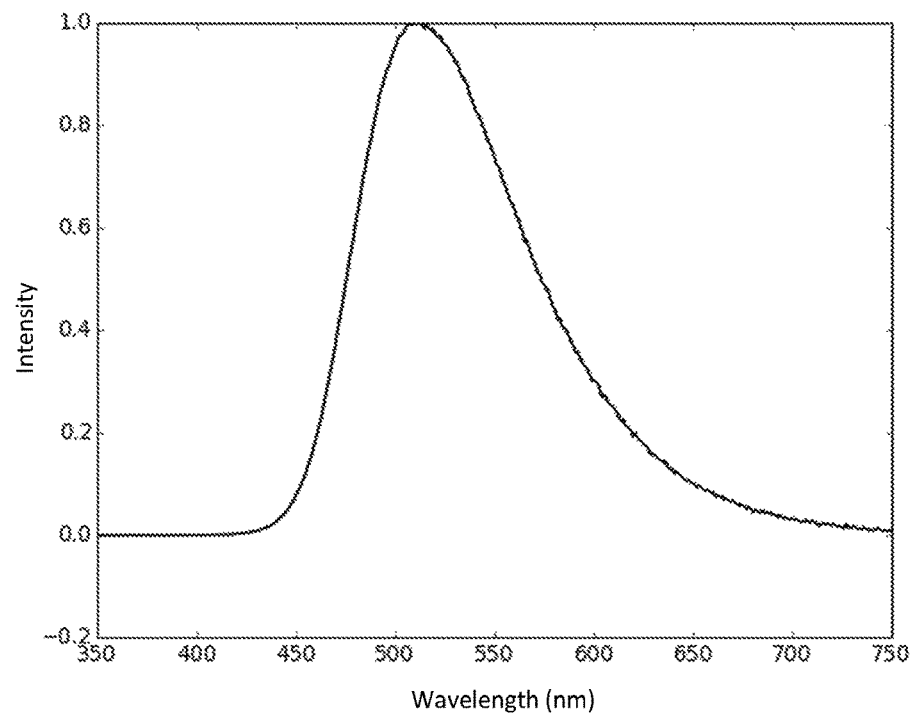
FIG. 18 illustrates an emission spectrum of Example 18 (10% in PMMA).

Example 18 was prepared according to GM4 (88% yield) and GM7 (90% yield).
MS (HPLC-MS), m/z (Retention time): 765, (16.18 min)
$R_f$=0.38 (cyclohexane/ethyl acetate 5:1).
FIG. 18 shows the emission spectrum of Example 18 (10% in PMMA). The emission maximum is at 513 nm. The photoluminescence quantum yield (PLQY) is 52% and the half-height width is 0.45 eV. The emission decay time is 34 µs.

Example 19

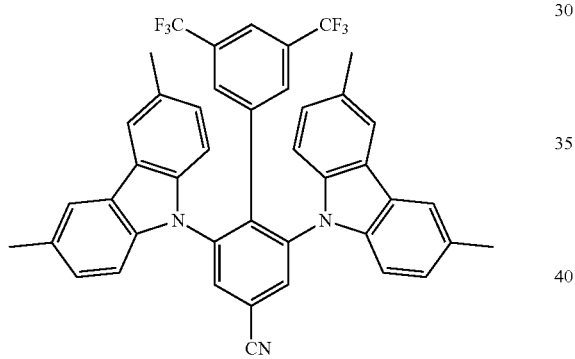

Figure 19:
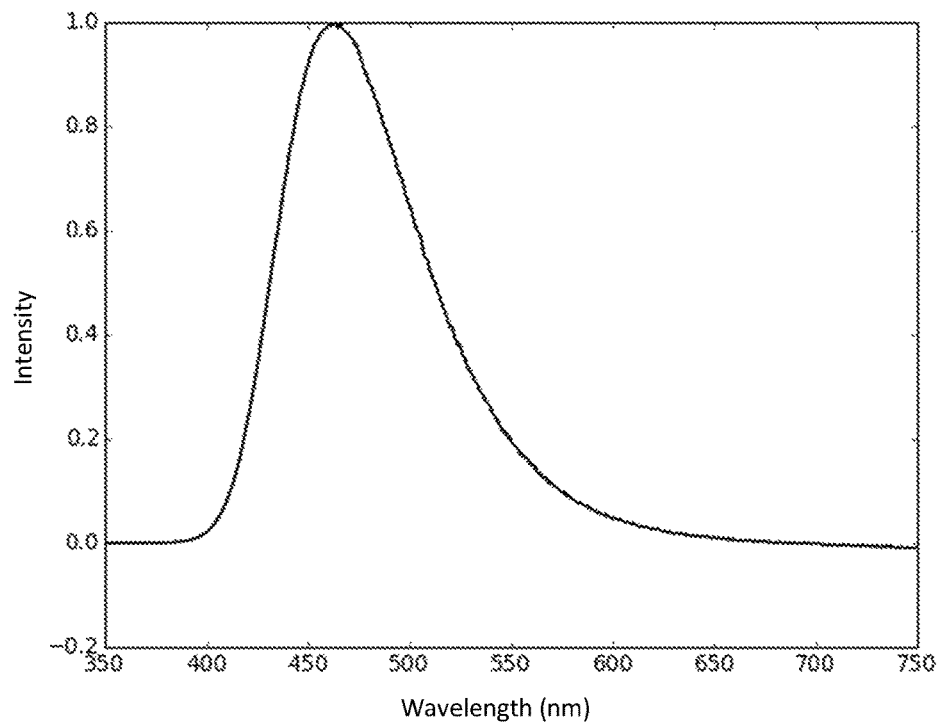
FIG. 19 illustrates an emission spectrum of Example 19 (10% in PMMA).

Example 19 was prepared according to GM3 (71% yield) and GM7 (31% yield).
MS (HPLC-MS), m/z (Retention time): 702, (20.85 min)
$R_f$=0.86 (cyclohexane/ethyl acetate 5:1).
FIG. 19 shows the emission spectrum of Example 19 (10% in PMMA). The emission maximum is at 463 nm. The photoluminescence quantum yield (PLQY) is 72% and the half-height width is 0.45 eV.

Example 20

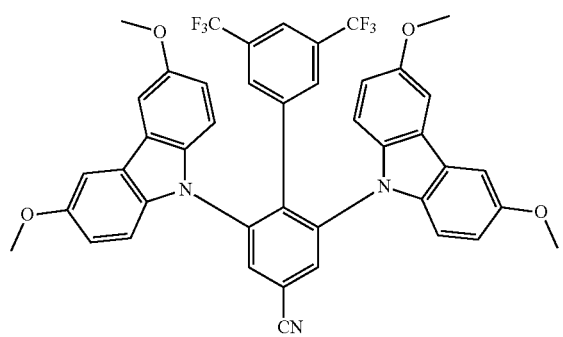

Figure 20:
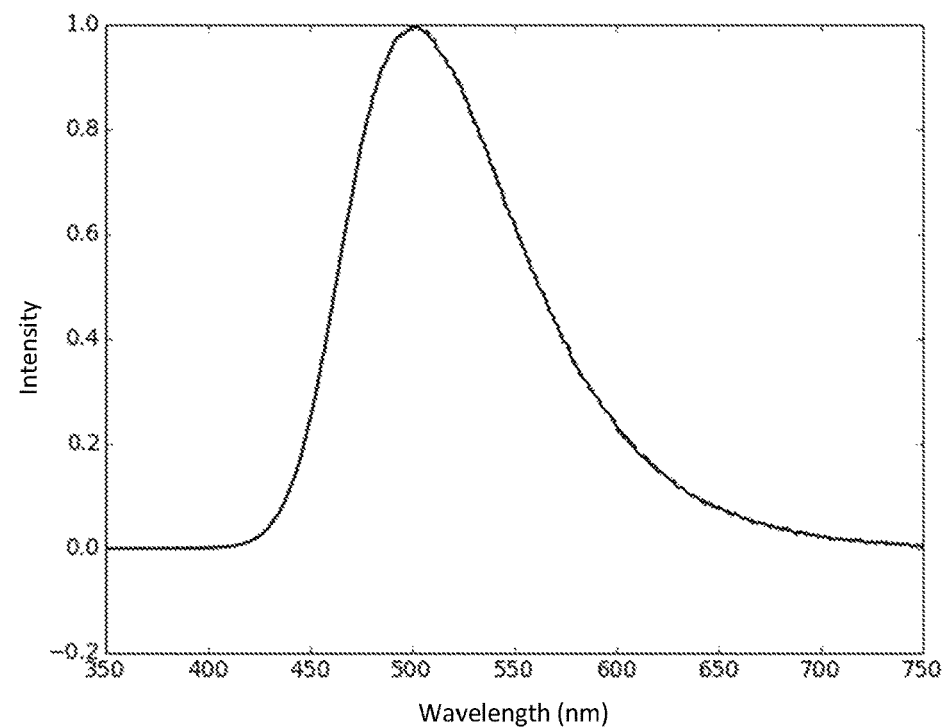
FIG. 20 illustrates an emission spectrum of Example 20 (10% in PMMA).

Example 20 was prepared according to GM3 (71% yield) and GM7 (54% yield).
MS (HPLC-MS), m/z (Retention time): 765, (15.05 min)
$R_f$=0.36 (cyclohexane/ethyl acetate 5:1).
FIG. 20 shows the emission spectrum of Example 20 (10% in PMMA). The emission maximum is at 500 nm. The photoluminescence quantum yield (PLQY) is 61% and the half-height width is 0.47 eV. The emission decay time is 11 µs.

Example 21

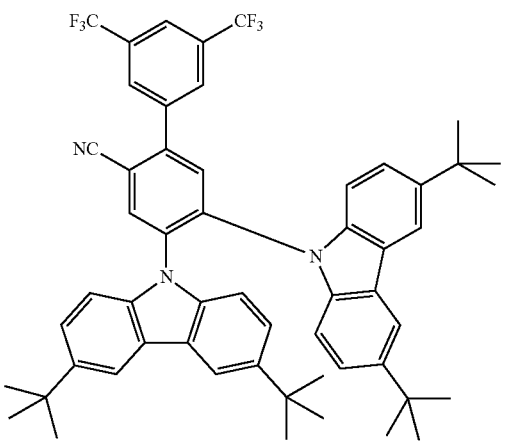 [SMILES: CC(C)(C)c1ccc2c(c1)c1cc(C(C)(C)C)ccc1n2-c1cc(C#N)c(-c2cc(C(F)(F)F)cc(C(F)(F)F)c2)cc1-n1c2ccc(C(C)(C)C)cc2c2cc(C(C)(C)C)ccc21]

Figure 21:
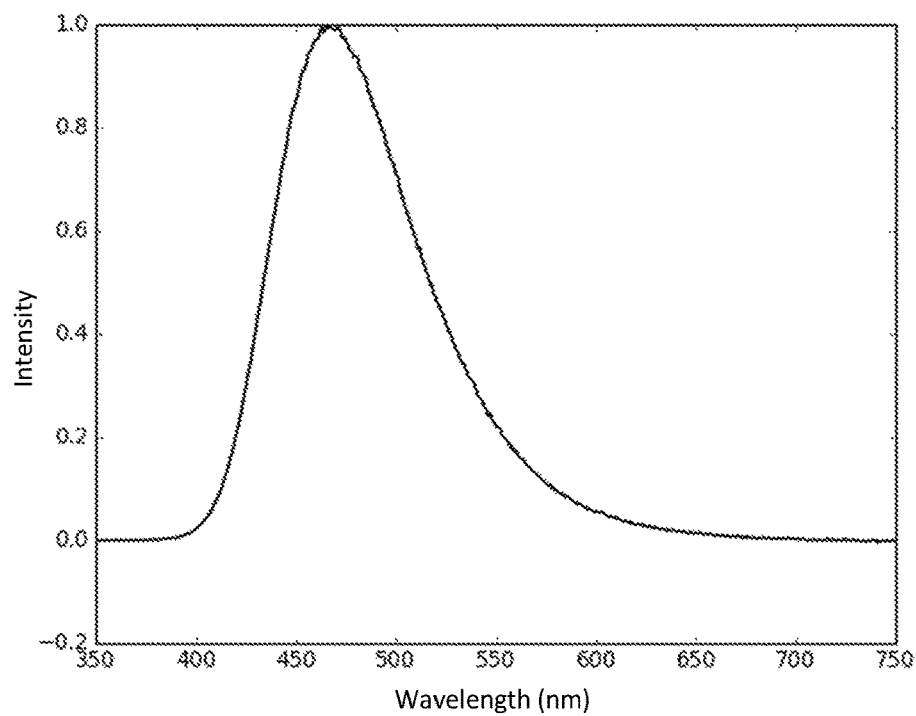
FIG. 21 illustrates an emission spectrum of Example 21 (10% in PMMA).

Example 21 was prepared according to GM5 (94% yield) and GM7 (31% yield).
FIG. 21 shows the emission spectrum of Example 21 (10% in PMMA). The emission maximum is at 468 nm. The photoluminescence quantum yield (PLQY) is 92% and the half-height width is 0.46 eV.

Example 22

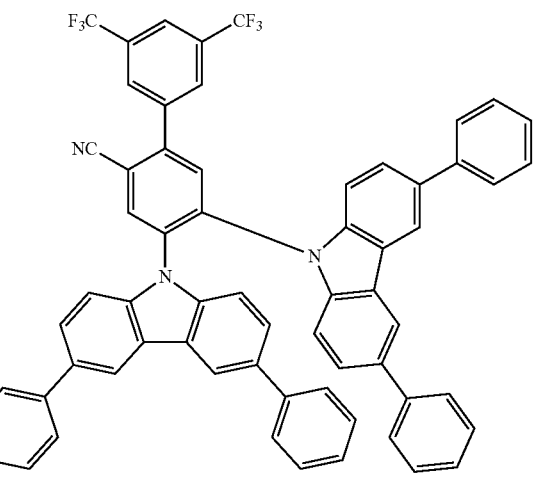

Figure 22:
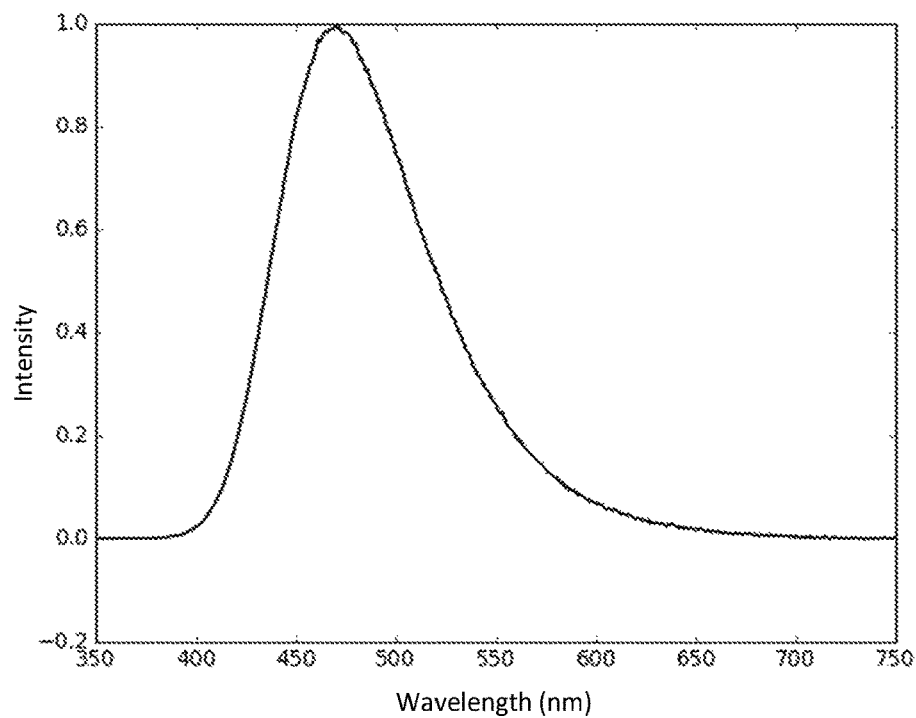
FIG. 22 illustrates an emission spectrum of Example 22 (10% in PMMA).

Example 22 was prepared according to GM5 (94% yield) and GM7 (68% yield).
FIG. 22 shows the emission spectrum of Example 22 (10% in PMMA). The emission maximum is at 470 nm. The photoluminescence quantum yield (PLQY) is 84% and the half-height width is 0.47 eV.

Example 23

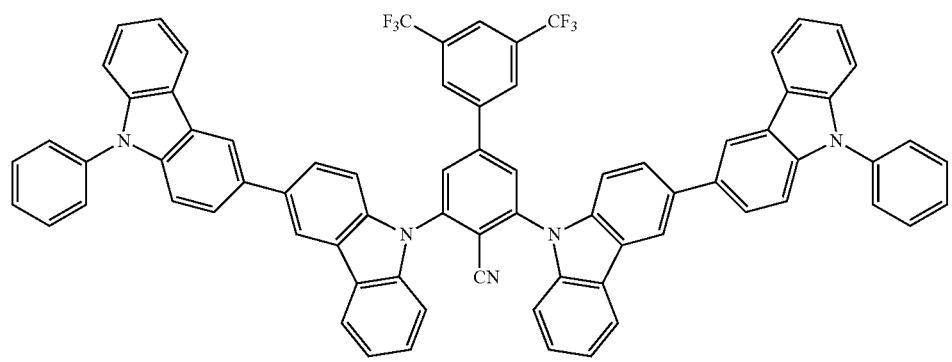 [SMILES: N#Cc1c(-n2c3ccccc3c3cc(-c4ccc5c(c4)c4ccccc4n5-c4ccccc4)ccc32)cc(-c2cc(C(F)(F)F)cc(C(F)(F)F)c2)cc1-n1c2ccccc2c2cc(-c3ccc4c(c3)c3ccccc3n4-c3ccccc3)ccc21]

Example 23 was prepared according to GM1 (99% yield) and GM7 (81% yield).

Figure 23:
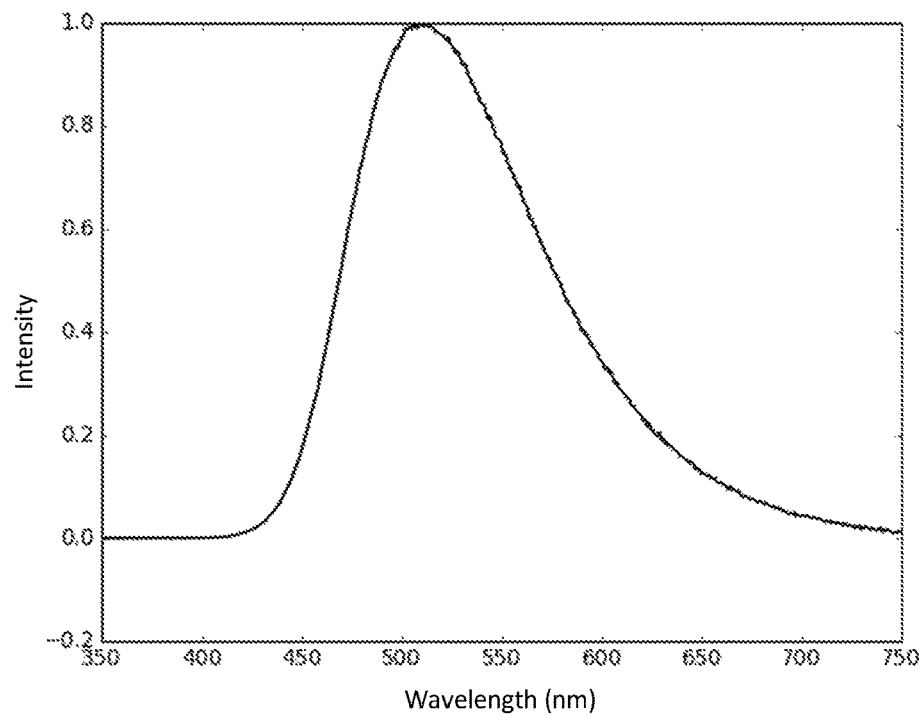
FIG. 23 illustrates an emission spectrum of Example 23 (10% in PMMA).

FIG. 23 shows the emission spectrum of Example 23 (10% in PMMA). The emission maximum is at 470 nm. The photoluminescence quantum yield (PLQY) is 47% and the half-height width is 0.50 eV. The emission decay time is 3 μs.

Example 24

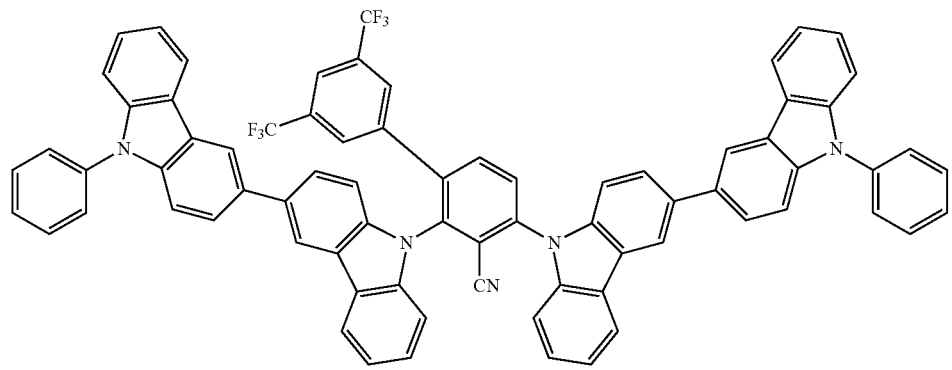 [SMILES: N#Cc1c(-n2c3ccccc3c3cc(-c4ccc5c(c4)c4ccccc4n5-c4ccccc4)ccc32)ccc(-c2cc(C(F)(F)F)cc(C(F)(F)F)c2)c1-n1c2ccccc2c2cc(-c3ccc4c(c3)c3ccccc3n4-c3ccccc3)ccc21]

Example 24 was prepared according to GM2 (52% yield) and GM7 (66% yield).

Figure 24:
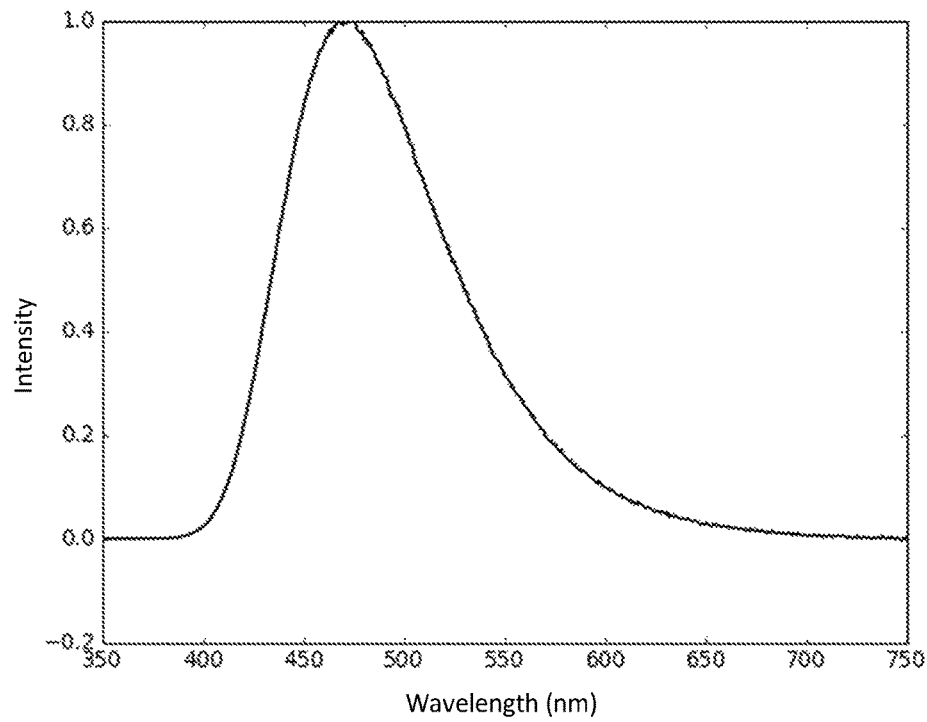
FIG. 24 illustrates an emission spectrum of Example 24 (10% in PMMA).

FIG. 24 shows the emission spectrum of Example 24 (10% in PMMA). The emission maximum is at 475 nm. The photoluminescence quantum yield (PLQY) is 62% and the half-height width is 0.51 eV.

Example 25

Figure 25:
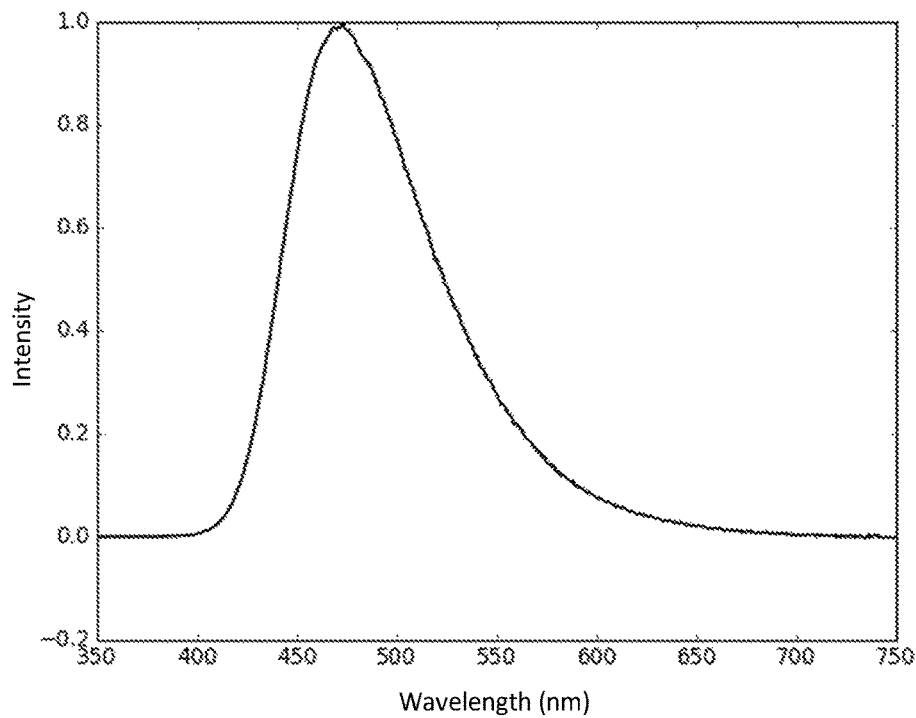
FIG. 25 illustrates an emission spectrum of Example 25 (10% in PMMA).

FIG. 25 shows the emission spectrum of Example 25 (10% in PMMA). The emission maximum is at 473 nm. The photoluminescence quantum yield (PLQY) is 84% and the half-height width is 0.45 eV.

Example 26

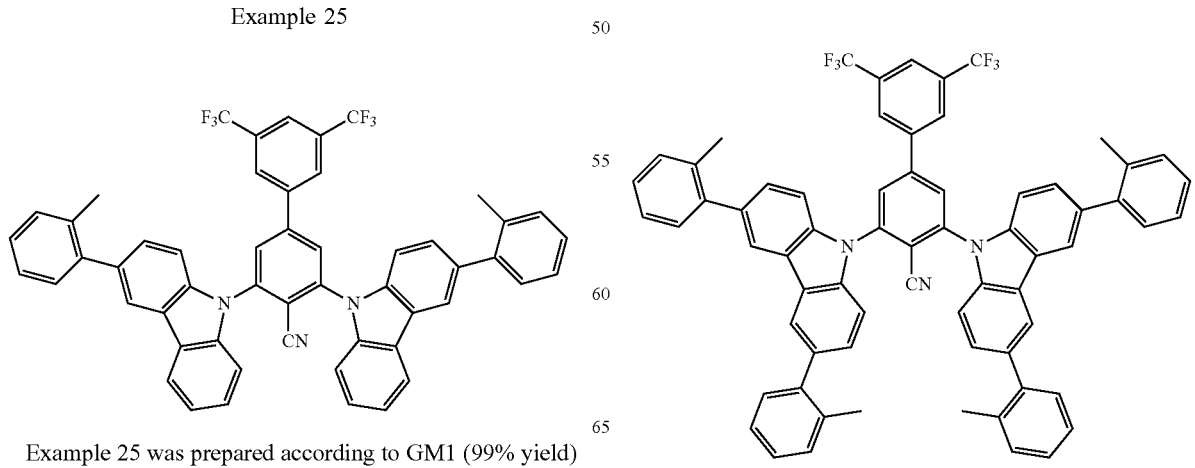

Example 25 was prepared according to GM1 (99% yield) and GM7 (64% yield).

Example 26 was prepared according to GM1 (99% yield) and GM7.

Figure 26:
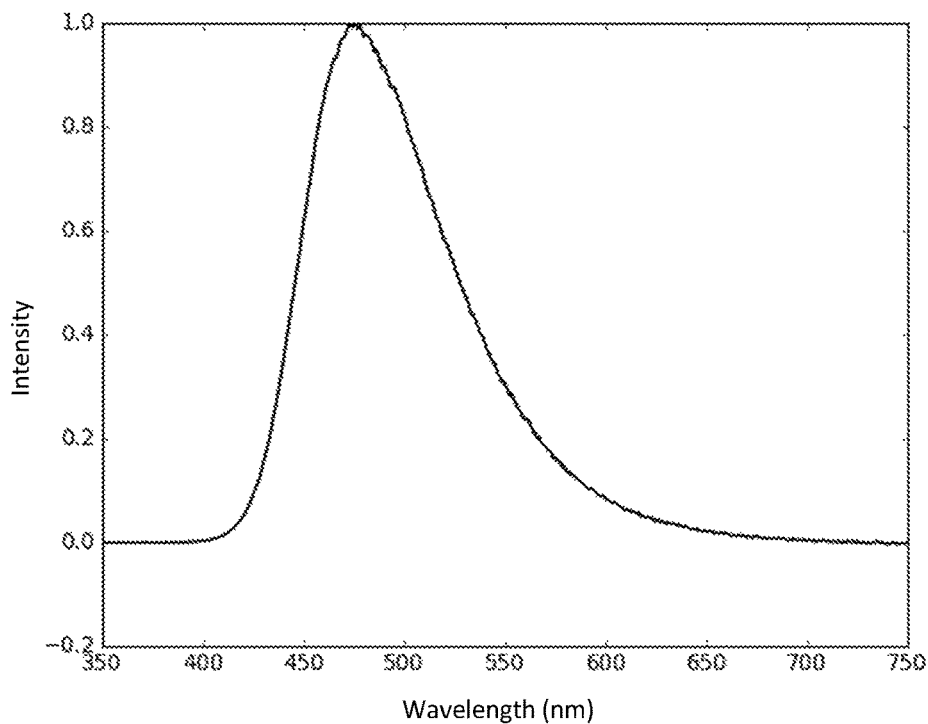
FIG. 26 illustrates an emission spectrum of Example 26 (10% in PMMA).

FIG. 26 shows the emission spectrum of Example 26 (10% in PMMA). The emission maximum is at 473 nm. The photoluminescence quantum yield (PLQY) is 87% and the half-height width is 0.43 eV. The emission decay time is 31 μs.

Example 27

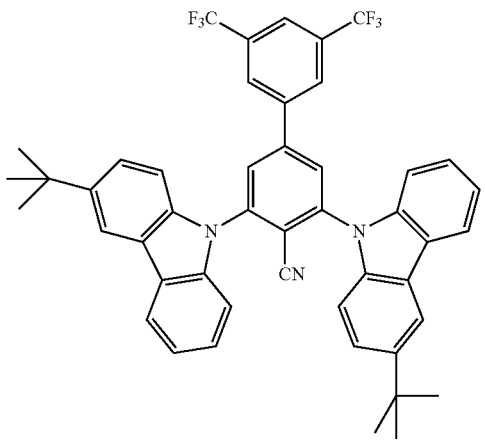 [SMILES: CC(C)(C)c1ccc2c(c1)c1ccccc1n2-c1cc(-c2cc(C(F)(F)F)cc(C(F)(F)F)c2)cc(-n2c3ccccc3c3cc(C(C)(C)C)ccc32)c1C#N]

Example 27 was prepared according to GM1 (99% yield) and GM7 (66% yield).

Figure 27:
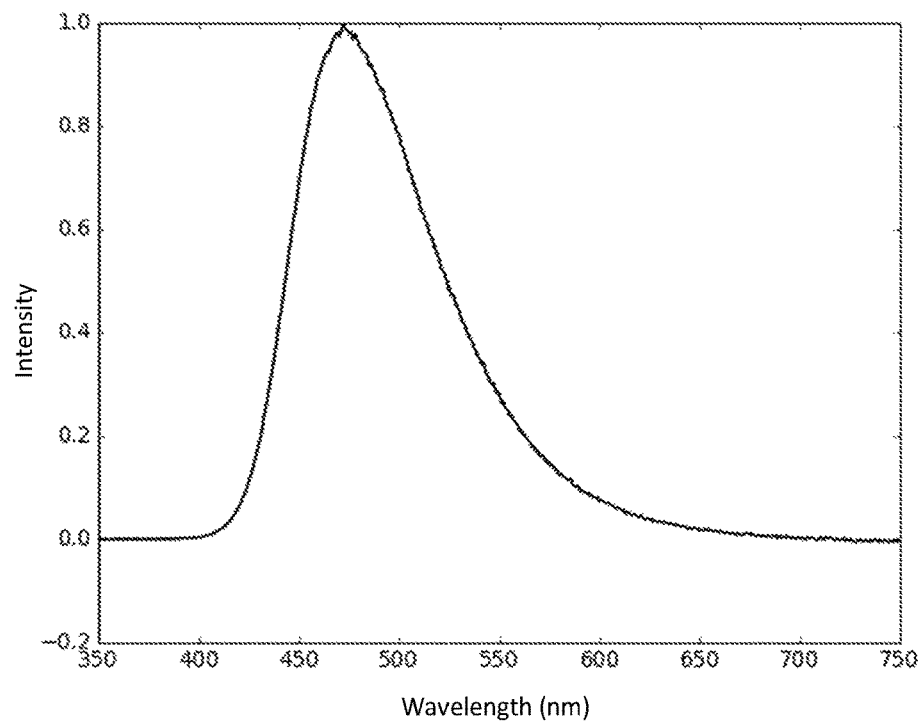
FIG. 27 illustrates an emission spectrum of Example 27 (10% in PMMA).

FIG. 27 shows the emission spectrum of Example 27 (10% in PMMA). The emission maximum is at 473 nm. The photoluminescence quantum yield (PLQY) is 82% and the half-height width is 0.43 eV. The emission decay time is 79 μs.

Example 28

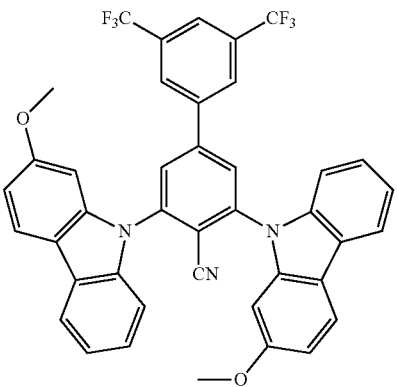 [SMILES: COc1ccc2c3ccccc3n(-c3cc(-c4cc(C(F)(F)F)cc(C(F)(F)F)c4)cc(-n4c5ccccc5c5ccc(OC)cc54)c3C#N)c2c1]

Example 28 was prepared according to GM1 (99% yield) and GM7 (53% yield).

Figure 28:
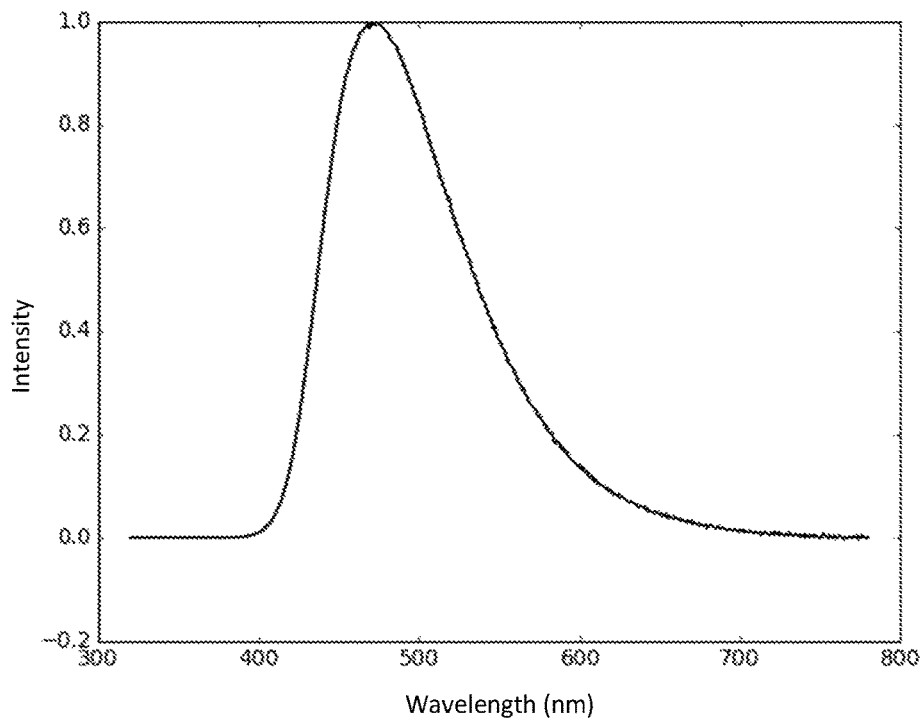
FIG. 28 illustrates an emission spectrum of Example 28 (10% in PMMA).

FIG. 28 shows the emission spectrum of Example 28 (10% in PMMA). The emission maximum is at 473 nm. The photoluminescence quantum yield (PLQY) is 61% and the half-height width is 0.52 eV.

Example 29

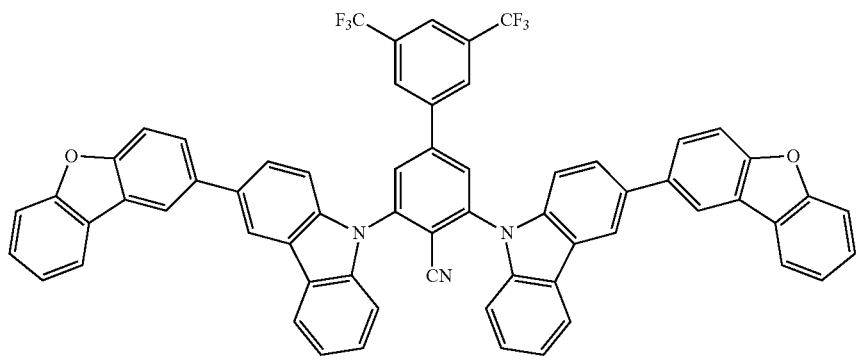 [SMILES: N#Cc1c(-n2c3ccccc3c3cc(-c4ccc5oc6ccccc6c5c4)ccc32)cc(-c2cc(C(F)(F)F)cc(C(F)(F)F)c2)cc1-n1c2ccccc2c2cc(-c3ccc4oc5ccccc5c4c3)ccc21]

Example 29 was prepared according to GM1 (99% yield) and GM7 (65% yield).

Figure 29:
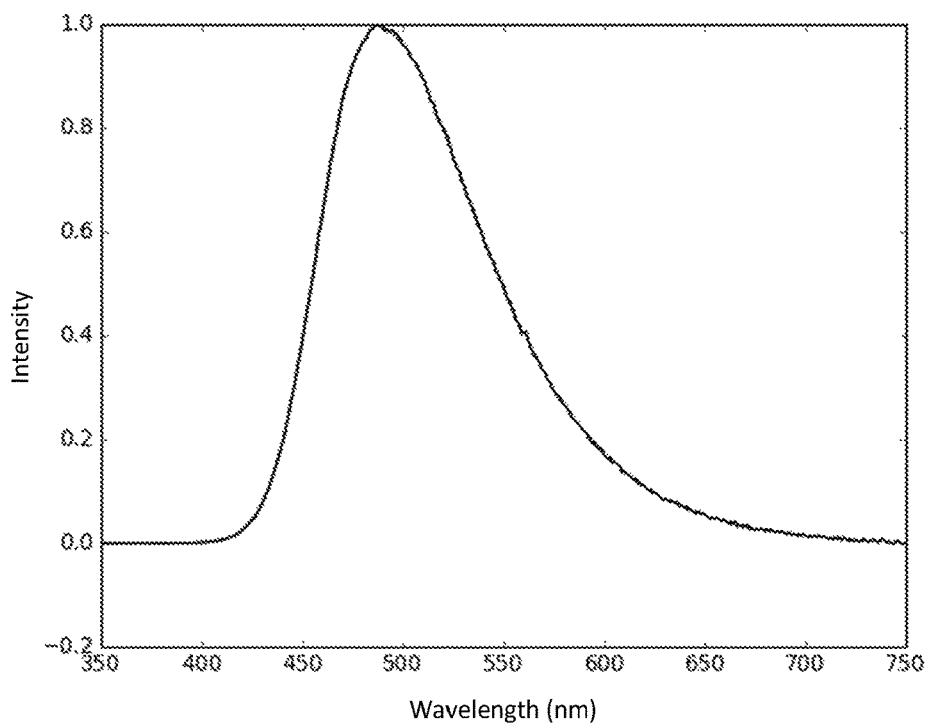
FIG. 29 illustrates an emission spectrum of Example 29 (10% in PMMA).

FIG. 29 shows the emission spectrum of Example 29 (10% in PMMA). The emission maximum is at 489 nm. The photoluminescence quantum yield (PLQY) is 73% and the half-height width is 0.47 eV. The emission decay time is 10 μs.

Example 30

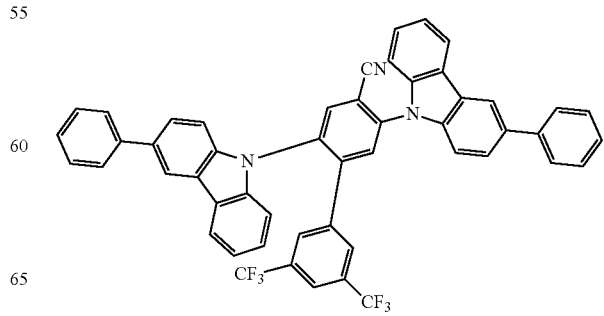

Example 30 was prepared according to GM4 (88% yield) and GM7 (38% yield).

Figure 30:
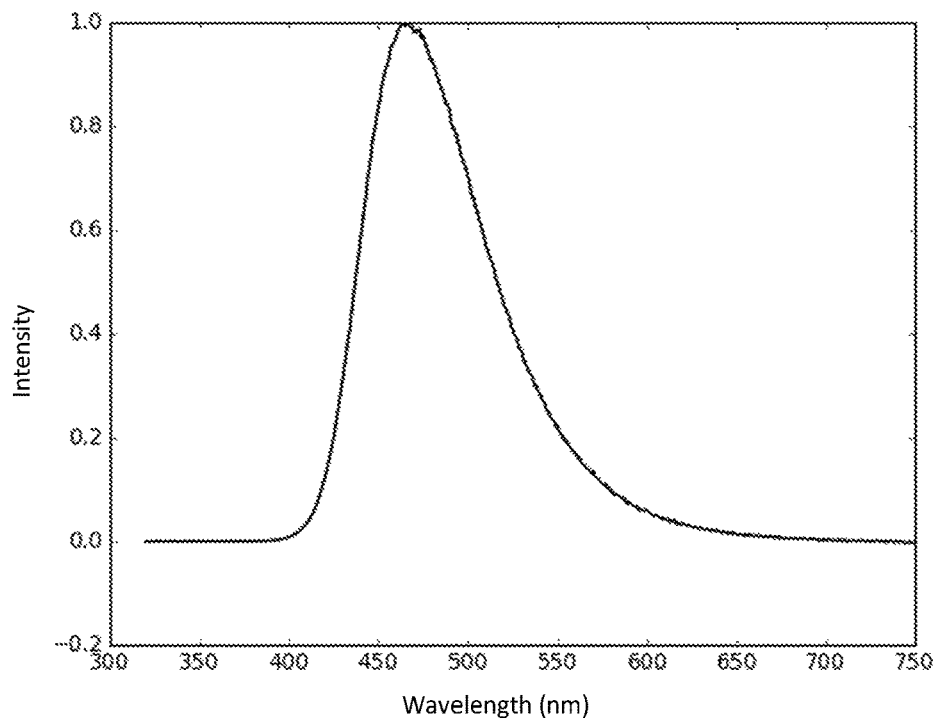
FIG. 30 illustrates an emission spectrum of Example 30 (10% in PMMA).

FIG. 30 shows the emission spectrum of Example 30 (10% in PMMA). The emission maximum is at 464 nm. The photoluminescence quantum yield (PLQY) is 86% and the half-height width is 0.43 eV.

Example 31

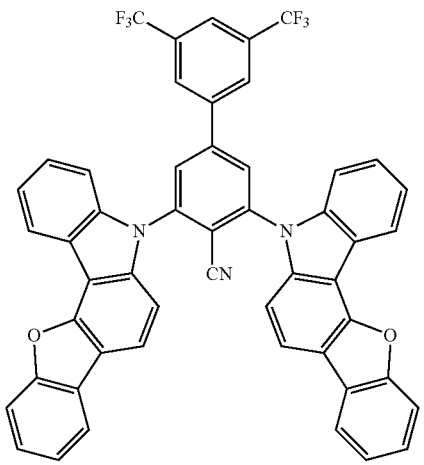 [SMILES: N#Cc1c(-n2c3ccccc3c3c4oc5ccccc5c4ccc32)cc(-c2cc(C(F)(F)F)cc(C(F)(F)F)c2)cc1-n1c2ccccc2c2c3oc4ccccc4c3ccc21]

Example 31 was prepared according to GM1 (99% yield) and GM7.

Figure 31:
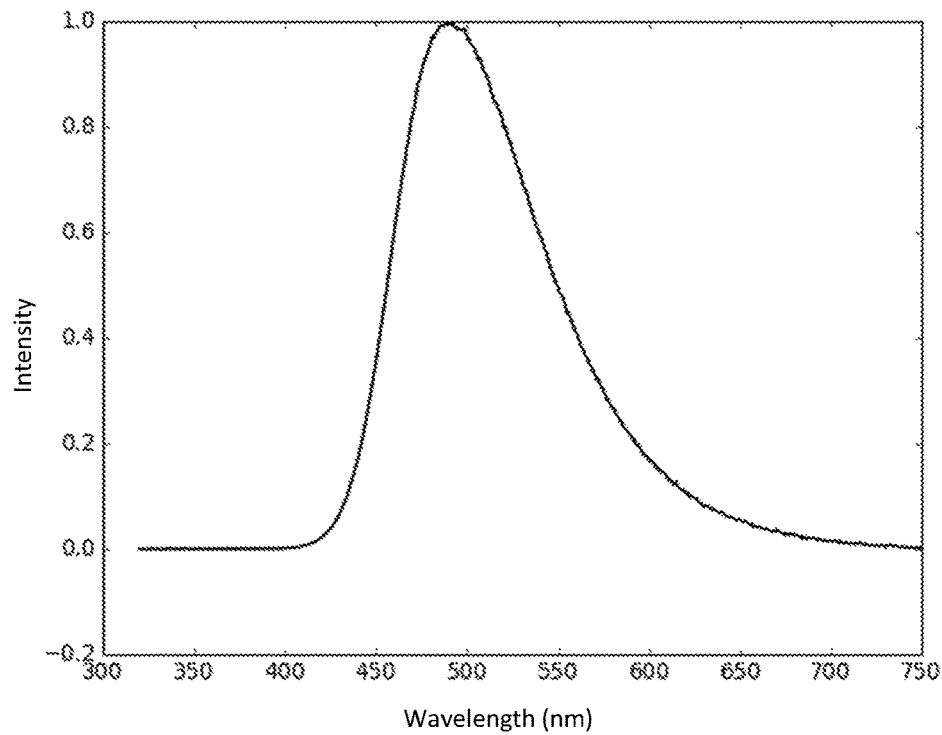
FIG. 31 illustrates an emission spectrum of Example 31 (10% in PMMA).

FIG. 31 shows the emission spectrum of Example 31 (10% in PMMA). The emission maximum is at 492 nm. The photoluminescence quantum yield (PLQY) is 78% and the half-height width is 0.46 eV. The emission decay time is 9 μs.

Example 32

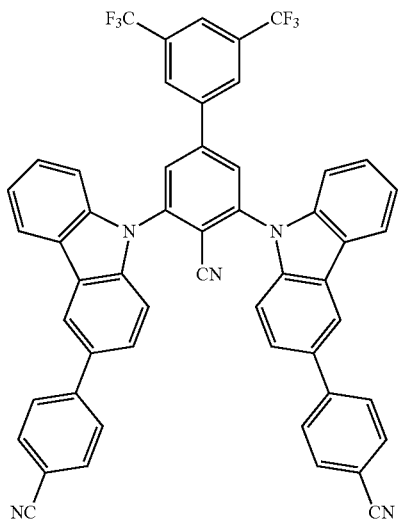 [SMILES: N#Cc1ccc(-c2ccc3c(c2)c2ccccc2n3-c2cc(-c3cc(C(F)(F)F)cc(C(F)(F)F)c3)cc(-n3c4ccccc4c4cc(-c5ccc(C#N)cc5)ccc43)c2C#N)cc1]

Example 32 was prepared according to GM1 (99% yield) and GM7 (92% yield).

Figure 32:
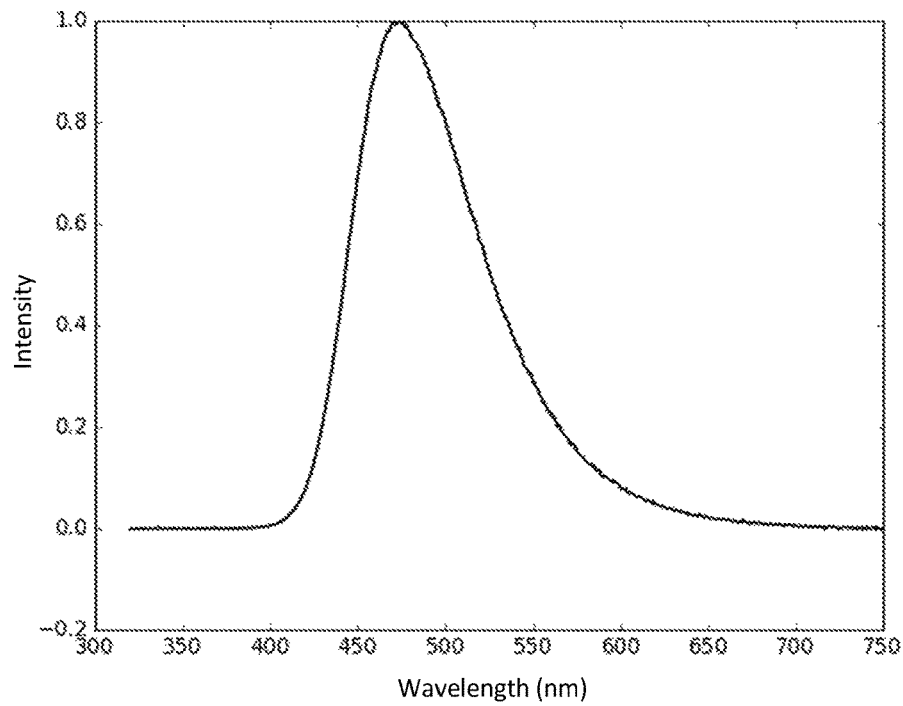
FIG. 32 illustrates an emission spectrum of Example 32 (10% in PMMA).

FIG. 32 shows the emission spectrum of Example 32 (10% in PMMA). The emission maximum is at 476 nm. The photoluminescence quantum yield (PLQY) is 72% and the half-height width is 0.44 eV.

Example 33

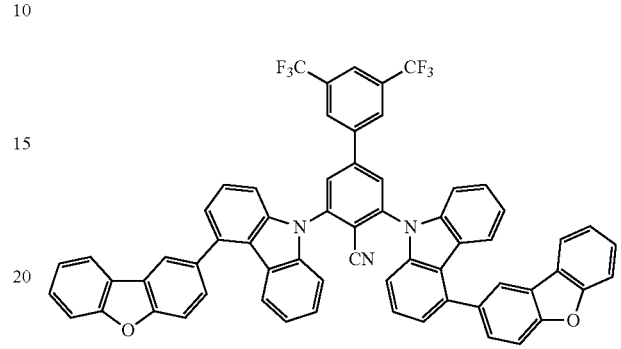

Example 33 was prepared according to GM1 (99% yield) and GM7 (78% yield).

Figure 33:
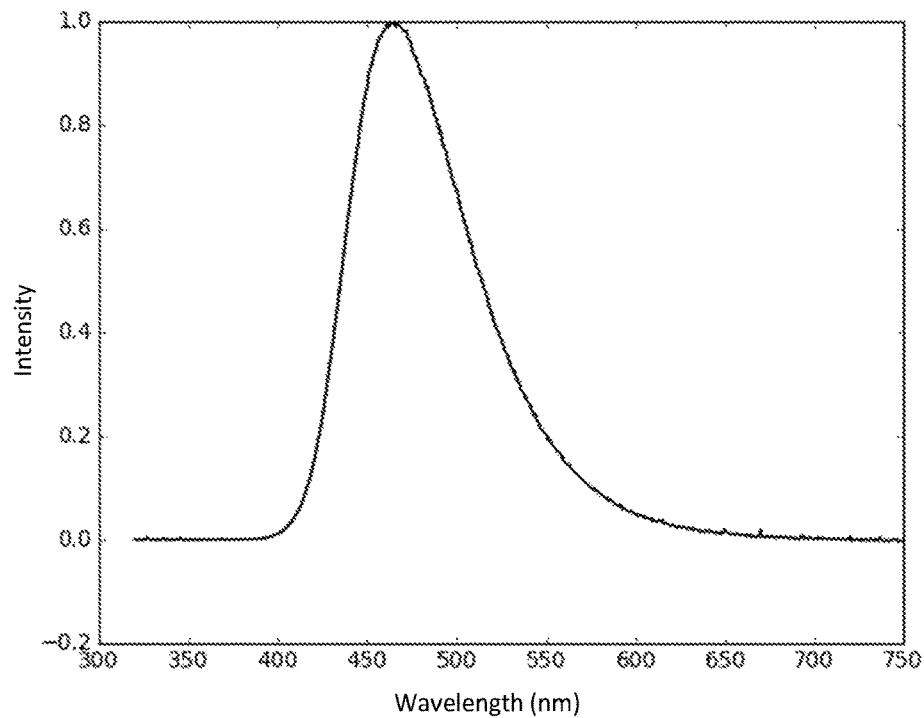
FIG. 33 illustrates an emission spectrum of Example 33 (10% in PMMA).

FIG. 33 shows the emission spectrum of Example 33 (10% in PMMA). The emission maximum is at 465 nm. The photoluminescence quantum yield (PLQY) is 93% and the half-height width is 0.44 eV.

Example 34

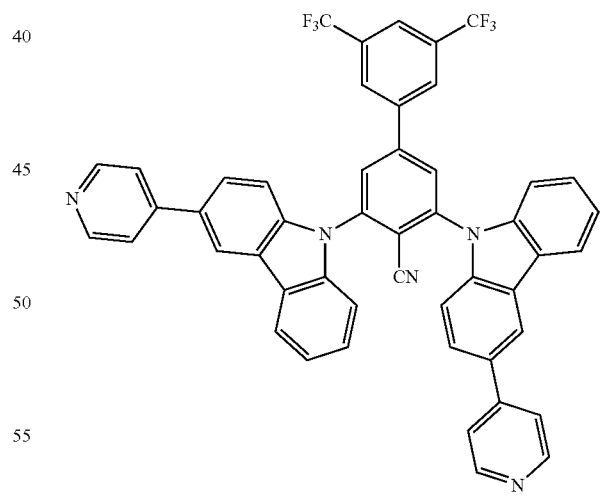

Example 34 was prepared according to GM1 (99% yield) and GM7 (92% yield).

Figure 34:
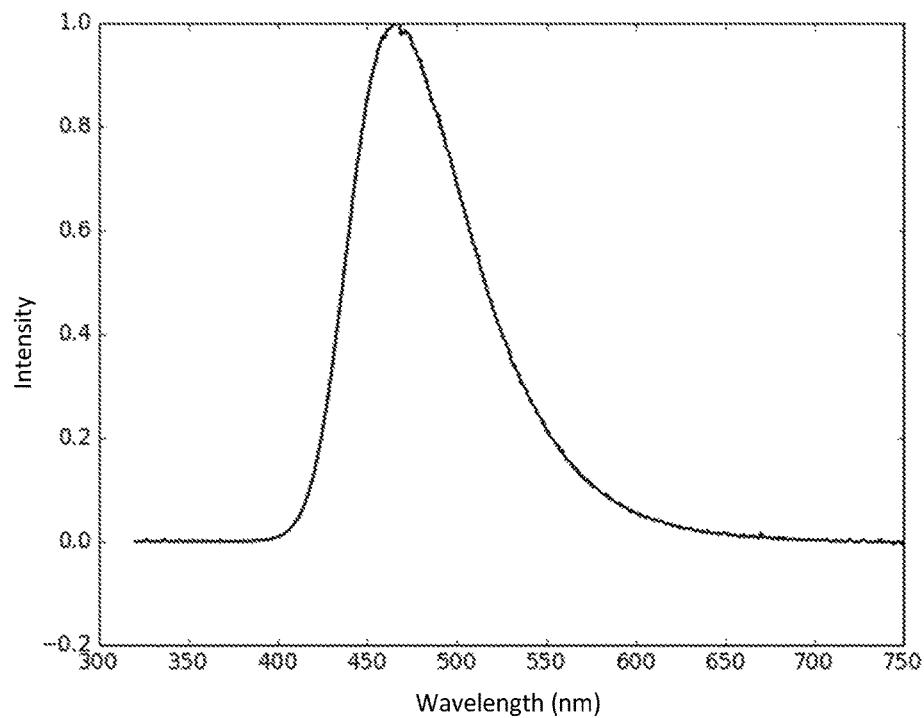
FIG. 34 illustrates an emission spectrum of Example 34 (10% in PMMA).

FIG. 34 shows the emission spectrum of Example 34 (10% in PMMA). The emission maximum is at 467 nm. The photoluminescence quantum yield (PLQY) is 83% and the half-height width is 0.43 eV.

Example 35

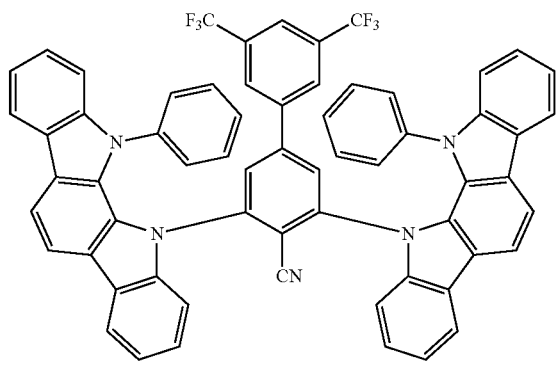 [SMILES: N#Cc1c(-n2c3ccccc3c3ccc4c5ccccc5n(-c5ccccc5)c4c32)cc(-c2cc(C(F)(F)F)cc(C(F)(F)F)c2)cc1-n1c2ccccc2c2ccc3c4ccccc4n(-c4ccccc4)c3c21]

Example 35 was prepared according to GM1 (99% yield) and GM7 (54% yield).

Figure 35:
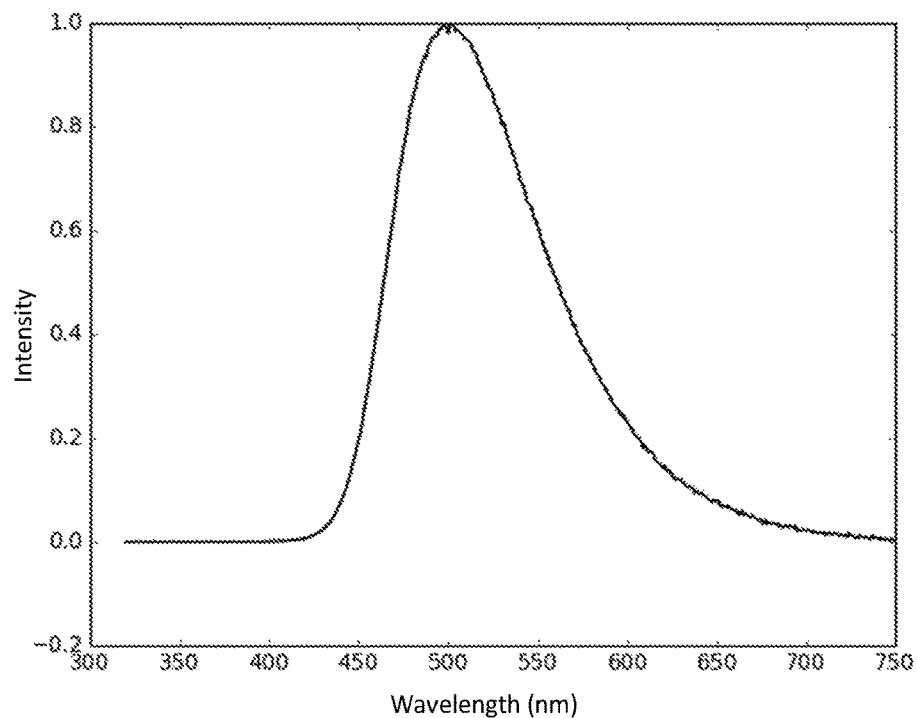
FIG. 35 illustrates an emission spectrum of Example 35 (10% in PMMA).

FIG. 35 shows the emission spectrum of Example 35 (10% in PMMA). The emission maximum is at 501 nm. The photoluminescence quantum yield (PLQY) is 62% and the half-height width is 0.47 eV. The emission decay time is 4 µs.

Example 36

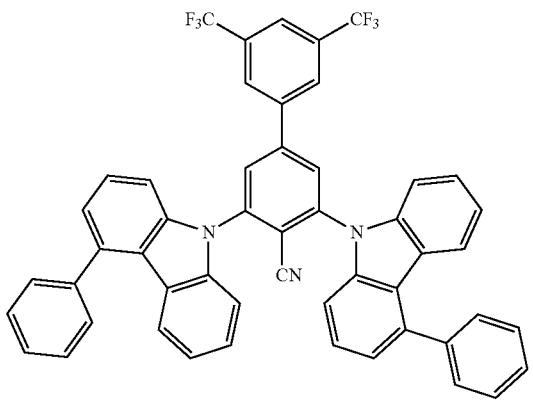 [SMILES: N#Cc1c(-n2c3ccccc3c3c(-c4ccccc4)cccc32)cc(-c2cc(C(F)(F)F)cc(C(F)(F)F)c2)cc1-n1c2ccccc2c2c(-c3ccccc3)cccc21]

Example 36 was prepared according to GM1 (99% yield) and GM7 (84% yield).

Figure 36:
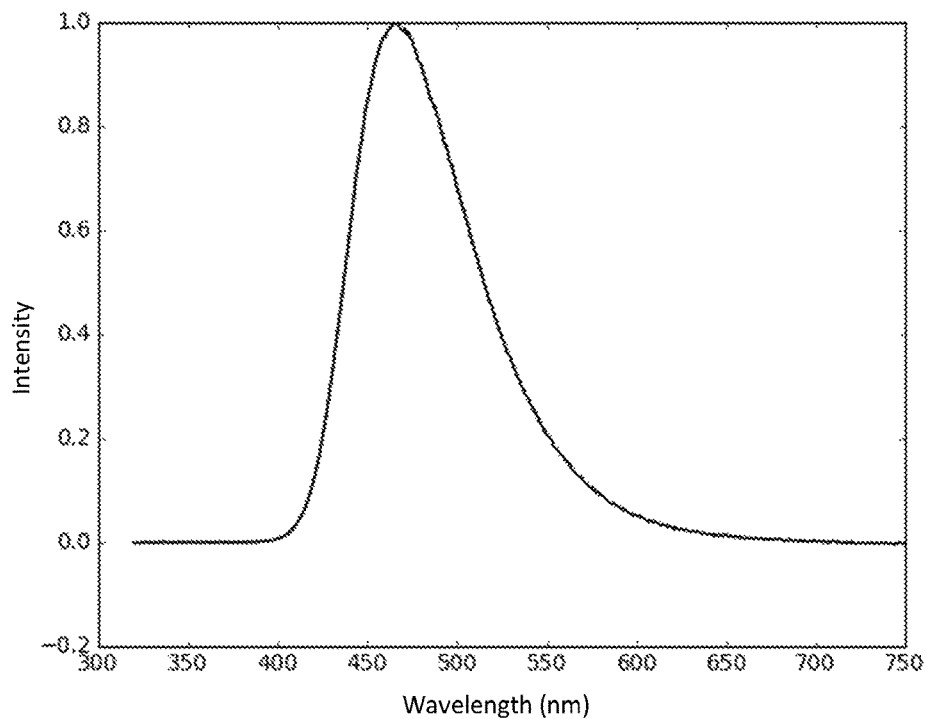
FIG. 36 illustrates an emission spectrum of Example 36 (10% in PMMA).

FIG. 36 shows the emission spectrum of Example 36 (10% in PMMA). The emission maximum is at 466 nm. The photoluminescence quantum yield (PLQY) is 76% and the half-height width is 0.43 eV.

Example 37

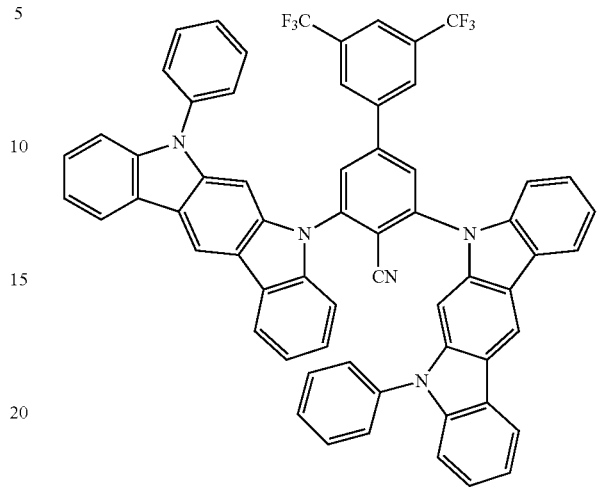

Example 37 was prepared according to GM1 (99% yield) and GM7 (43% yield).

Figure 37:
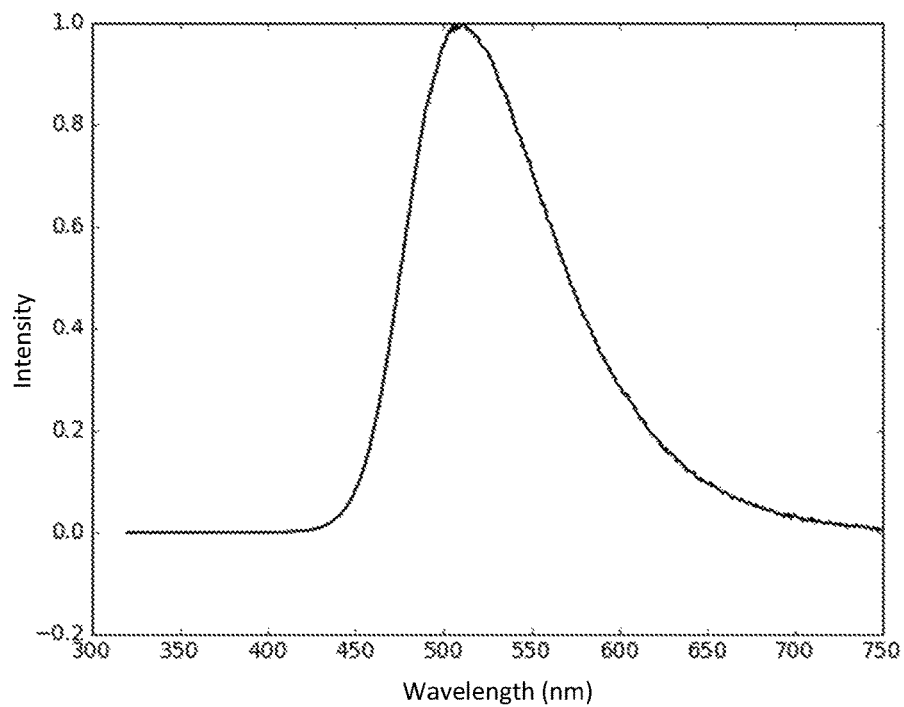
FIG. 37 illustrates an emission spectrum of Example 37 (10% in PMMA).

FIG. 37 shows the emission spectrum of Example 37 (10% in PMMA). The emission maximum is at 509 nm. The photoluminescence quantum yield (PLQY) is 59% and the half-height width is 0.44 eV. The emission decay time is 3 µs.

Example 38

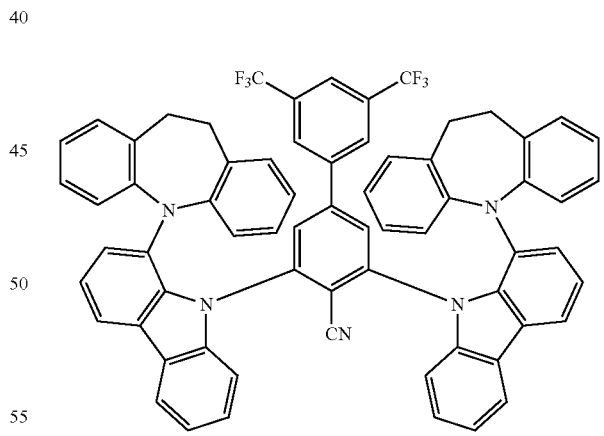

Example 38 was prepared according to GM1 (99% yield) and GM7 (3% yield).

Figure 38:
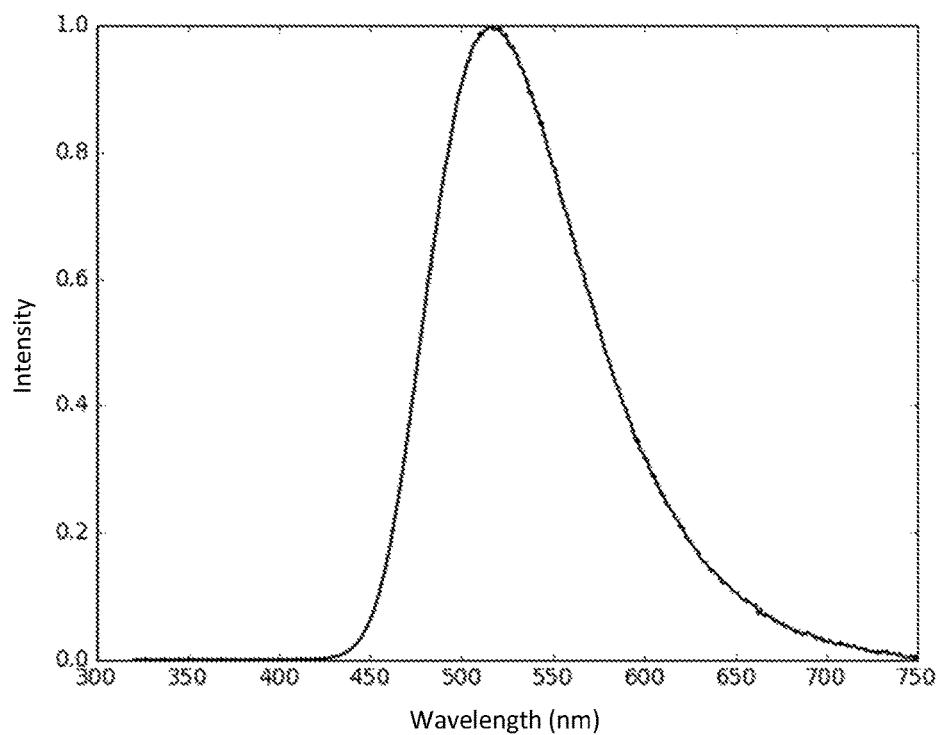
FIG. 38 illustrates an emission spectrum of Example 38 (10% in PMMA).

FIG. 38 shows the emission spectrum of Example 38 (10% in PMMA). The emission maximum is at 521 nm. The photoluminescence quantum yield (PLQY) is 72% and the half-height width is 0.45 eV. The emission decay time is 37 µs.

Example 39

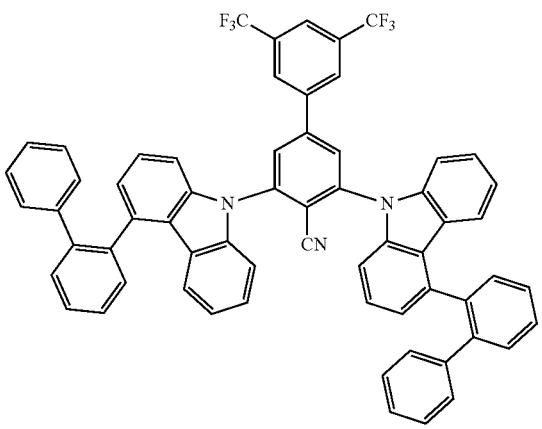 [SMILES: N#Cc1c(-n2c3ccccc3c3c(-c4ccccc4-c4ccccc4)cccc32)cc(-c2cc(C(F)(F)F)cc(C(F)(F)F)c2)cc1-n1c2ccccc2c2c(-c3ccccc3-c3ccccc3)cccc21]

Example 39 was prepared according to GM1 (99% yield) and GM7 (14% yield).

Figure 39:
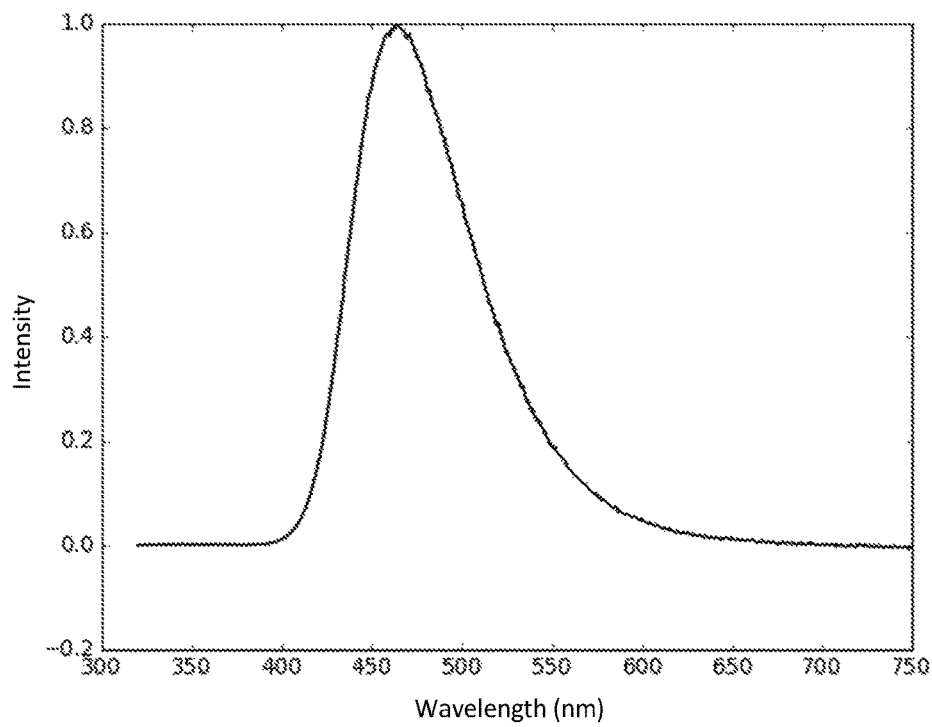
FIG. 39 illustrates an emission spectrum of Example 39 (10% in PMMA).

FIG. 39 shows the emission spectrum of Example 39 (10% in PMMA). The emission maximum is at 463 nm. The photoluminescence quantum yield (PLQY) is 60% and the half-height width is 0.43 eV.

Example 40

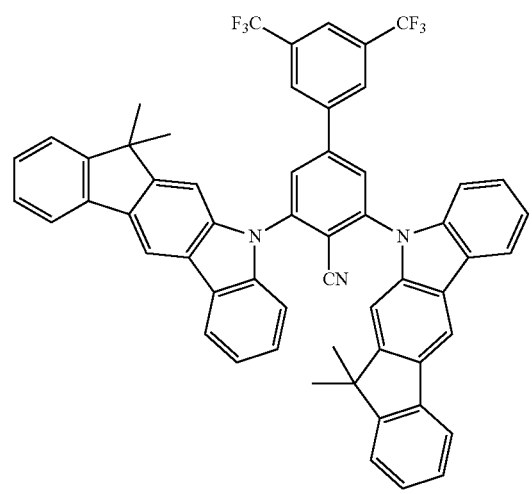 [SMILES: CC1(C)c2ccccc2-c2cc3c4ccccc4n(-c4cc(-c5cc(C(F)(F)F)cc(C(F)(F)F)c5)cc(-n5c6ccccc6c6cc7c(cc65)C(C)(C)c5ccccc5-7)c4C#N)c3cc21]

Example 40 was prepared according to GM1 (99% yield) and GM7 (38% yield).

Figure 40:
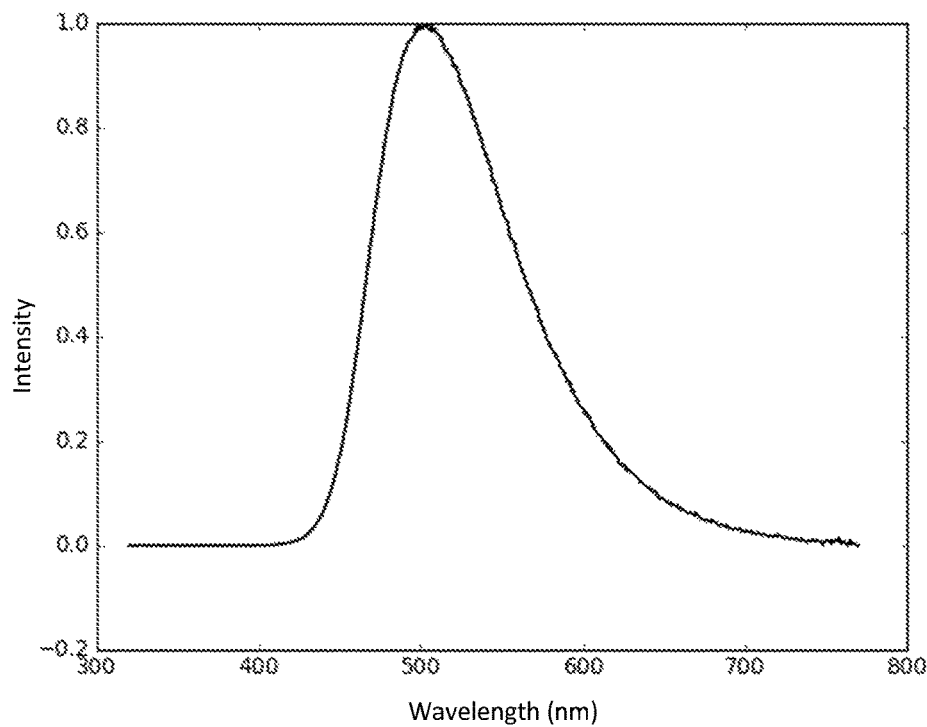
FIG. 40 illustrates an emission spectrum of Example 40 (10% in PMMA).

FIG. 40 shows the emission spectrum of Example 40 (10% in PMMA). The emission maximum is at 504 nm. The photoluminescence quantum yield (PLQY) is 57% and the half-height width is 0.47 eV. The emission decay time is 4 μs.

Example 41

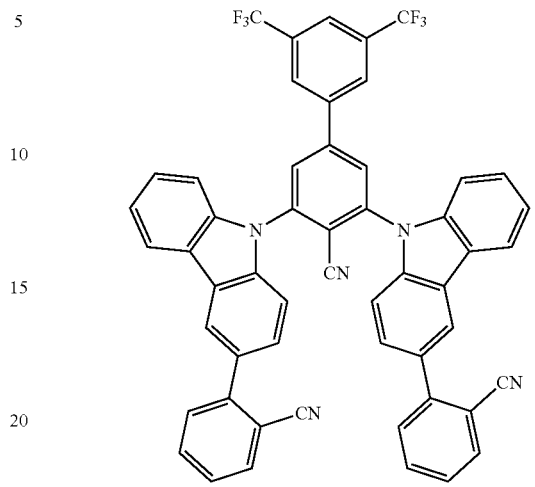

Example 41 was prepared according to GM1 (99% yield) and GM7 (74% yield).

Figure 41:
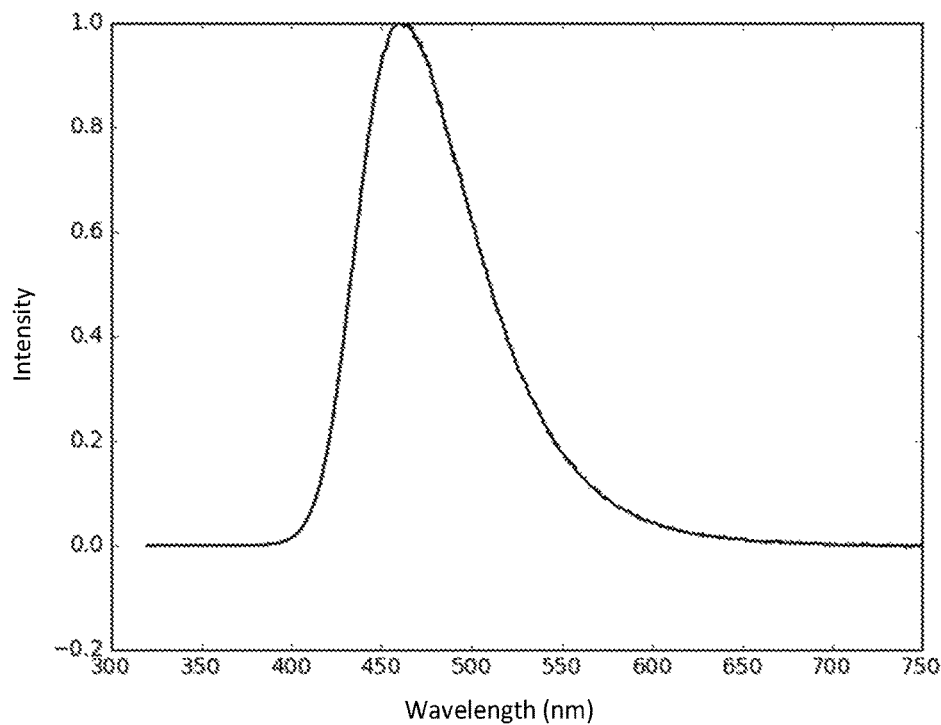
FIG. 41 illustrates an emission spectrum of Example 41 (10% in PMMA).

FIG. 41 shows the emission spectrum of Example 41 (10% in PMMA). The emission maximum is at 462 nm. The photoluminescence quantum yield (PLQY) is 78% and the half-height width is 0.44 eV.

Example 42

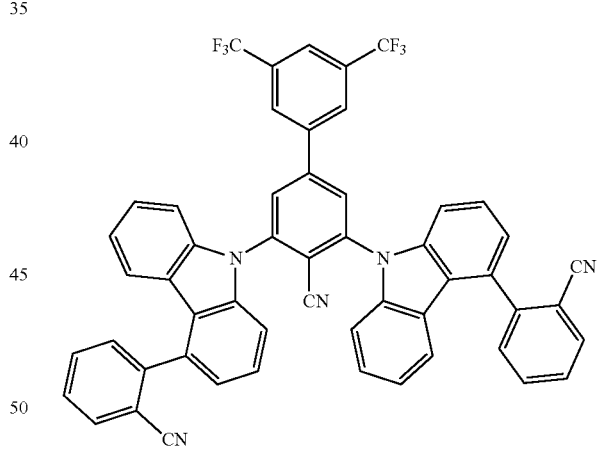

Example 42 was prepared according to GM1 (99% yield) and GM7 (75% yield).

Figure 42:
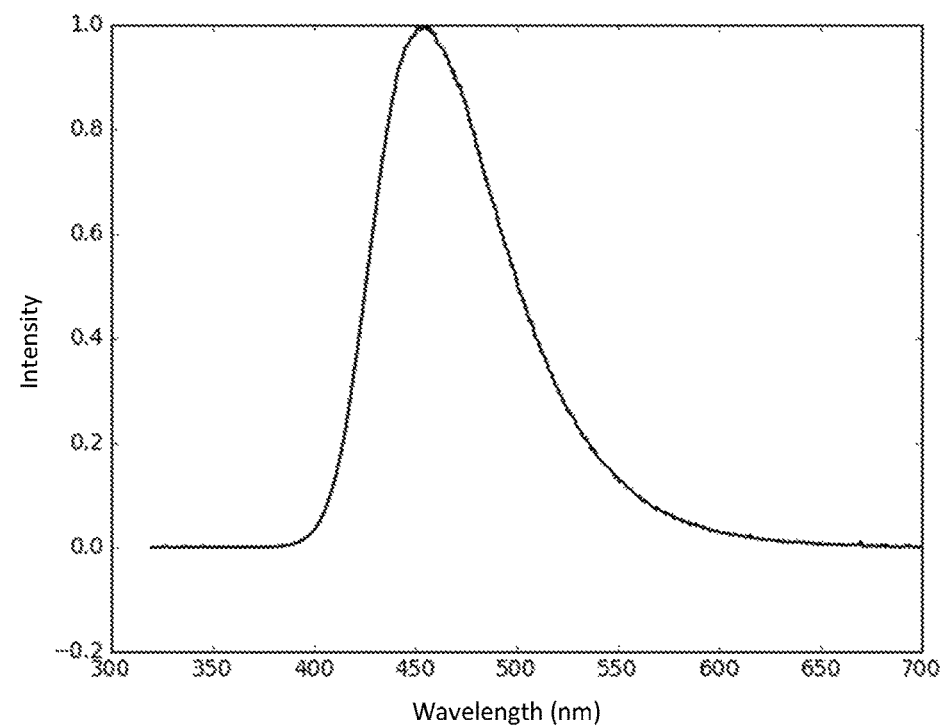
FIG. 42 illustrates an emission spectrum of Example 42 (10% in PMMA).

FIG. 42 shows the emission spectrum of Example 42 (10% in PMMA). The emission maximum is at 455 nm. The photoluminescence quantum yield (PLQY) is 77% and the half-height width is 0.44 eV.

Example D1

Example 4 was tested in an OLED component ("component D1") with the following structure (the proportion of the molecule according to the invention in the emission layer is reported in percent by mass):

| Layer | Thickness | D1 |
|---|---|---|
| 7 | 100 nm | Al |
| 6 | 2 nm | Liq |
| 5 | 40 nm | NBPhen |
| 4 | 20 nm | 4 (20%):mCBP |
| 3 | 10 nm | TCTA |
| 2 | 80 nm | NPB |
| 1 | 130 nm | ITO |
| Substrate | | glass |

| | Maximum values | at 1000 cd/m$^2$ |
|---|---|---|
| External quantum efficiency (EQE): | 14.2 ± 0.7% | 10.9 ± 0.3% |

The emission maximum is at 480 nm; CIEx was determined as 0.19 and CIEy as 0.36 at 6 V.

Example D2

Example 9 was tested in an OLED component ("component D2") with the following structure (the proportion of the molecule according to the invention in the emission layer is reported in percent by mass):

| Layer | Thickness | D2 |
|---|---|---|
| 7 | 100 nm | Al |
| 6 | 2 nm | Liq |
| 5 | 40 nm | NBPhen |
| 4 | 20 nm | 9 (10%): mCBP |
| 3 | 10 nm | TCTA |
| 2 | 80 nm | NPB |
| 1 | 130 nm | ITO |
| Substrate | | glass |

| | Maximum values | at 1000 cd/m$^2$ | LT80 (at 500 cd/m$^2$) |
|---|---|---|---|
| External quantum efficiency (EQE): | — | 14.7 ± 0.1% | 325 h |

The emission maximum is at 486 nm; CIEx was determined as 0.21 and CIEy as 0.39 at 6 V.

Example D3

Example 9 was tested in the OLED component D3 with the following structure (proportion of the molecule according to the invention and the two host molecules in the emission layer is reported in percent by mass in each case):

| Layer | Thickness | Material |
|---|---|---|
| 8 | 100 nm | Al |
| 7 | 2 nm | Liq |
| 6 | 30 nm | NBPhen |
| 5 | 10 nm | T2T |
| 4 | 20 nm | Example 9 (10%): mCBP (75%): T2T(15%) |
| 3 | 10 nm | TCTA |
| 2 | 80 nm | NPB |
| 1 | 130 nm | ITO |
| Substrate | | glass |

The emission maximum is at 493 nm; CIEx was determined as 0.22 and CIEy as 0.46 at 6 V. The EQE at 1000 cd/m$^2$ is 23.6±0.4% and the LT80 at 500 cd/m$^2$ is 416 h.

Example D4

Example 9 was tested in the OLED component D4 with the following structure (proportion of the molecule according to the invention and the two host molecules in the emission layer is reported in percent by mass in each case):

| Layer | Thickness | Material |
|---|---|---|
| 7 | 100 nm | Al |
| 6 | 2 nm | Liq |
| 5 | 40 nm | NBPhen |
| 4 | 20 nm | Example 9 (10%): 9-[3,5-bis(2-dibenzofuranyl)phenyl]-9H-carbazole (60%): T2T(30%) |
| 3 | 10 nm | TCTA |
| 2 | 80 nm | NPB |
| 1 | 130 nm | ITO |
| Substrate | | glass |

The emission maximum is at 487 nm; CIEx was determined as 0.21 and CIEy as 0.42 at 6 V. The EQE at 1000 cd/m$^2$ is 15.1±0.6% and the LT80 at 500 cd/m$^2$ is 1017 h.

Example D5

Example 31 was tested in the OLED component D5 with the following structure (proportion of the molecule according to the invention and the two host molecules in the emission layer is reported in percent by mass in each case):

| Layer | Thickness | Material |
|---|---|---|
| 8 | 100 nm | Al |
| 7 | 2 nm | Liq |
| 6 | 30 nm | NBPhen |
| 5 | 10 nm | T2T |
| 4 | 20 nm | Example 31 (10%): 9-[3,5-bis(2-dibenzofuranyl)phenyl]-9H-carbazole (75%): T2T(15%) |
| 3 | 10 nm | TCTA |
| 2 | 80 nm | NPB |
| 1 | 130 nm | ITO |
| Substrate | | glass |

The emission maximum is at 485 nm; CIEx was determined as 0.21 and CIEy as 0.41 at 6 V. The EQE at 1000 cd/m$^2$ is 16.1±0.5% and the LT80 at 500 cd/m$^2$ is 260 h.

Example D6

Example 35 was tested in OLED component D6 having the same structure as OLED component D1, except that Example 4 was replaced by Example 35. The emission maximum is at 504 nm; CIEx was determined as 0.27 and CIEy as 0.48 at 6 V. The EQE at 1000 cd/m$^2$ is 9.5±0.3% and the LT80 at 500 cd/m$^2$ is 162 h.

Example D7

Example 1 was tested in the OLED component D7 with the following structure (proportion of the molecule according to the invention and the two host molecules in the emission layer is reported in percent by mass in each case):

| Layer | Thickness | Material |
|---|---|---|
| 8 | 100 nm | Al |
| 7 | 2 nm | Liq |

-continued

| Layer | Thickness | Material |
|---|---|---|
| 6 | 30 nm | TPBi |
| 5 | 10 nm | DPEPO |
| 4 | 20 nm | Example 1 (20%): DPEPO (80%) |
| 3 | 10 nm | CzSi |
| 2 | 20 nm | TCTA |
| 2 | 70 nm | NPB |
| 2 | 20 nm | m-MTDATA |
| 1 | 130 nm | ITO |
| Substrate | | glass |

The emission maximum is at 460 nm; CIEx was determined as 0.16 and CIEy as 0.19 at 6 V. The EQE at 1000 cd/m$^2$ is 8.0±0.4%.

Example D8

Example 27 was tested in OLED component D8 having the same structure as OLED component D1, except that Example 1 was replaced by Example 27. The emission maximum is at 473 nm; CIEx was determined as 0.18 and CIEy as 0.29 at 6 V. The EQE at 1000 cd/m$^2$ is 10.6±0.4%.

A Further Illustrative OLED Component Comprises the Following Structure:

| Layer | Thickness | Material |
|---|---|---|
| 9 | 100 nm | Al |
| 8 | 2 nm | Liq |
| 7 | 30 nm | NBPhen |
| 6 | 10 nm | T2T |
| 5 | 20 nm | Example 9 (20%): mCBP (60%): T2T(20%) |
| 4 | 10 nm | mCBP |
| 3 | 10 nm | TCTA |
| 2 | 80 nm | NPB |
| 1 | 130 nm | ITO |
| Substrate | | glass |

Further Examples of Organic Molecules According to the Invention:

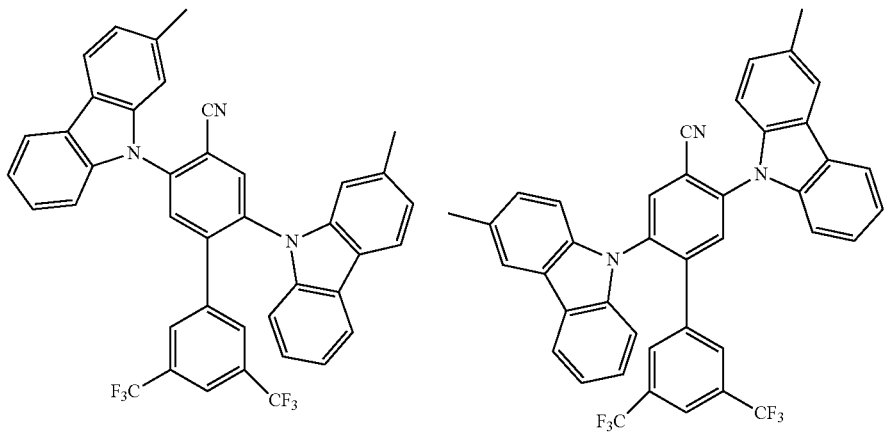

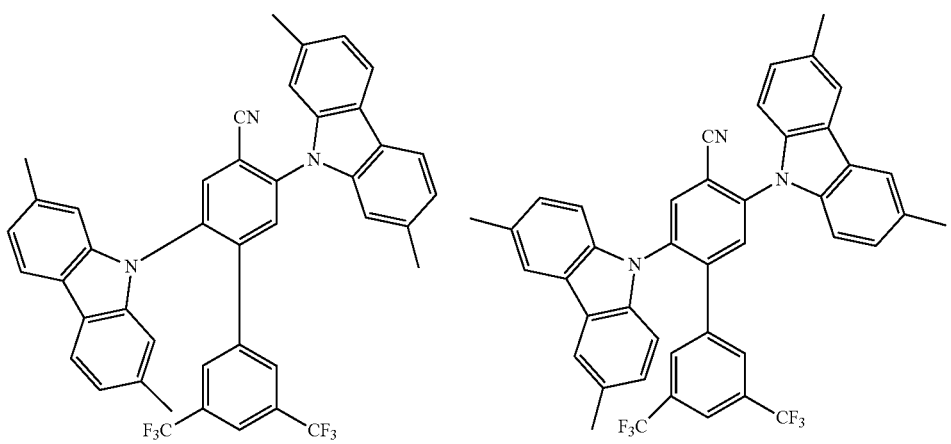

73
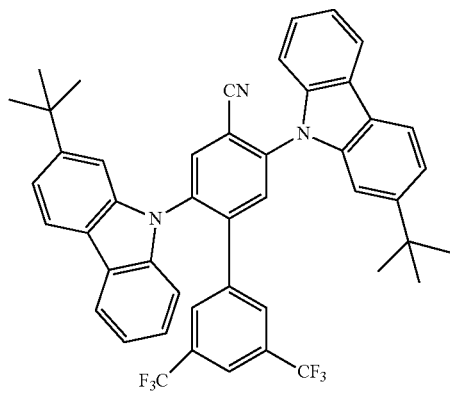
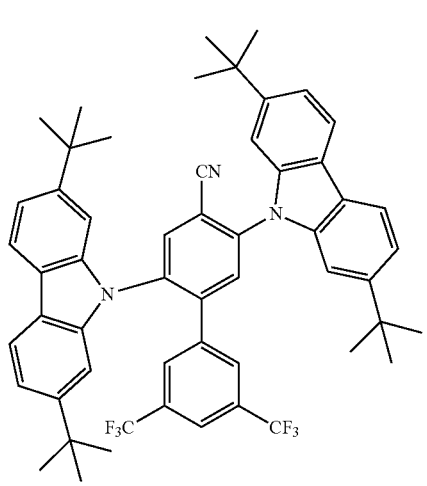
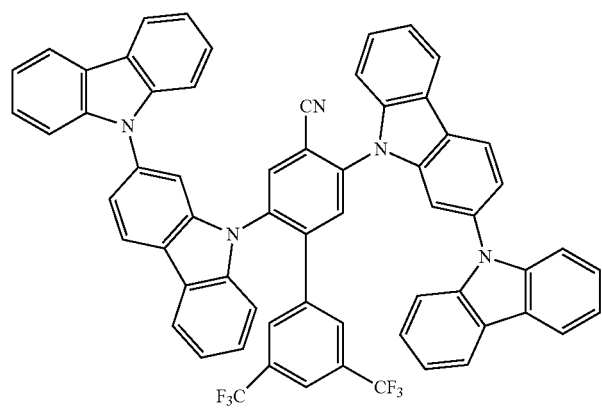
74
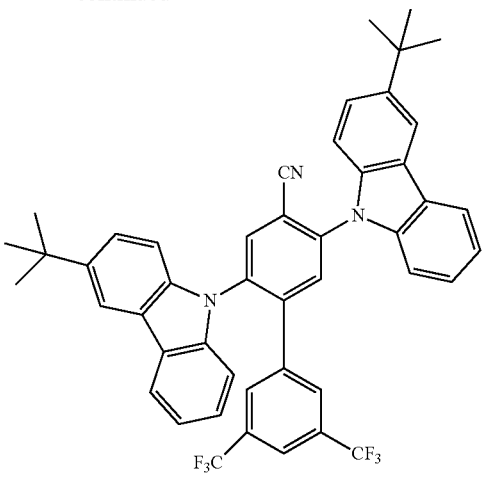
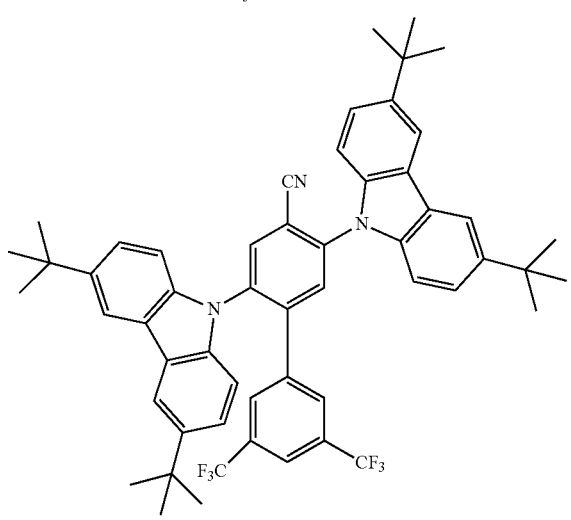
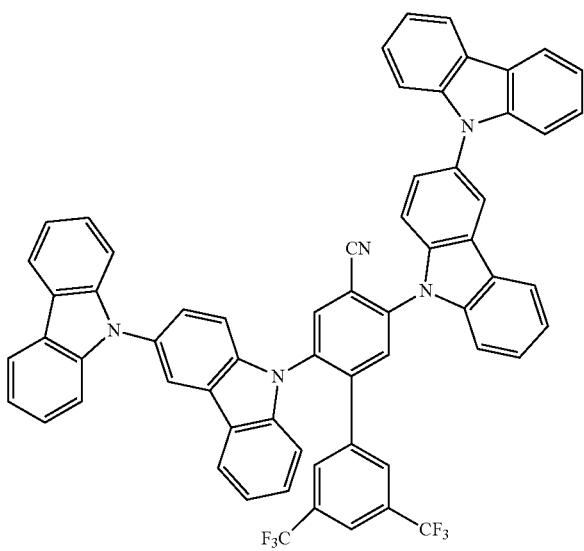

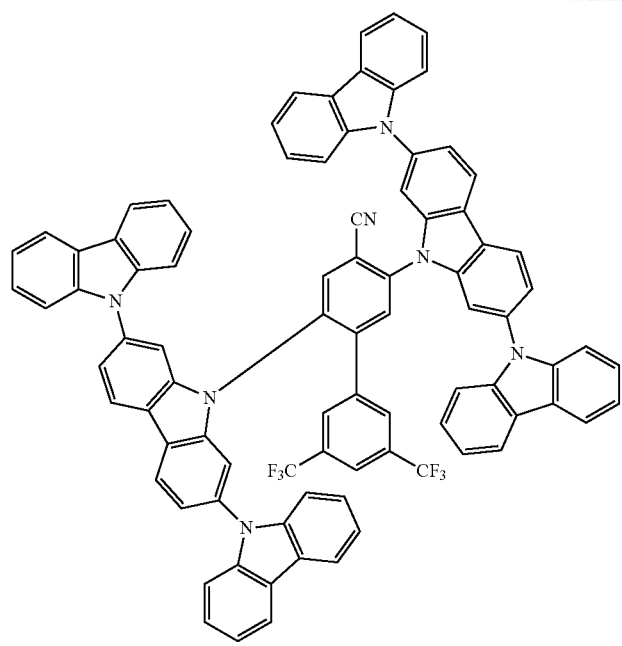
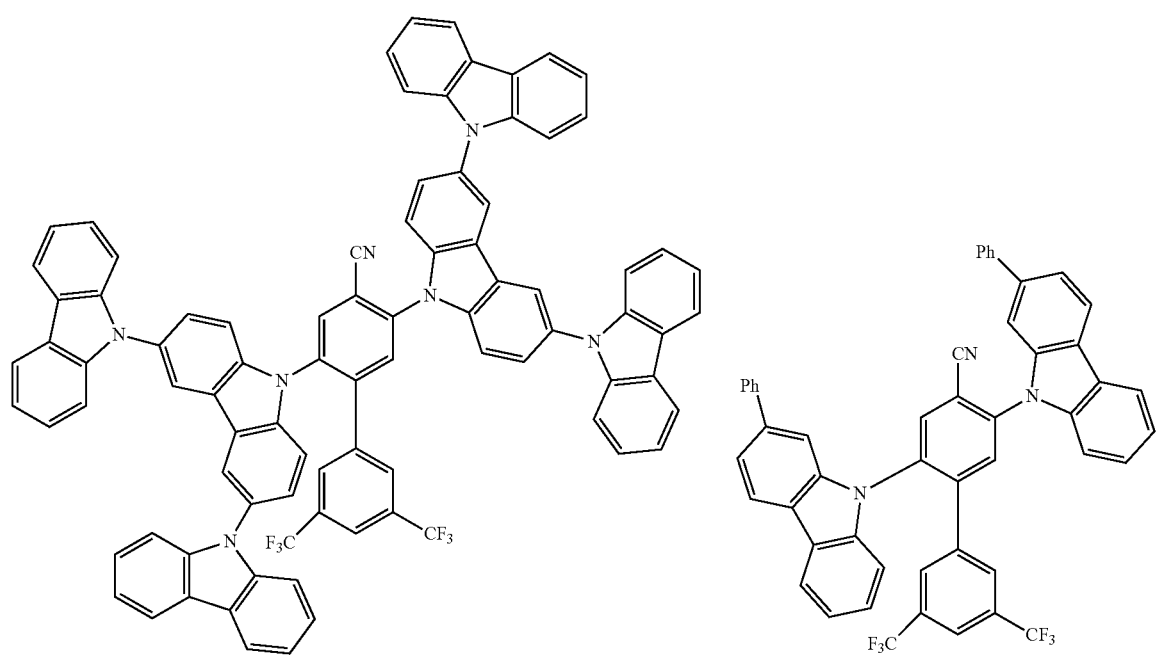

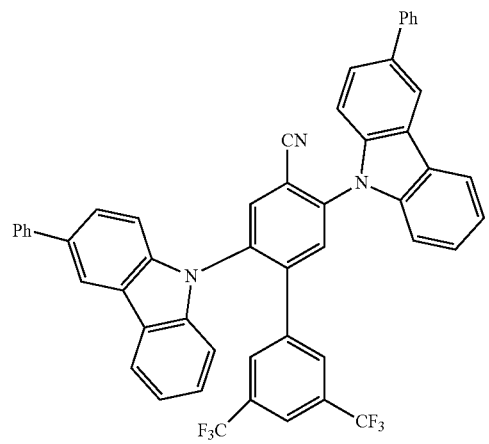
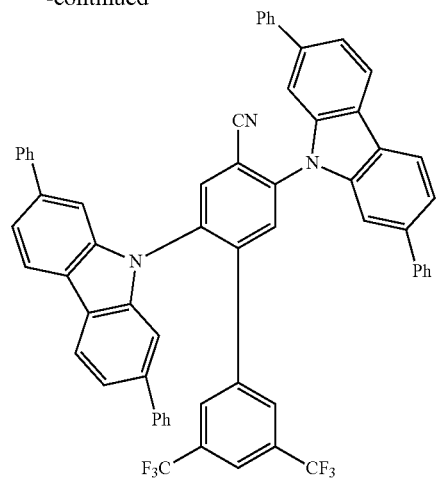
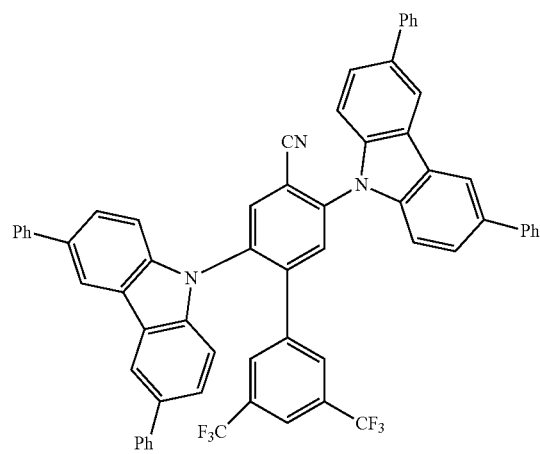
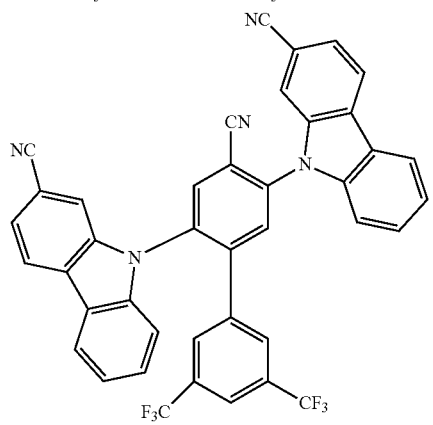
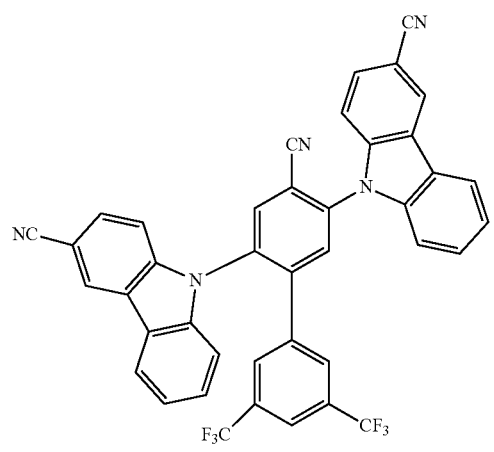
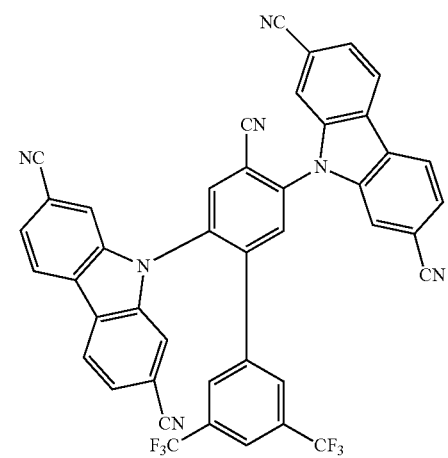

-continued
79
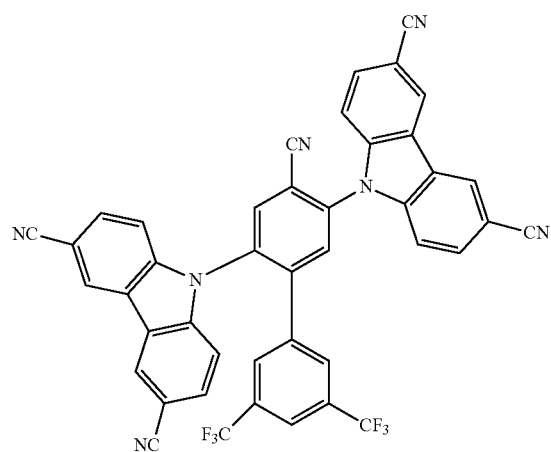
80
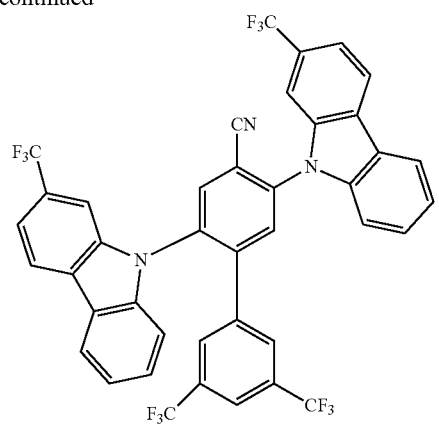
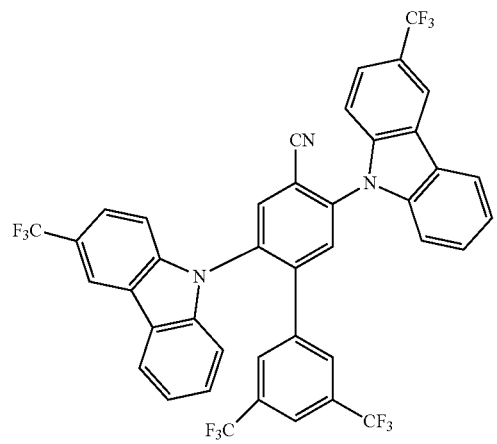
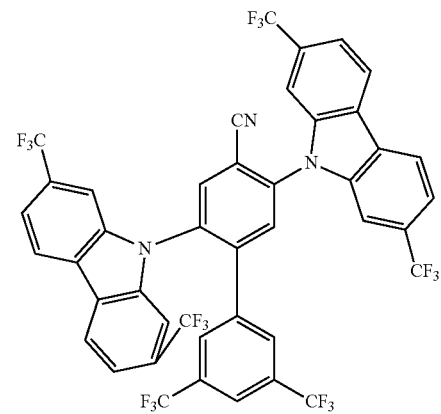
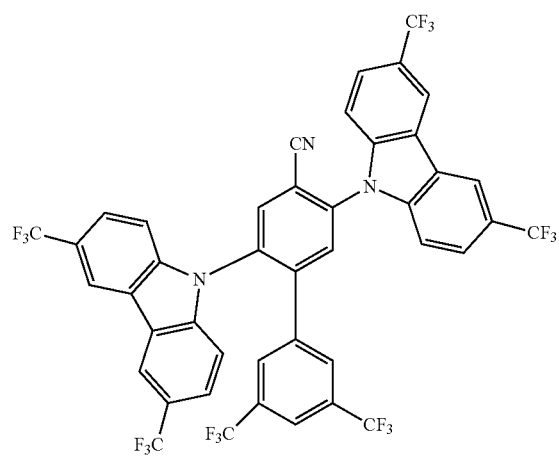
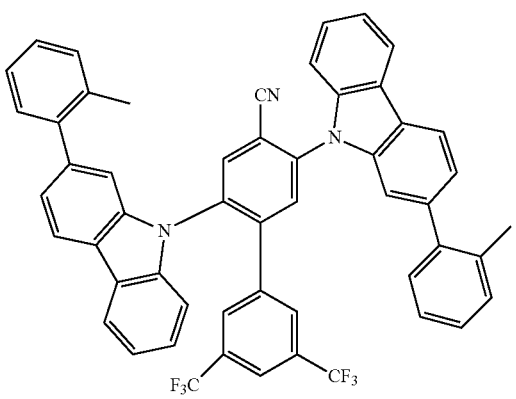

-continued
| 81 | 82 |
|---|---|
| 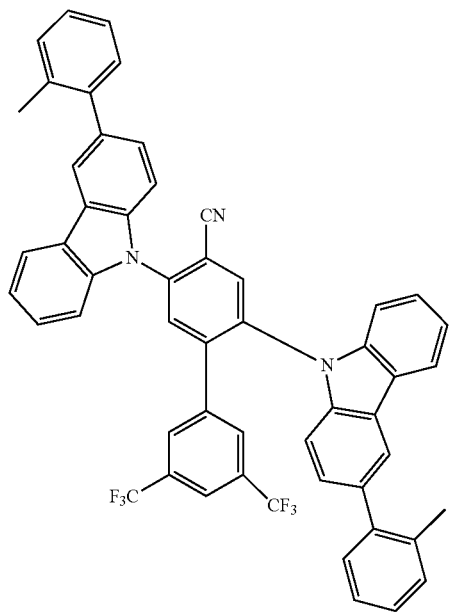 | 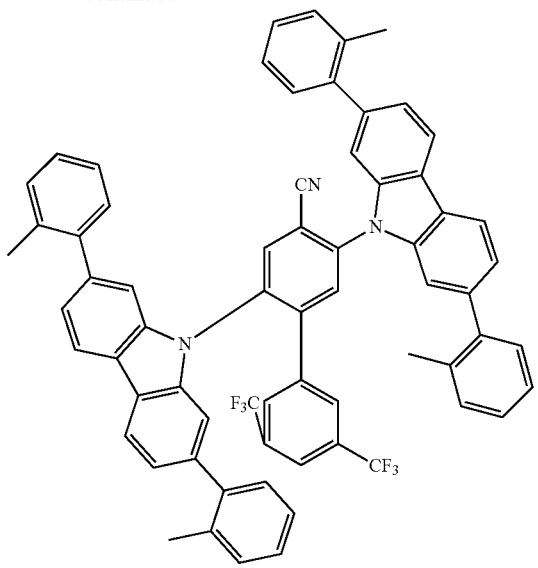 |
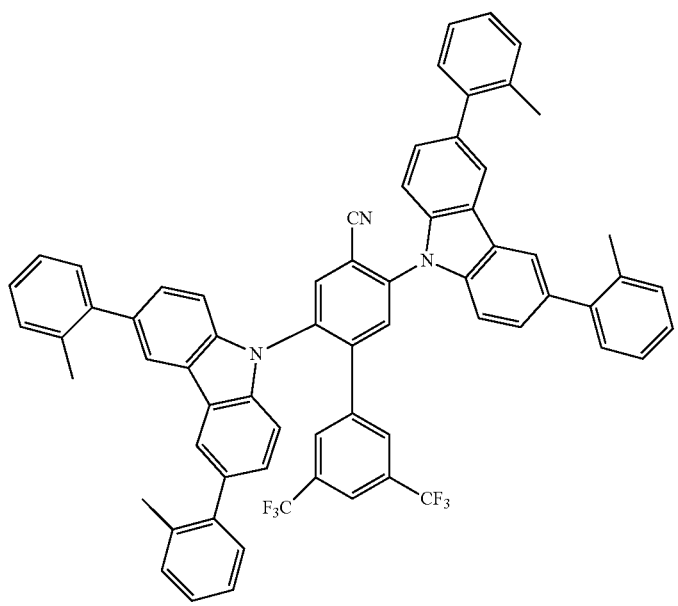

83 84
-continued
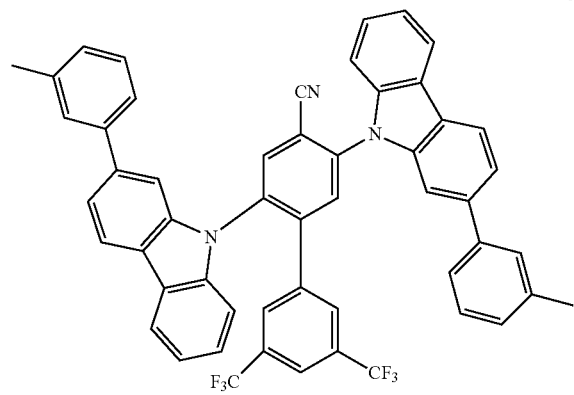
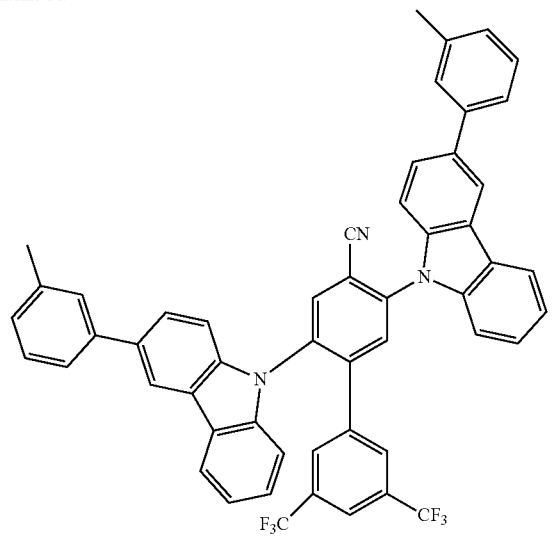
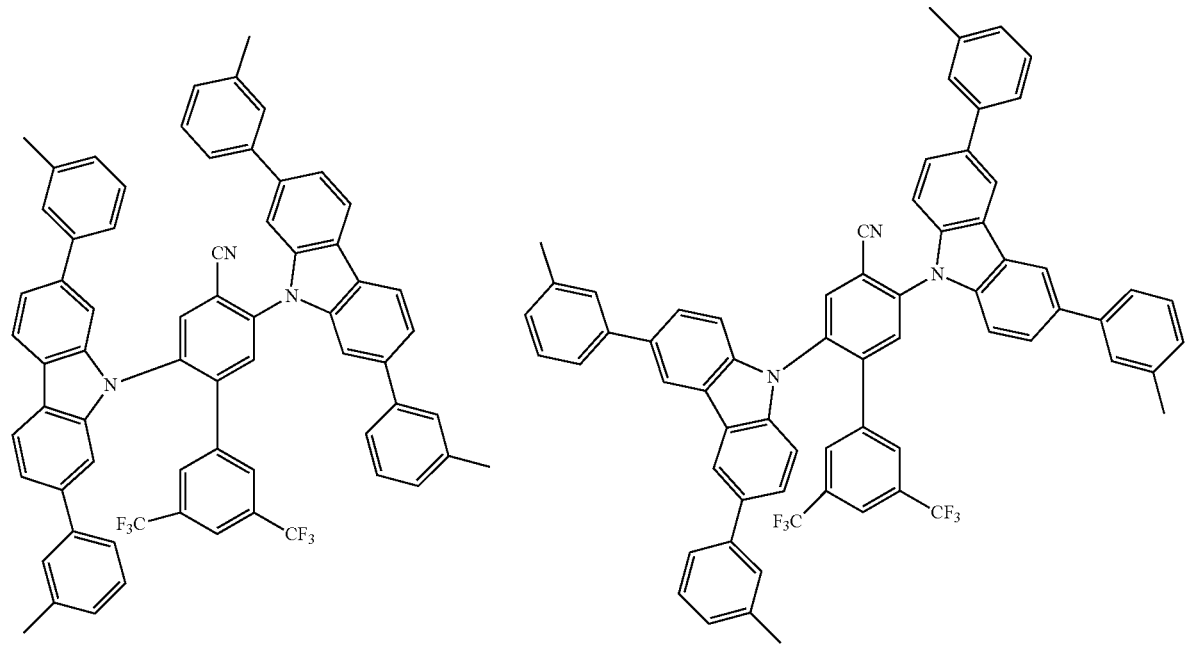

85 86
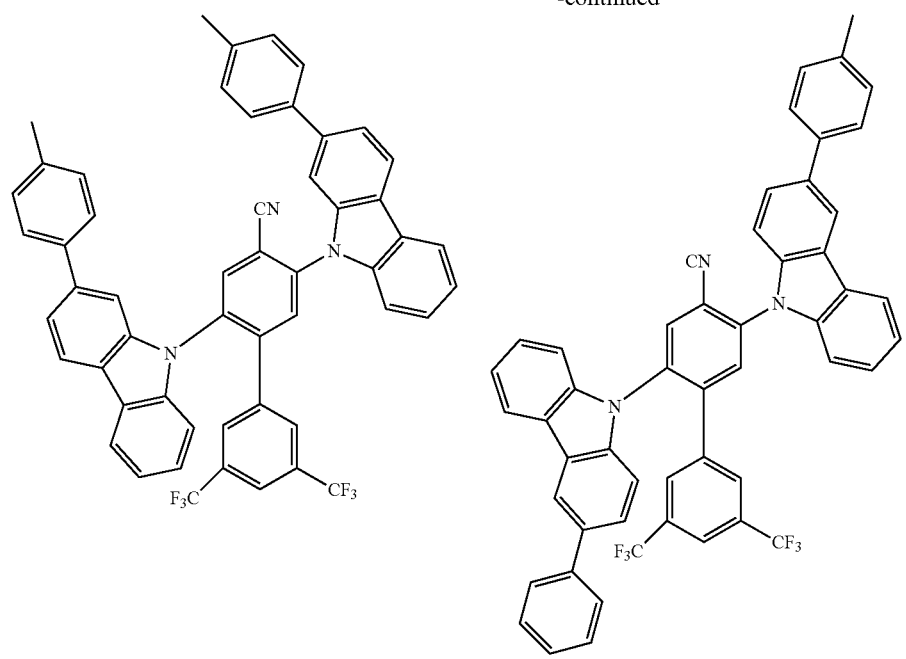
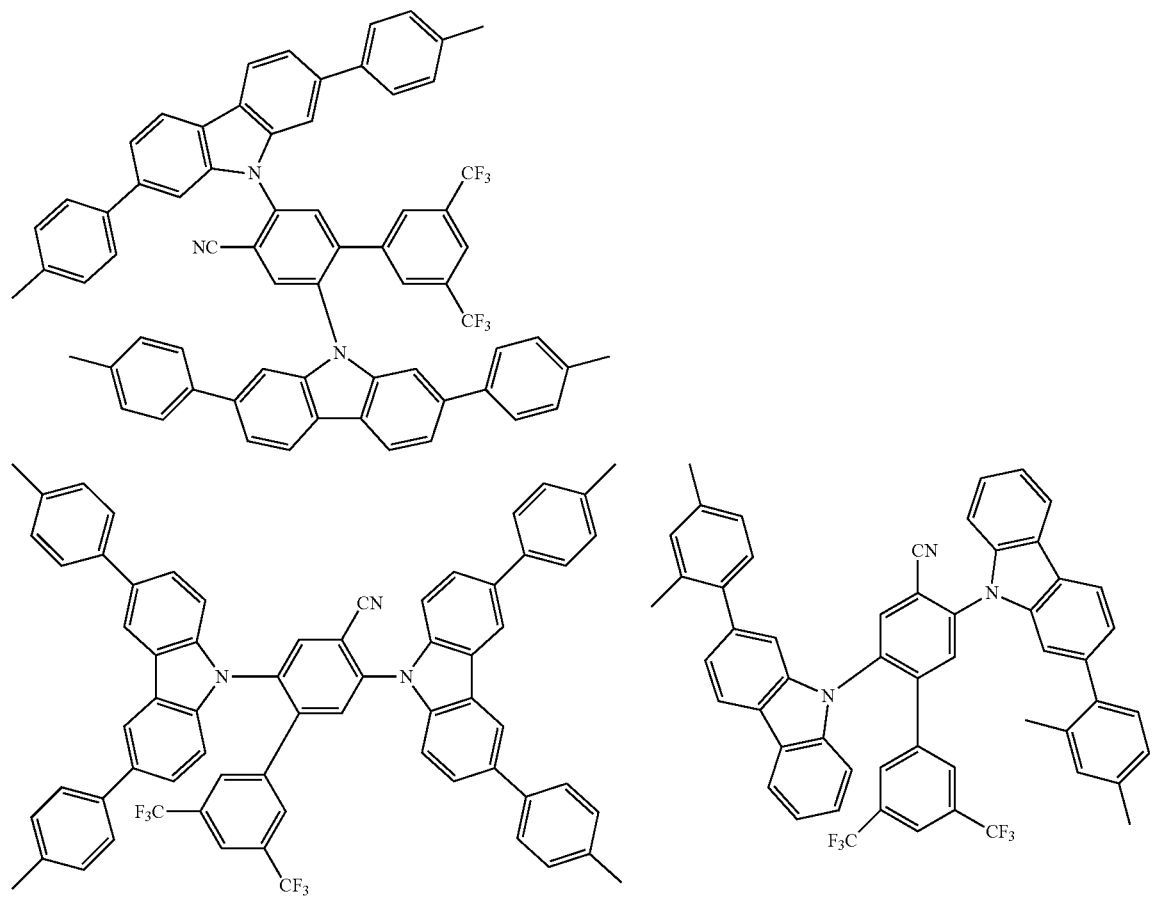

-continued
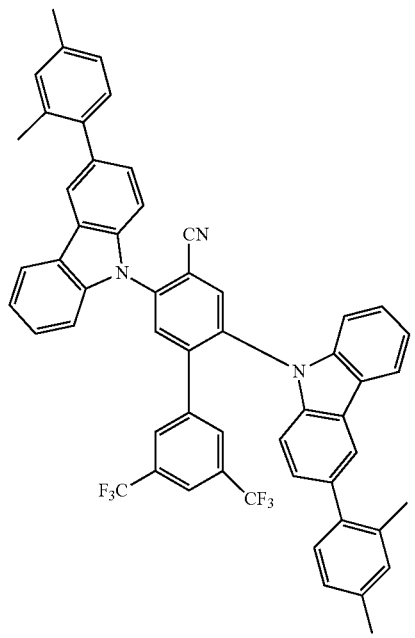
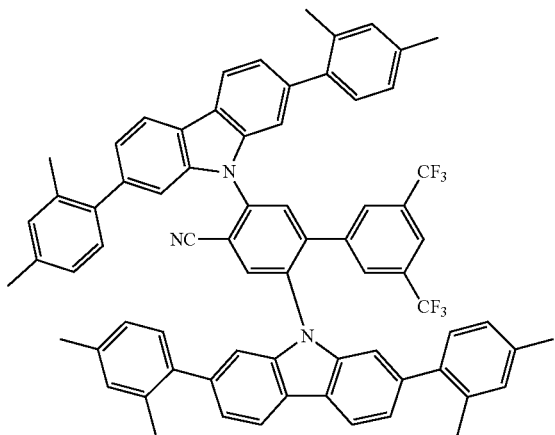
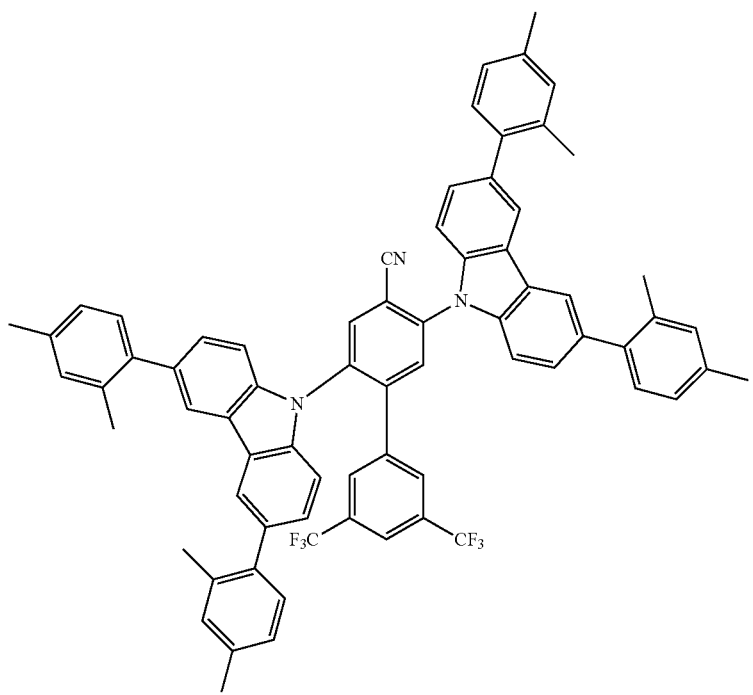

-continued
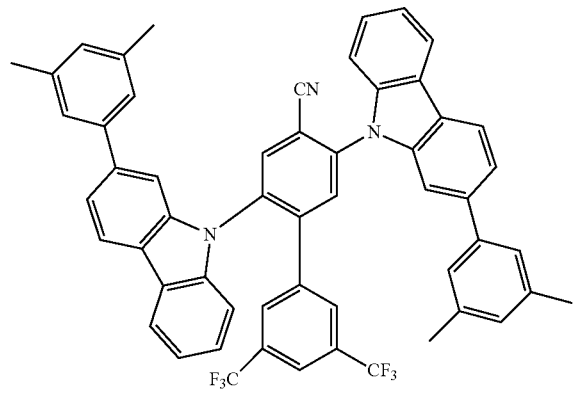
89
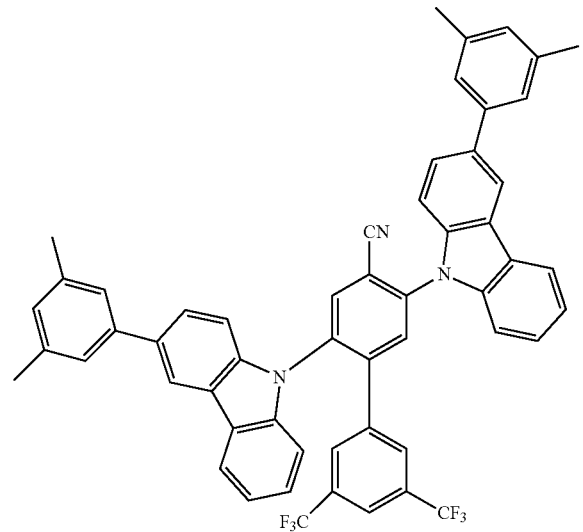
90
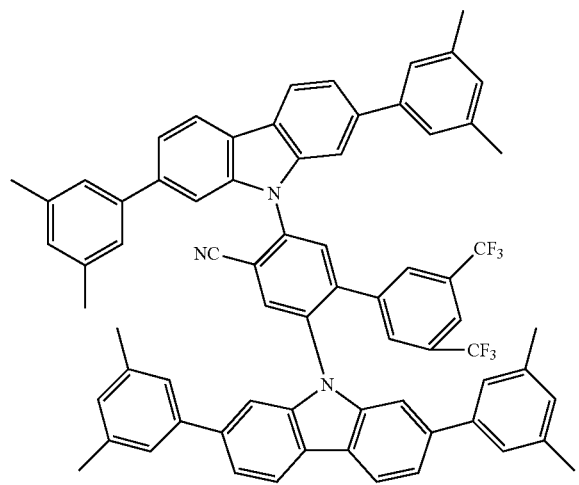
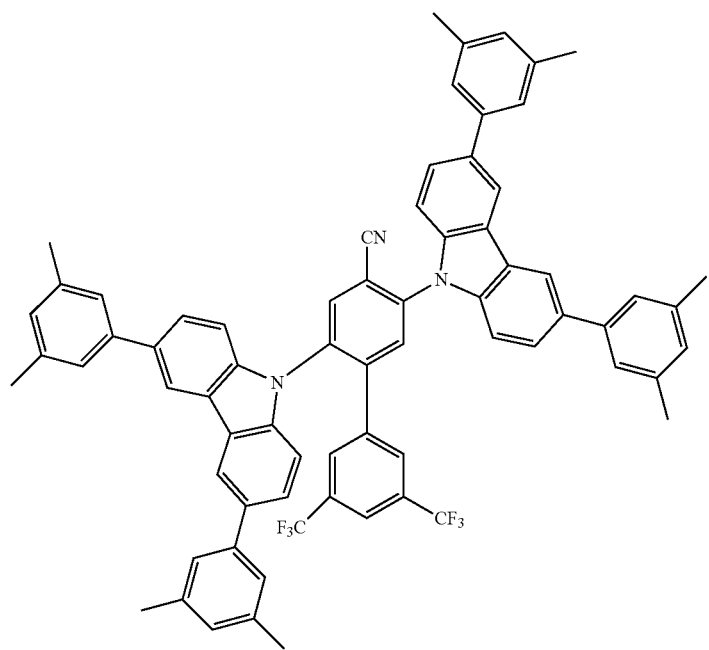

91
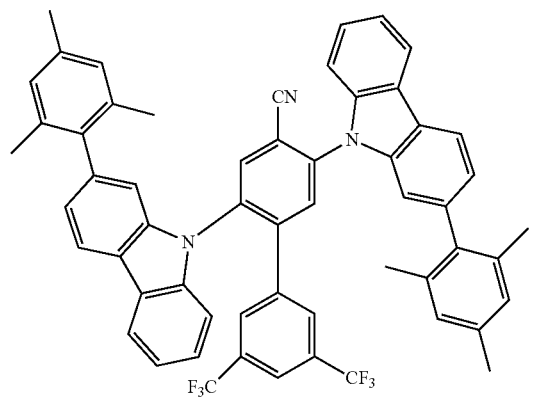
92
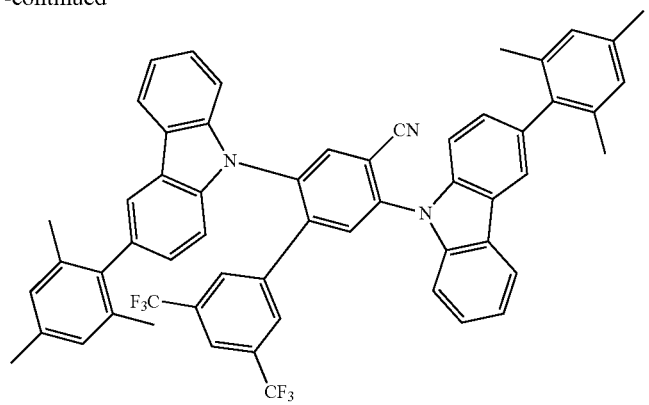
-continued
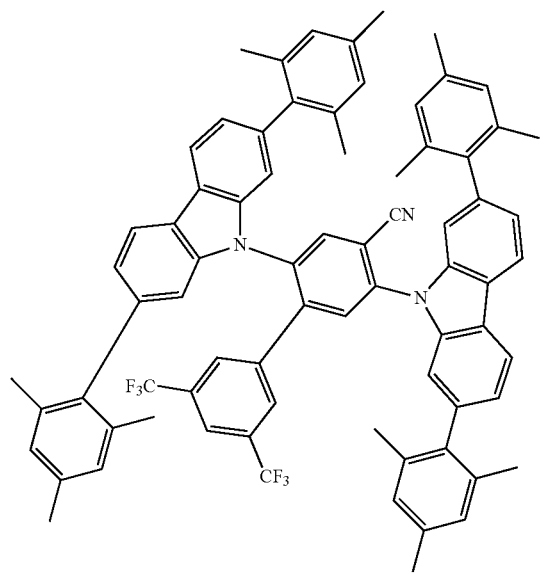
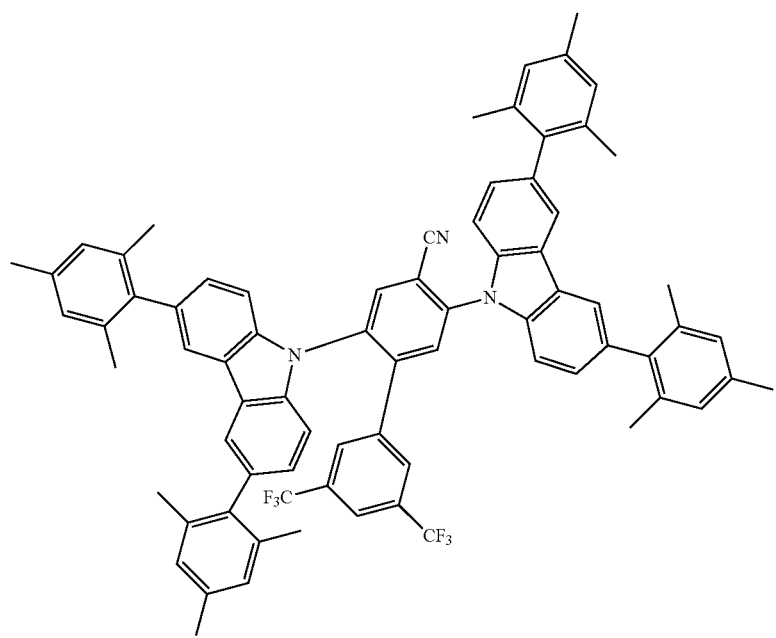

-continued
93
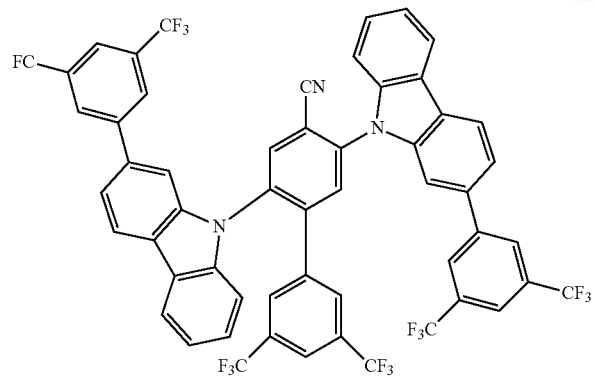
94
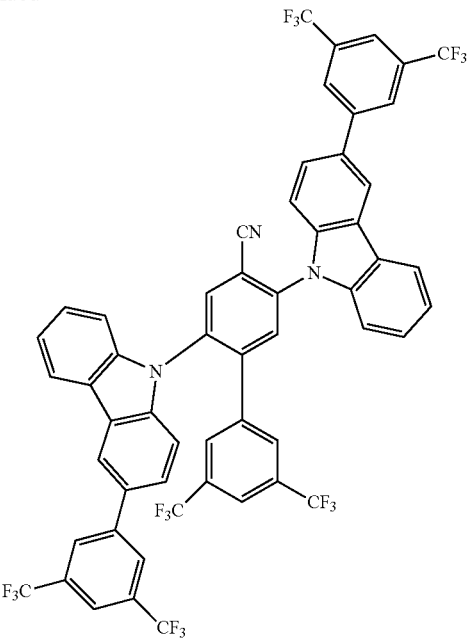
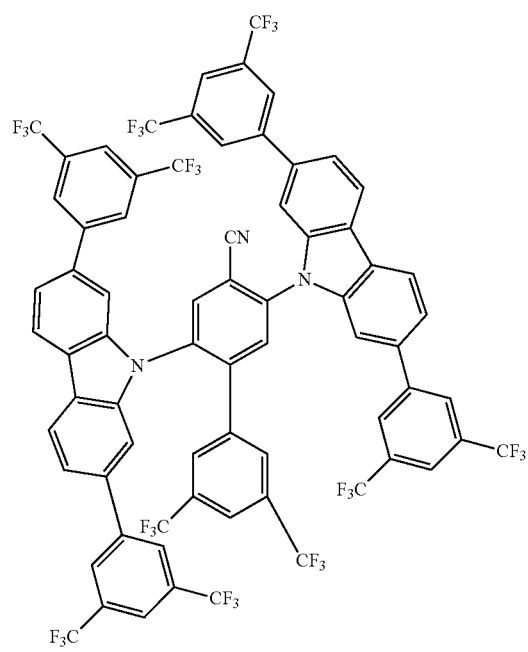
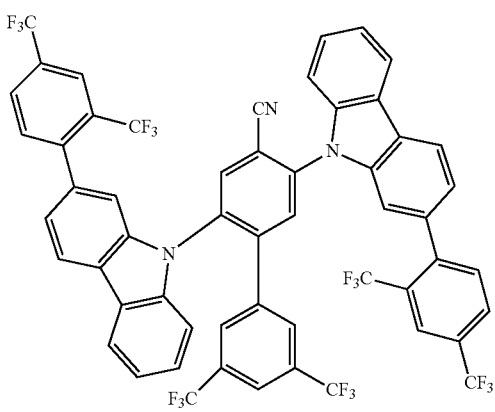

-continued
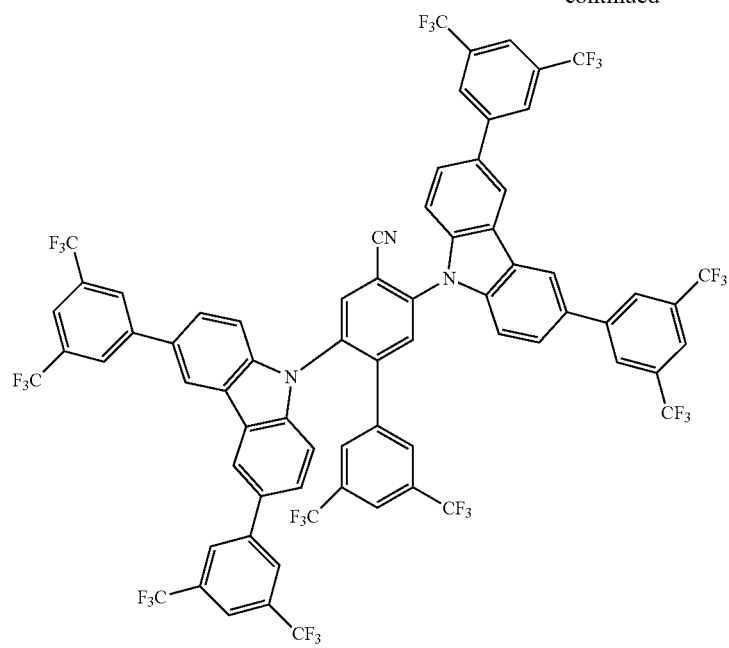
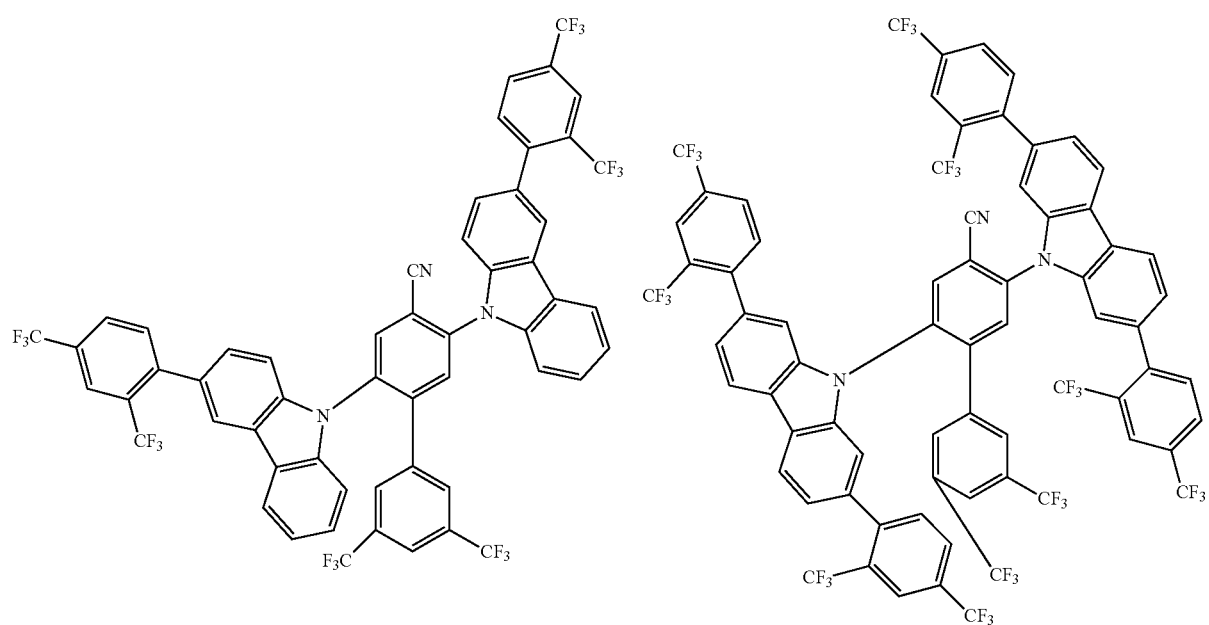

-continued
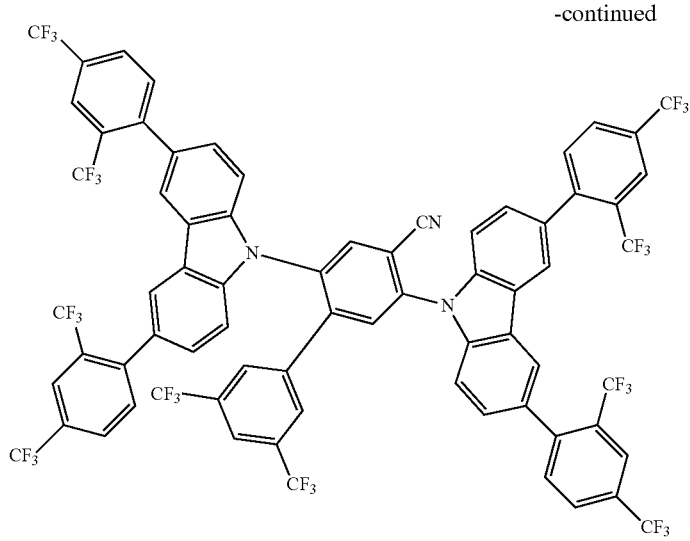
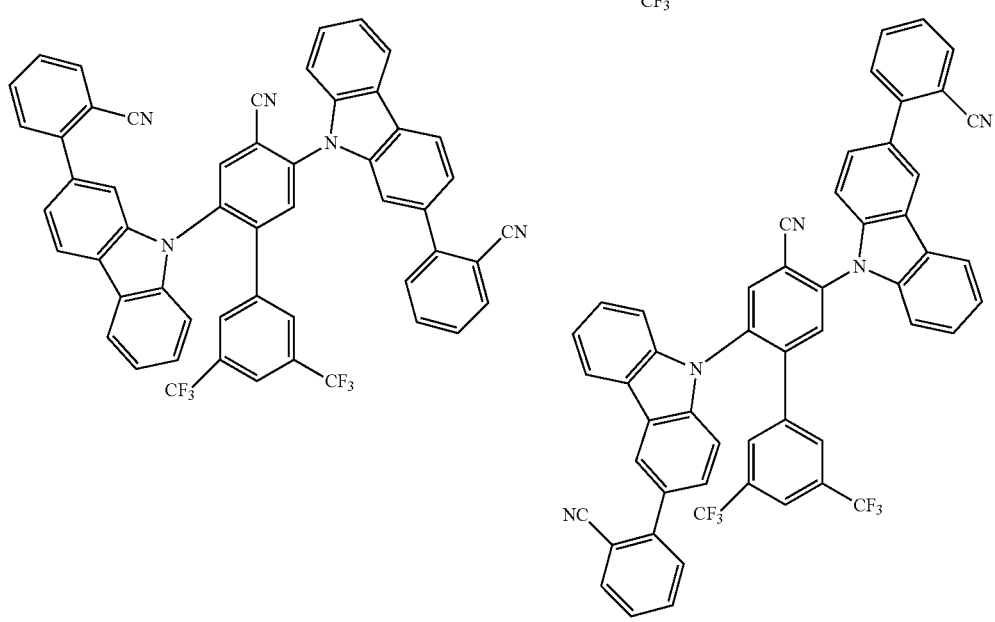
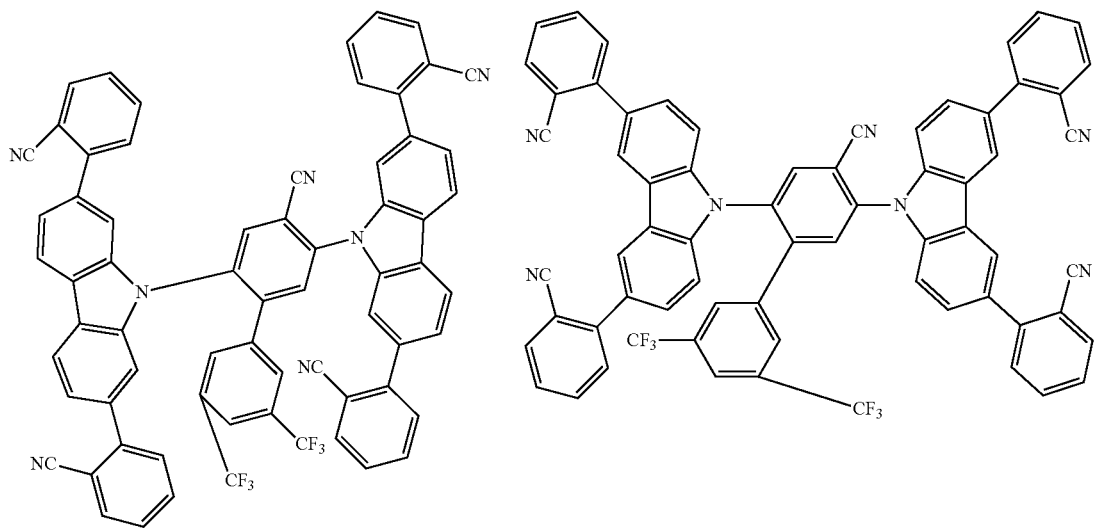

99
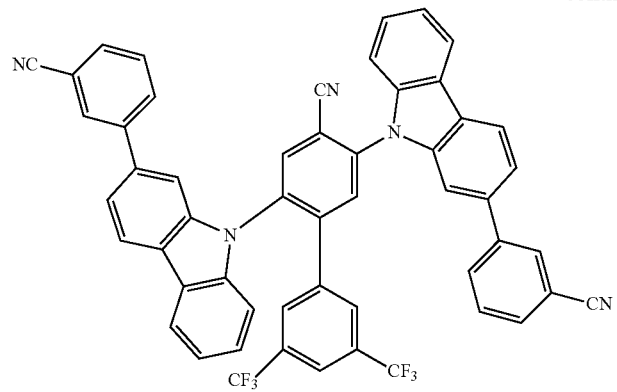
100
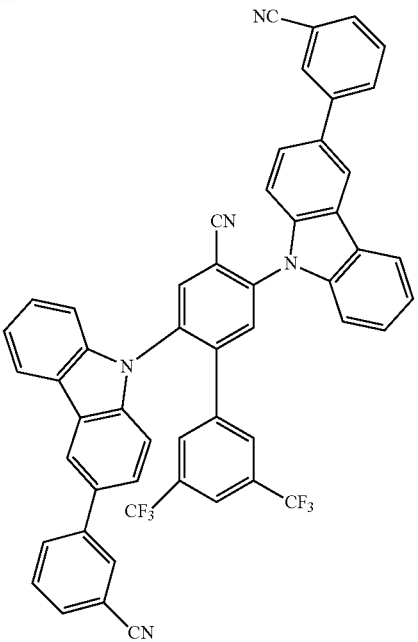
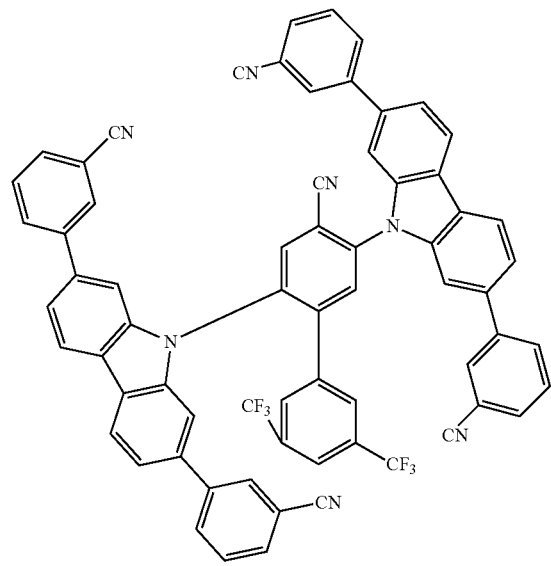
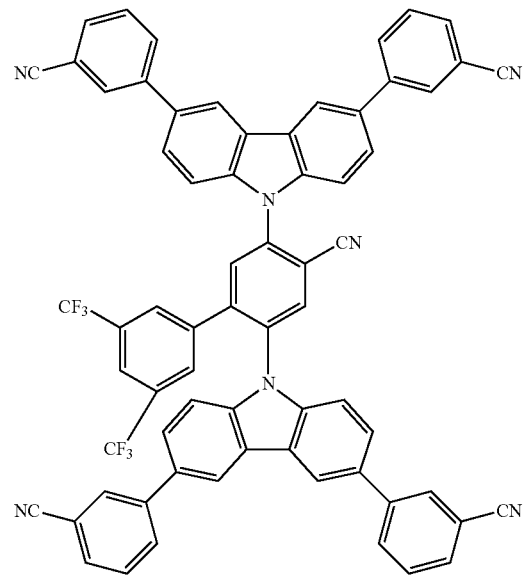

-continued
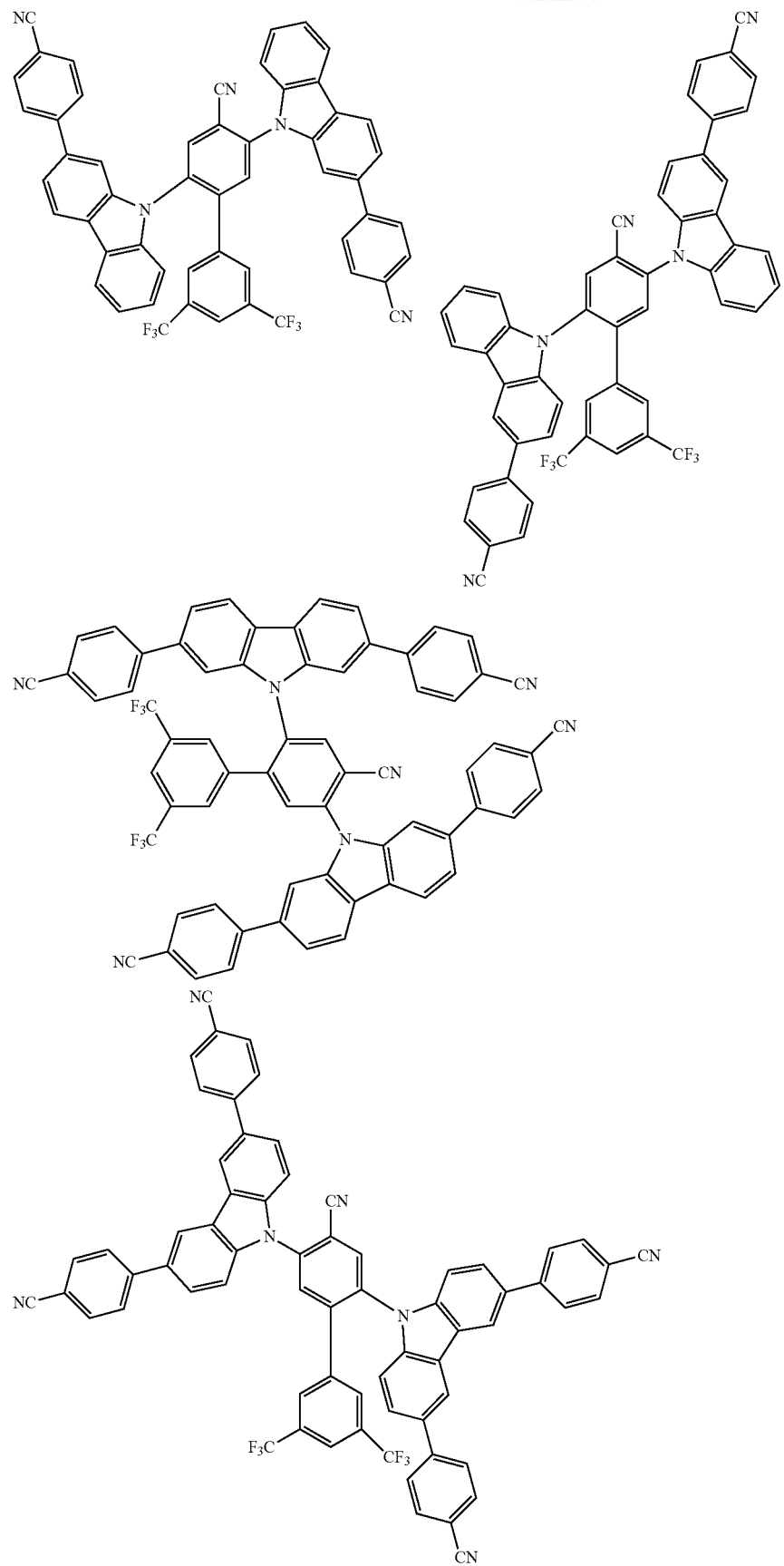

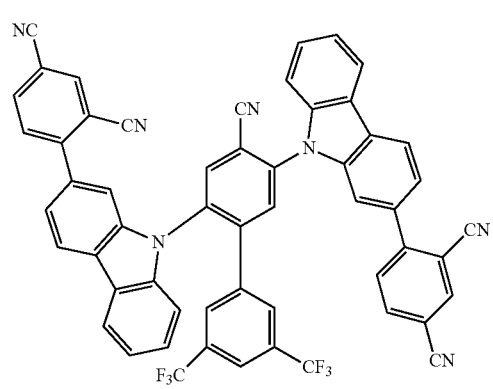
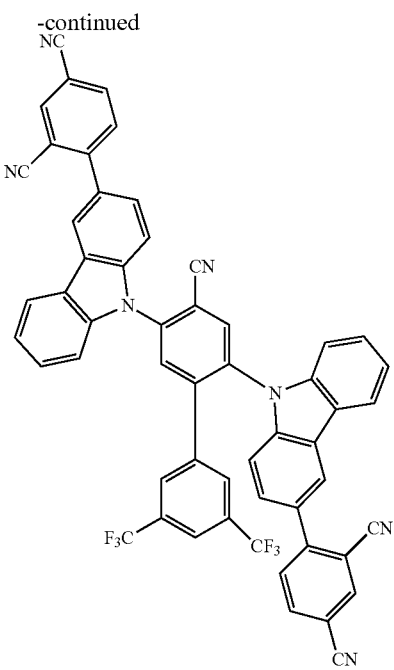
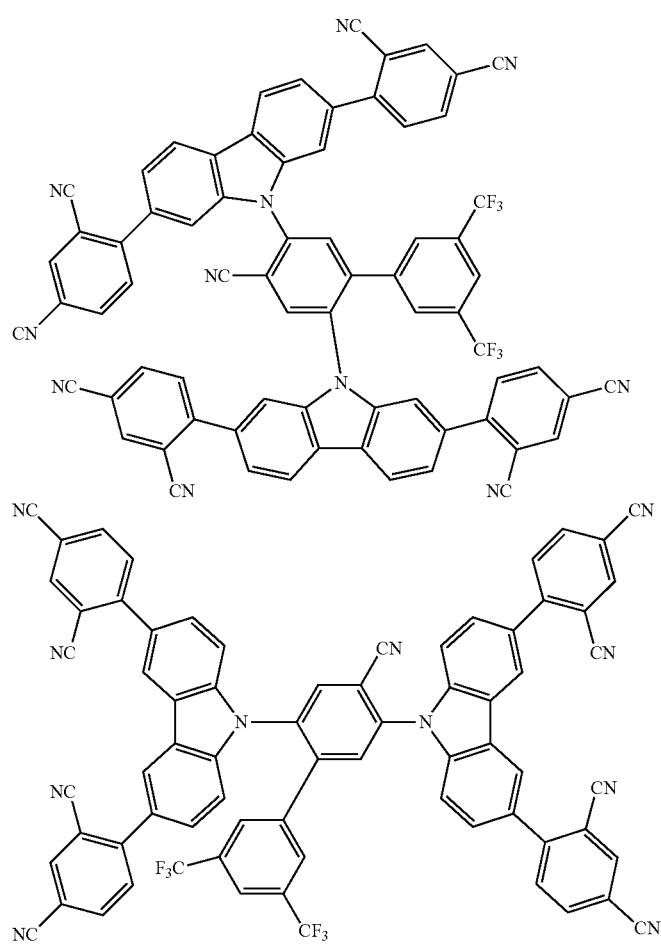

-continued
105 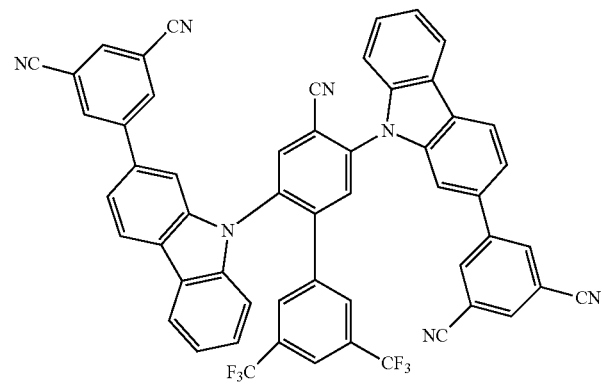
106 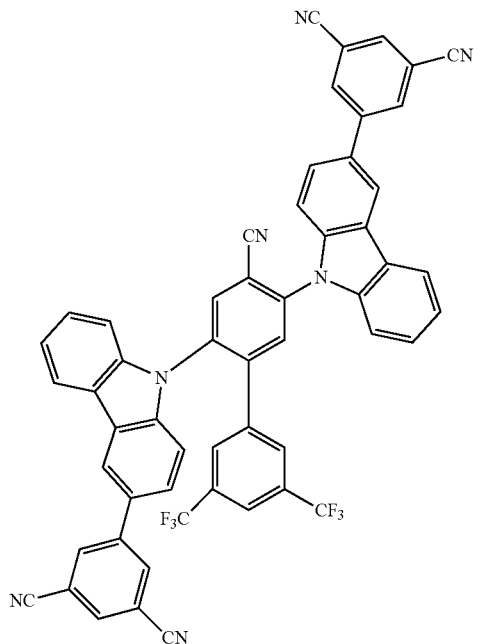
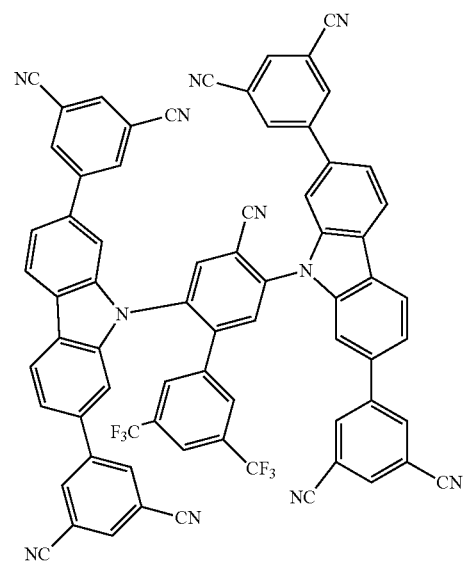
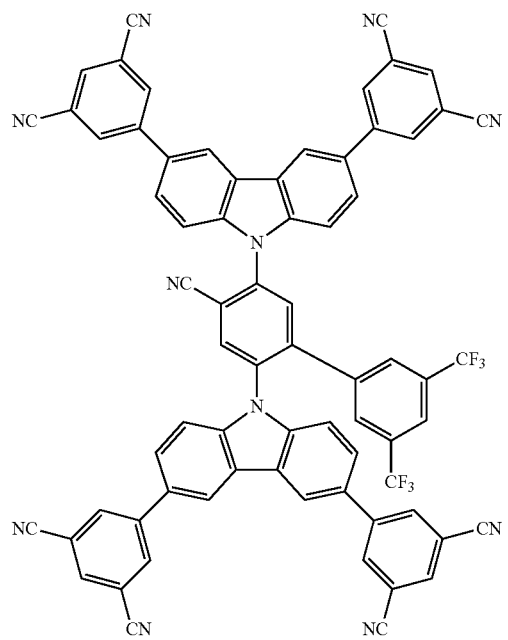

-continued
107
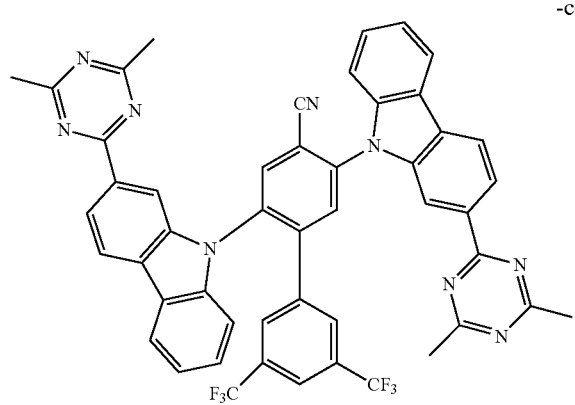
108
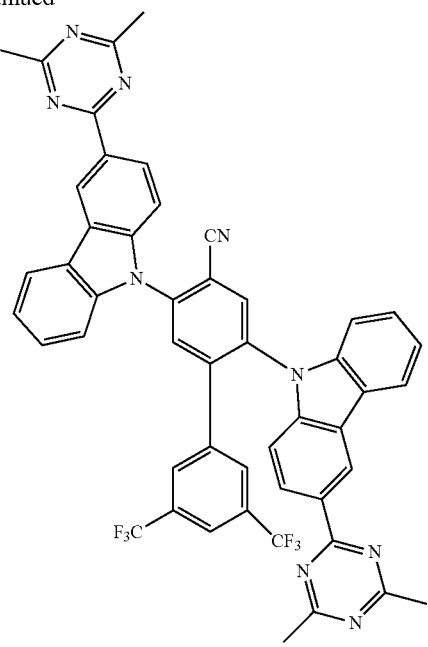
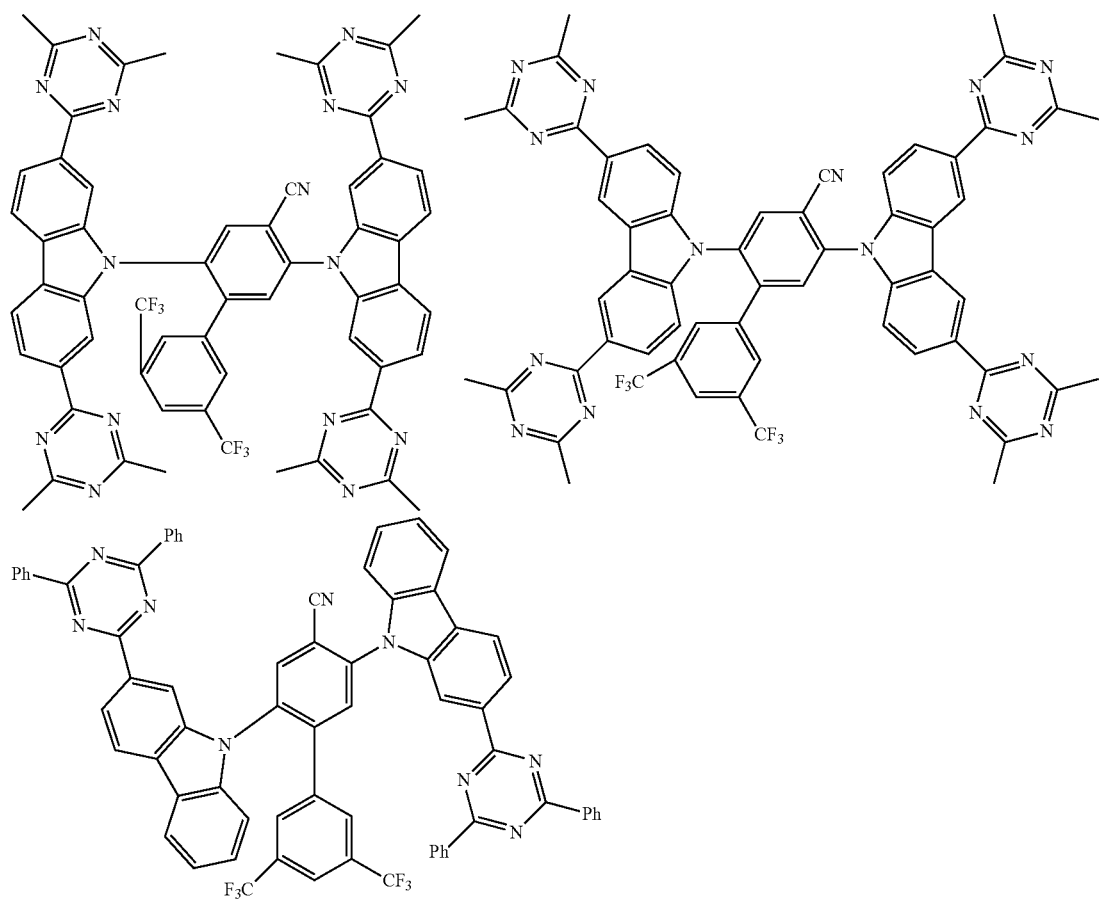

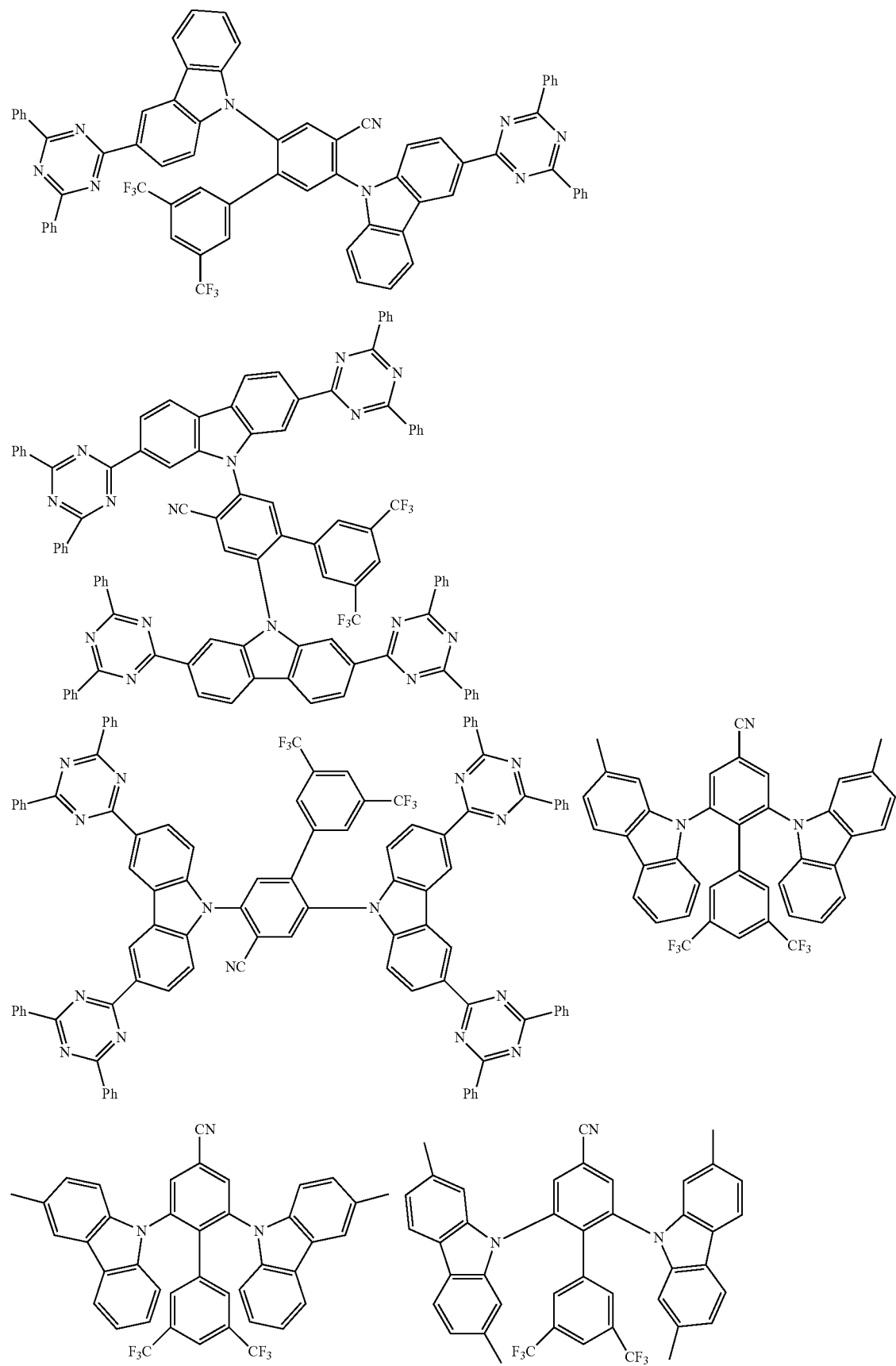

-continued
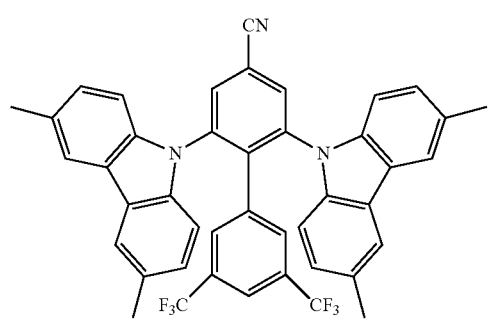
111
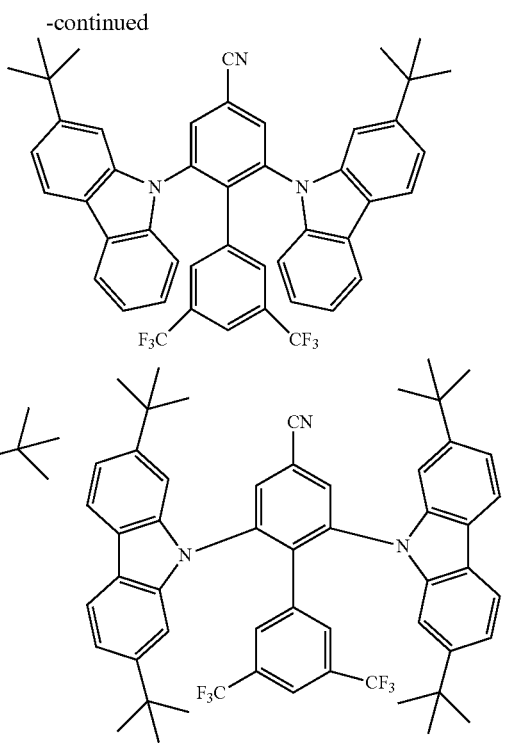
112
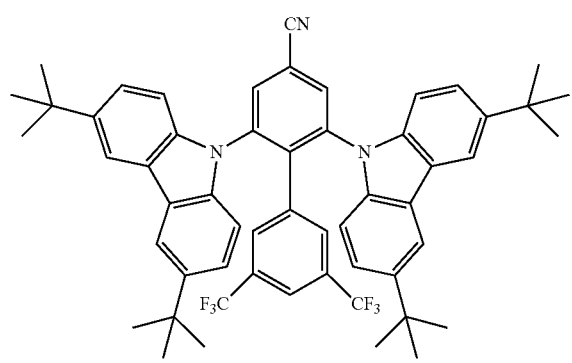
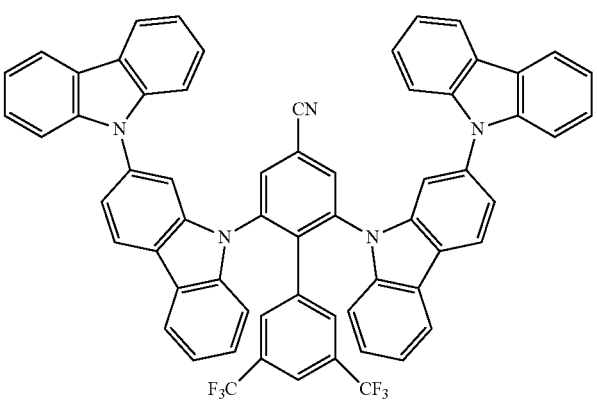
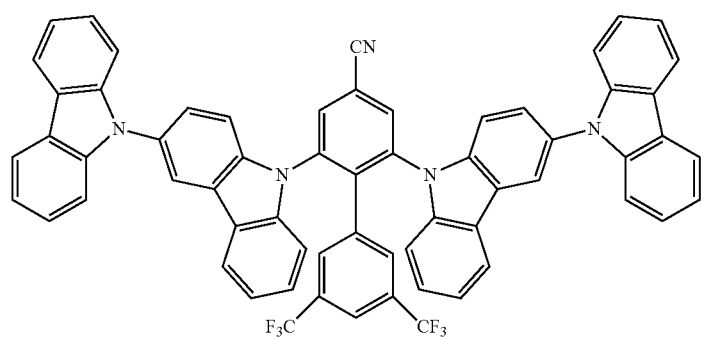

-continued
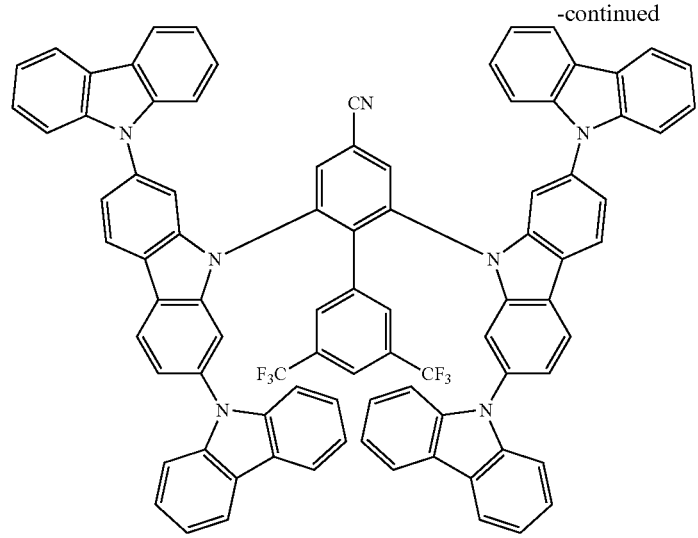
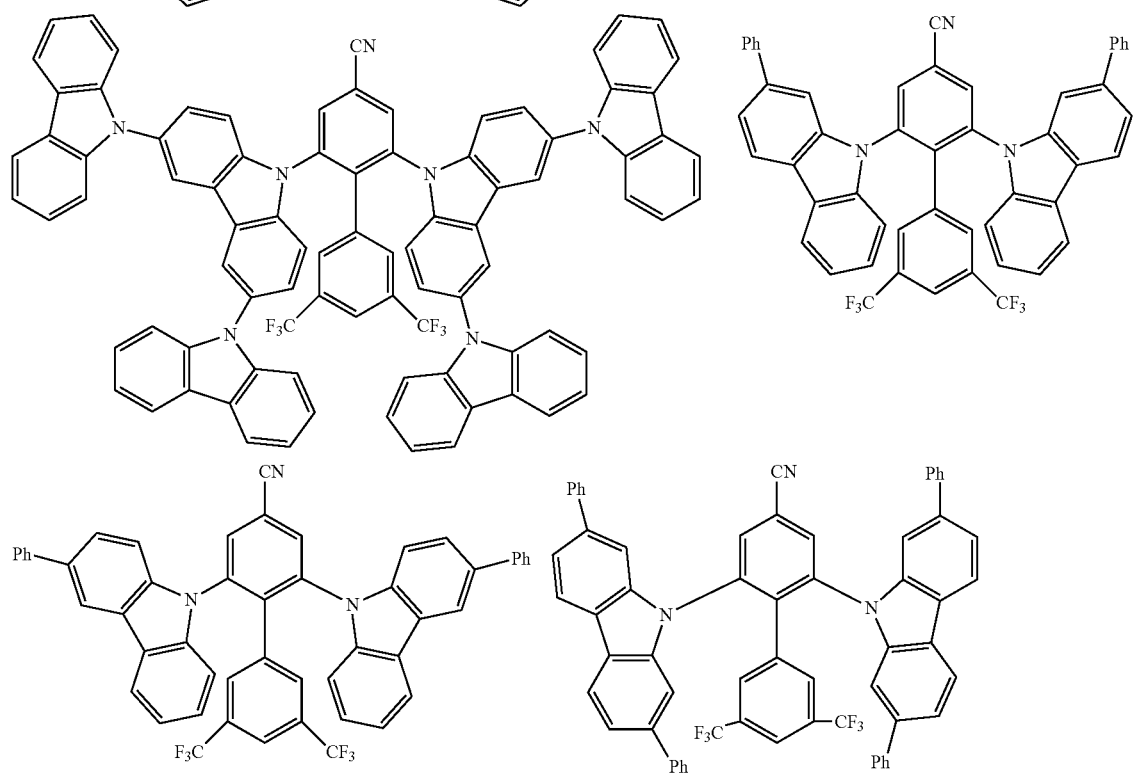
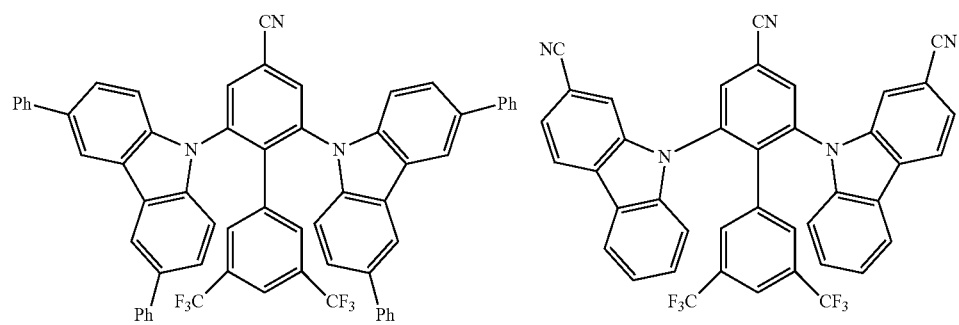

-continued
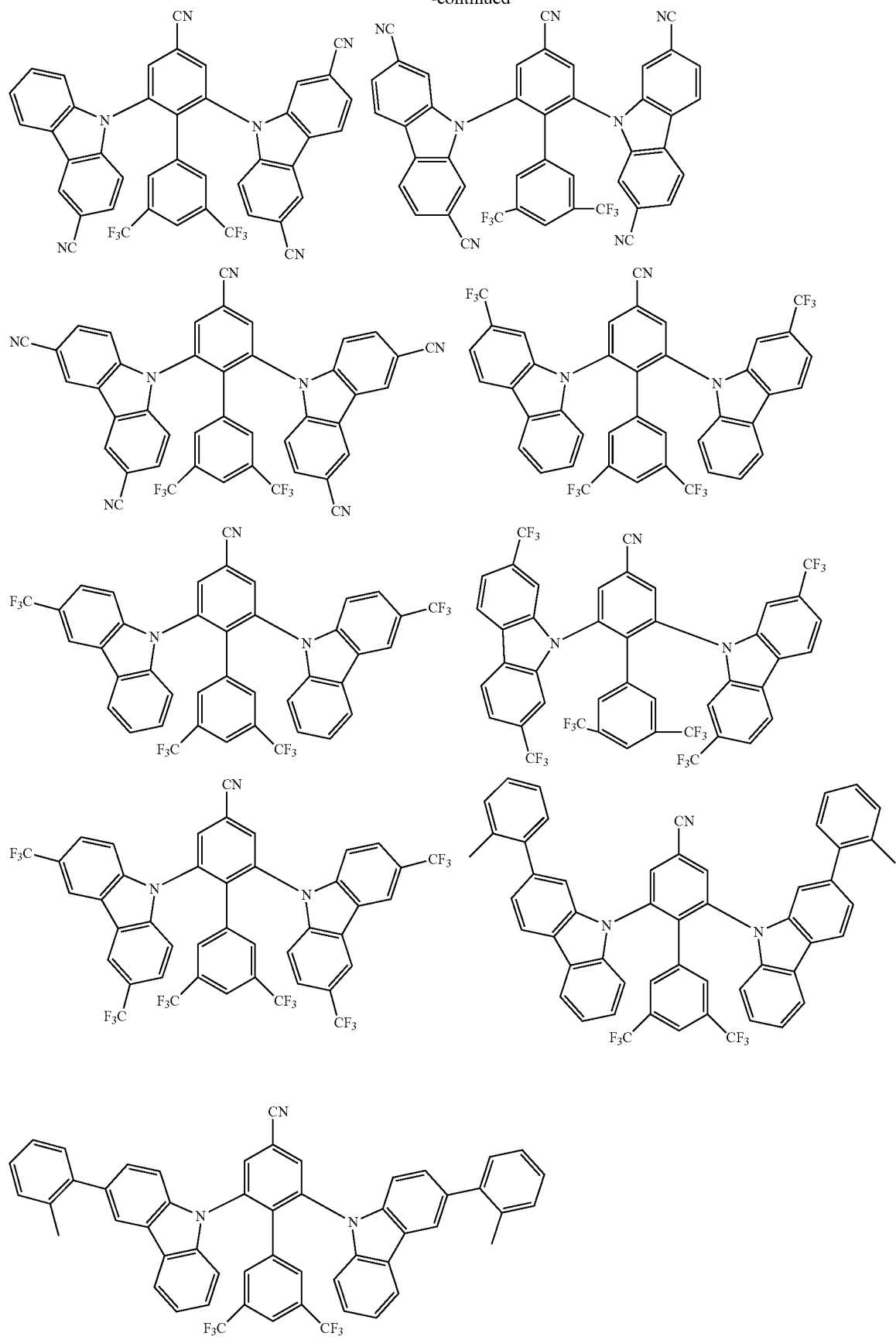

-continued
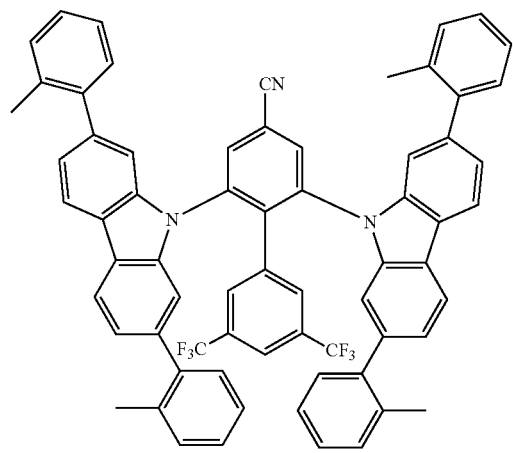
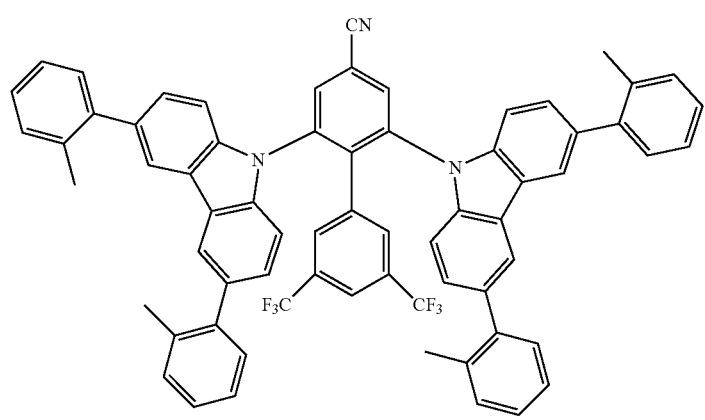
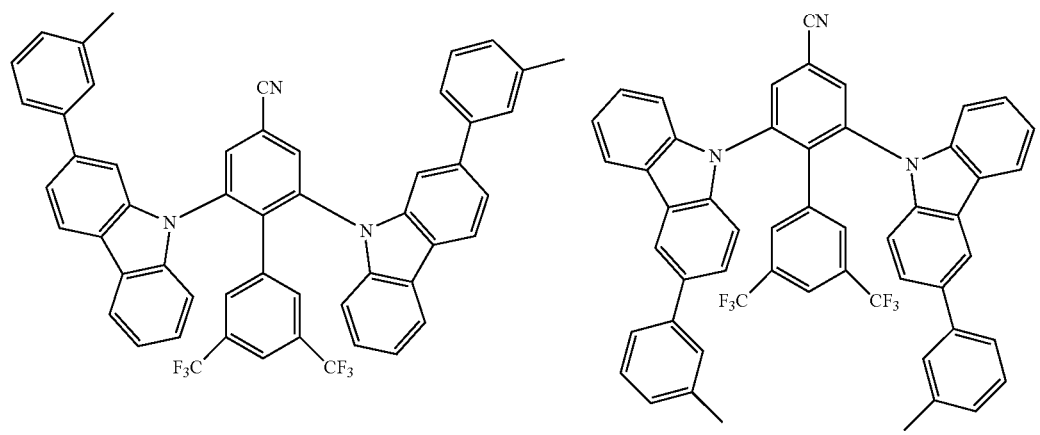

-continued
119
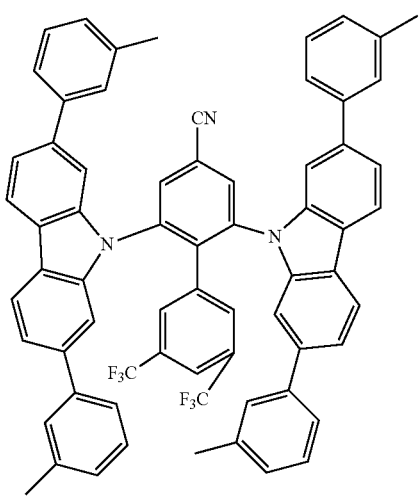
120
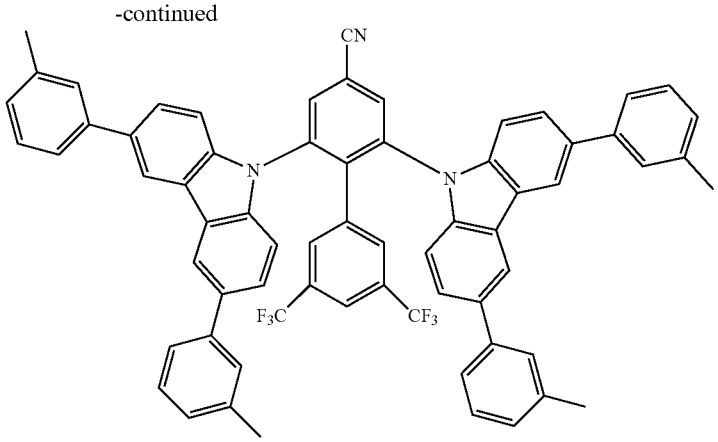
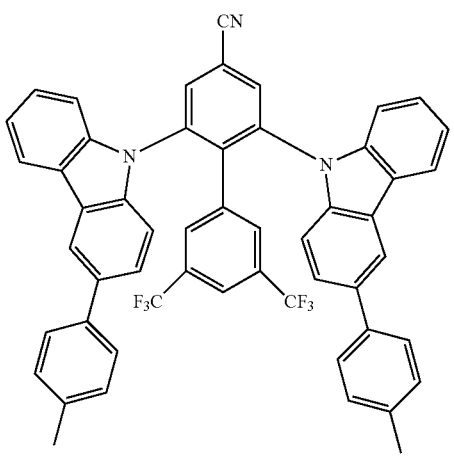
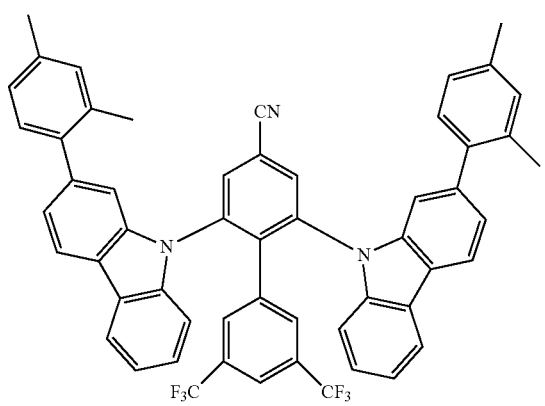
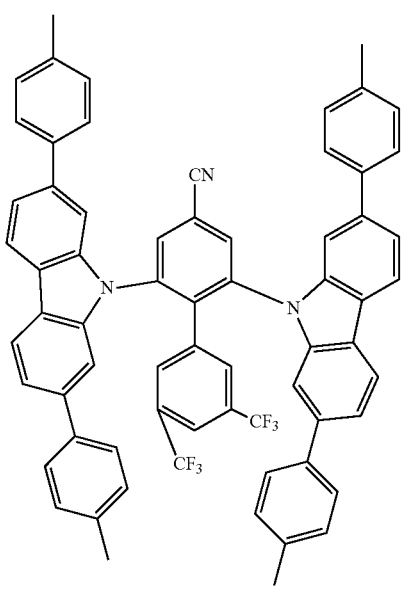

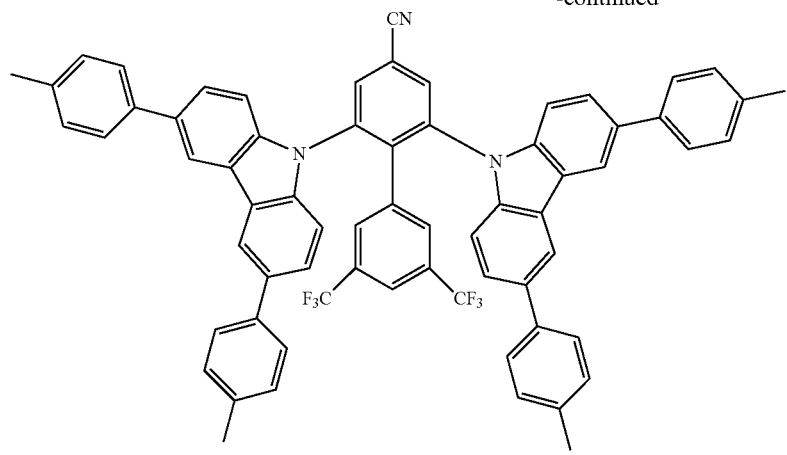
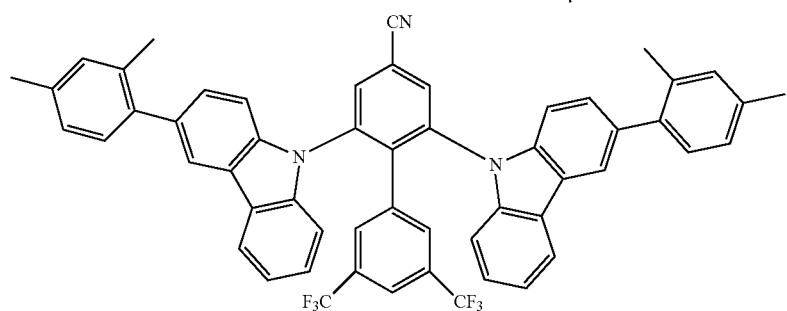
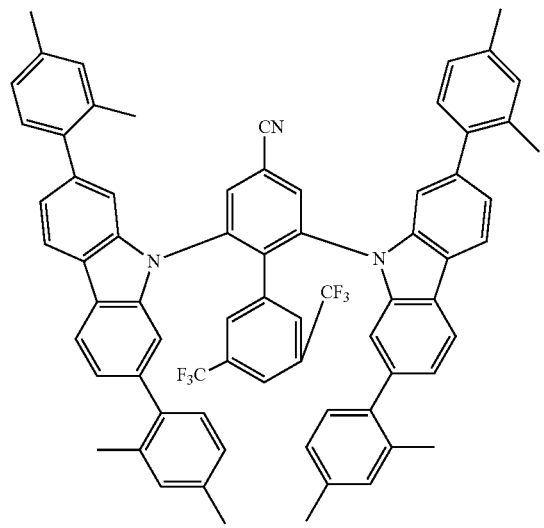
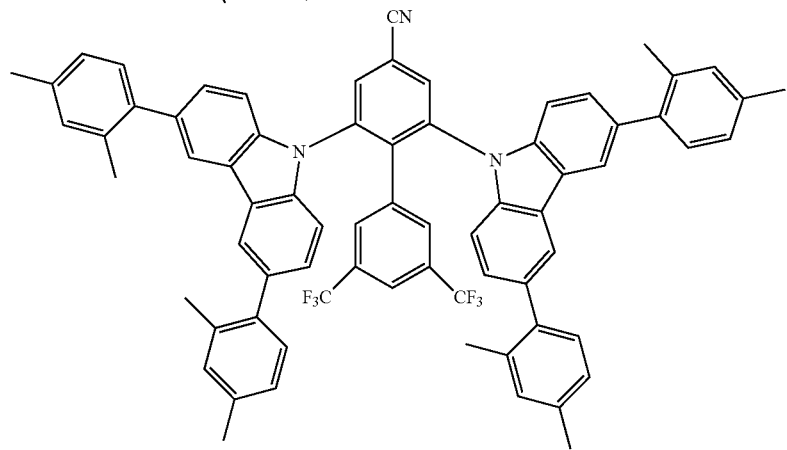

-continued
123
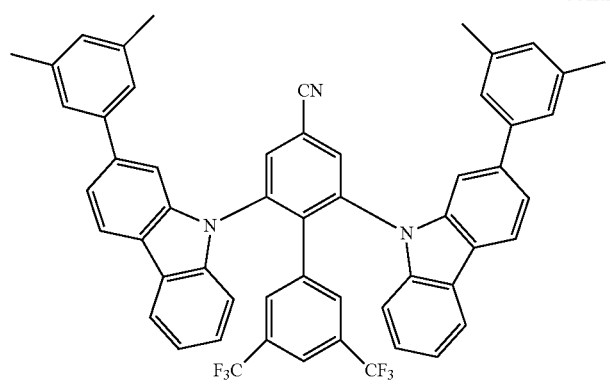
124
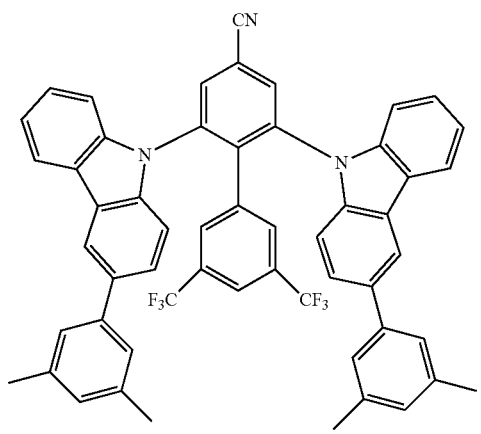
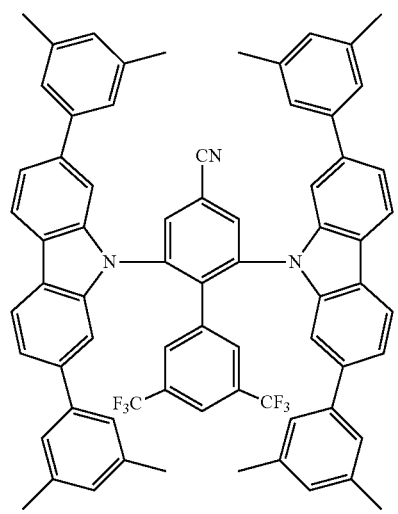
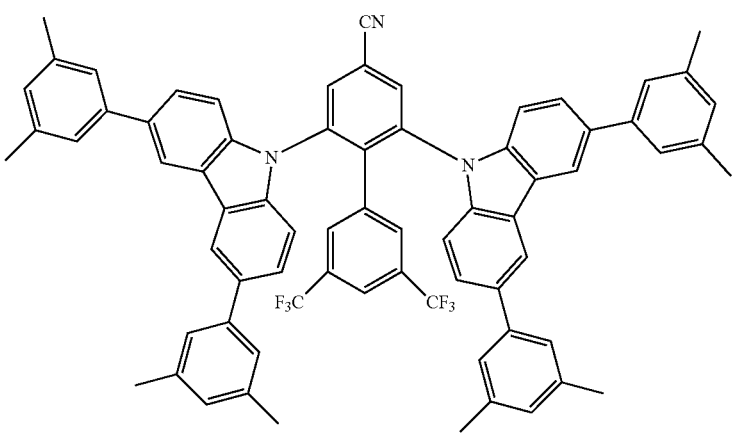
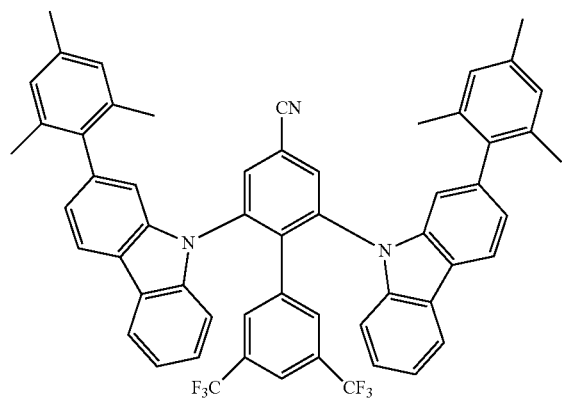
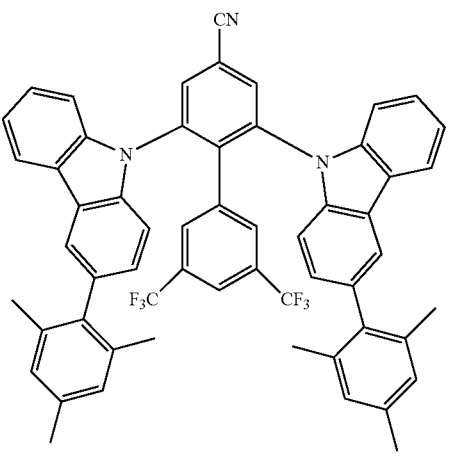

-continued
125
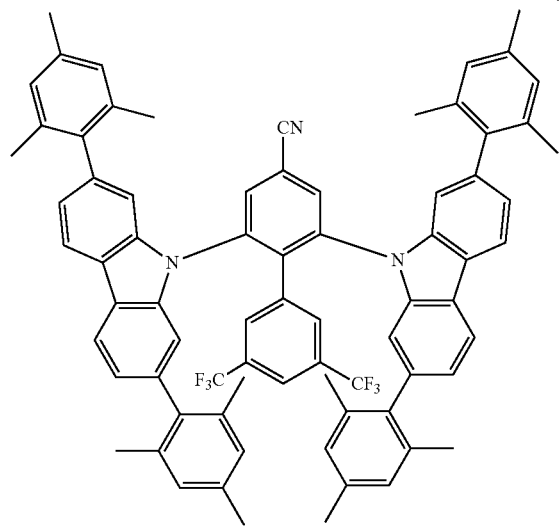
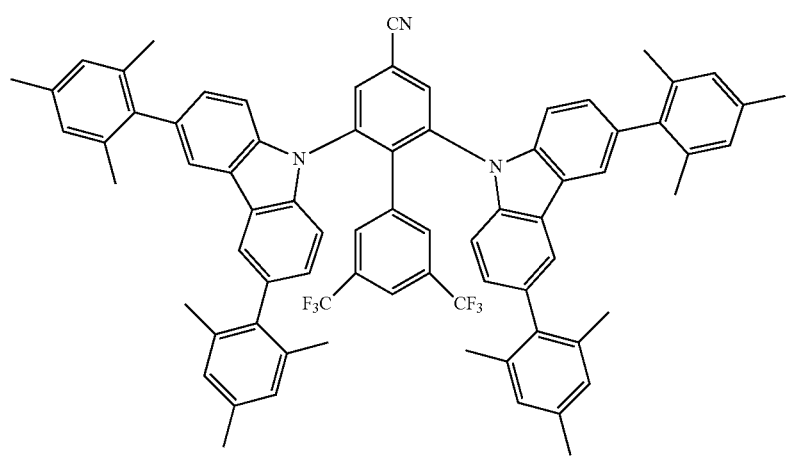
126
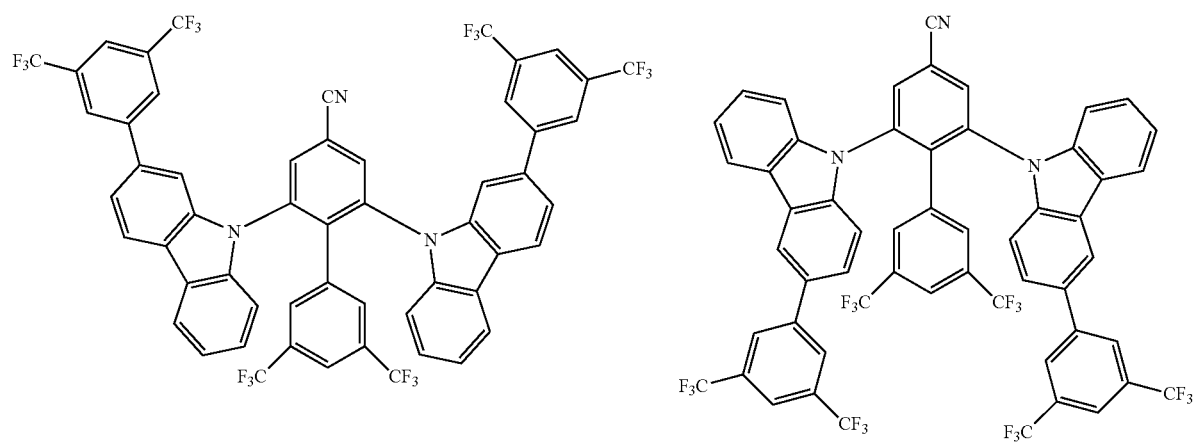

127 128
-continued
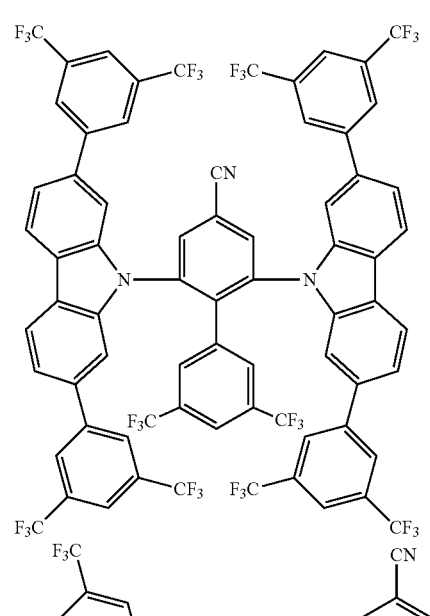
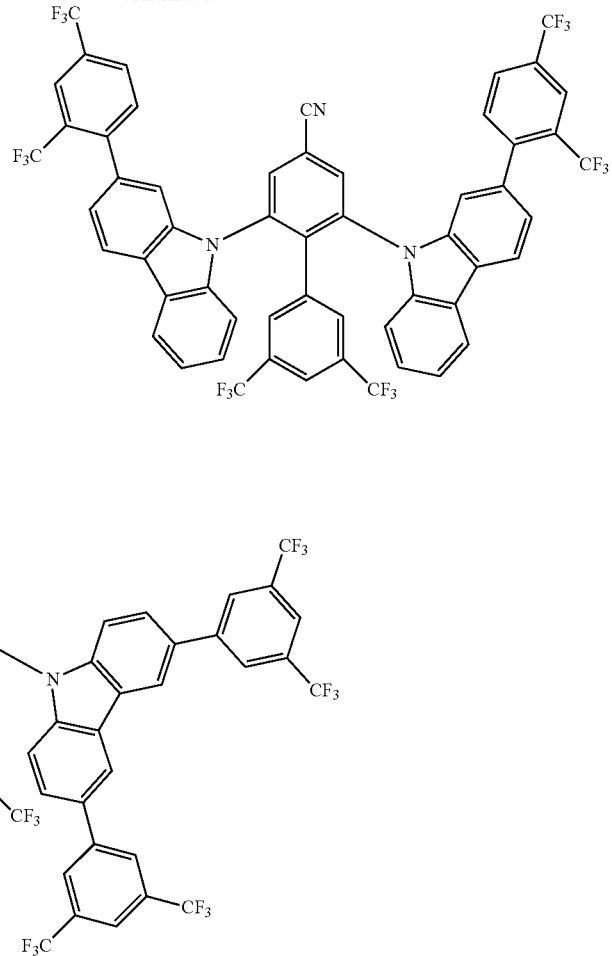
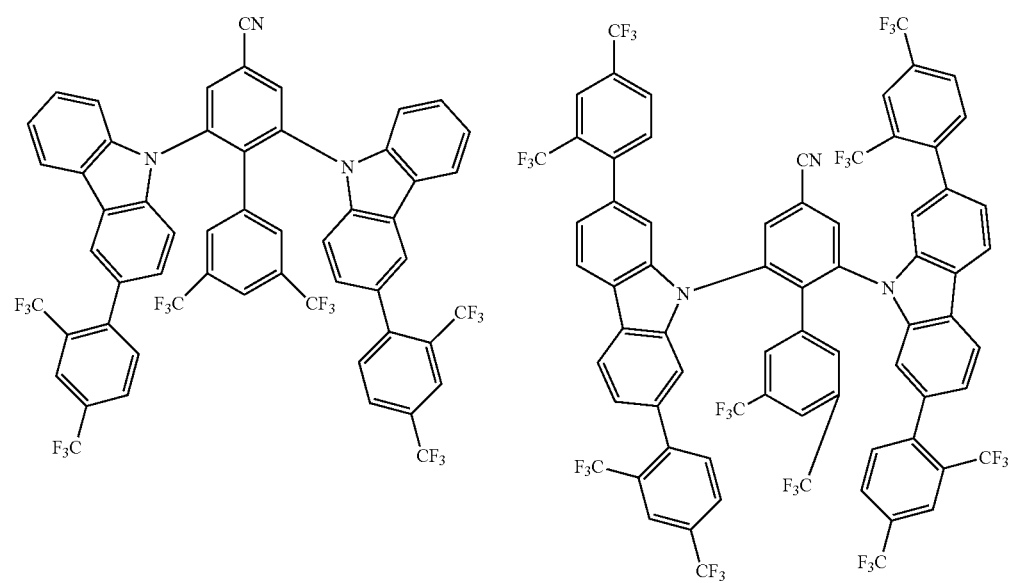

-continued
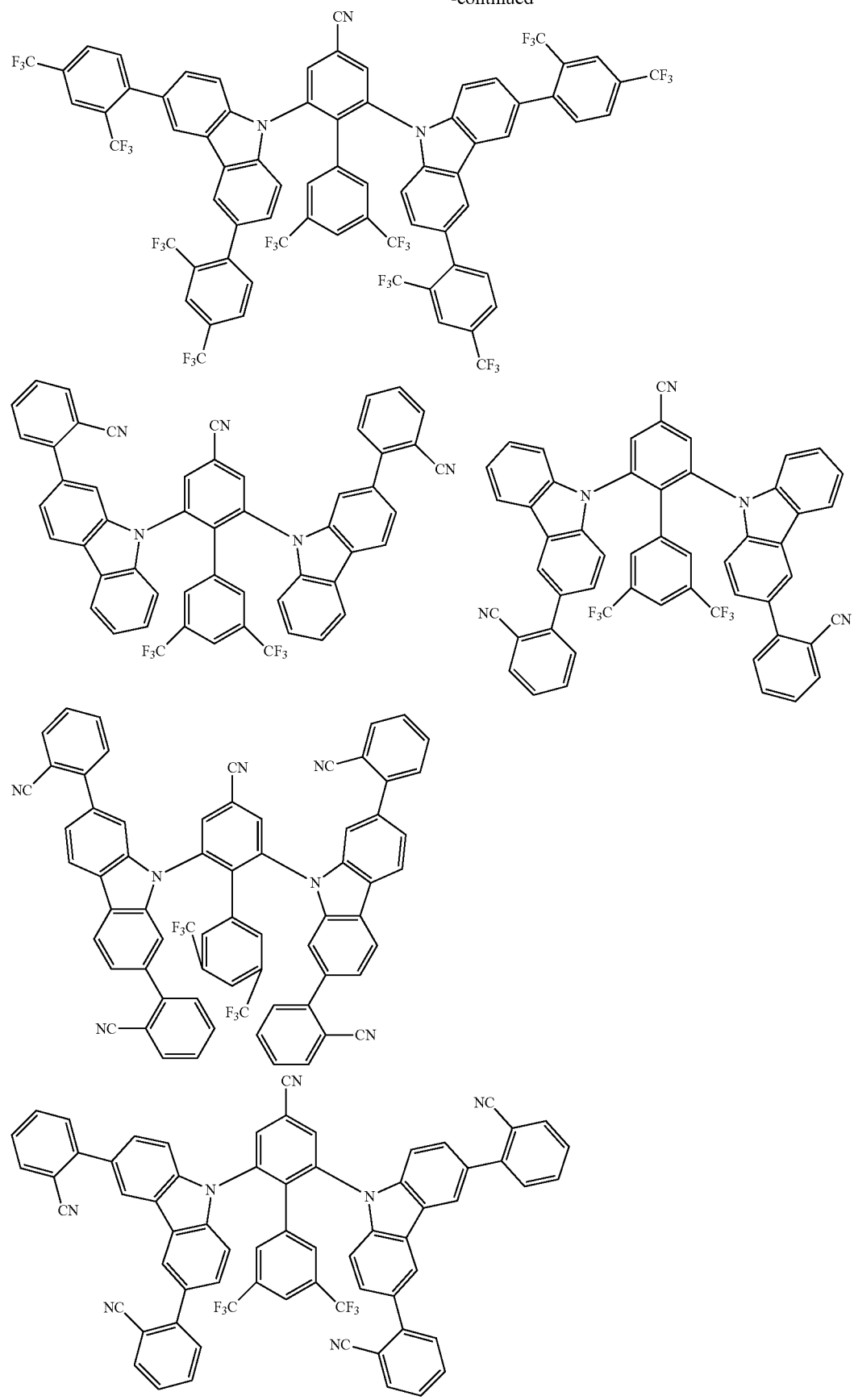

-continued
131
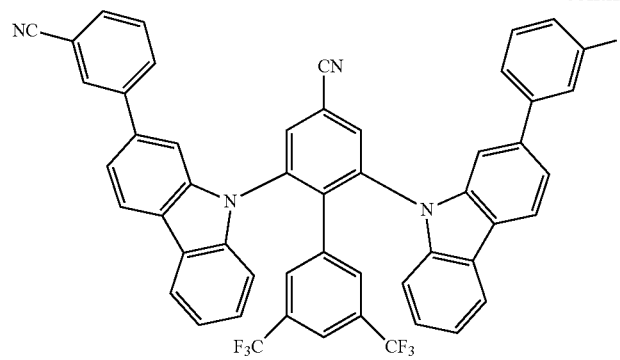
132
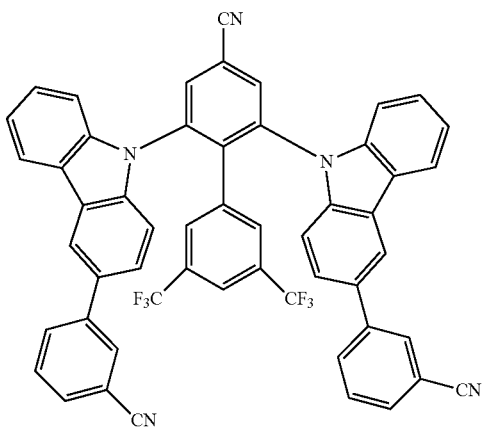
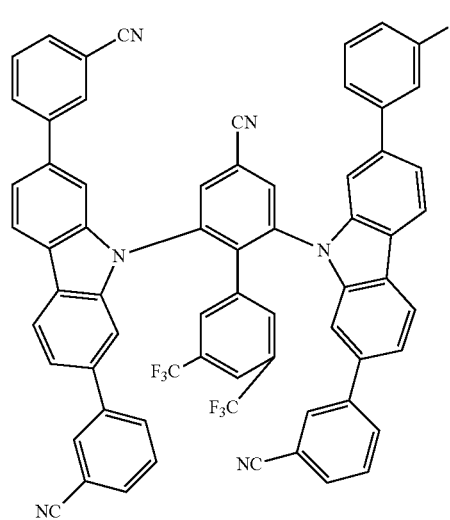
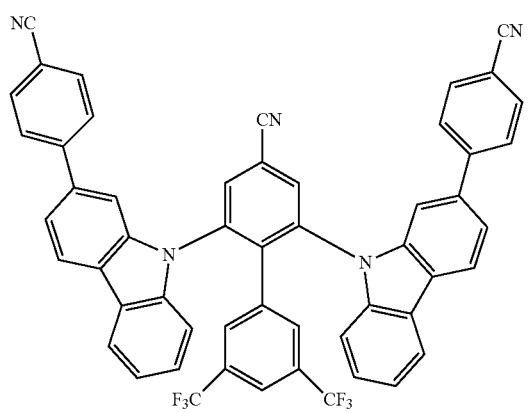
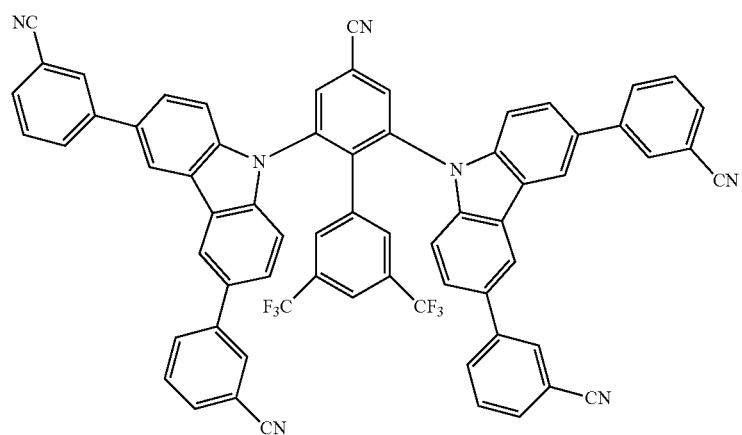

-continued
| 133 | 134 |
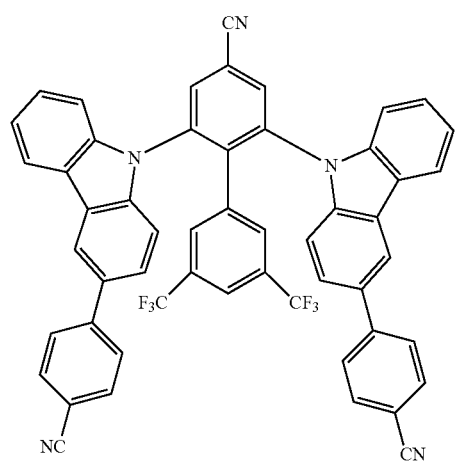
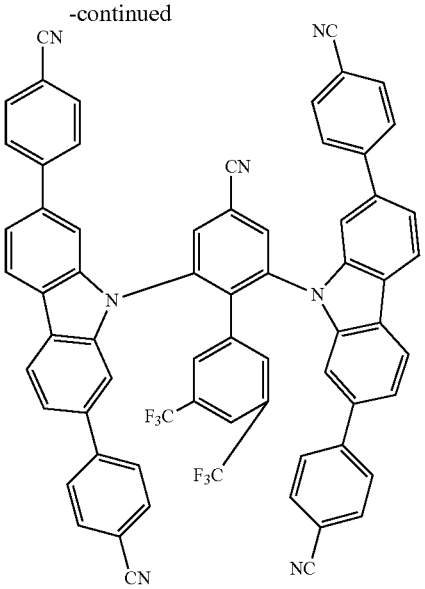
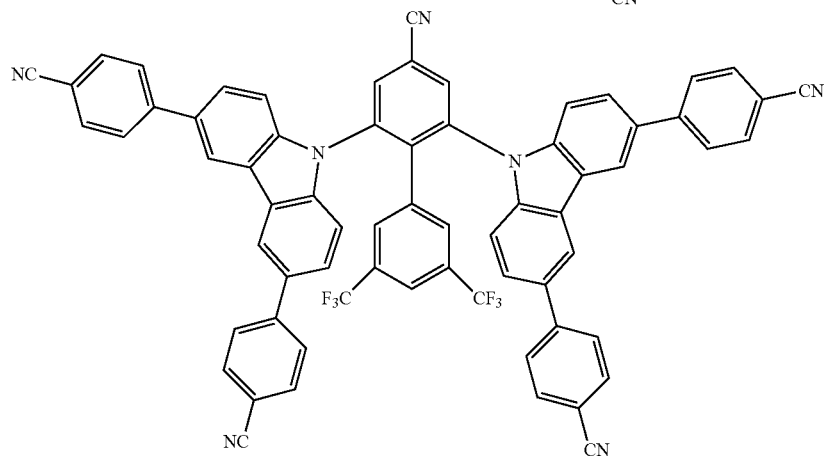
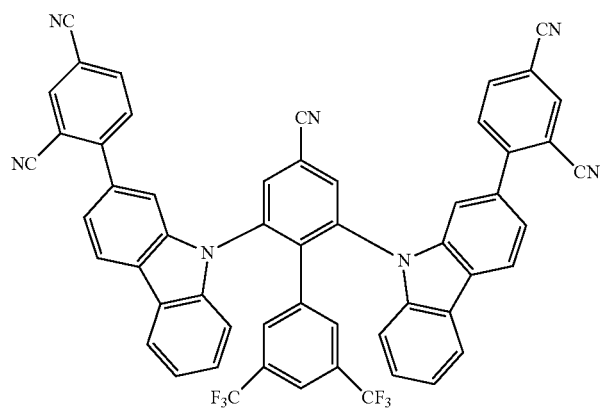
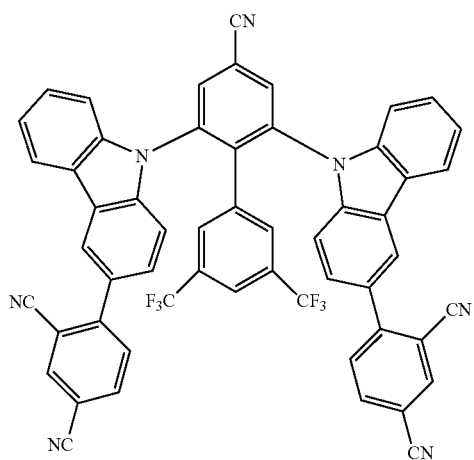

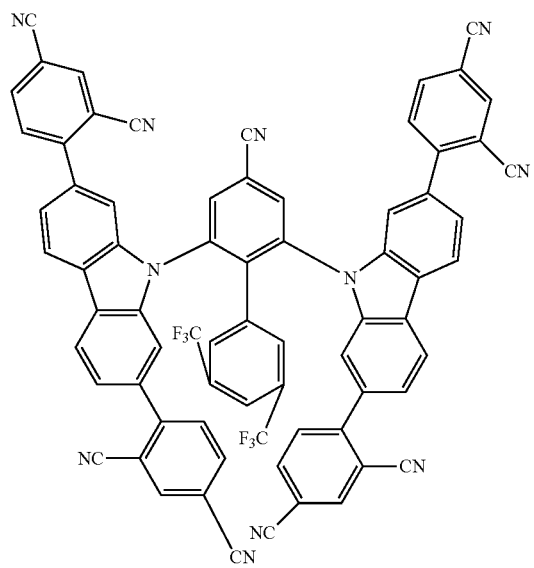
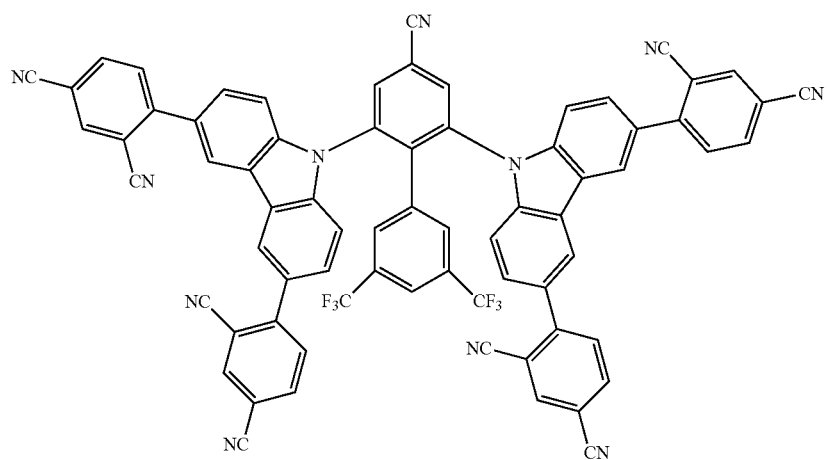
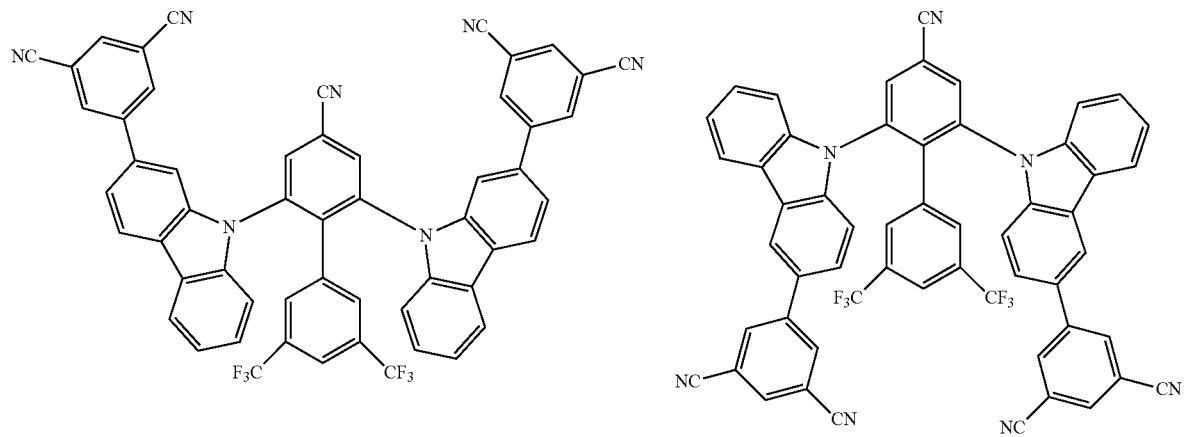

137
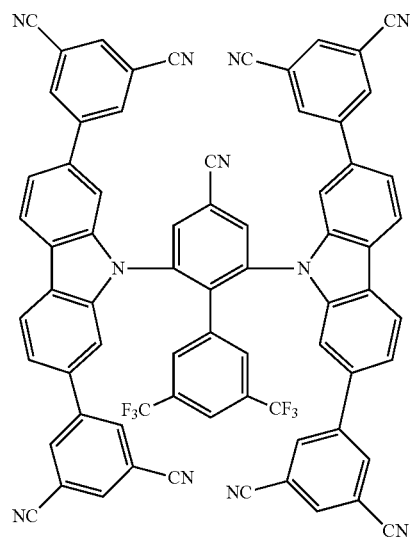
138
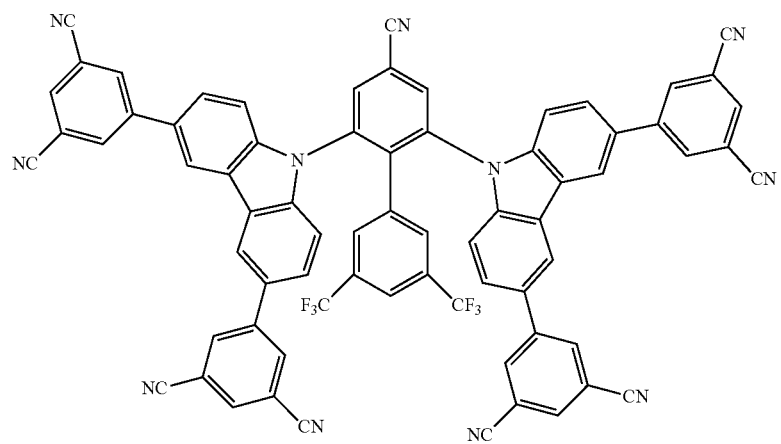
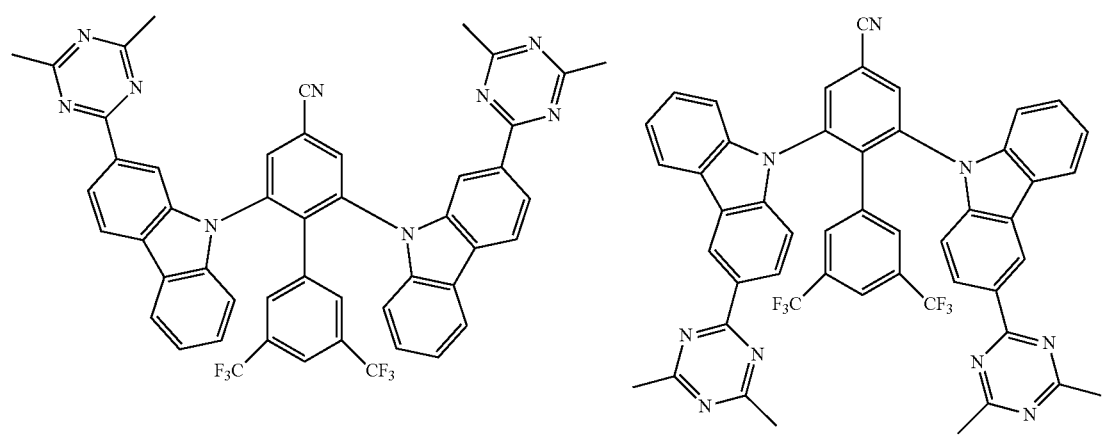

139
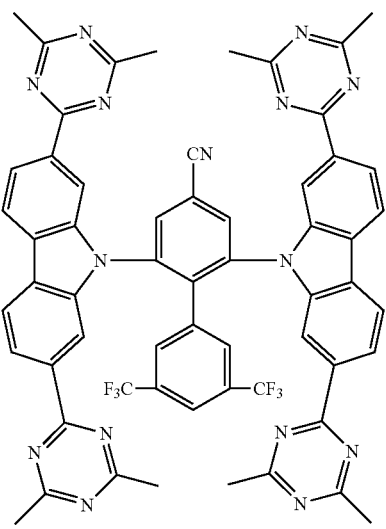
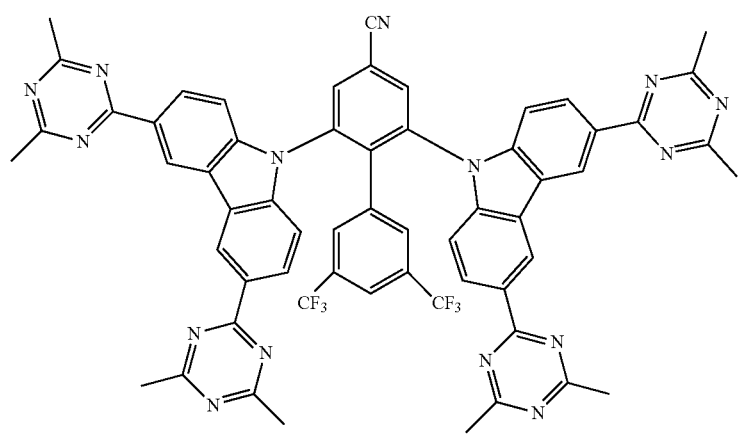
140
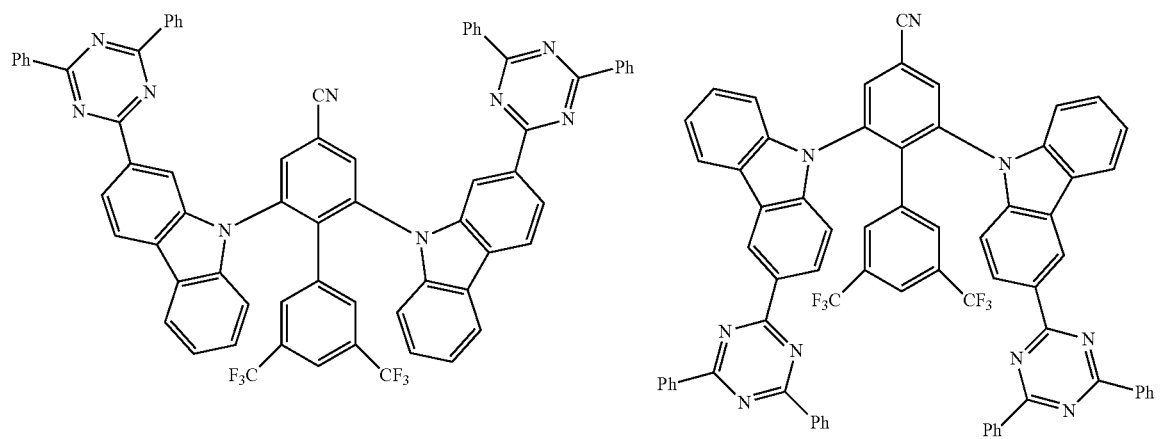

141
142
-continued
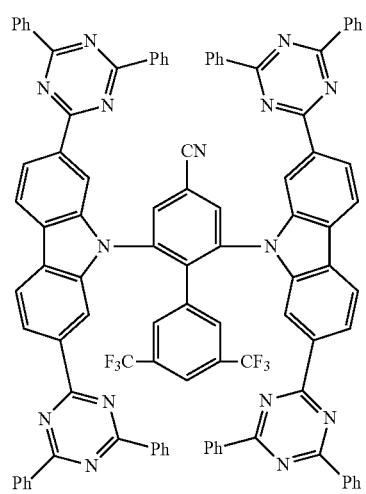
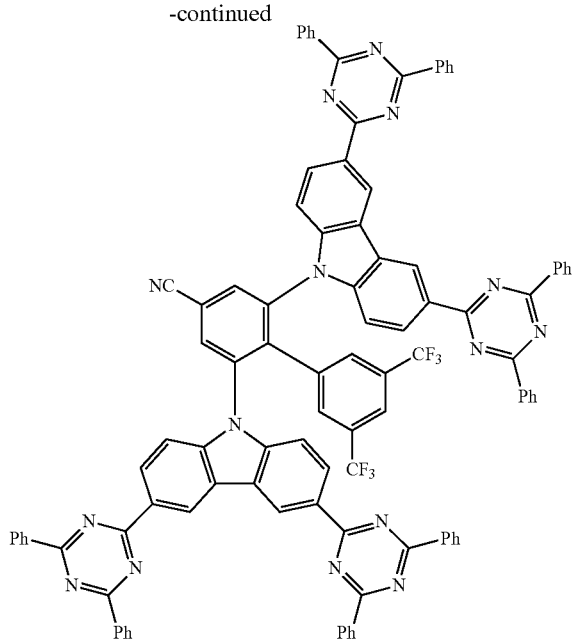
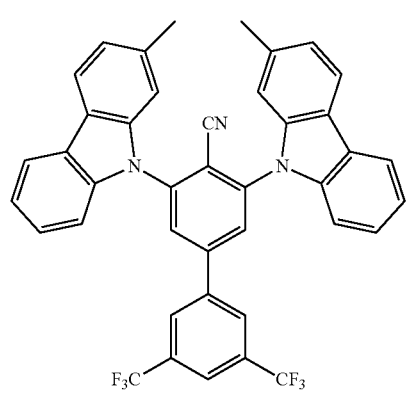
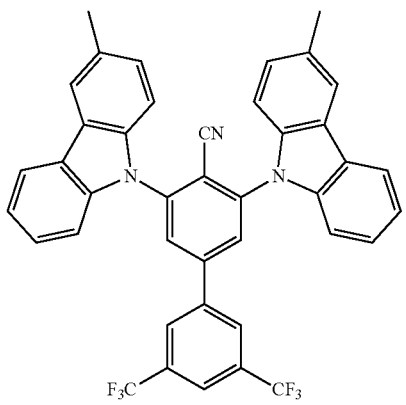
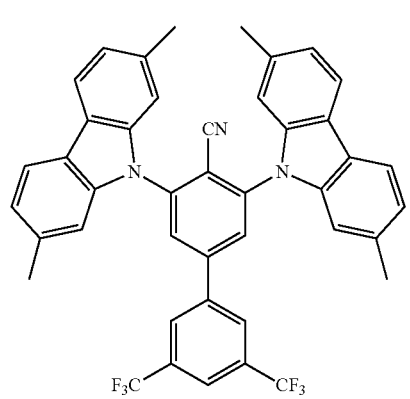
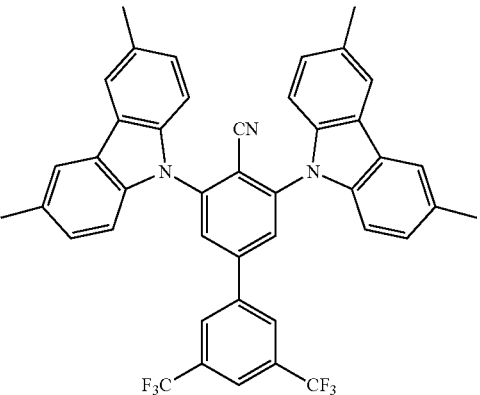

-continued
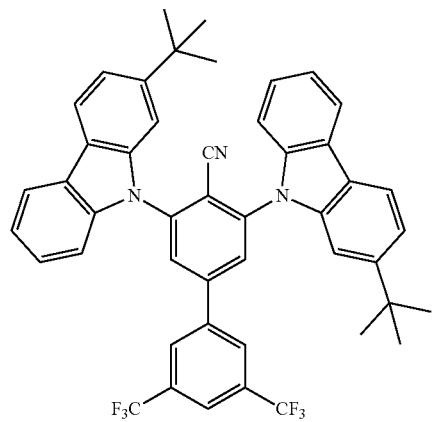
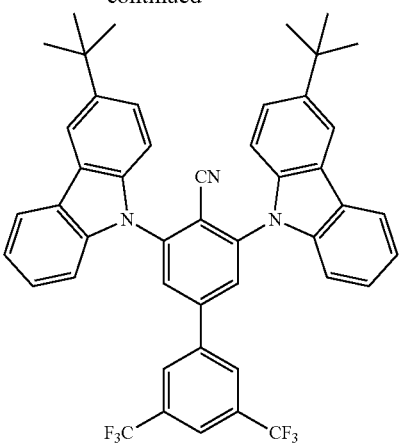
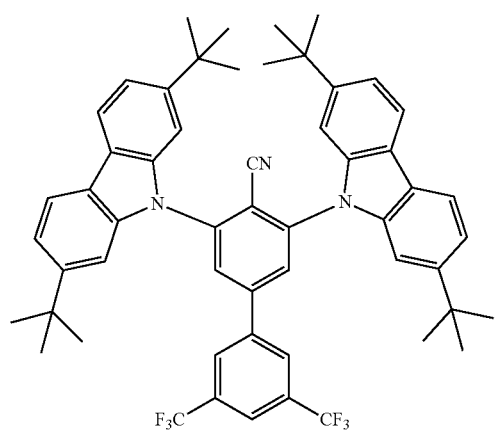
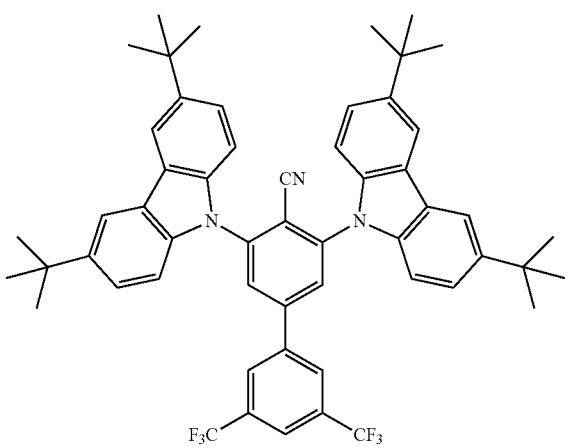
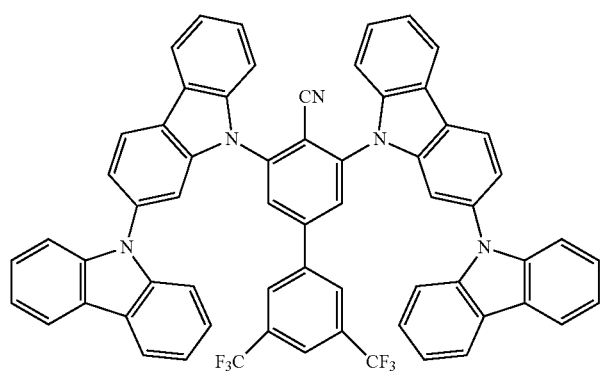
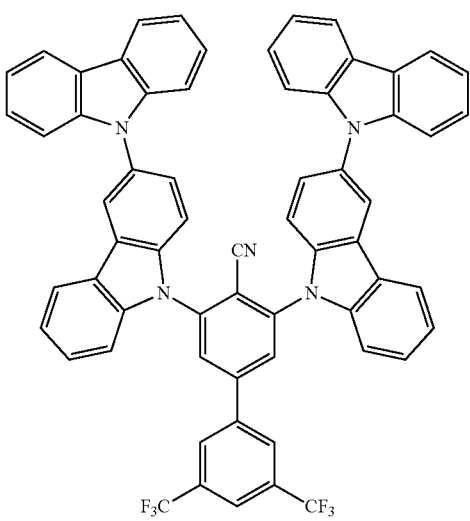

-continued
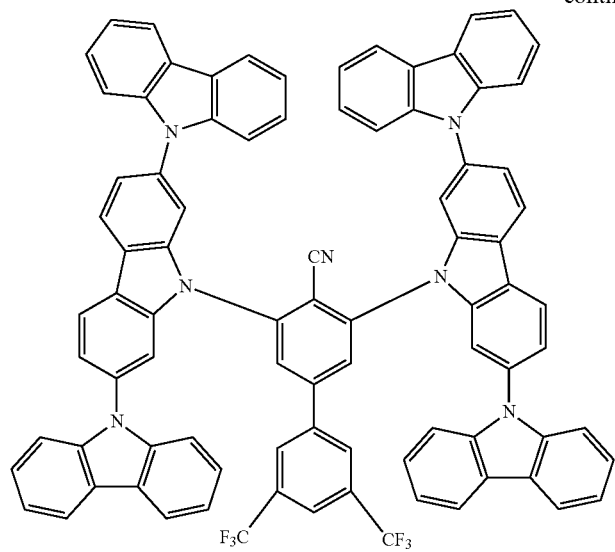
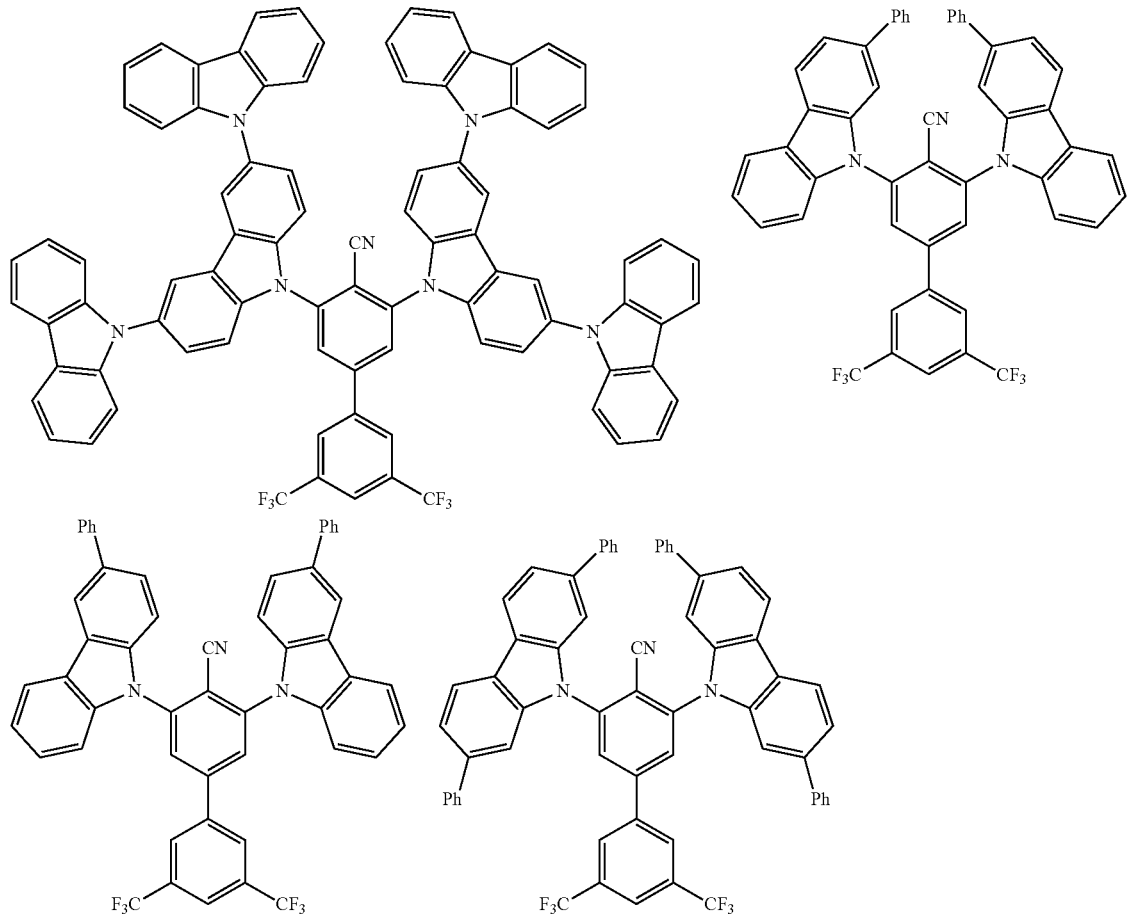

-continued
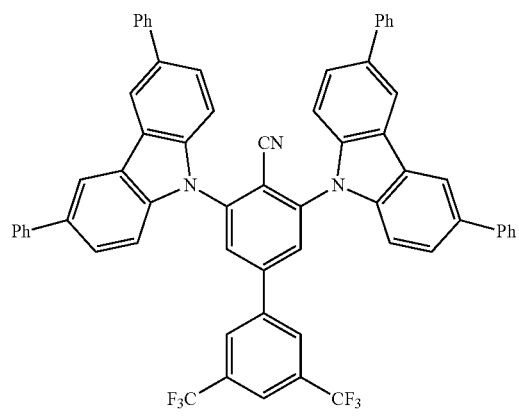
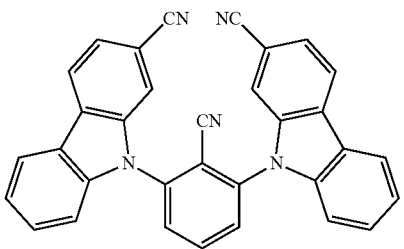
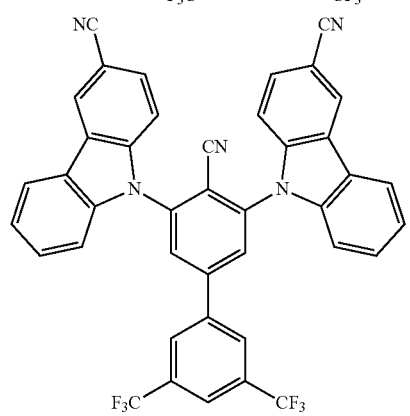
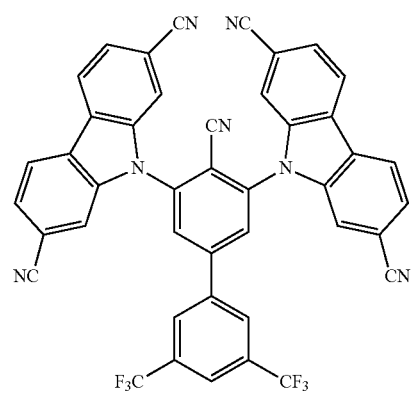
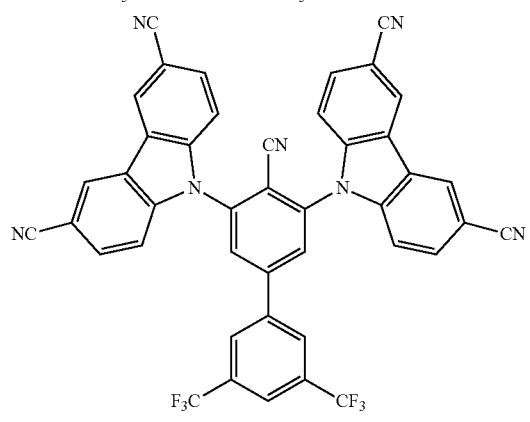
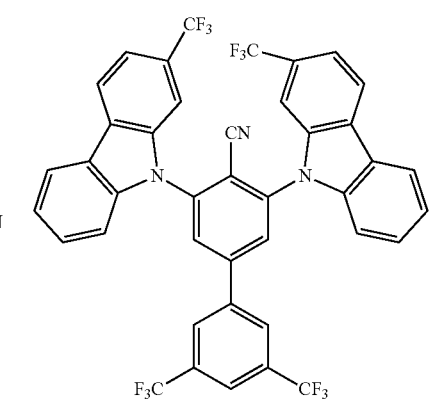
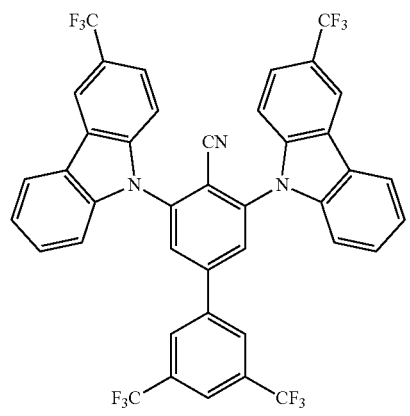
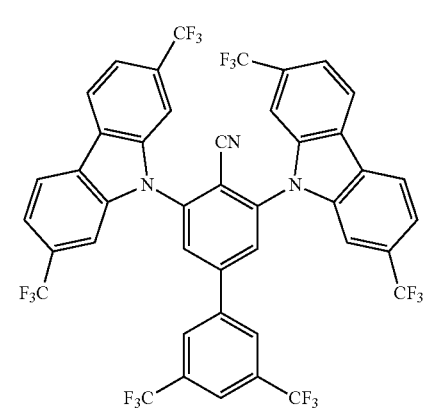

-continued
149
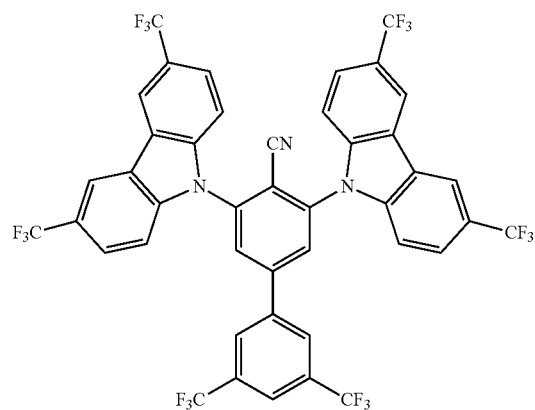
150
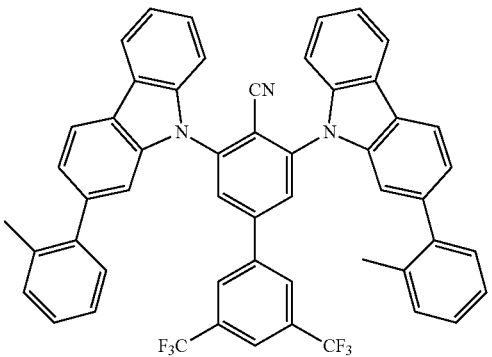
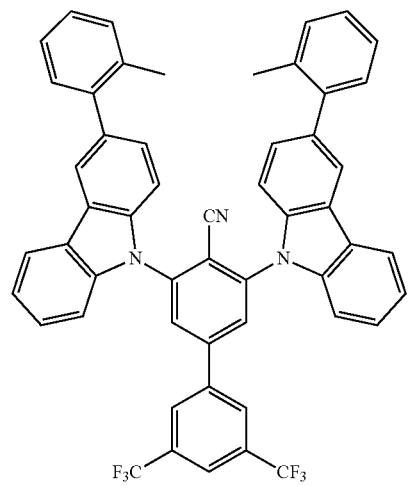
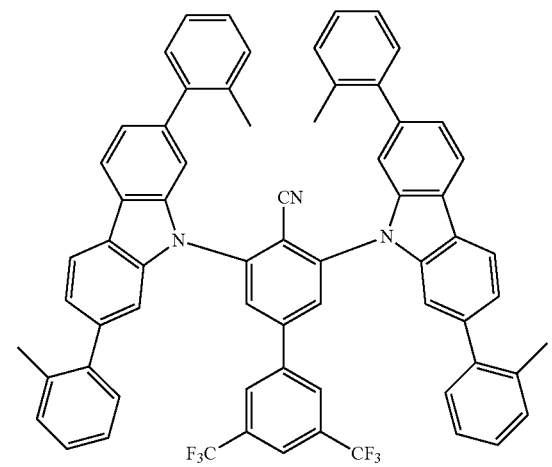
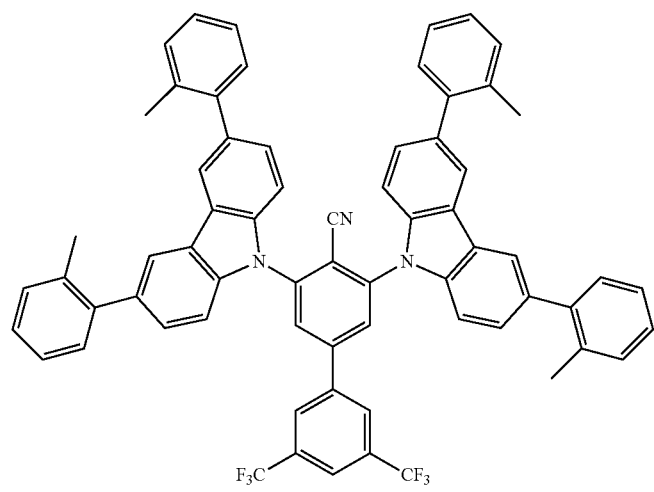
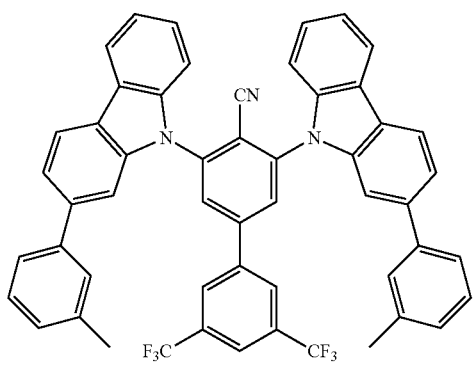

-continued
151
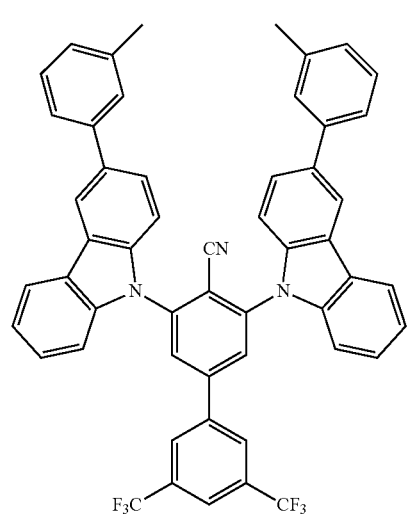
152
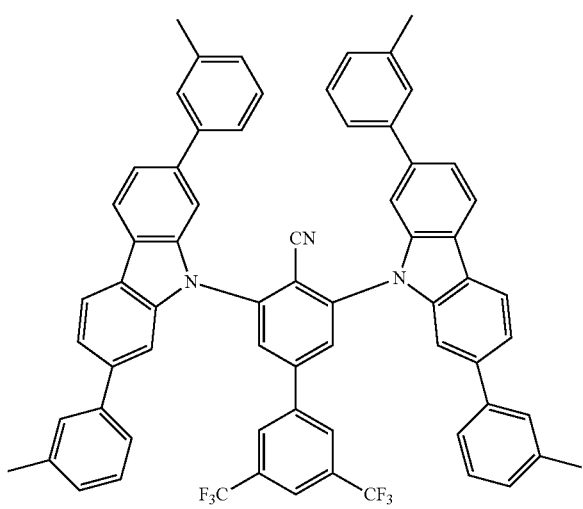
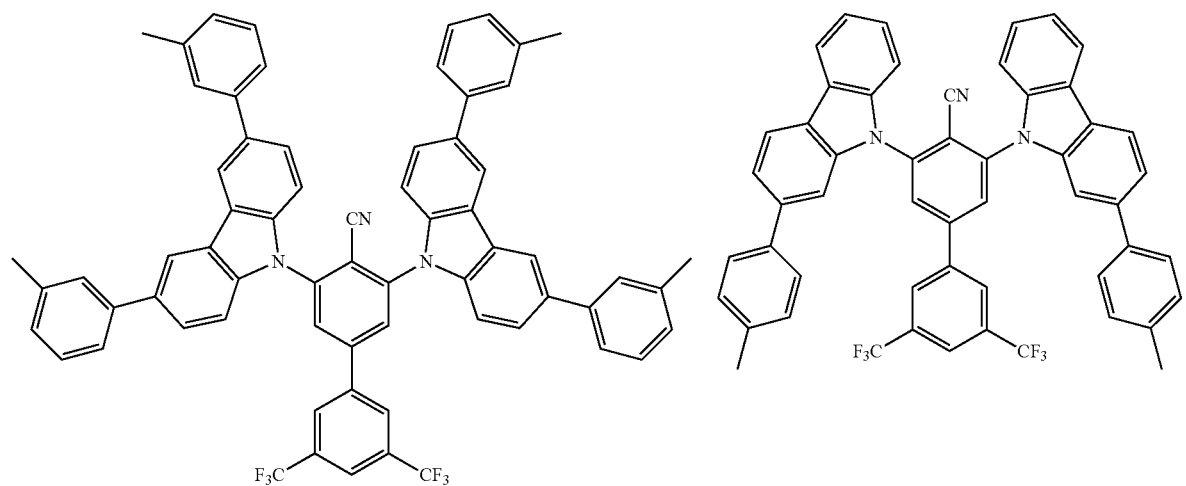
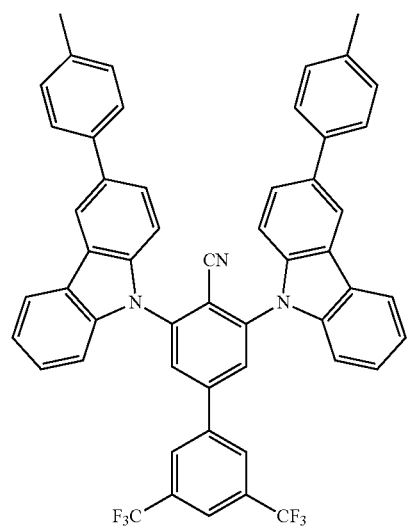
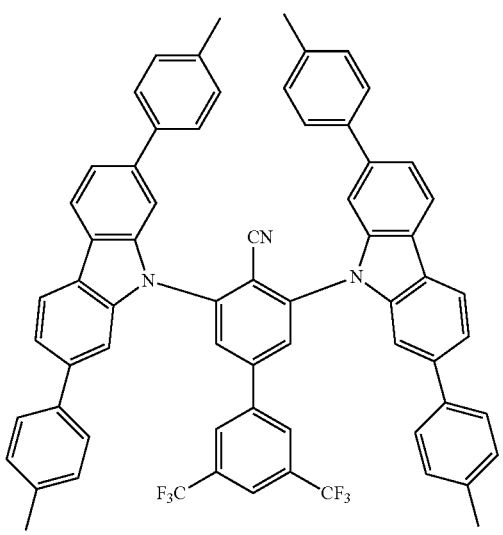

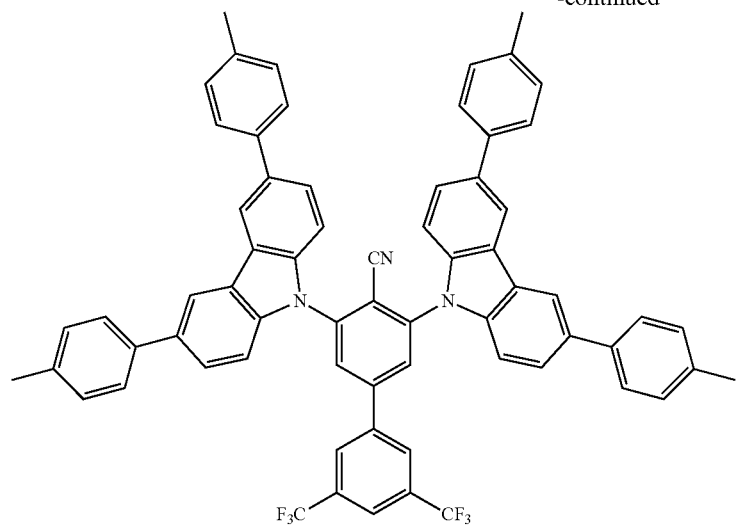
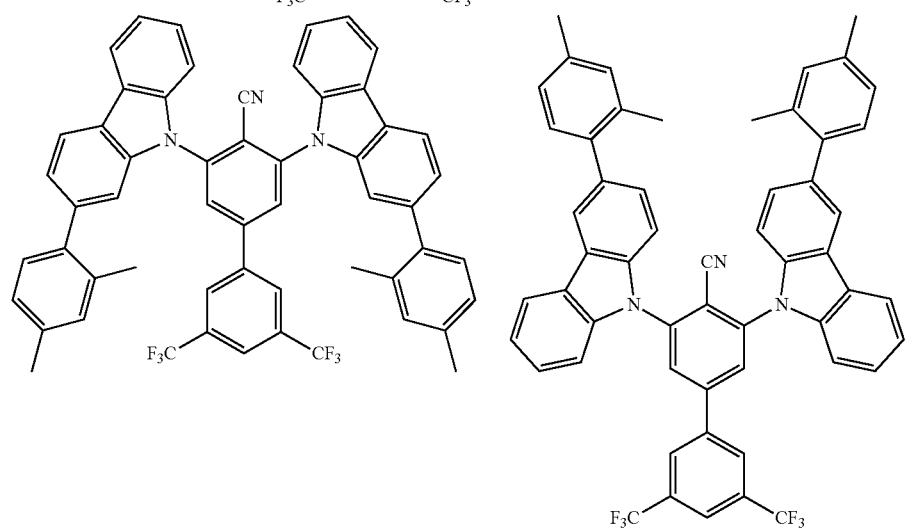
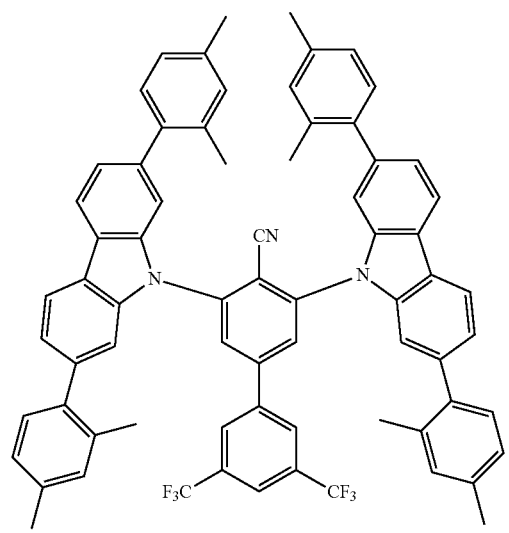

-continued
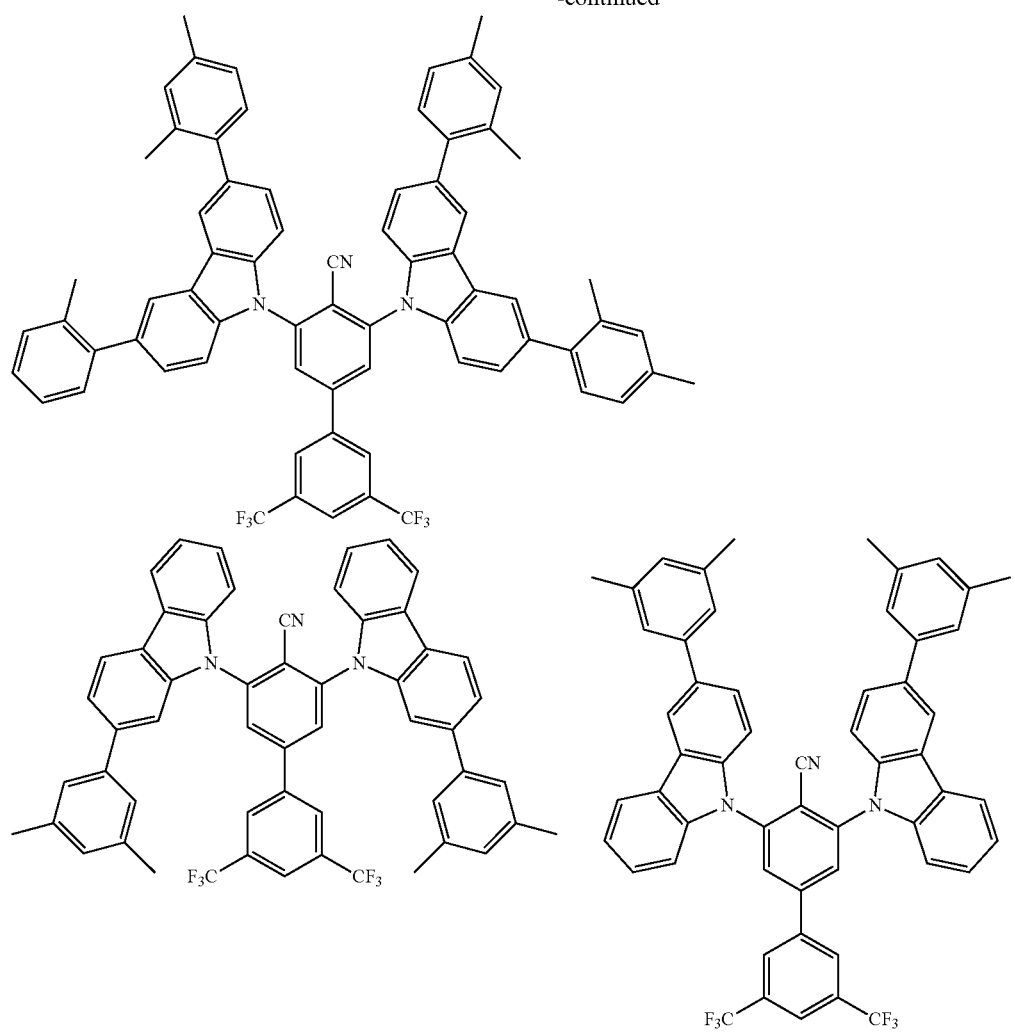
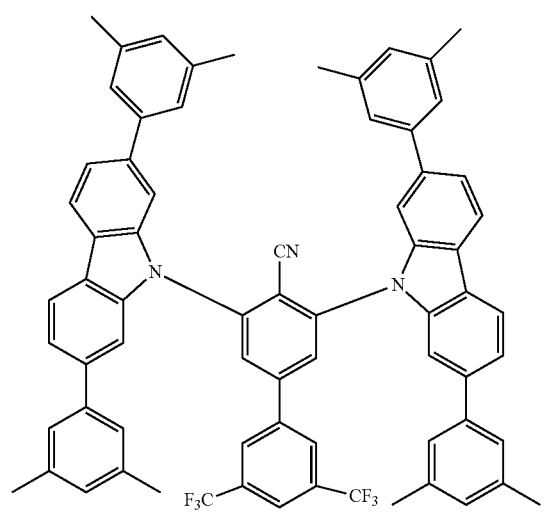

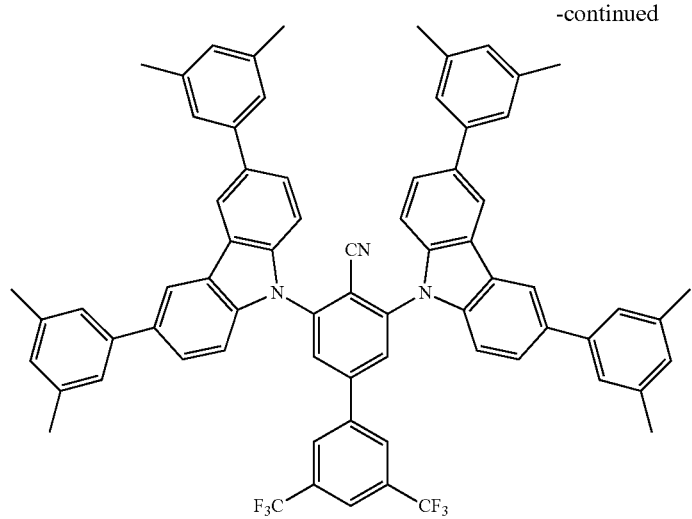
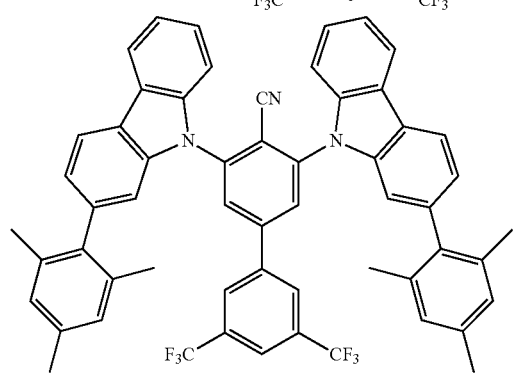
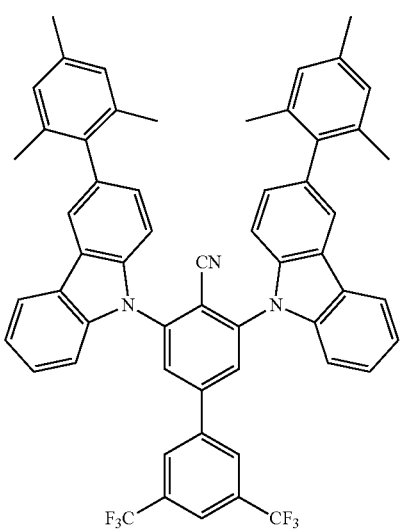
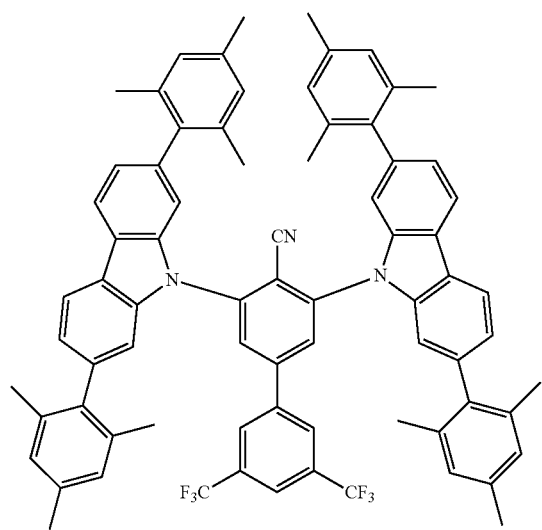

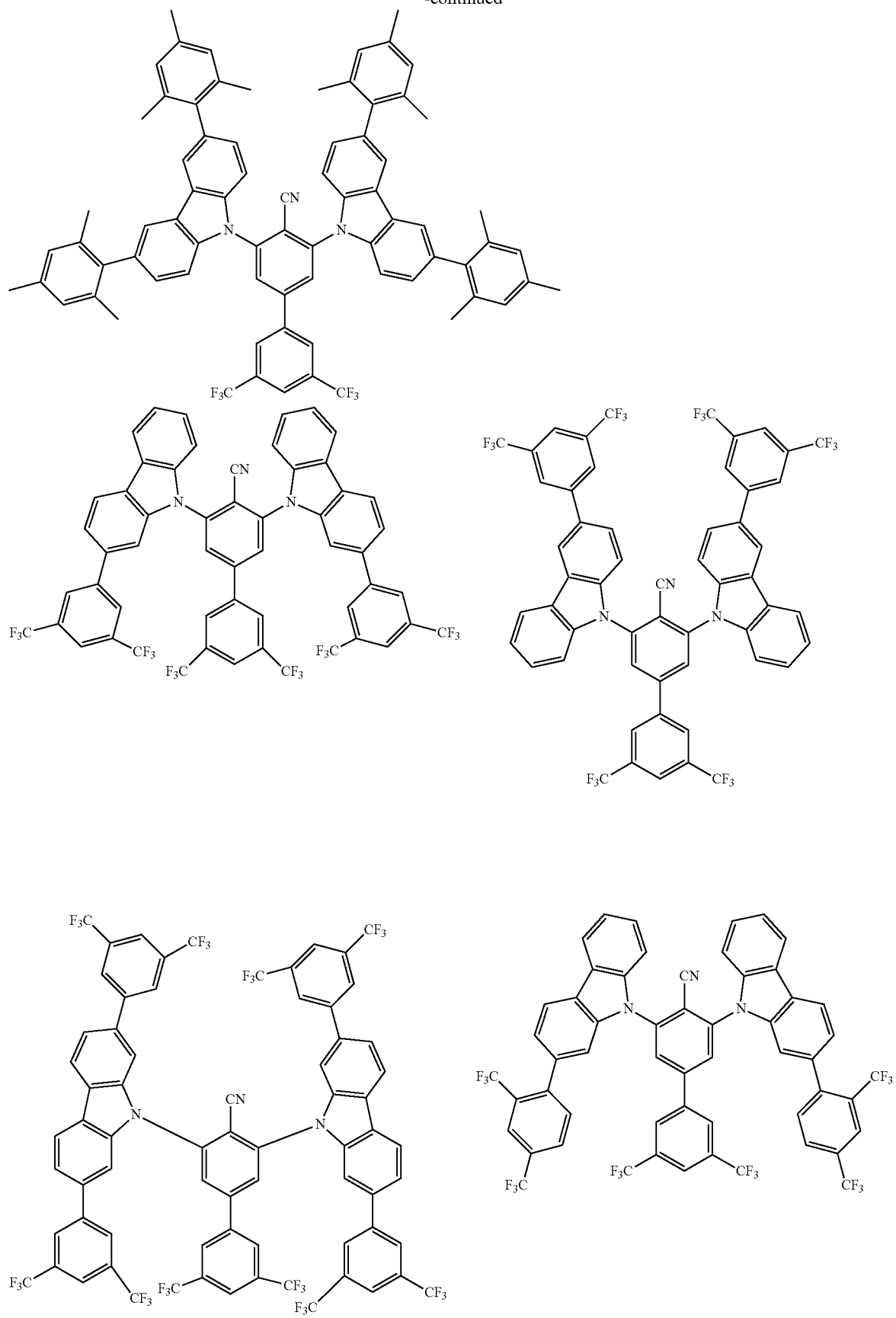

-continued
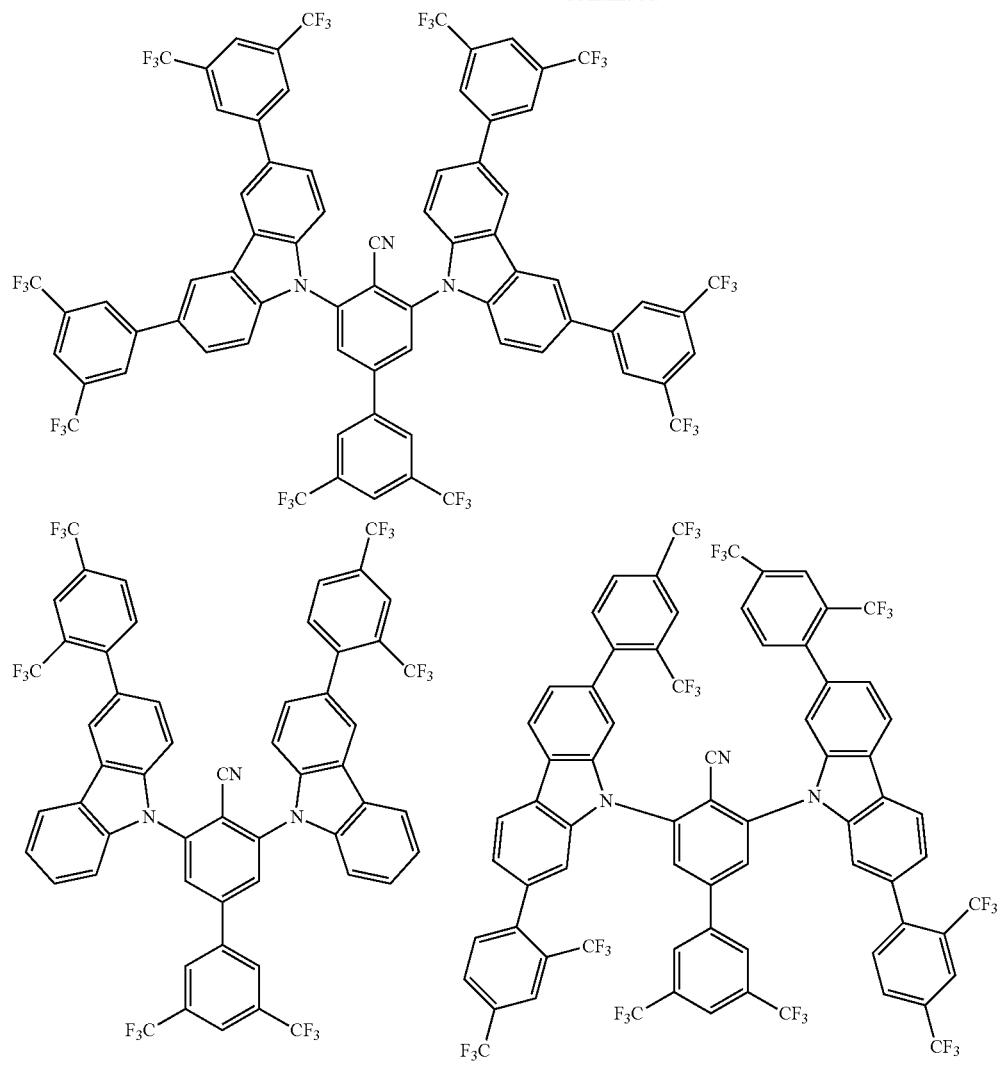
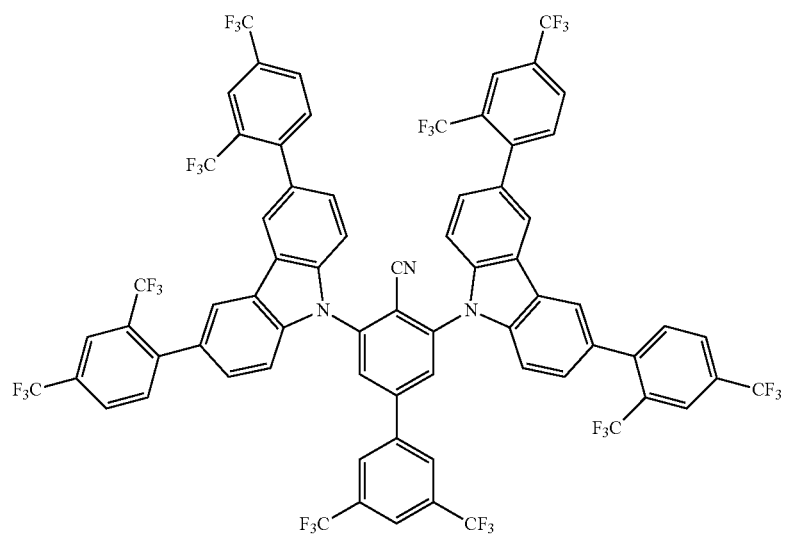

163
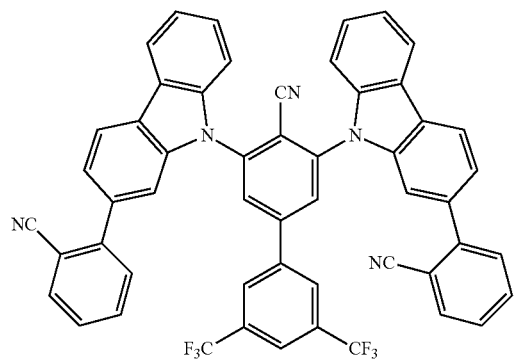
164
-continued
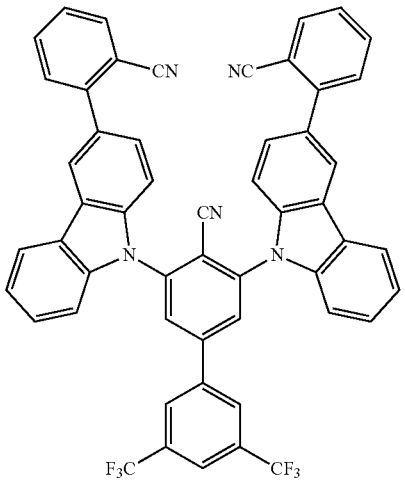
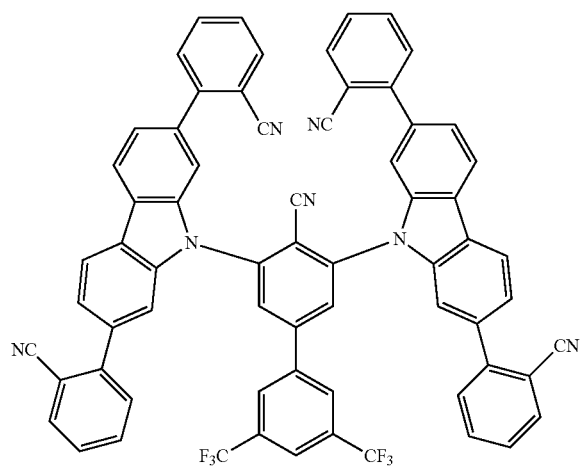
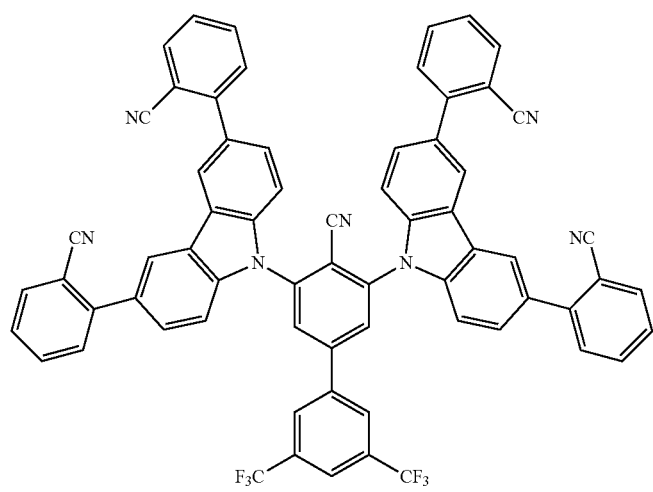

165
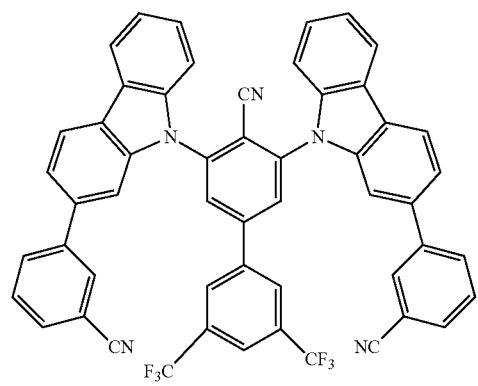
166
-continued
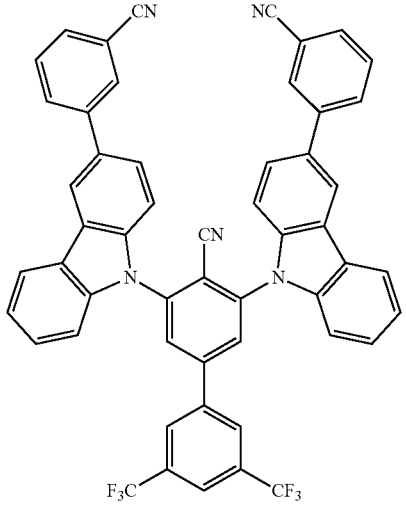
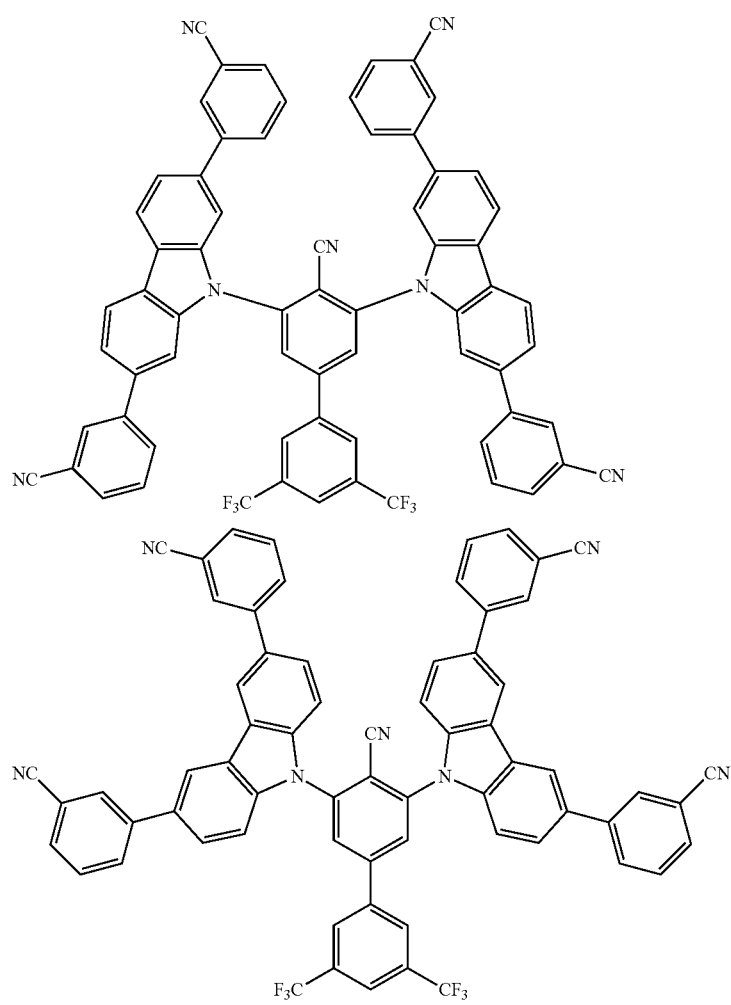

167
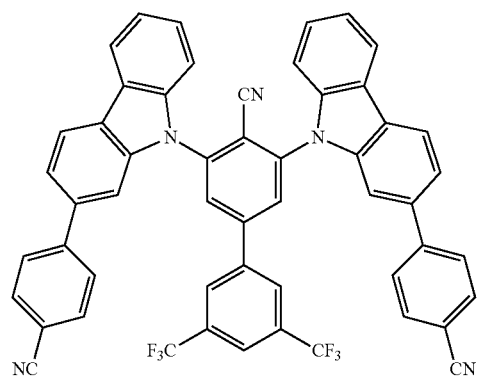
-continued
168
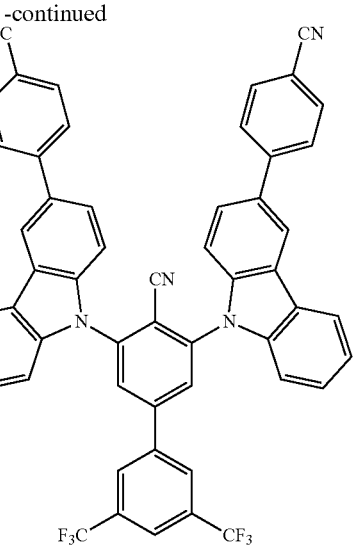
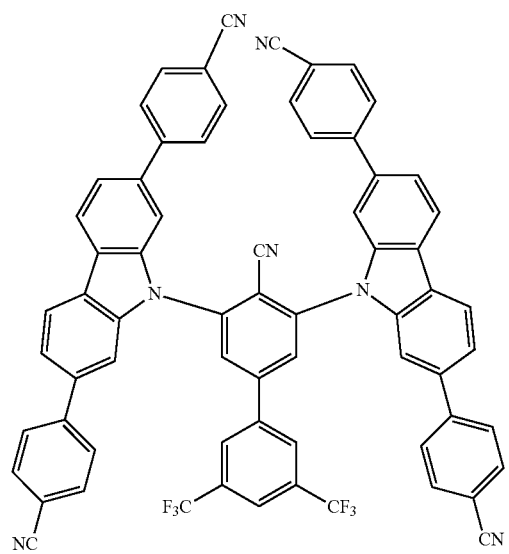
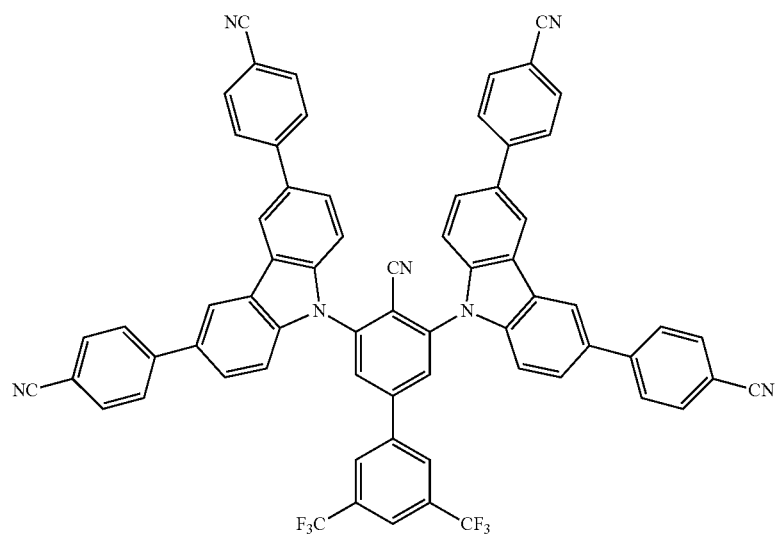

169
170
-continued
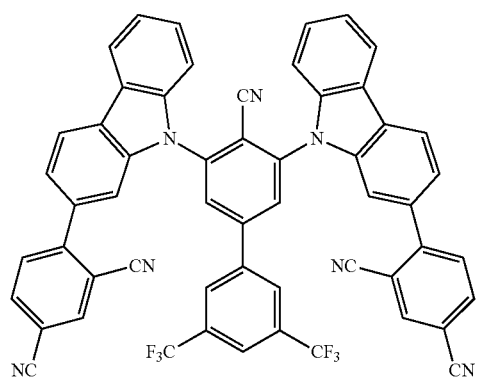
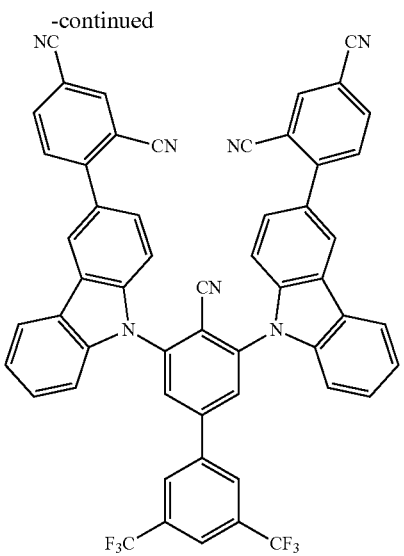
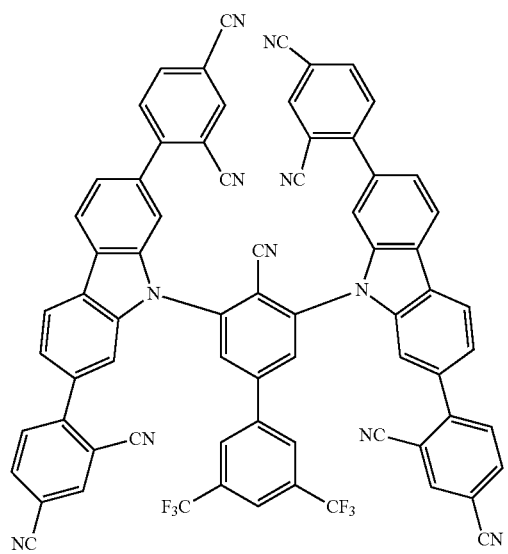
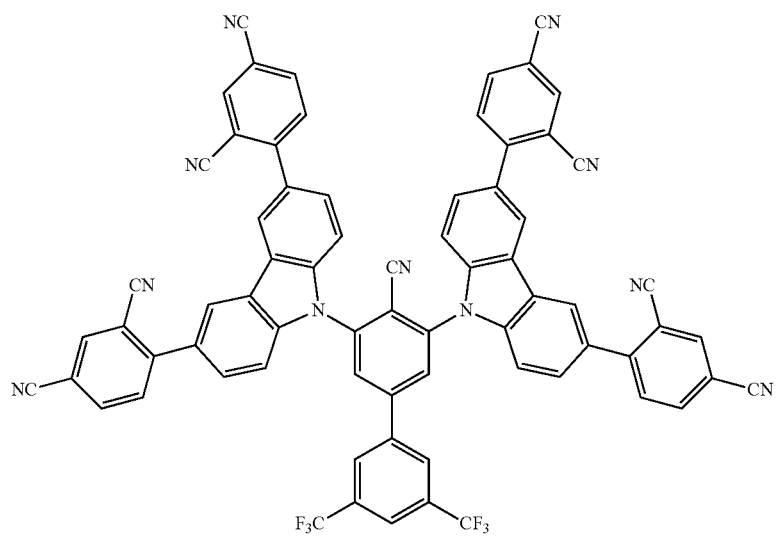

171
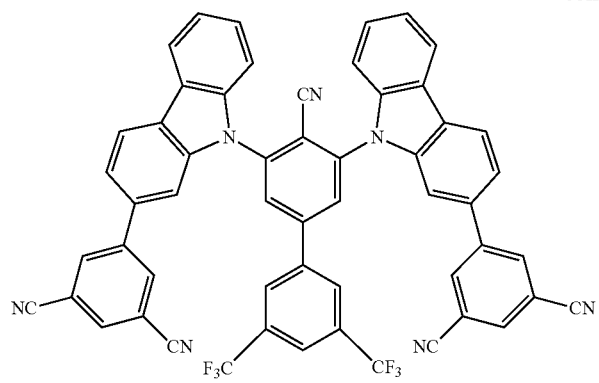
172
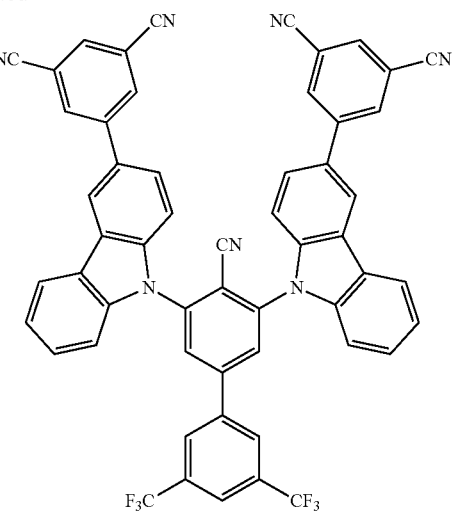
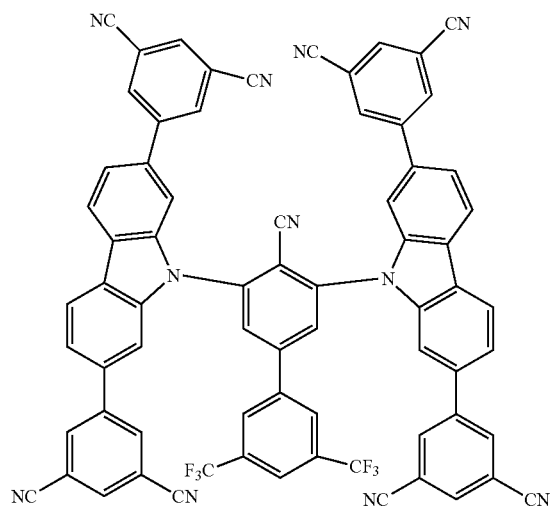
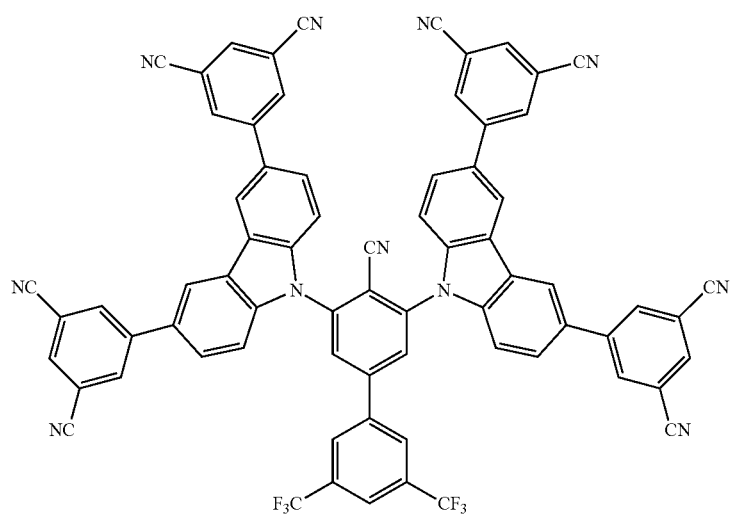

173
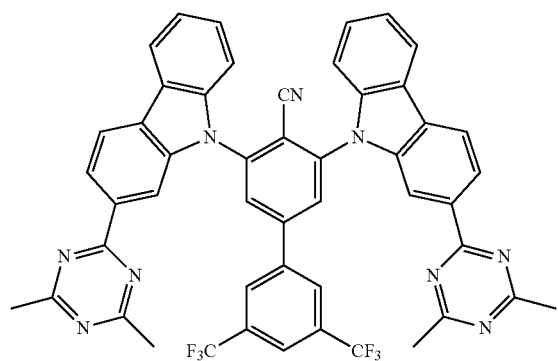
174
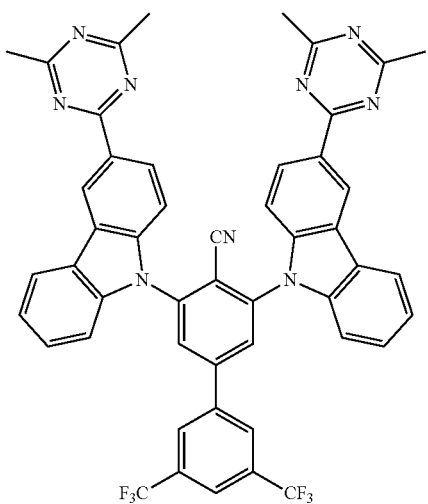
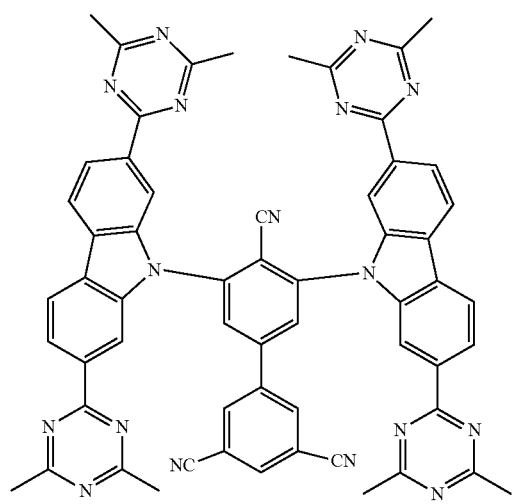
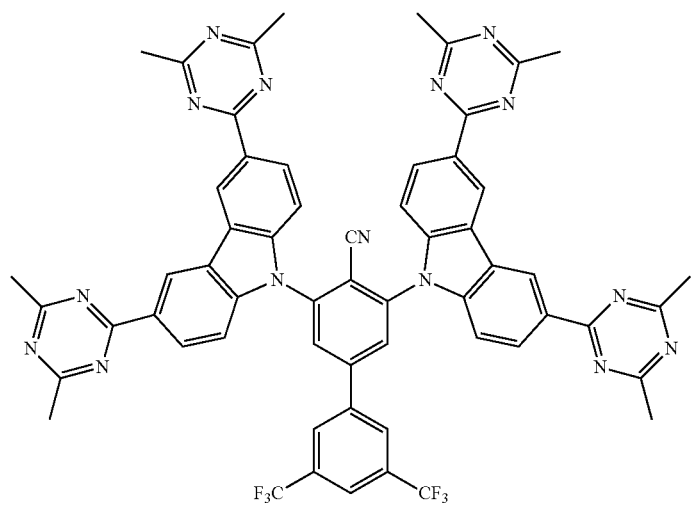

-continued
175
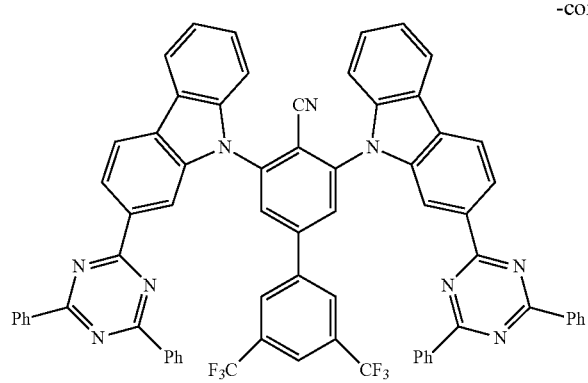
176
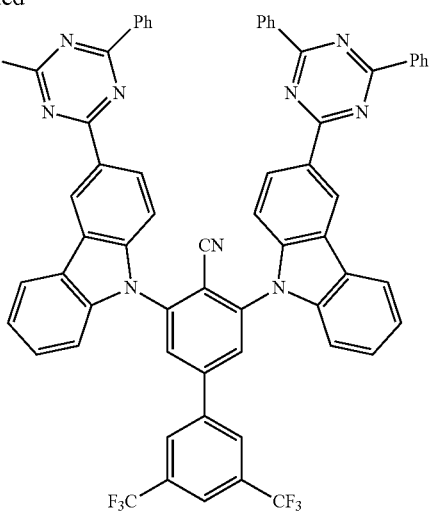
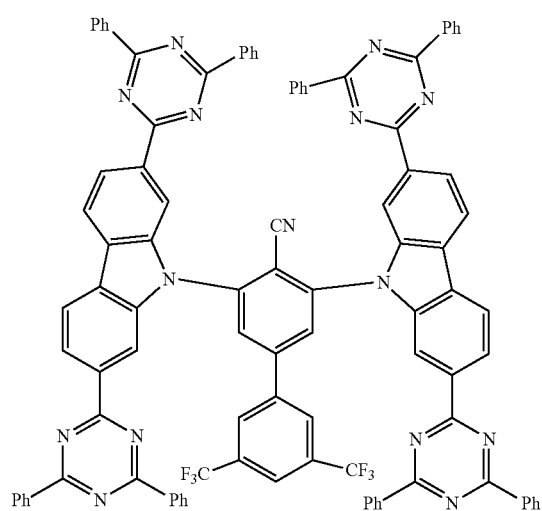
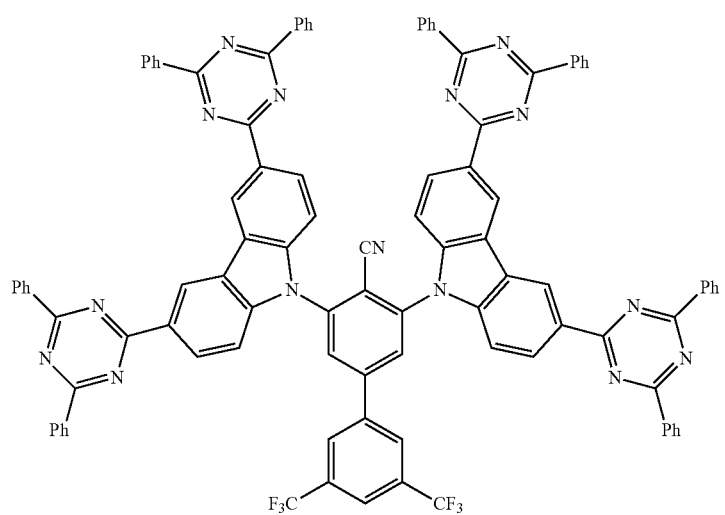

-continued
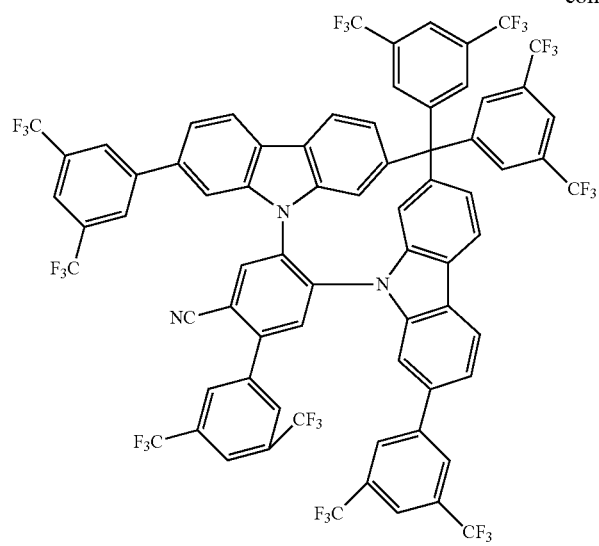
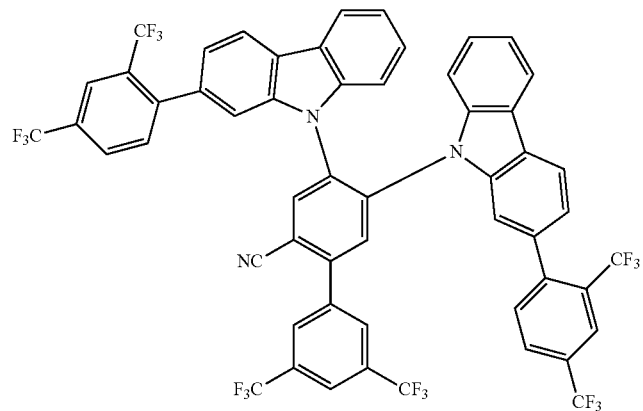
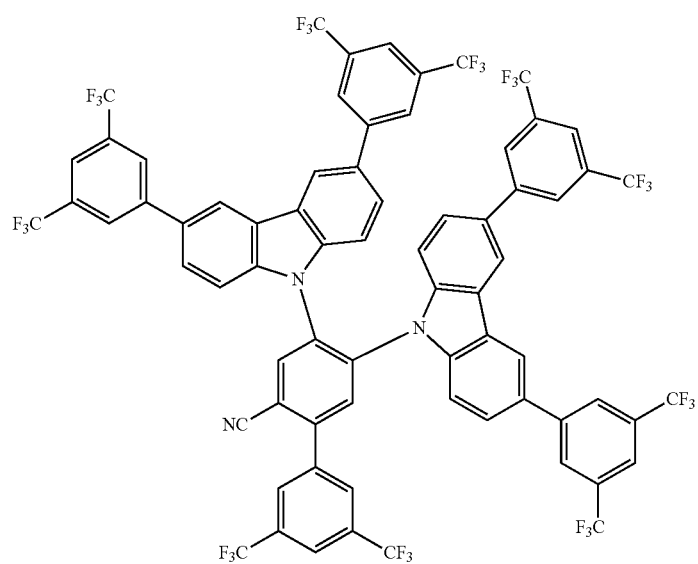

-continued
179
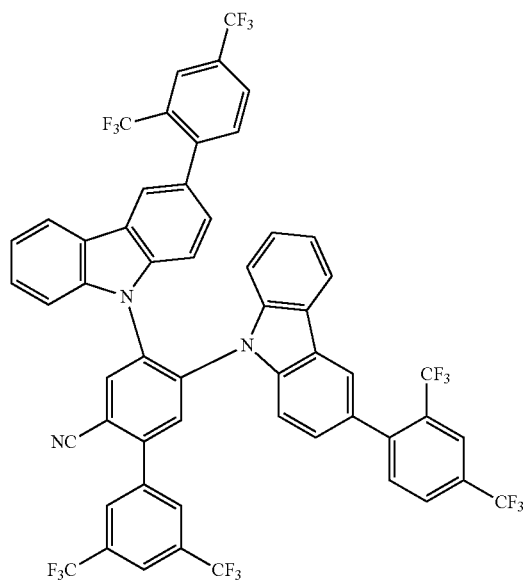
180
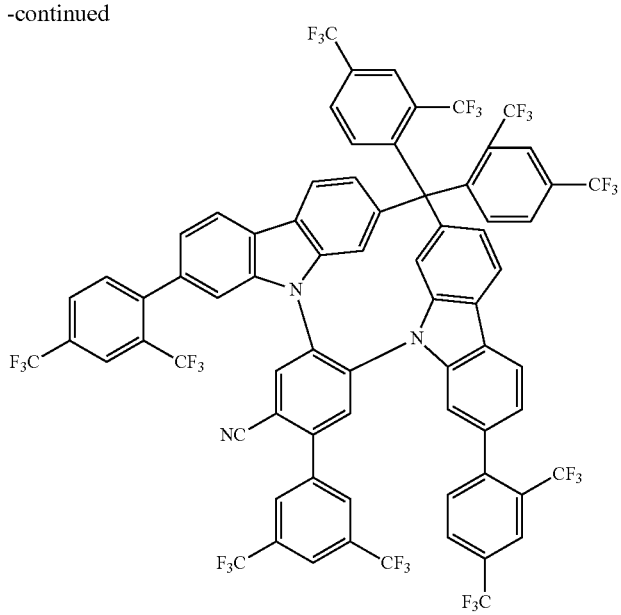
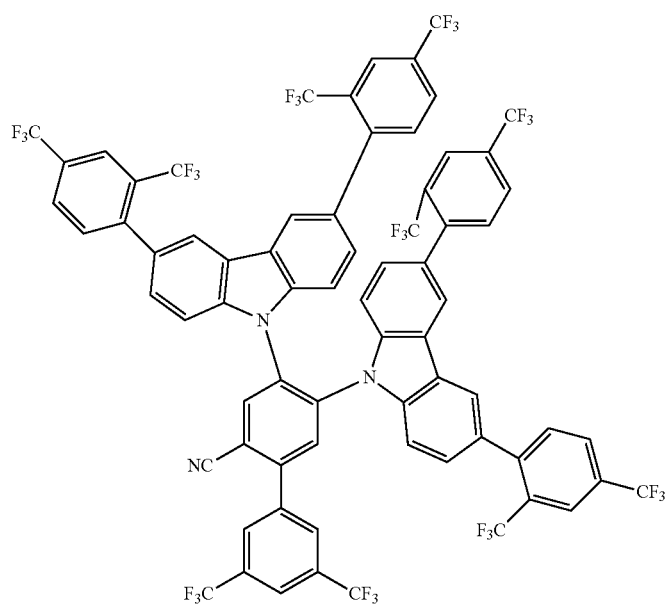
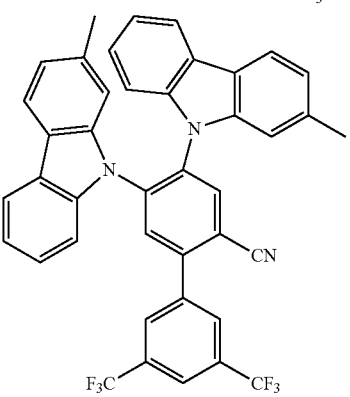
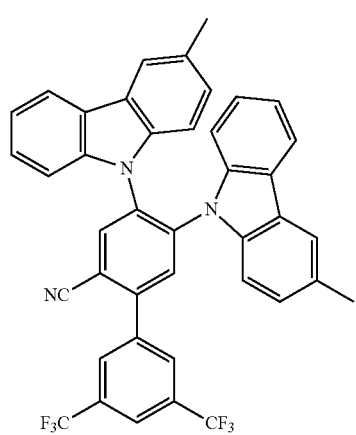
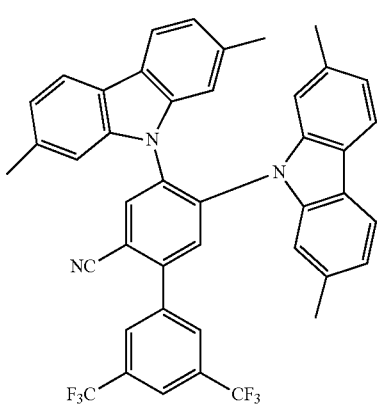
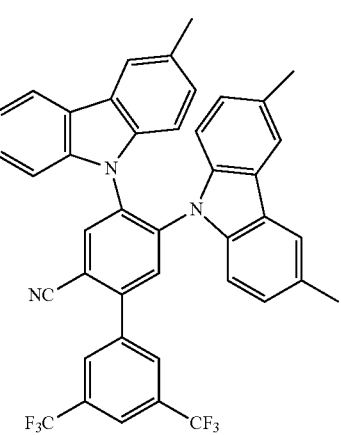

-continued
181 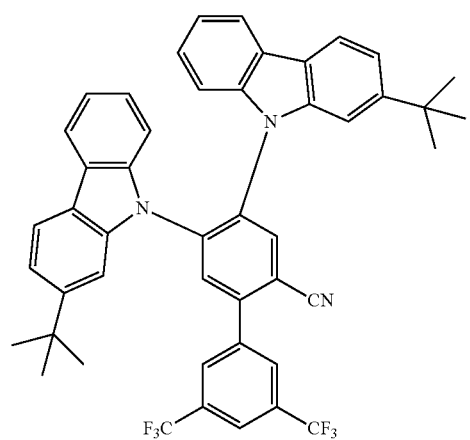
182 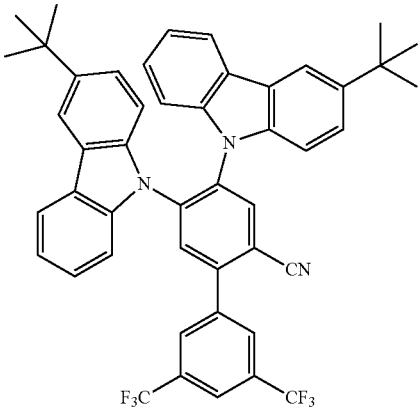
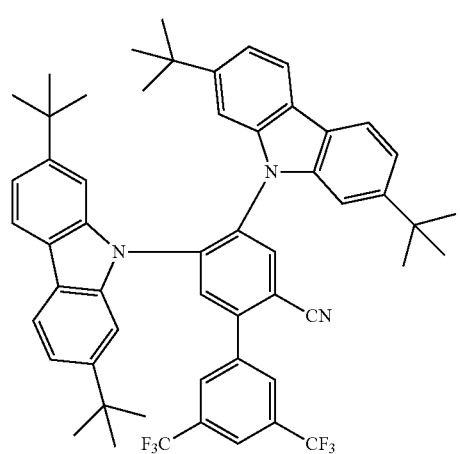
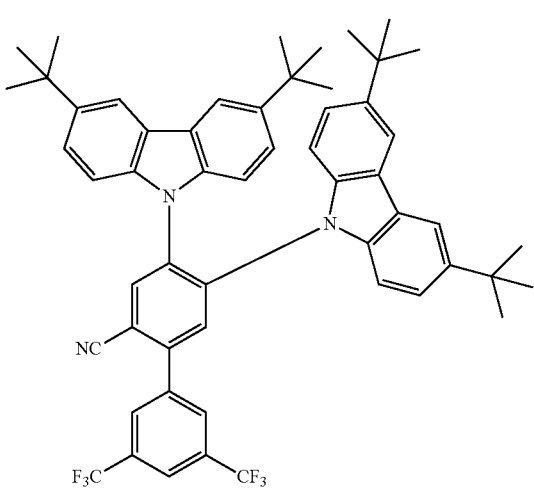
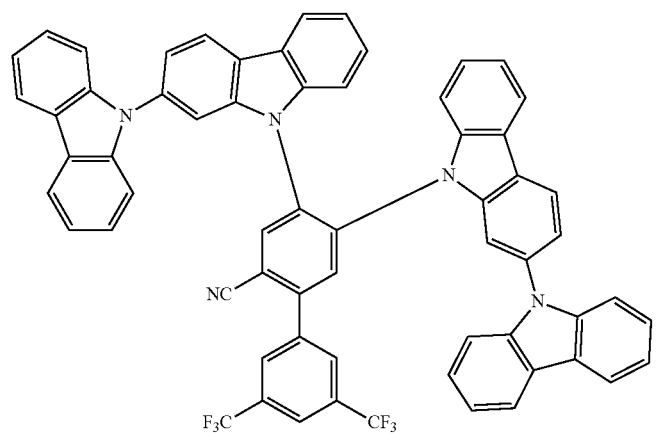
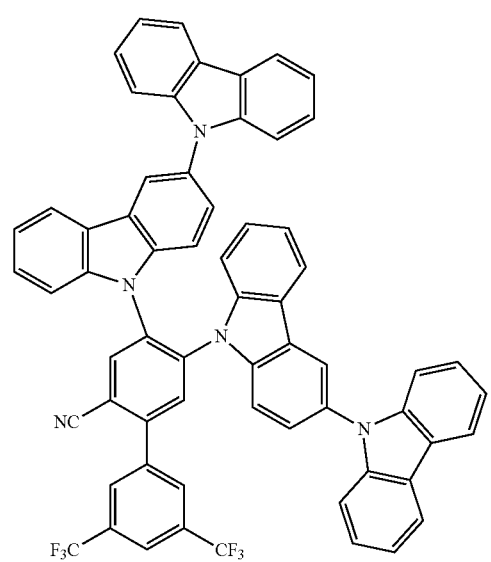

-continued
183 184
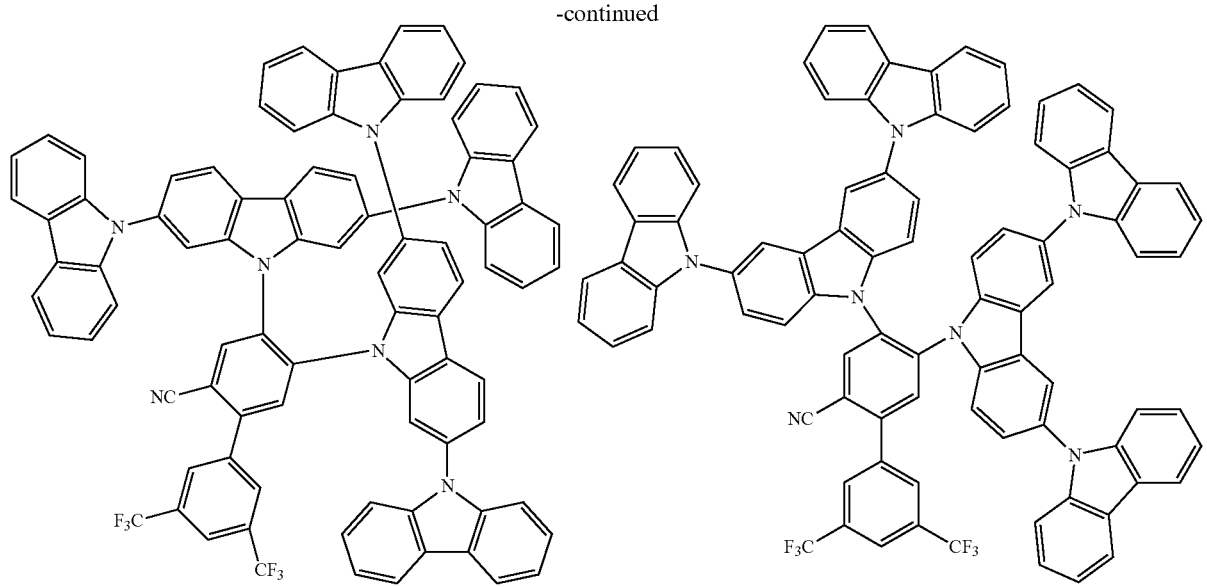
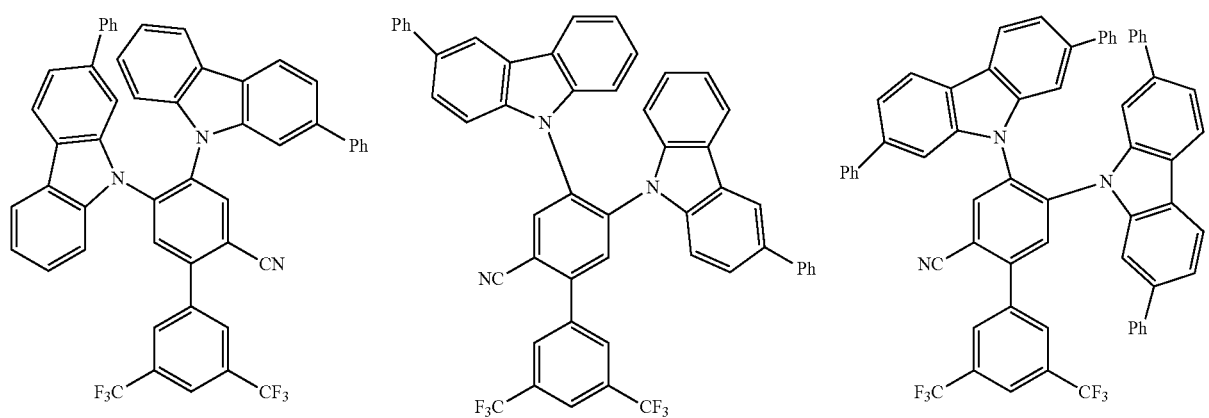
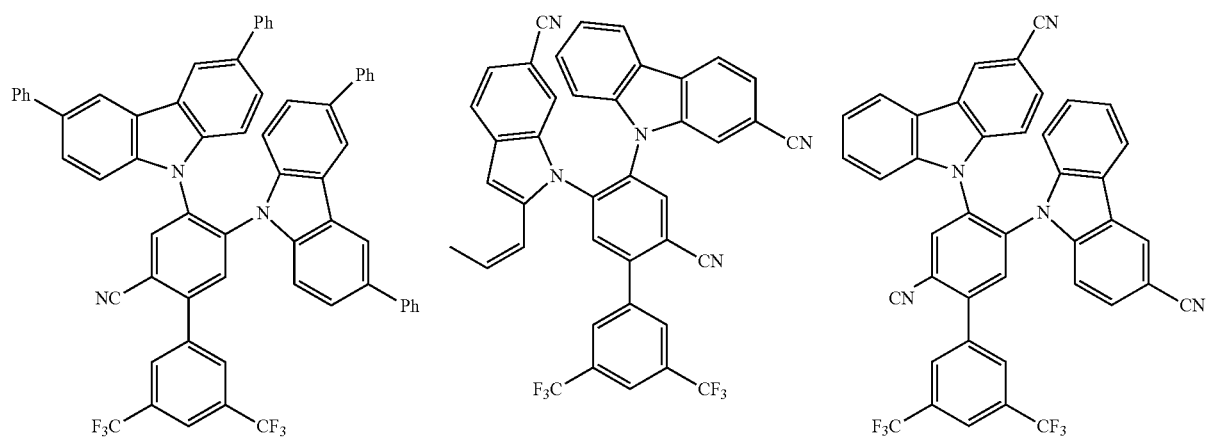

185
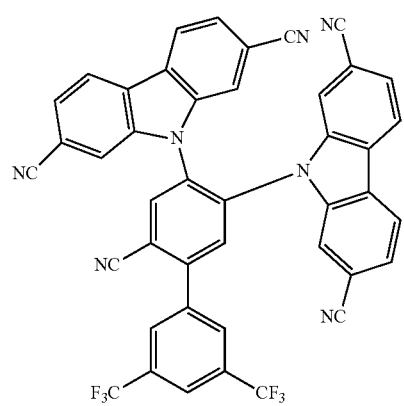
186
-continued
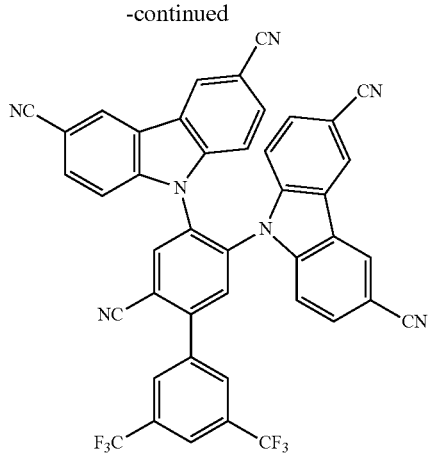
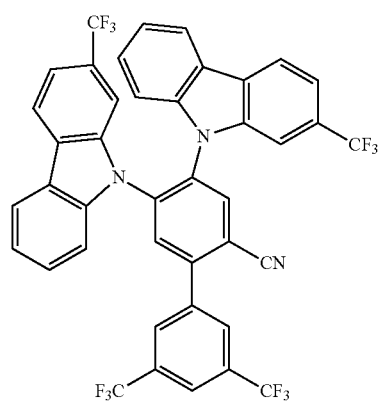
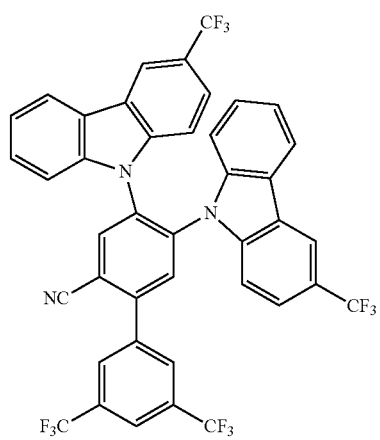
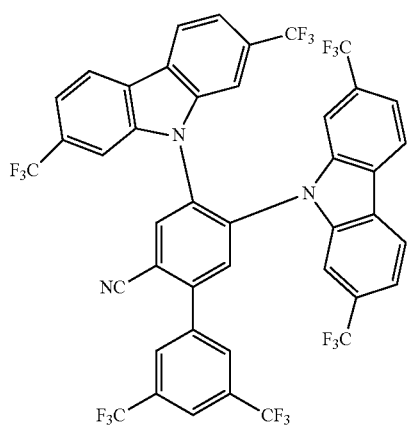
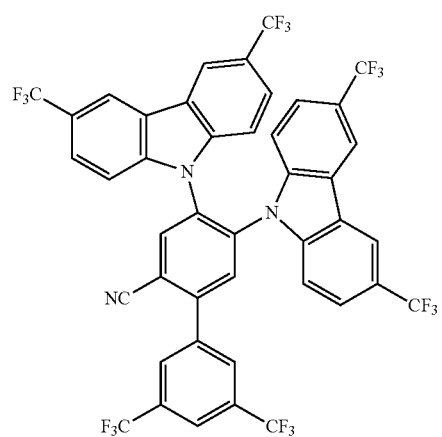
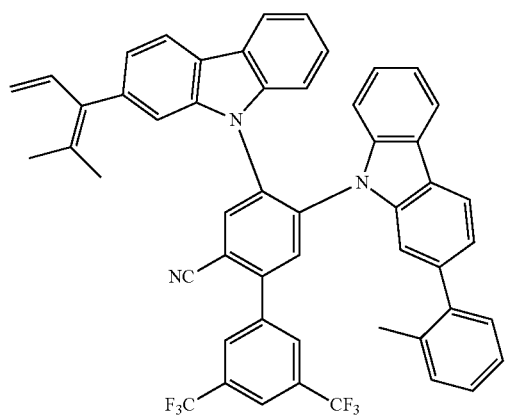

187
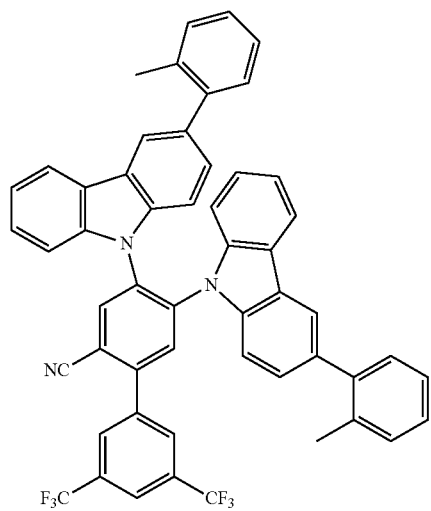
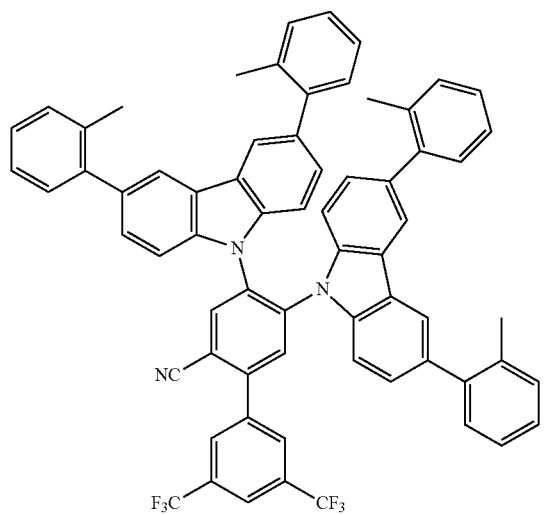
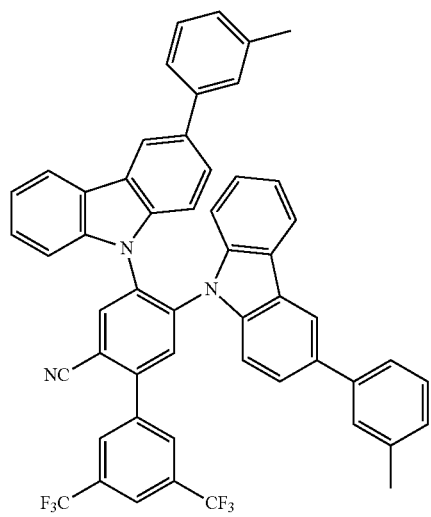
188
-continued
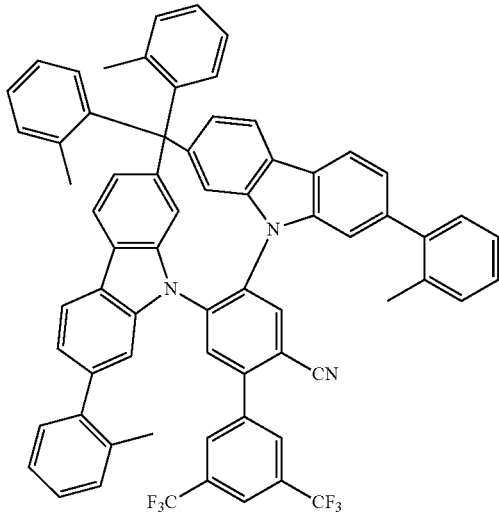
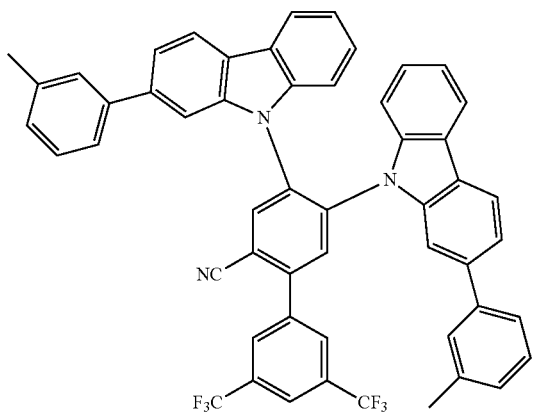
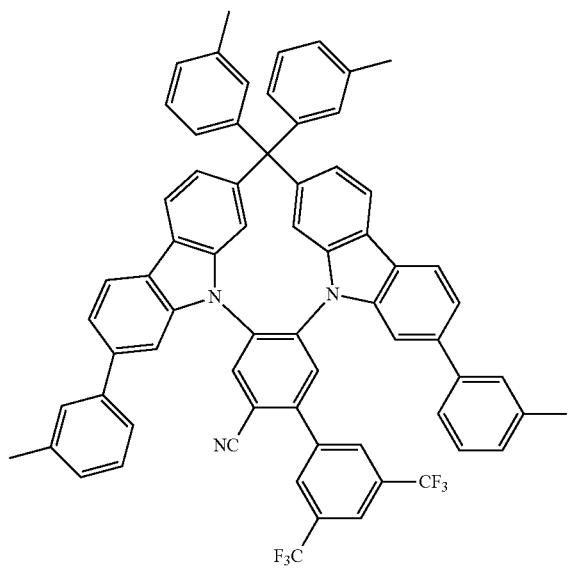

-continued
189
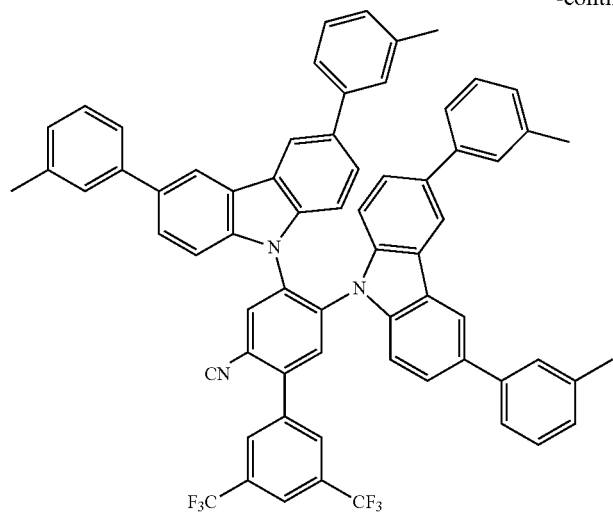
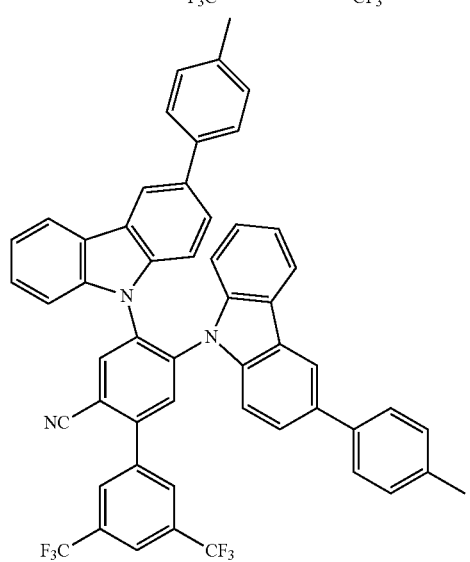
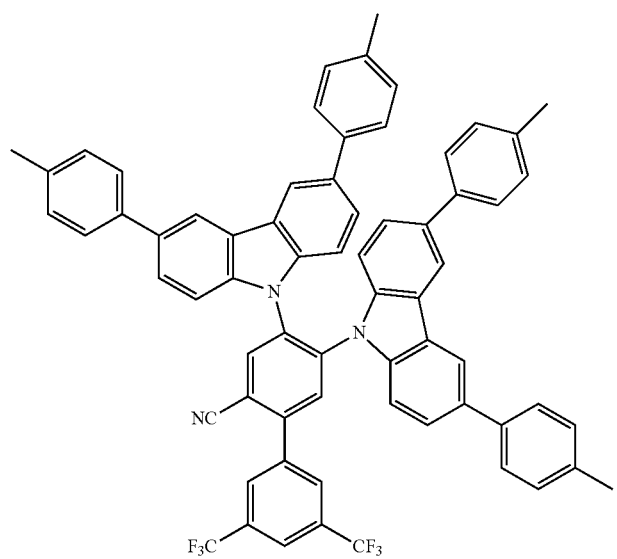
190
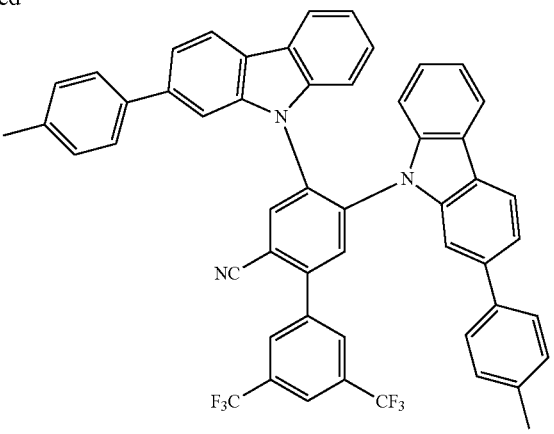
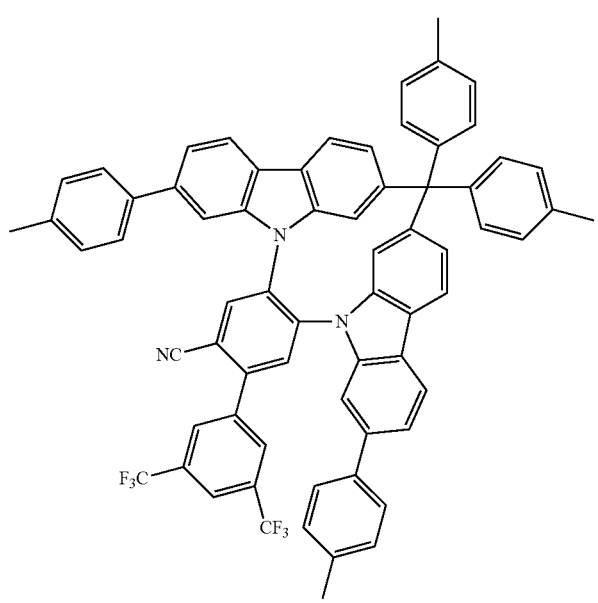
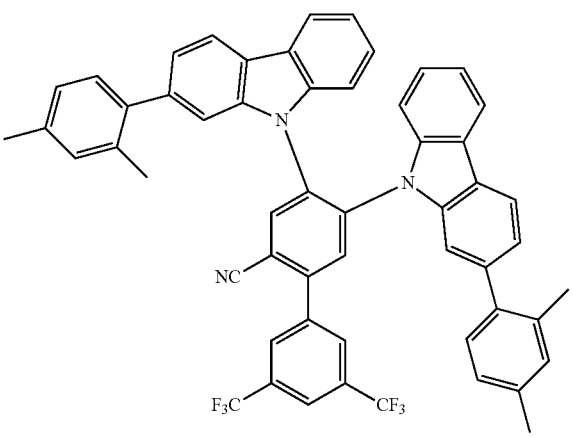

191
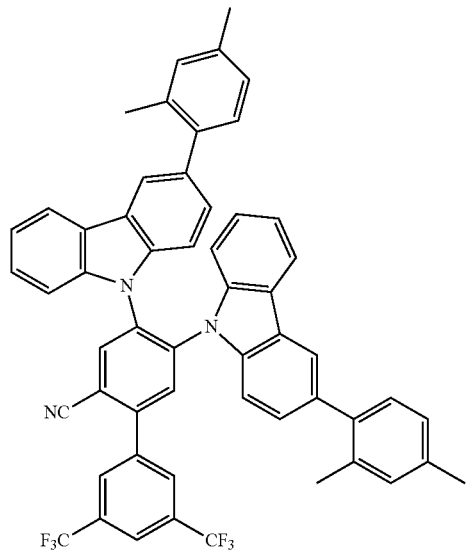
192
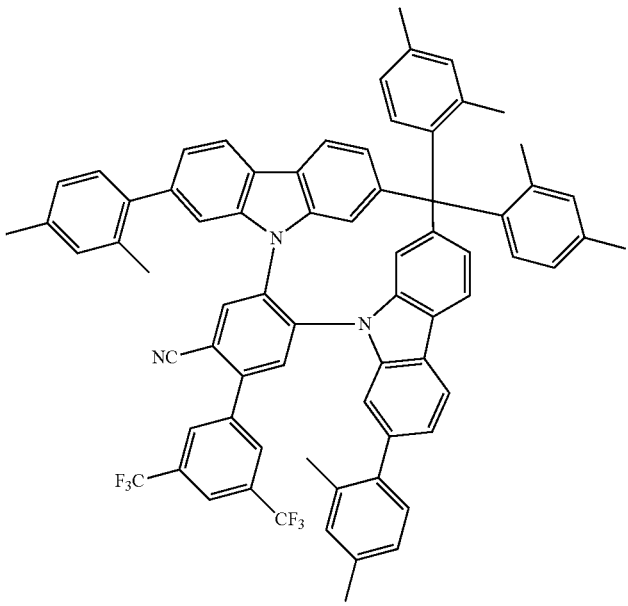
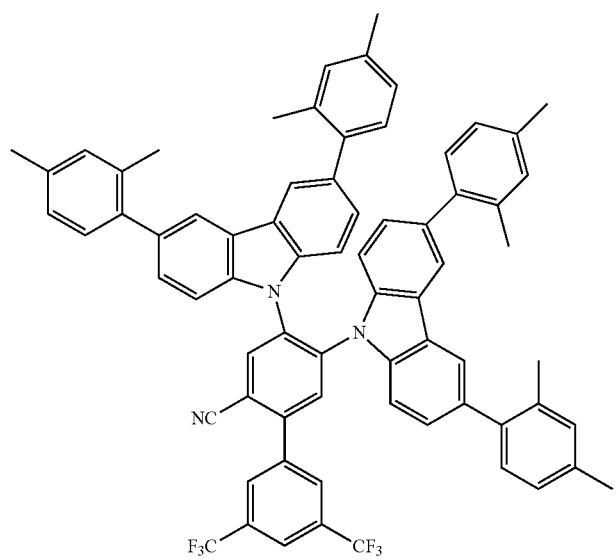
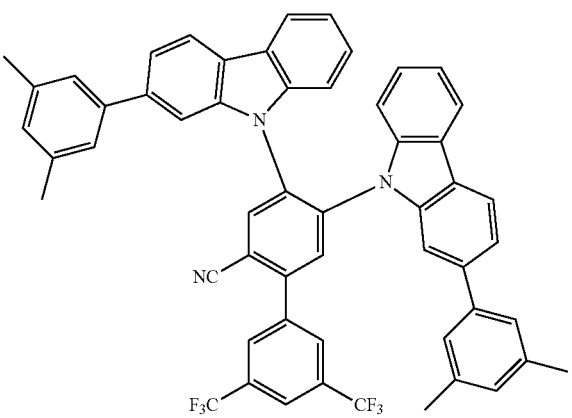
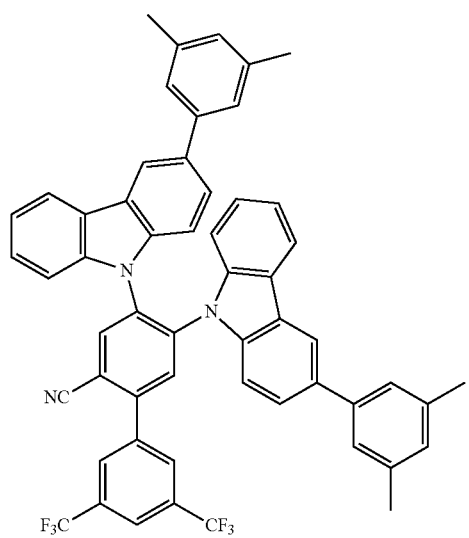
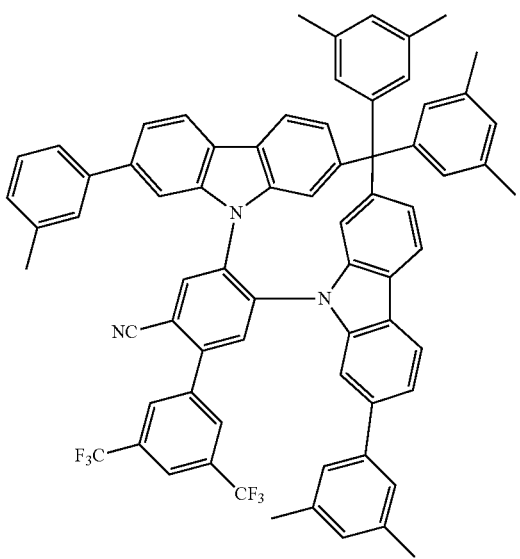

-continued
193
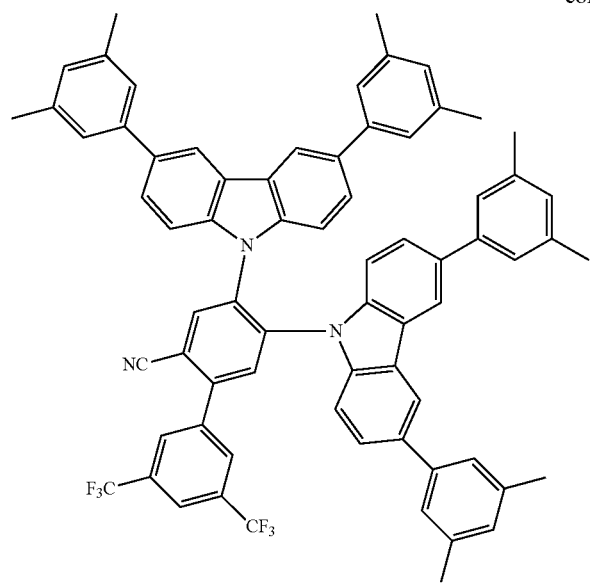
194
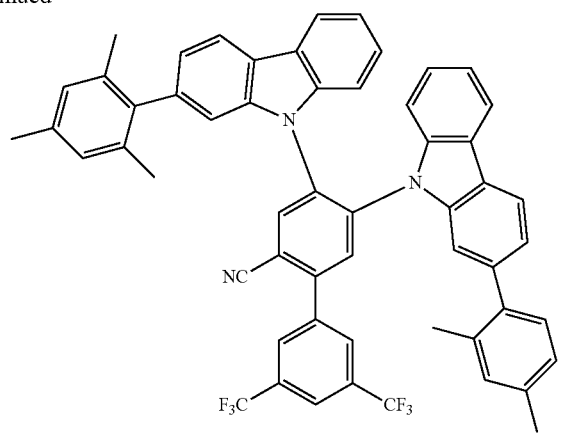
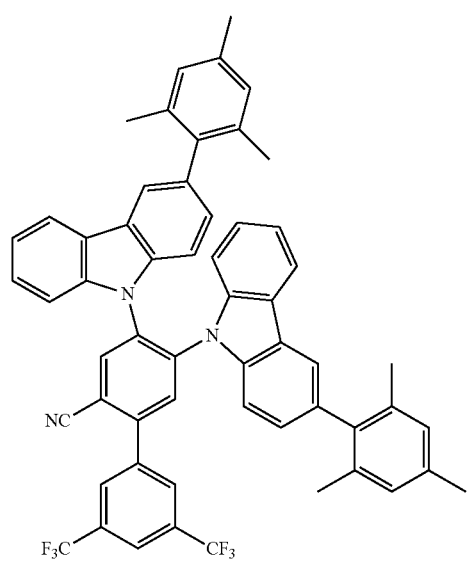
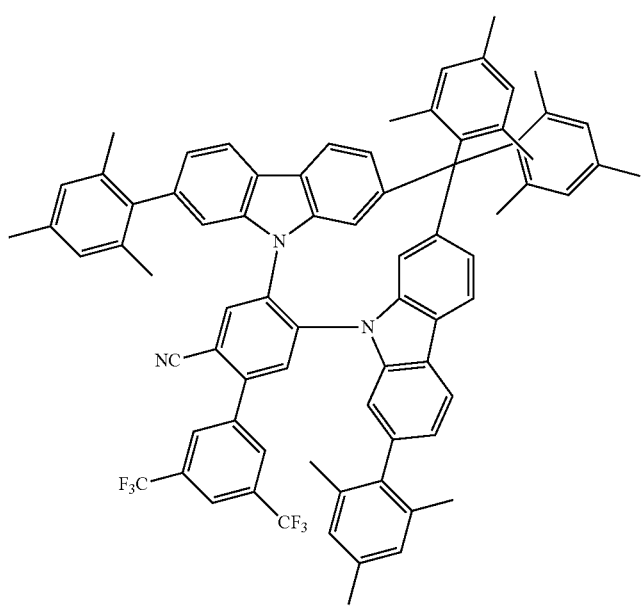

-continued
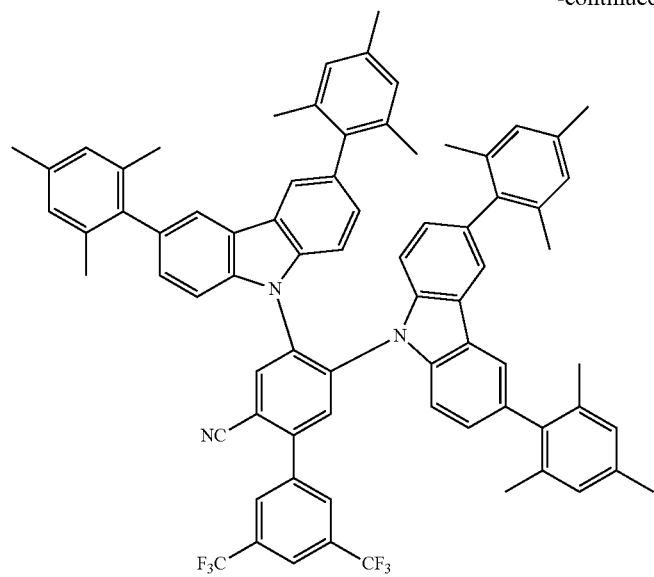
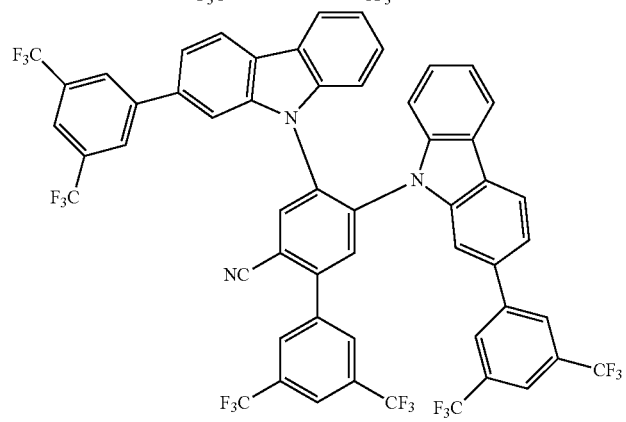
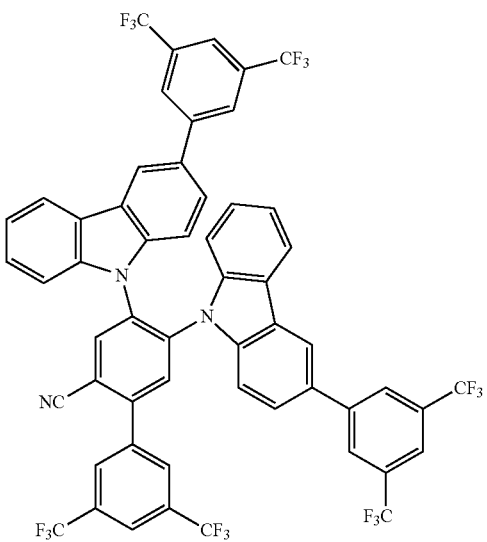
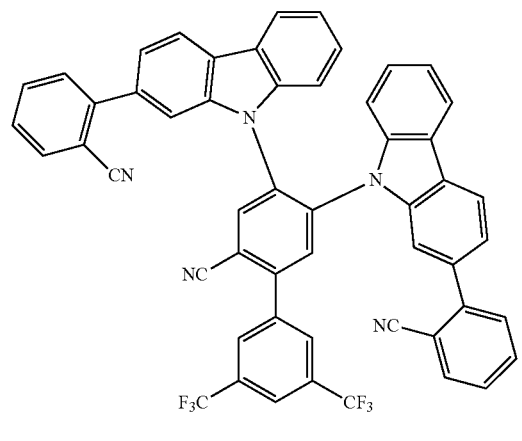
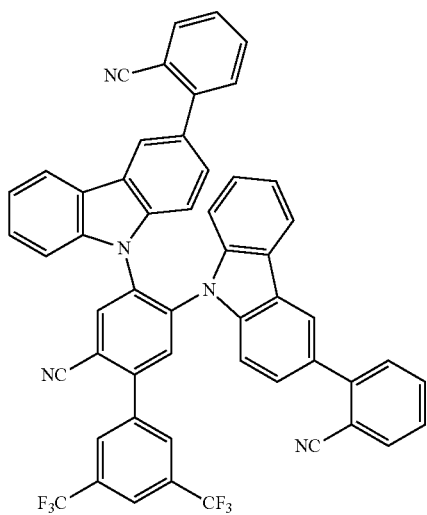

-continued
197
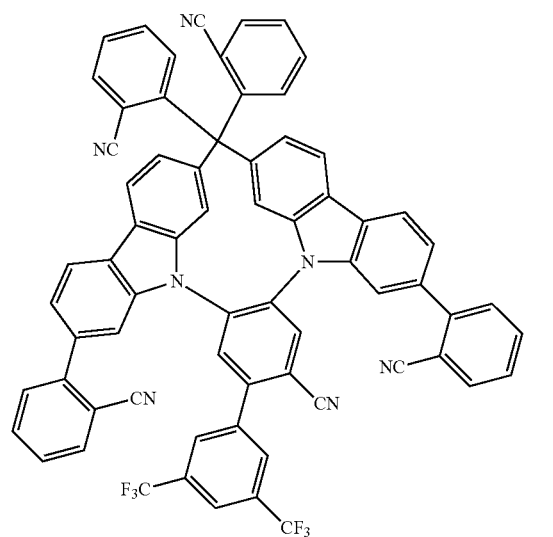
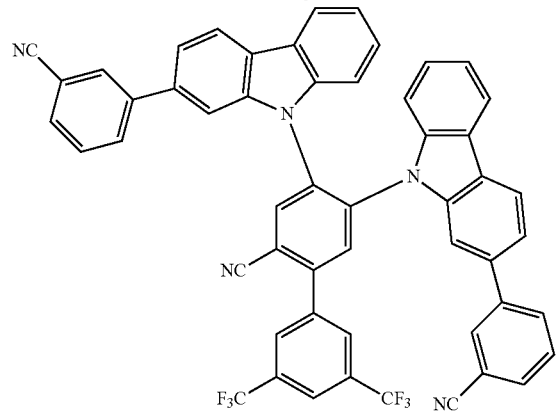
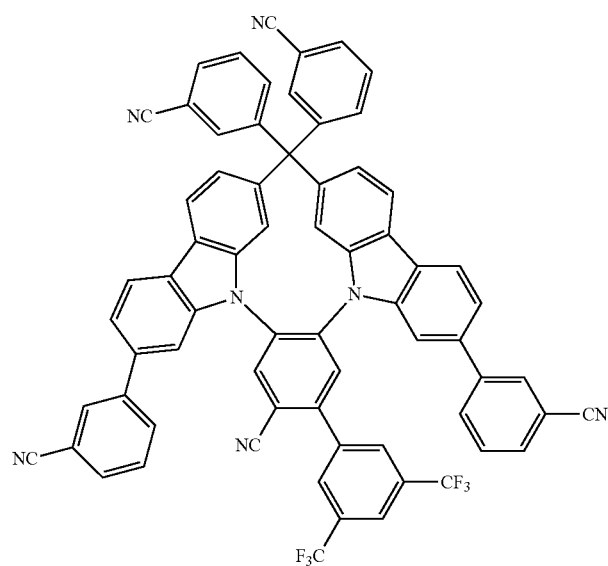
198
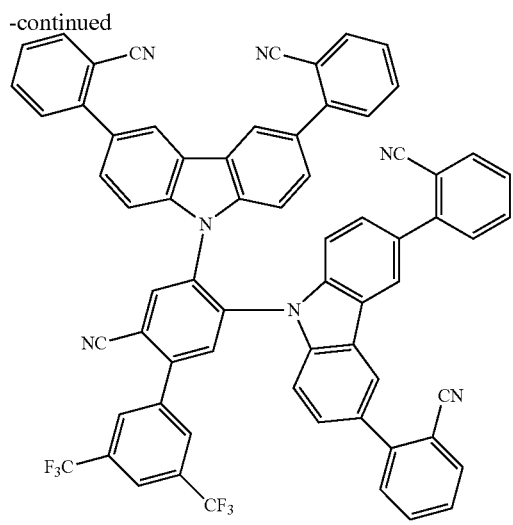
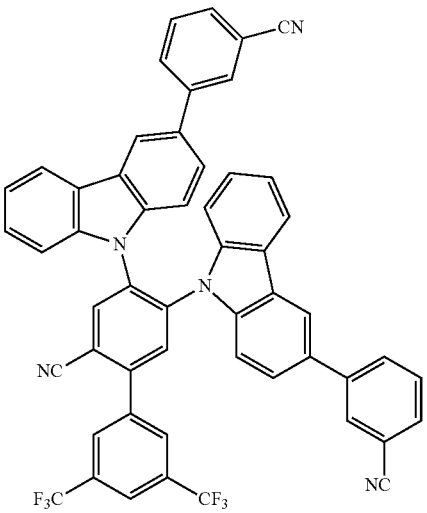
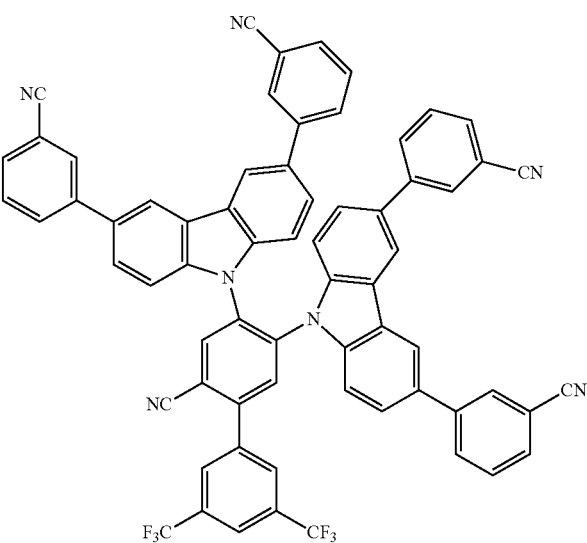

-continued
199
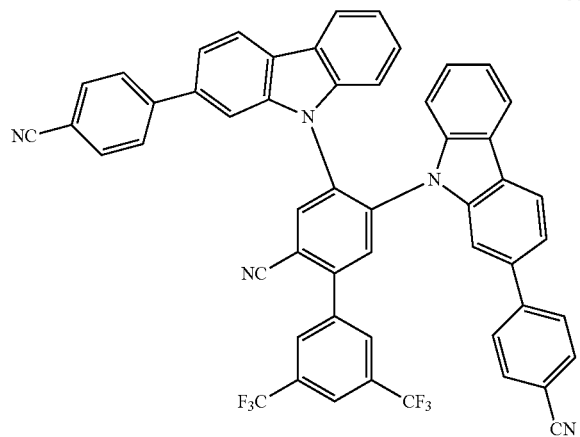
200
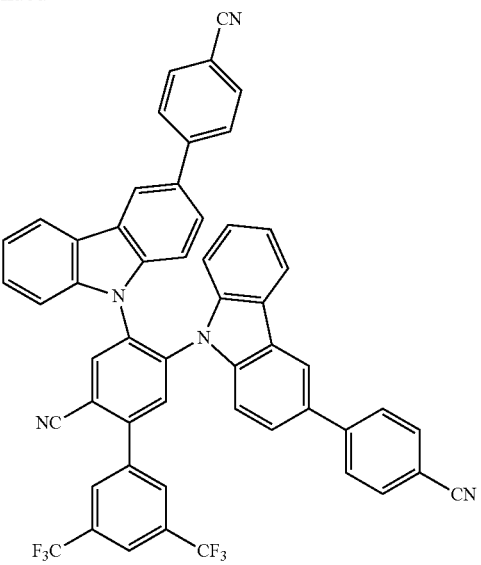
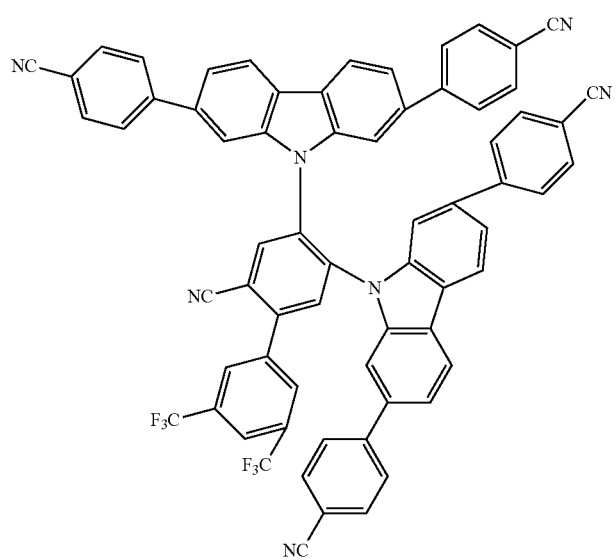
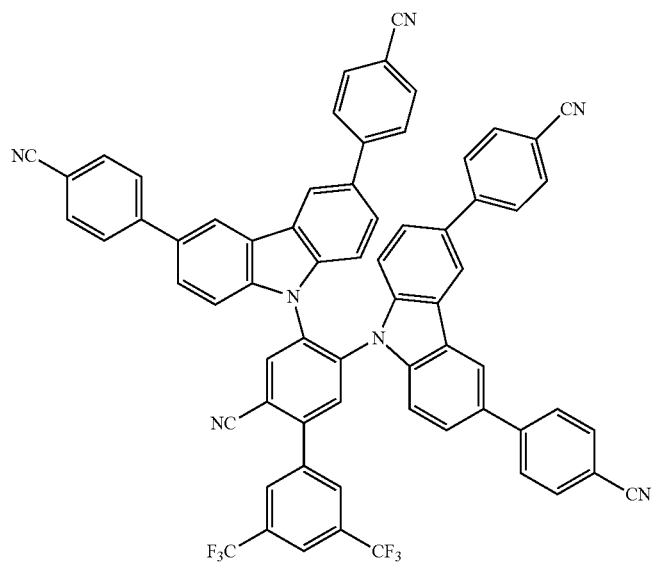

-continued
201
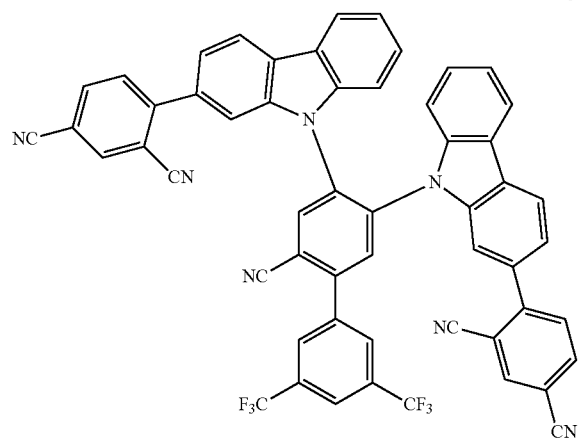
202
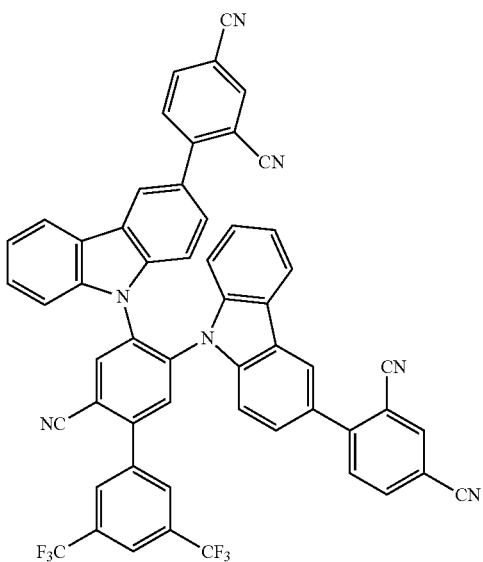
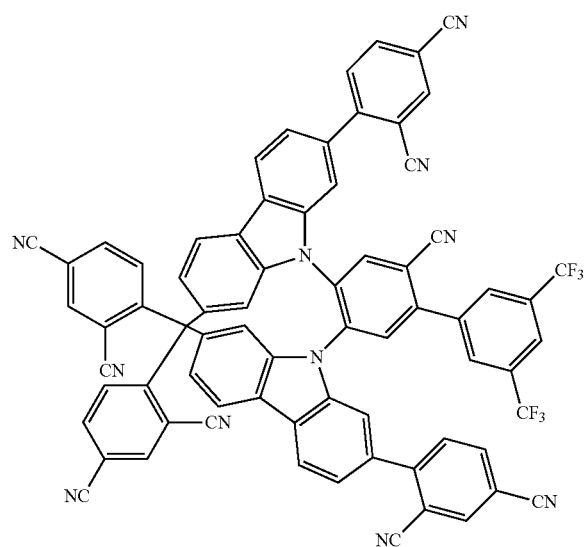
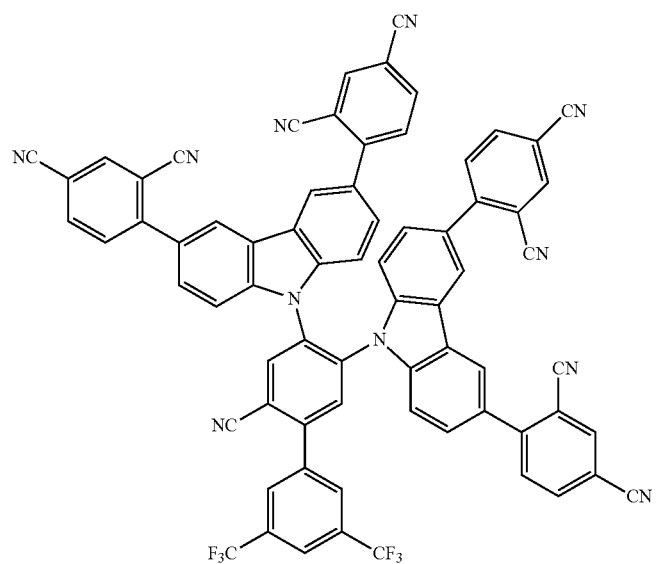

-continued
203
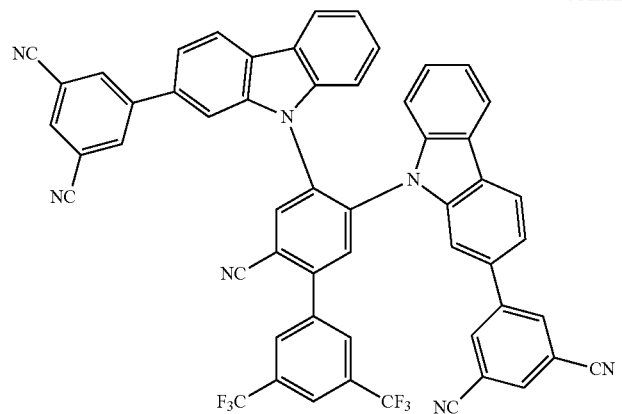
204
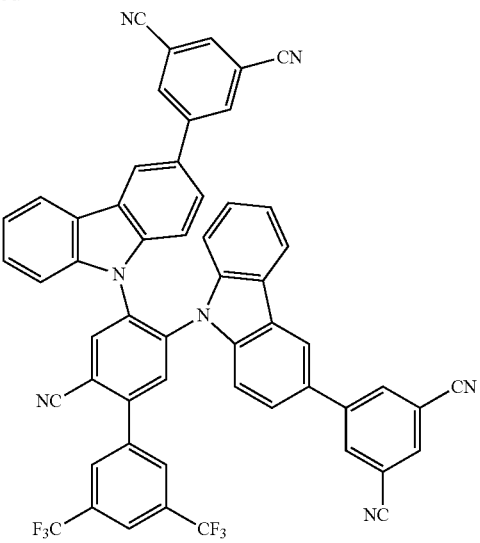
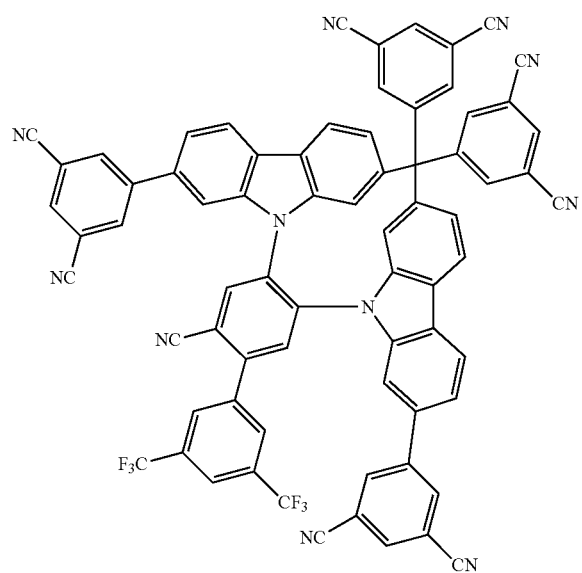
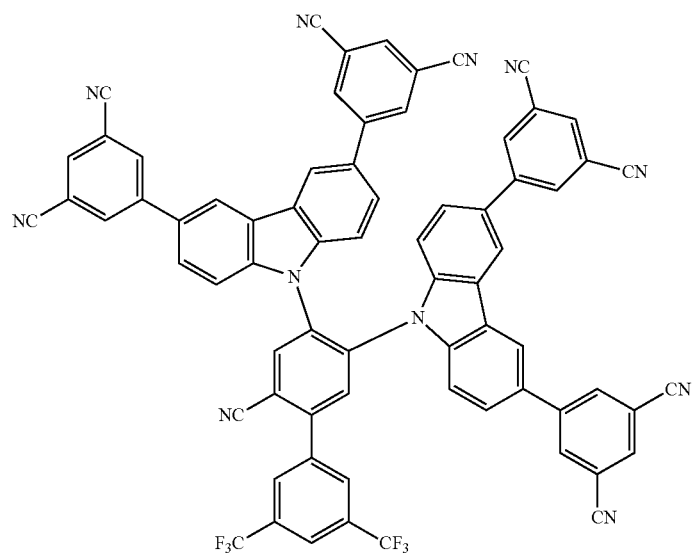

-continued
| 205 | 206 |
|---|---|
| 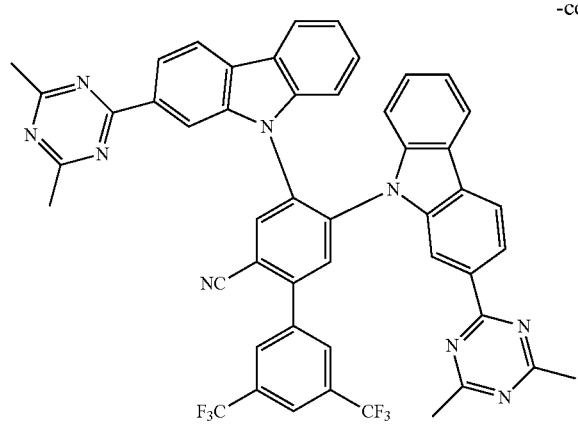 | 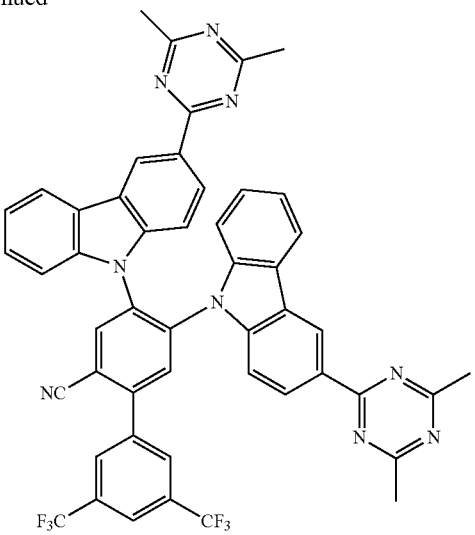 |
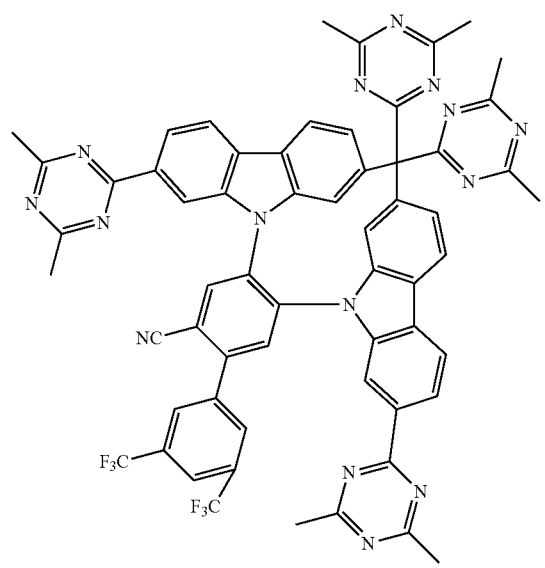
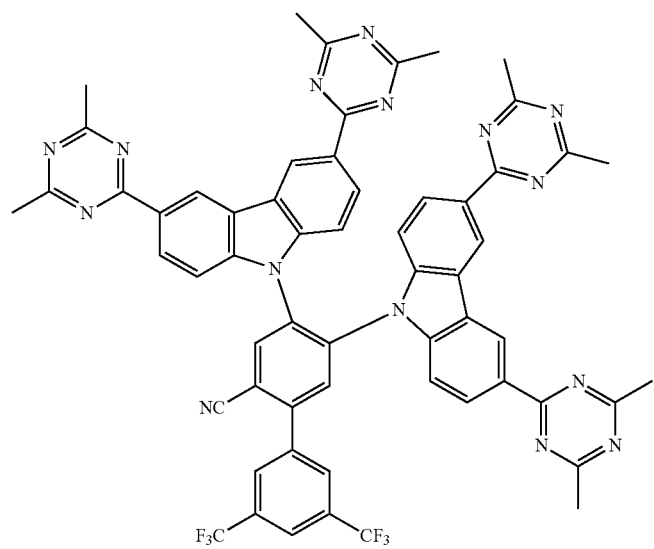

-continued
207
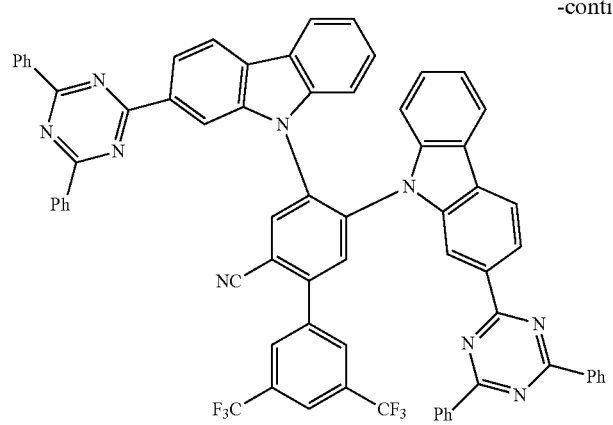
208
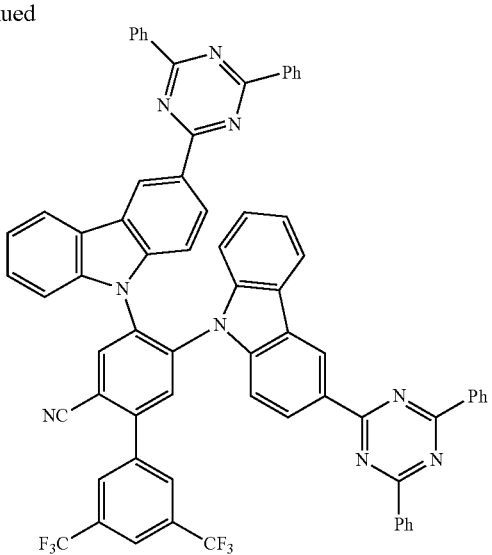
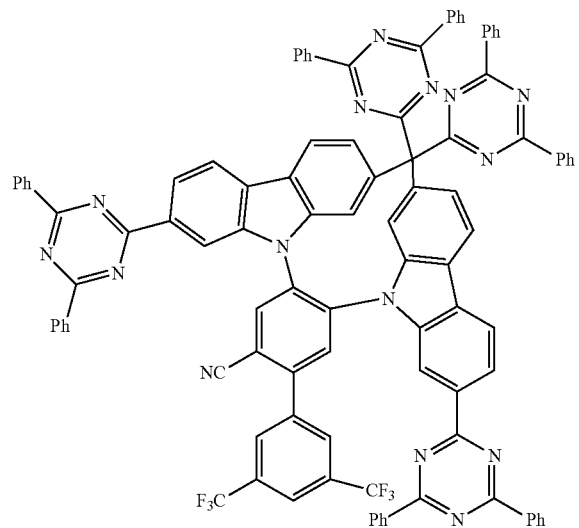
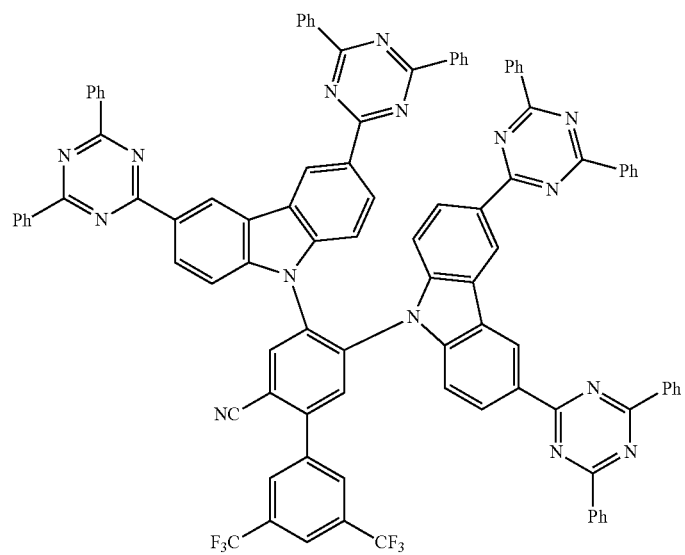

The invention claimed is:
1. An organic molecule comprising
a first chemical unit comprising a structure of formula I

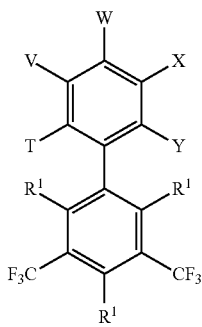

Formula I and two second chemical units each comprising a structure of formula II

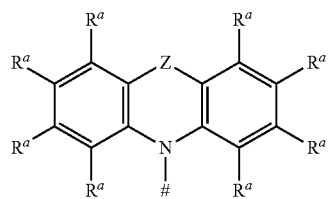

Formula II wherein the first chemical unit is joined to each of the two second chemical units via a single bond;
wherein:
T is an attachment point of the single bond between the first chemical unit and a second chemical unit or is H;
V is an attachment point of the single bond between the first chemical unit and a second chemical unit or is H;
W is an attachment point of the single bond between the first chemical unit and a second chemical unit or is selected from the group consisting of H, CN and $CF_3$;
X is an attachment point of the single bond between the first chemical unit and a second chemical unit or is selected from the group consisting of H, CN and $CF_3$;
Y is an attachment point of the single bond between the first chemical unit and a second chemical unit or is selected from the group consisting of H, CN and $CF_3$;
# indicates an attachment point of the single bond between a second chemical unit and the first chemical unit;
Z is the same or different for each of the two second chemical units and is a direct bond or selected from the group consisting of $CR^3R^4$, $C=CR^3R^4$, $C=O$, $C=NR^3$, $NR^3$, O, $SiR^3R^4$, S, S(O) and $S(O)_2$;
$R^1$ is the same or different at each occurrence on the first chemical unit and is selected from the group consisting of:
H, deuterium;
a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium; and
an aromatic or heteroaromatic ring system which has 5 to 15 aromatic ring atoms and may be substituted in each case by one or more $R^6$ radicals;

$R^a$, $R^3$ and $R^4$ are the same or different at each occurrence and are selected from the group consisting of:
H, deuterium, $N(R^5)_2$, OH, $Si(R^5)_3$, $B(OR^5)_2$, $OSO_2R^5$, $CF_3$, CN, F, Br, I;
a linear alkyl, alkoxy or thioalkoxy group which has 1 to 40 carbon atoms and may be substituted in each case by one or more $R^5$ radicals, wherein one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more hydrogen atoms may be replaced by deuterium, CN, $CF_3$ or $NO_2$;
a linear alkenyl or alkynyl group which has 2 to 40 carbon atoms and may be substituted in each case by one or more $R^5$ radicals, wherein one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more hydrogen atoms may be replaced by deuterium, CN, $CF_3$ or $NO_2$;
a branched or cyclic alkyl, alkenyl, alkynyl, alkoxy or thioalkoxy group which has 3 to 40 carbon atoms and may be substituted in each case by one or more $R^5$ radicals, wherein one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more hydrogen atoms may be replaced by deuterium, CN, $CF_3$ or $NO_2$;
an aromatic or heteroaromatic ring system which has 5 to 60 aromatic ring atoms and may he substituted in each case by one or more $R^5$ radicals;
an aryloxy or heteroaryloxy group which has 5 to 60 aromatic ring atoms and may be substituted in each case by one or more $R^5$ radicals; and
a diarylamino group, diheteroarylamino group or arylheteroarylamino group which has 10 to 40 aromatic ring atoms and may be substituted in each case by one or more $R^5$ radicals;
$R^5$ is the same or different at each occurrence and is selected from the group consisting of:
H, deuterium, $N(R^6)_2$, OH, $Si(R^6)_3$, $B(OR^6)_2$, $OSO_2R^6$, $CF_3$, CN, F, Br, I;
a linear alkyl, alkoxy or thioalkoxy group which has 1 to 40 carbon atoms and may be substituted in each case by one or more $R^6$ radicals, wherein one or more nonadjacent $CH_2$ groups may be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more hydrogen atoms may be replaced by deuterium, CN, $CF_3$ or $NO_2$;
a linear alkenyl or alkynyl group which has 2 to 40 carbon atoms and may be substituted in each case by one or more $R^6$ radicals, wherein one or more nonadjacent $CH_2$ groups may be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more hydrogen atoms may be replaced by deuterium, CN, $CF_3$ or $NO_2$;
a branched or cyclic alkyl, alkenyl, alkynyl, alkoxy or thioalkoxy group which has 3 to 40 carbon atoms and may be substituted in each case by one or more $R^6$ radicals, wherein one or more nonadjacent $CH_2$ groups may be replaced by $R^6C=CR^6$, $C\equiv C$, $Si(R^6)_2$, $Ge(R^6)_2$, $Sn(R^6)_2$, $C=O$, $C=S$, $C=Se$, C=NR$^6$, P(=O)(R$^6$), SO, SO$_2$, NR$^6$, O, S or CONR$^6$ and wherein one or more hydrogen atoms may be replaced by deuterium, CN, CF$_3$ or NO$_2$;

an aromatic or heteroaromatic ring system which has 5 to 60 aromatic ring atoms and may be substituted in each case by one or more R$^6$ radicals;

an aryloxy or heteroaryloxy group which has 5 to 60 aromatic ring atoms and may be substituted in each case by one or more R$^6$ radicals; and a diarylamino group, diheteroarylamino group or arylheteroarylamino group which has 10 to 40 aromatic ring atoms and may be substituted in each case by one or more R$^6$ radicals;

R$^6$ is the same or different at each occurrence and is selected from the group consisting of:

H, deuterium, OH, CF$_3$, CN, F;

a linear alkyl, alkoxy or thioalkoxy group having 1 to 5 carbon atoms, wherein one or more hydrogen atoms may be replaced by deuterium, CN, CF$_3$ or NO$_2$;

a linear alkenyl or alkynyl group having 2 to 5 carbon atoms, wherein one or more hydrogen atoms may be replaced by deuterium, CN, CF$_3$ or NO$_2$;

a branched or cyclic alkyl, alkenyl, alkynyl, alkoxy or thioalkoxy group having 3 to 5 carbon atoms, wherein one or more hydrogen atoms may be replaced by deuterium, CN, CF$_3$ or NO$_2$;

an aromatic or heteroaromatic ring system having 5 to 60 aromatic ring atoms;

an aryloxy or heteroaryloxy group having 5 to 60 aromatic ring atoms; and a diarylamino group; diheteroarylamino group or arylheteroarylamino group having 10 to 40 aromatic ring atoms;

wherein each of the R$^a$, R$^3$, R$^4$ or R$^5$ radicals together with one or more further R$^a$, R$^3$, R$^4$ or R$^5$ radicals may form a mono- or polycyclic, aliphatic, aromatic and/or benzofused ring system; and wherein exactly one radical selected from the group consisting of W, X and Y is CN or CF$_3$, and exactly two radicals selected from the group consisting of T, V, W, X and Y are an attachment point of the single bond between the first chemical unit and a second chemical unit.

2. The organic molecule according to claim 1, wherein R$^1$ is H, methyl or phenyl.

3. The organic molecule according to claim 1, wherein W is CN.

4. The organic molecule according to claim 1, wherein the each of the two second chemical units is the same or different from each other and comprises a structure of the formula IIa:

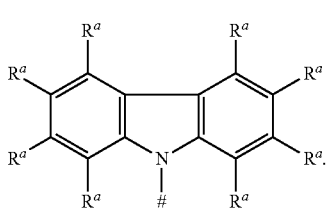

Formula IIa

5. The organic molecule according to claim 1, wherein each of the two second chemical units comprises a structure of the formula IIb:

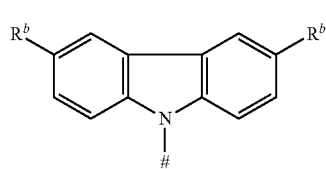

Formula IIb wherein R$^b$ is the same or different at each occurrence and is selected from the group consisting of:

N(R$^5$)$_2$, OH, Si(R$^5$)$_3$, B(OR$^5$)$_2$, OSO$_2$R$^5$, CF$_3$, CN, F, Br, I;

a linear alkyl, alkoxy or thioalkoxy group which has 1 to 40 carbon atoms and may be substituted in each case by one or more R$^5$ radicals, wherein one or more nonadjacent CH$_2$ groups may be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more hydrogen atoms may be replaced by deuterium, CN, CF$_3$ or NO$_2$;

a linear alkenyl or alkynyl group which has 2 to 40 carbon atoms and may be substituted in each case by one or more R$^5$ radicals, wherein one or more nonadjacent CH$_2$ groups may he replaced by R$^5$C=CR$^5$, C≡C, Si(R$^5$)$_2$, Ge(R$^5$ )$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more hydrogen atoms may be replaced by deuterium, CN, CF$_3$ or NO$_2$;

a branched or cyclic alkyl, alkenyl, alkynyl, alkoxy or thioalkoxy group which has 3 to 40 carbon atoms and may be substituted in each case by one or more R$^5$ radicals, wherein one or more nonadjacent CH$_2$ groups may be replaced by R$^5$C=CR$^5$, C≡C, Si (R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more hydrogen atoms may be replaced by deuterium, CN, CF$_3$ or NO$_2$;

an aromatic or heteroaromatic ring system which has 5 to 60 aromatic ring atoms and may be substituted in each case by one or more R$^5$ radicals;

an aryloxy or heteroaryloxy group which has 5 to 60 aromatic ring atoms and may be substituted in each case by one or more R$^5$ radicals; and a diarylamino group, diheteroarylamino group or arylheteroarylamino group which has 10 to 40 aromatic ring atoms and may be substituted in each case by one or more R$^5$ radicals.

6. The organic molecule according to claim 1, wherein each of the two second chemical units comprises a structure of the formula IIc:

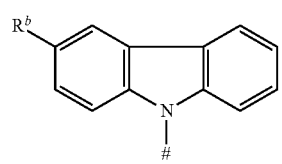

Formula IIc wherein R$^b$ is the same or different at each occurrence and is selected from the group consisting of:

N(R$^5$)$_2$, OH, Si(R$^5$)$_3$, B(OR$^5$)$_2$, OSO$_2$R$^5$, CF$_3$, CN, F, Br, I;

a linear alkyl, alkoxy or thioalkoxy group which has 1 to 40 carbon atoms and may be substituted in each case by one or more $R^5$ radicals, wherein one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more hydrogen atoms may be replaced by deuterium, CN, $CF_3$ or $NO_2$;

a linear alkenyl or alkynyl group which has 2 to 40 carbon atoms and may be substituted in each case by one or more $R^5$ radicals, wherein one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more hydrogen atoms may be replaced by deuterium, CN, $CF_3$ or $NO_2$;

a branched or cyclic alkyl, alkenyl, alkynyl, alkoxy or thioalkoxy group which has 3 to 40 carbon atoms and may be substituted in each case by one or more $R^5$ radicals, wherein one or more nonadjacent $CH_2$ groups may be replaced by $R^5C=CR^5$, $C\equiv C$, Si$(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more hydrogen atoms may be replaced by deuterium, CN, $CF_3$ or $NO_2$;

an aromatic or heteroaromatic ring system which has 5 to 60 aromatic ring atoms and may be substituted in each case by one or more $R^5$ radicals;

an aryloxy or heteroaryloxy group which has 5 to 60 aromatic ring atoms and may be substituted in each case by one or more $R^5$ radicals; and a diarylamino group, diheteroarylamino group or arylheteroarylamino group which has 10 to 40 aromatic ring atoms and may be substituted in each case by one or more $R^5$ radicals.

7. The organic molecule according to claim 5, wherein $R^b$ is $N(Ph)_2$ or is Me, $^iPr$, $^tBu$, CN, $CF_3$, Ph, pyridinyl, pyrimidinyl or carbazolyl, which may be substituted in each case by one or more radicals selected from Me, $^iPr$, $^tBu$, CN, $CF_3$ and Ph.

8. The organic molecule according to claim 6, wherein $R^b$ is $N(Ph)_2$ or is Me, $^iPr$, $^tBu$, CN, $CF_3$, Ph, pyridinyl, pytitnidinyl or carbazolyl, which may be substituted in each case by one or more radicals selected from Me, $^iPr$, $^tBu$, CN, $CF_3$ and Ph.

9. A process for preparing the organic molecule according to claim 1, wherein a 2,4,6-$R^1$-substituted 3,5-bis(trifluoromethyl)phenylboronic acid or a corresponding 2,4,6-$R^1$-substituted 3,5-bis(trifluoromethyl)phenylboronic ester is used as reactant.

10. An organic optoelectronic device comprising at least one of a luminescent emitter, electron transport material, hole injection material, and hole blocker material, wherein the luminescent emitter, the electron transport material, the hole injection material, and the hole blocker material comprise the organic molecule according to claim 1.

11. The organic optoelectronic device according to claim 10, wherein the organic optoelectronic device is selected from the group consisting of an organic light-emitting diode (OLED), a light-emitting electrochemical cell, an OLED sensor, an organic diode, an organic solar cell, an organic transistor, an organic field-effect transistor, an organic laser and a down-conversion element.

12. A composition comprising:
at least one organic molecule according to claim 1 in the form of an emitter;
at least one of an emitter and a host material not comprising the organic molecule according to claim 1; and
at least one of a dye and a solvent.

13. An organic optoelectronic device comprising the composition according to claim 12, wherein the organic optoelectronic device is selected from the group consisting of an organic light-emitting diode (OLED), a light-emitting electrochemical cell, an OLED sensor, an organic diode, an organic solar cell, an organic transistor, an organic field-effect transistor, an organic laser and a down-conversion element.

14. The organic optoelectronic device according to claim 13, comprising:
a substrate;
an anode;
a cathode, wherein the anode or cathode is on the substrate; and
at least one light-emitting layer arranged between the anode and the cathode, wherein the at least one light-emitting layer comprises the composition according to claim 12.

15. A method for manufacturing an optoelectronic component, comprising performing processing of the organic molecule according to claim 1 from a solution or by using a vacuum evaporation process.

16. The organic molecule of claim 1, wherein the organic molecule does not contain any metal ions.

* * * * *

UNITED STATES PATENT AND TRADEMARK OFFICE
CERTIFICATE OF CORRECTION

PATENT NO. : 10,439,151 B2
APPLICATION NO. : 15/685166
DATED : October 8, 2019
INVENTOR(S) : Martha Fabio et al.

It is certified that error appears in the above-identified patent and that said Letters Patent is hereby corrected as shown below:

In the Claims

Column 210, Claim 1, Line 50, please delete "$SO_{,2}$," and insert --$SO_2$,--

Signed and Sealed this
Tenth Day of December, 2019

Andrei Iancu
*Director of the United States Patent and Trademark Office*